United States Patent
Obrecht et al.

(10) Patent No.: US 8,895,499 B2
(45) Date of Patent: Nov. 25, 2014

(54) β-HAIRPIN PEPTIDOMIMETICS

(75) Inventors: Daniel Obrecht, Bättwil (CH); Frank Otto Gombert, Basel (CH); John Anthony Robinson, Wermatswil (CH); Krystyna Patora-Komisarska, Zürich (CH)

(73) Assignees: Polyphor AG, Allschwil (CH); Universität Zurich, Zurich (CH)

( * ) Notice: Subject to any disclaimer, the term of this patent is extended or adjusted under 35 U.S.C. 154(b) by 0 days.

(21) Appl. No.: 13/814,398

(22) PCT Filed: Aug. 5, 2010

(86) PCT No.: PCT/EP2010/061445
§ 371 (c)(1),
(2), (4) Date: Apr. 3, 2013

(87) PCT Pub. No.: WO2012/016595
PCT Pub. Date: Feb. 9, 2012

(65) Prior Publication Data
US 2013/0189363 A1   Jul. 25, 2013

(51) Int. Cl.
A61K 38/00 (2006.01)
C07K 7/54 (2006.01)
A01N 47/44 (2006.01)
C07K 7/64 (2006.01)

(52) U.S. Cl.
CPC . *C07K 7/54* (2013.01); *A01N 47/44* (2013.01); *C07K 7/64* (2013.01)
USPC .......................................................... 514/1.1

(58) Field of Classification Search
None
See application file for complete search history.

(56) References Cited

FOREIGN PATENT DOCUMENTS

| WO | WO 02/070547 A1 | 9/2002 |
|----|-----------------|--------|
| WO | WO 2004/010503 A1 | 3/2004 |
| WO | WO 2007/079597 A1 | 7/2007 |

OTHER PUBLICATIONS

Robinson et al., Bioorganic & Medicinal Chemistry, 2005, 13, 2055 2064.*
International Search Report for International Patent Application No. PCT/EP2010/061445, dated Dec. 22, 2010.
Robinson et al., "Properties and structure-activity studies of cyclic β-hairpin peptidomimetics based on the cationic antimicrobial peptide protegrin I," Bioorganic & Medicinal Chemistry, vol. 13, pp. 2055-2064.
International Preliminary Report on Patentability for International Patent Application No. PCT/EP2010/061445, dated Feb. 5, 2013.

* cited by examiner

*Primary Examiner* — Marcela M Cordero Garcia
*Assistant Examiner* — Kaipeen Yang
(74) *Attorney, Agent, or Firm* — Birch, Stewart, Kolasch & Birch, LLP

(57) ABSTRACT

β-Hairpin peptidomimetics of the general formula Cyclo(-$Xaa^1$-$Xaa^2$-$Xaa^3$-$Xaa^4$-$Xaa^5$-$Xaa^6$-$Xaa^7$-$Xaa^8$-$Xaa^9$-$Xaa^{10}$-$Xaa^{11}$-$Xaa^{12}$-$Xaa^{13}$-$Xaa^{14}$-), enantiomers and pharmaceutically acceptable salts thereof, with $Xaa^1$-$Xaa^{14}$ being amino acid residues of certain types which are defined in the description and the claims, have anti-infective activity, e.g. to selectively inhibit the growth of or to kill microorganisms such as *Bacillus subtilis* and/or *Shigella boydii*. They can be used as medicaments to treat or prevent infections or as disinfectants for foodstuffs, cosmetics, medicaments or other nutrient-containing materials. These peptidomimetics can be manufactured by a process which is based on a mixed solid- and solution phase synthetic strategy.

16 Claims, No Drawings

β-HAIRPIN PEPTIDOMIMETICS

The present invention provides β-hairpin peptidomimetics having selective anti-infective activity.

The β-hairpin peptidomimetics of the invention are Cyclo (-$Xaa^1$-$Xaa^2$-$Xaa^3$-$Xaa^4$-$Xaa^5$-$Xaa^6$-$Xaa^7$-$Xaa^8$-$Xaa^9$-$Xaa^{10}$-$Xaa^{11}$-$Xaa^{12}$-$Xaa^{13}$-$Xaa^{14}$-), and pharmaceutically acceptable salts thereof, with $Xaa^1$ to $Xaa^{14}$ being as described herein below.

In addition, the present invention provides an efficient synthetic process by which these compounds can, if desired, be made in parallel library-format. These β-hairpin peptidomimetics show a significantly enhanced ratio between anti-infective activity on the one hand, and reduced hemolysis of red blood cells and reduced or no cytotoxicity on the other.

A major cause of death worldwide and a leading cause of mortality in developed countries are infectious diseases. They result from the presence of pathogenic microbial agents including pathogenic viruses and pathogenic bacteria. The growing problem of bacterial resistance to established antibiotics has stimulated intense interest in developing novel antimicrobial agents with new modes of action (D. Obrecht, J. A. Robinson, F. Bernadini, C. Bisang, S. J. DeMarco, K. Moehle, F. O. Gombert, *Curr. Med. Chem.* 2009, 16, 42-65; H. Breithaupt, *Nat. Biotechnol.* 1999, 17, 1165-1169). One emerging class of antibiotics is based on naturally occurring cationic peptides (T. Ganz, R. I. Lehrer, *Mol. Medicine Today* 1999, 5, 292-297; R. M. Epand, H. J. Vogel, *Biochim. Biophys. Acta* 1999, 1462, 11-28). These include disulfide-bridged β-hairpin and β-sheet peptides (such as the protegrins [V. N. Kokryakov, S. S. L. Harwig, E. A. Panyutich, A. A. Shevchenko, G. M. Aleshina, O. V. Shamova, H. A. Korneva, R. I. Lehrer, *FEBS Lett.* 1993, 327, 231-236], tachyplesins [T. Nakamura, H. Furunaka, T. Miyata, F. Tokunaga, T. Muta, S. Iwanaga, M. Niwa, T. Takao, Y. Shimonishi, *J. Biol. Chem.* 1988, 263, 16709-16713], and the defensins [R. I. Lehrer, A. K. Lichtenstein, T. Ganz, *Annu. Rev. Immunol.* 1993, 11, 105-128], amphipathic α-helical peptides (e.g. cecropins, dermaseptins, magainins, and mellitins [A. Tossi, L. Sandri, A. Giangaspero, *Biopolymers* 2000, 55, 4-30]), as well as other linear and loop-structured peptides. Although the mechanisms of action of antimicrobial cationic peptides are not yet fully understood, their primary site of interaction is the microbial cell membrane (H. W. Huang, *Biochemistry* 2000, 39, 8347-8352). Upon exposure to these agents, the cell membrane undergoes permeabilization, which is followed by rapid cell death. However, more complex mechanisms of action, for example, involving receptor-mediated signaling, cannot presently be ruled out (M. Wu, E. Maier, R. Benz, R. E. Hancock, *Biochemistry* 1999, 38, 7235-7242).

Unlike most antibiotics, antiviral agents do not destroy the target viruses but they are able to inhibit the development of viral pathogens at different stages of their replication cycle, for example, by preventing the entry of the viruses to the target cells or by blocking essential steps during the viral synthesis within the target cells. Common diseases caused by viruses are, for example, influenza, avian influenza, swine influenza, severe acute respiratory syndrome (SARS), or acquired immune deficiency syndrome (AIDS). Encephalitis, meningitis, pharyngitis parotitis, gingivostomatitis, hepatitis, myelitis, gastroenteritis, pancreatitis, certain skin infections or cardiovascular diseases as well as pneumonia or sexually transmitted diseases can be caused by viral infections.

In the compounds described below, a new strategy is introduced to stabilize β-hairpin conformations in backbone-cyclic cationic peptide mimetics exhibiting selective anti-infective activity. This involves transplanting the hairpin sequence onto a template, whose function is to restrain the peptide loop backbone into a hairpin geometry.

Template-bound hairpin mimetic peptides have been described in the literature (D, Obrecht, M. Altorfer, J. A. Robinson, *Adv. Med. Chem.* 1999, 4, 1-68; J. A. Robinson, *Syn. Lett.* 2000, 4, 429-441) and the ability to generate β-hairpin peptidomimetics using combinatorial and parallel synthesis methods has now been established (L. Jiang, K. Moehle, B. Dhanapal, D. Obrecht, J. A. Robinson, *Helv. Chim. Acta.* 2000, 83, 3097-3112). Antibacterial template-fixed peptidomimetics and methods for their synthesis have been described in International Patent applications WO02/070547 A1, WO2004/018503 A1 and WO2007/079605 A2 but these molecules do not show high potency and selectivity against *Bacillus subtilis* and/or *Shigella boydii*.

The β-hairpin peptidomimetics of the present invention are compounds of the general formula Cyclo(-$Xaa^1$-$Xaa^2$-$Xaa^3$-$Xaa^4$-$Xaa^5$-$Xaa^6$-$Xaa^7$-$Xaa^8$-$Xaa^9$-$Xaa^{10}$-$Xaa^{11}$-$Xaa^{12}$-$Xaa^{13}$-$Xaa^{14}$-), wherein the amino acid residues $Xaa^1$ to $Xaa^{14}$ are:

$Xaa^1$: amino acid residue of type C, or of type D,
  as described herein below;
$Xaa^2$: amino acid residue of type E,
  as described herein below;
$Xaa^3$: amino acid residue of type C, or of type F,
  as described herein below;
$Xaa^4$: amino acid residue of type C, or of type E,
  as described herein below;
$Xaa^5$: amino acid residue of type C,
  as described herein below;
$Xaa^6$: amino acid residue of type E, as described herein below; or the D-isomer of an amino acid residue of type E, as described herein below;
$Xaa^7$: amino acid residue of type F,
  as described herein below, or Gly;
$Xaa^8$: amino acid residue of type E,
  as described herein below;
$Xaa^9$: amino acid residue of type E,
  as described herein below;
$Xaa^{10}$: amino acid residue of type C, or of type F,
  as described herein below;
$Xaa^{11}$: amino acid residue of type E, or of type F,
  as described herein below;
$Xaa^{12}$: amino acid residue of type C, or of type E, or of type F, as described herein below;
$Xaa^{13}$: amino acid residue of formula -A-CO—,
  as described herein below;
$Xaa^{14}$: amino acid residue of formula —B—CO—,
  as described herein below;
with the proviso that if
  $Xaa^9$ is an amino acid residue of type E,
    as described herein below,
  then $Xaa^9$ is Dab; and/or if
  $Xaa^{12}$ is an amino acid residue of type F,
    as described herein below,
  then $Xaa^n$ is Gln; and/or
at least two of the amino acid residues of Cyclo(-$Xaa^1$-$Xaa^2$-$Xaa^3$-$Xaa^4$-$Xaa^5$-$Xaa^6$-$Xaa^7$-$Xaa^8$-$Xaa^9$-$Xaa^{10}$-$Xaa^{11}$-$Xaa^{12}$-$Xaa^{13}$-$Xaa^{14}$-) are non-canonical amino acid residues, as described herein below;
or
compounds of the general formula Cyclo(-$Xaa^1$-$Xaa^2$-$Xaa^3$-$Xaa^4$-$Xaa^5$-$Xaa^8$-$Xaa^9$-$Xaa^8$-$Xaa^9$-$Xaa^{10}$-$Xaa^{11}$-$Xaa^{12}$-$Xaa^{13}$-$Xaa^{14}$-), wherein the amino acid residues $Xaa^1$ to $Xaa^{14}$ are:
  $Xaa^1$: amino acid residue of type D,
    as described herein below;

Xaa²: amino acid residue of type E,
   as described herein below;
Xaa³: amino acid residue of type C, or of type F,
   as described herein below;
Xaa⁴: amino acid residue of type E,
   as described herein below;
Xaa⁵: amino acid residue of type C,
   as described herein below;
Xaa⁶: amino acid residue of type E, or the D-isomer of an amino acid residue of type E, as described herein below;
Xaa⁷: amino acid residue of type C, or of type D, or of type E, or of type F, as described herein below, or Gly;
Xaa⁸: amino acid residue of type F,
   as described herein below;
Xaa⁹: amino acid residue of type E,
   as described herein below;
Xaa¹⁰: amino acid residue of type C, or of type D, or of type F, as described herein below;
Xaa¹¹: amino acid residue of type E, or or type F,
   as described herein below;
Xaa¹²: amino acid residue of type C or of type E,
   as described herein below;
Xaa¹³: amino acid residue of formula-A-CO—,
   as described herein below;
Xaa¹⁴: amino acid residue of formula —B—CO—,
   as described herein below;
with the proviso that if
   Xaa⁷ is an amino acid residue of type F,
      as described herein below,
   then Xaa⁷ is Gln or Thr; and/or if
   Xaa¹⁰ is an amino acid residue of type F,
      as described herein below,
   then Xaa¹⁰ is Ser; and/or
at least one of the amino acid residues of Cyclo(-Xaa¹-Xaa²-Xaa³-Xaa⁴-Xaa⁵-Xaa⁶-Xaa⁷-Xaa⁸-Xaa⁹-Xaa¹⁰-Xaa¹¹-Xaa¹²-Xaa¹³-Xaa¹⁴-) is a non-canonical amino acid residue, as described herein below;
or
compounds of the general formula Cyclo(-Xaa¹-Xaa²-Xaa³-Xaa⁴-Xaa⁵-Xaa⁶-Xaa⁷-Xaa⁸-Xaa⁹-Xaa¹⁰-Xaa¹¹-Xaa¹²-Xaa¹³-Xaa¹⁴-), wherein the amino acid residues Xaa¹ to Xaa¹⁴ are:
   Xaa¹: amino acid residue of type D,
      as described herein below;
   Xaa²: amino acid residue of type E,
      as described herein below;
   Xaa³: amino acid residue of type C,
      as described herein below;
   Xaa⁴: amino acid residue of type E,
      as described herein below;
   Xaa⁵: amino acid residue of type C,
      as described herein below;
   Xaa⁶: amino acid residue of type E, as described herein below, or the D-isomer of an amino acid residue of type E, as described herein below;
   Xaa⁷: amino acid residue of type F,
      as described herein below;
   Xaa⁸: amino acid residue of type D,
      as described herein below;
   Xaa⁹: amino acid residue of type E,
      as described herein below;
   Xaa¹⁰: amino acid residue of type F,
      as described herein below;
   Xaa¹¹: amino acid residue of type E,
      as described herein below;
   Xaa¹²: amino acid residue of type E,
      as described herein below;
   Xaa¹³: amino acid residue of formula-A-CO—,
      as described herein below;
   Xaa¹⁴: amino acid residue of formula —B—CO—,
      as described herein below;
or
compounds of the general formula Cyclo(-Xaa¹-Xaa²-Xaa³-Xaa⁴-Xaa⁵-Xaa⁶-Xaa⁷-Xaa⁸-Xaa⁹-Xaa¹⁰-Xaa¹¹-Xaa¹²-Xaa¹³-Xaa¹⁴-), wherein the amino acid residues Xaa¹ to Xaa¹⁴ are:
   Xaa¹: amino acid residue of type D,
      as described herein below;
   Xaa²: amino acid residue of type E,
      as described herein below;
   Xaa³: amino acid residue of type E,
      as described herein below;
   Xaa⁴: amino acid residue of type E,
      as described herein below;
   Xaa⁵: amino acid residue of type C,
      as described herein below, or Gly;
   Xaa⁶: amino acid residue of type E, or of type F, as described herein below, or the D-isomer of an amino acid residue of type E, as described herein below, or —B—CO—, as described herein below or Gly;
   Xaa⁷: amino acid residue of type E, as described herein below, or the D-isomer of an amino acid residue of type E, as described herein below, or Gly;
   Xaa⁸: amino acid residue of type F,
      as described herein below, or Gly;
   Xaa⁹: amino acid residue of type E,
      as described herein below;
   Xaa¹⁰: amino acid residue of type F,
      as described herein below;
   Xaa¹¹: amino acid residue of type E,
      as described herein below;
   Xaa¹²: amino acid residue of type E,
      as described herein below;
   Xaa¹³: amino acid residue of formula-A-CO—,
      as described herein below;
   Xaa¹⁴: amino acid residue of formula —B—CO—,
      as described herein below;
with the proviso that at least one of the amino acid residues of Cyclo(-Xaa¹-Xaa²-Xaa³-Xaa⁴-Xaa⁵-Xaa⁶-Xaa⁷-Xaa⁸-Xaa⁹-Xaa¹⁰-Xaa¹¹-Xaa¹²-Xaa¹³-Xaa¹⁴-) is a non-canonical amino acid residue, as described herein below;
or
compounds of the general formula Cyclo(-Xaa¹-Xaa²-Xaa³-Xaa⁴-Xaa⁵-Xaa⁶-Xaa⁷-Xaa⁸-Xaa⁹-Xaa¹⁰-Xaa¹¹-Xaa¹²-Xaa¹³-Xaa¹⁴-), wherein the amino acid residues Xaa¹ to Xaa¹⁴ are:
   Xaa¹: amino acid residue of type E,
      as described herein below;
   Xaa²: amino acid residue of type E,
      as described herein below;
   Xaa³: amino acid residue of type C, or of type F,
      as described herein below;
   Xaa⁴: amino acid residue of type E,
      as described herein below;
   Xaa⁵: amino acid residue of type C, or of type F,
      as described herein below;
   Xaa⁶: amino acid residue of type E, as described herein below, or the D-isomer of an amino acid residue of type E, as described herein below;
   Xaa⁷: Gly;
   Xaa⁸: amino acid residue of type E, or of type F,
      as described herein below;

Xaa⁹: amino acid residue of type E,
    as described herein below;
Xaa¹⁰: amino acid residue of type C, or of type F,
    as described herein below;
Xaa¹¹: amino acid residue of type E,
    as described herein below;
Xaa¹²: amino acid residue of type E,
    as described herein below;
Xaa¹³: amino acid residue of formula-A-CO—,
    as described herein below;
Xaa¹⁴: amino acid residue of formula —B—CO—,
    as described herein below;
with the proviso that at least two of the amino acid residues of Cyclo(-Xaa¹-Xaa²-Xaa³-Xaa⁴-Xaa⁵-Xaa⁶-Xaa⁷-Xaa⁸-Xaa⁹-Xaa¹⁰-Xaa¹¹-Xaa¹²-Xaa¹³-Xaa¹⁴-) are non-canonical amino acid residues;
or
compounds of the general formula Cyclo(-Xaa¹-Xaa²-Xaa³-Xaa⁴-Xaa⁵-Xaa⁶-Xaa⁷-Xaa⁸-Xaa⁹-Xaa¹⁰-Xaa¹¹-Xaa¹²-Xaa¹³-Xaa¹⁴-), wherein the amino acid residues Xaa¹ to Xaa¹⁴ are:
    Xaa¹: amino acid residue of type E,
        as described herein below;
    Xaa²: amino acid residue of type C, or of type F,
        as described herein below;
    Xaa³: amino acid residue of type E,
        as described herein below;
    Xaa⁴: amino acid residue of type E,
        as described herein below;
    Xaa⁵: amino acid residue of type C,
        as described herein below;
    Xaa⁶: amino acid residue of type E,
        as described herein below;
    Xaa⁷: Gly;
    Xaa⁸: amino acid residue of type F,
        as described herein below;
    Xaa⁹: amino acid residue of type E,
        as described herein below;
    Xaa¹⁰: amino acid residue of type E, or of type F,
        as described herein below;
    Xaa¹¹: amino acid residue of type E, or of type F,
        as described herein below;
    Xaa¹²: amino acid residue of type E,
        as described herein below;
    Xaa¹³: amino acid residue of formula-A-CO—,
        as described herein below;
    Xaa¹⁴: amino acid residue of formula —B—CO—,
        as described herein below;
    the amino acid residues Xaa² and Xaa¹¹, taken together, can form an amino acid residue of type H, as described herein below;
with the proviso that at least one of the amino acid residues of Cyclo(-Xaa¹-Xaa²-Xaa³-Xaa⁴-Xaa⁵-Xaa⁶-Xaa⁷-Xaa⁸-Xaa⁹-Xaa¹⁰-Xaa¹¹-Xaa¹²-Xaa¹³-Xaa¹⁴-) are non-canonical amino acid residues;
or
compounds of the general formula Cyclo(-Xaa¹-Xaa²-Xaa³-Xaa⁴-Xaa⁵-Xaa⁶-Xaa⁷-Xaa⁸-Xaa⁹-Xaa¹⁰-Xaa¹¹-Xaa¹²-Xaa¹³-Xaa¹⁴-), wherein the amino acid residues Xaa¹ to Xaa¹⁴ are:
    Xaa¹: amino acid residue of type, E or of type F,
        as described herein below;
    Xaa²: amino acid residue of type C, or of type D, or of type E, or of type F, as described herein below;
    Xaa³: amino acid residue of type E, as described herein below, or the D-isomer of an amino acid residue of type E, as described herein below, or Gly;
    Xaa⁴: amino acid residue of type C, or of type D, or of type E, or of type F, as described herein below;
    Xaa⁵: amino acid residue of type E,
        as described herein below;
    Xaa⁶: amino acid residue of type E, or of type F,
        as described herein below, or Gly;
    Xaa⁷: amino acid residue of type D, or of type E, or of type F, as described herein below, or Gly;
    Xaa⁸: amino acid residue of type E,
        as described herein below;
    Xaa⁹: amino acid residue of type D, or of type E,
        as described herein below;
    Xaa¹⁰: amino acid residue of type C, or of type D, or of type E, or of type F, as described herein below;
    Xaa¹¹: amino acid residue of type D, or of type E, or of type F, as described herein below, or Gly;
    Xaa¹²: amino acid residue of type C, or of type D, or of type E, or of type F, as described herein below;
    Xaa¹³: amino acid residue of formula-A-CO—,
        as described herein below;
    Xaa¹⁴: amino acid residue of formula —B—CO—,
        as described herein below;
    the amino acid residues Xaa² and Xaa¹¹, taken together, can form an amino acid residue of type H, as described herein below;
with the proviso that at least two of the amino acid residues of Cyclo(-Xaa¹-Xaa²-Xaa³-Xaa⁴-Xaa⁵-Xaa⁶-Xaa⁷-Xaa⁸-Xaa⁹-Xaa¹⁰-Xaa¹¹-Xaa¹²-Xaa¹³-Xaa¹⁴-) are non-canonical amino acid residues;
—B—CO— is Gly, NMeGly or the residue of an L-α-amino acid with B being a residue of formula —NR²⁰CH(R⁷¹)—, or —NR²⁰CH(R⁷²)—, or —NR²⁰CH(R⁷³)—, or —NR²⁰CH(R⁷⁴)—, or —NR²⁰CH(R⁸⁴)—, or the enantiomer of one of the groups A1 to A69 as defined hereinafter;
A of -A-CO— is a group of one of the formulae

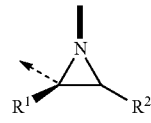

A1

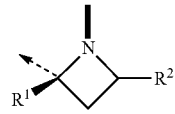

A2

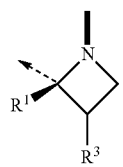

A3

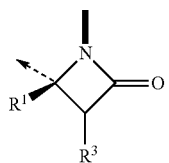

A4

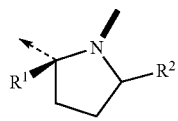

A5

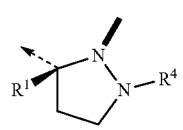 A6
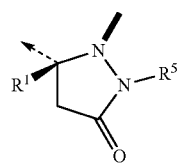 A7
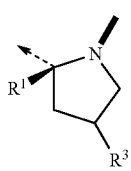 A8
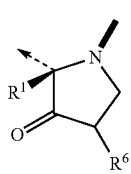 A9
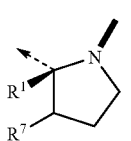 A10
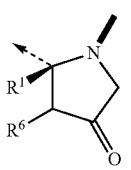 A11
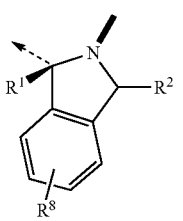 A12
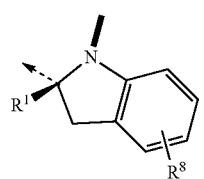 A13
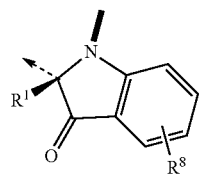 A14
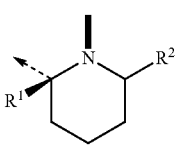 A15
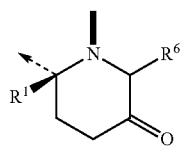 A16
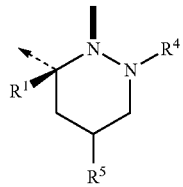 A17
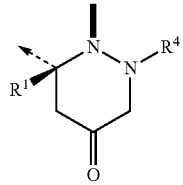 A18
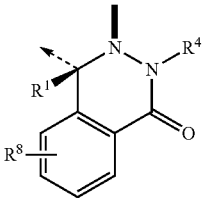 A19
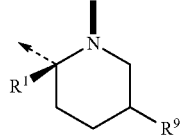 A20
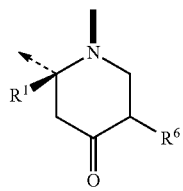 A21
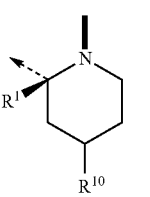 A22

-continued
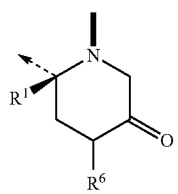
A23
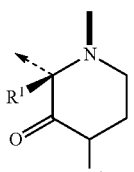
A24
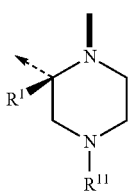
A25
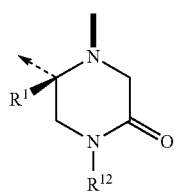
A26
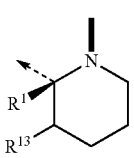
A27
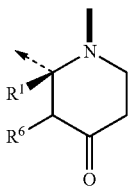
A28
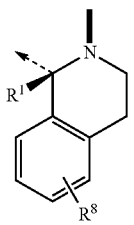
A29
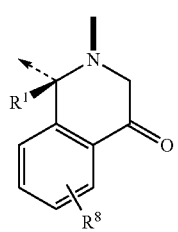
A30
-continued
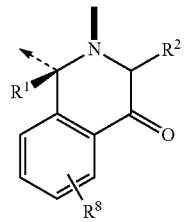
A31
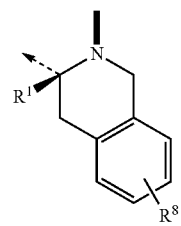
A32
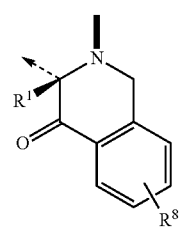
A33
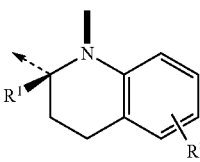
A34
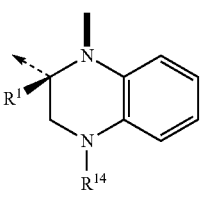
A35
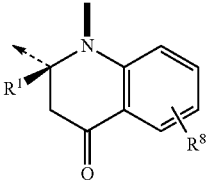
A36
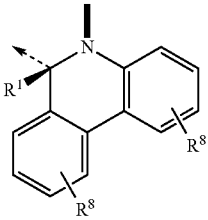
A37
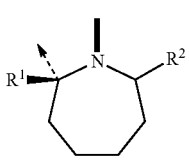
A38

-continued
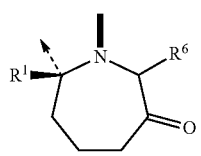
A39
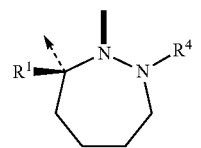
A40
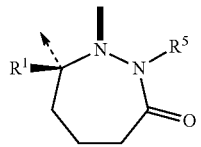
A41
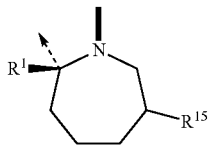
A42
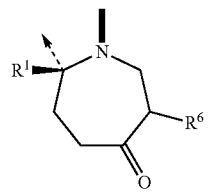
A43
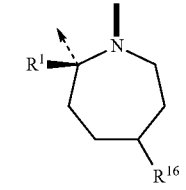
A44
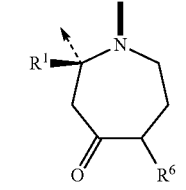
A45
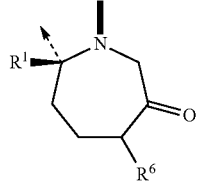
A46
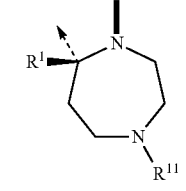
A47
-continued
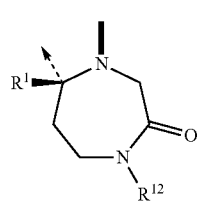
A48
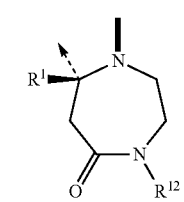
A49
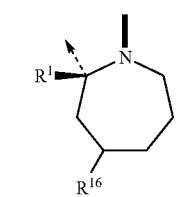
A50
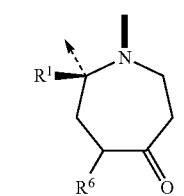
A51
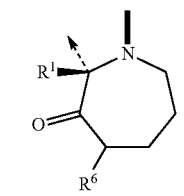
A52
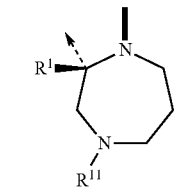
A53
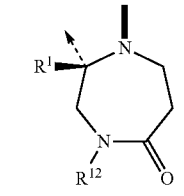
A54
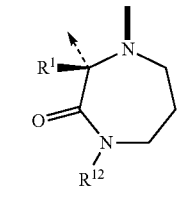
A55

13
-continued
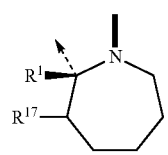
A56
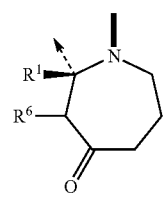
A57
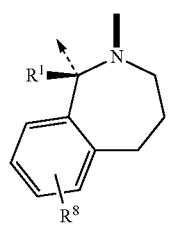
A58
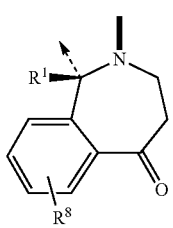
A59
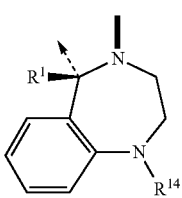
A60
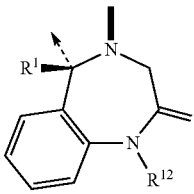
A61
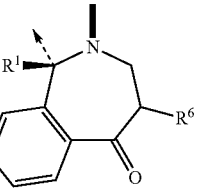
A62
14
-continued
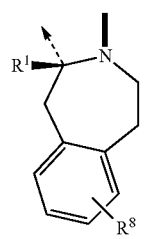
A63
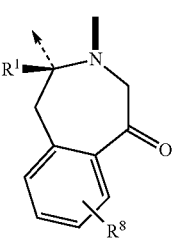
A64
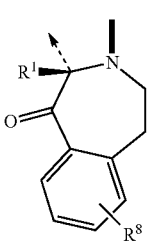
A65
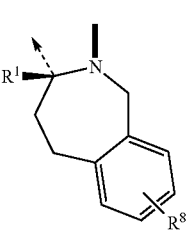
A66
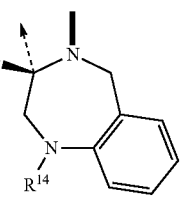
A67
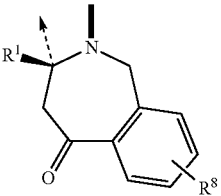
A68
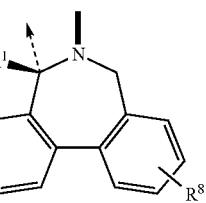
A69

| | |
|---|---|
| A70 ![R18,R19,N-R20 structure] | A79 ![pyrrolidine N-R20, N-R11] |
| A71 ![R18,R19,CH2,N-R20] | A80 ![tetrahydrothiophene N-R20] |
| A72 ![R18,R19,N-R20] | A81 ![tetrahydrofuran N-R20] |
| A73 ![cyclopropane R21, N-R20] | A82 ![pyrrolidinone N-R20, N-R12] |
| A74 ![cyclobutane R22, N-R20] | A83 ![pyrazolidine N-R20, N-R26, N-R25] |
| A75 ![cyclobutane R23, N-R20] | A84 ![indane N-R20, R8] |
| A76 ![azetidine N-R20, N-R11] | A85 ![indanone N-R20, R8] |
| A77 ![cyclopentane R22, N-R20] | |
| A78 ![cyclopentane R24, N-R20] | |

| | |
|---|---|
| 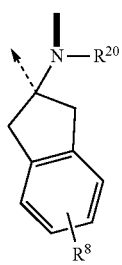 A86 | 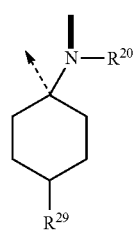 A93 |
| 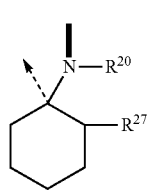 A87 | 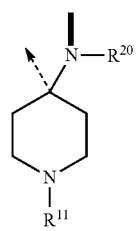 A94 |
| 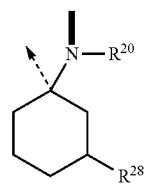 A88 | 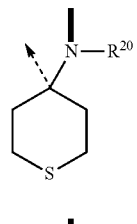 A95 |
| 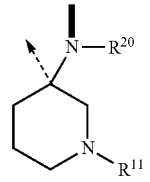 A89 | 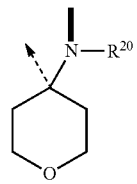 A96 |
| 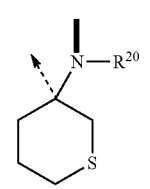 A90 | 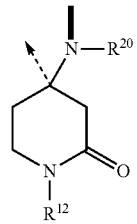 A97 |
| 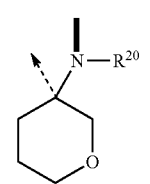 A91 | 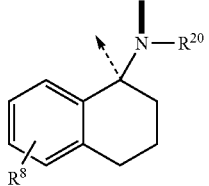 A98 |
| 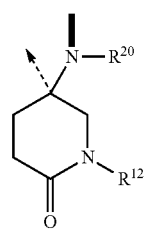 A92 | 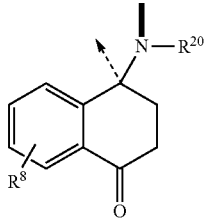 A99 |

-continued

A100 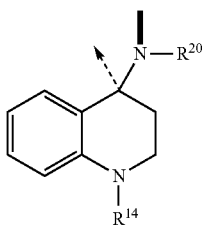

A101 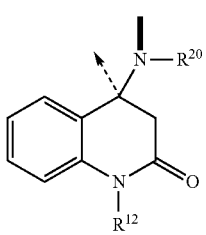

A102 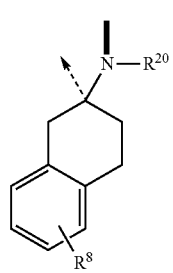

A103 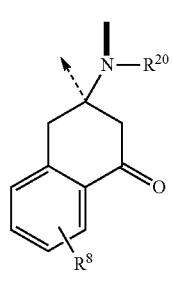

A104 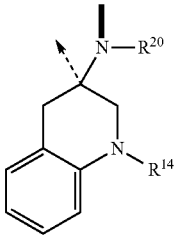

$R^1$ is H; lower alkyl; lower cycloalkyl; lower alkyl-aryl or aryl-lower alkyl;

$R^2$ is H; alkyl; alkenyl; $-(CH_2)_p(CHR^{61})_sOR^{55}$;
$-(CH_2)_p(CHR^{61})_sSR^{56}$;
$-(CH_2)_p(CHR^{61})_sNR^{33}R^{34}$; $-(CH_2)_p(CHR^{61})_sOCONR^{33}R^{75}$;
$-(CH_2)_p(CHR^{61})_sNR^{20}CONR^{33}R^{82}$; $-(CH_2)_o(CHR^{61})_sCOOR^{57}$;
$-(CH_2)_o(CHR^{61})_sCONR^{58}R^{59}$; $-(CH_2)_o(CHR^{61})_sPO(OR^{60})_2$;
$-(CH_2)_o(CHR^{61})_sSO_2R^{62}$; or $-(CH_2)_o(CHR^{61})_sR^{77}$;

$R^3$ is alkyl; alkenyl; $-(CH_2)_o(CHR^{61})_sOR^{55}$; $-(CH_2)_o(CHR^{61})_sSR^{56}$;
$-(CH_2)_o(CHR^{61})_sNR^{33}R^{34}$;
$-(CH_2)_o(CHR^{61})_sOCONR^{33}R^{75}$; $-(CH_2)_o(CHR^{61})_sNR^{20}CONR^{33}R^{82}$;
$-(CH_2)_o(CHR^{61})_sCOOR^{57}$; $-(CH_2)_o(CHR^{61})_sCONR^{58}R^{59}$;
$-(CH_2)_o(CHR^{61})_sPO(OR^{60})_2$;
$-(CH_2)_o(CHR^{61})_sSO_2R^{62}$; or $-(CH_2)_o(CHR^{61})_sC_6H_4R^8$;

$R^4$ is H; alkyl; alkenyl; $-(CH_2)_m(CHR^{61})_sOR^{55}$; $-(CH_2)_m(CHR^{61})_sSR^{56}$;
$-(CH_2)_m(CHR^{61})_sNR^{33}R^{34}$;
$-(CH_2)_m(CHR^{61})_sOCONR^{33}R^{75}$; $-(CH_2)_m(CHR^{61})_sNR^{20}CONR^{33}R^{82}$;
$-(CH_2)_p(CHR^{61})_sCOOR^{57}$; $-(CH_2)_p(CHR^{61})_sCONR^{58}R^{59}$;
$-(CH_2)_p(CHR^{61})_sPO(OR^{60})_2$;
$-(CH_2)_p(CHR^{61})_sSO_2R^{62}$; or $-(CH_2)_o(CHR^{61})_sC_6H_4R^8$;

$R^5$ is H; alkyl; alkenyl; $-(CH_2)_m(CHR^{61})_sOR^{55}$;
$-(CH_2)_m(CHR^{61})_sSR^{56}$;
$-(CH_2)_m(CHR^{61})_sNR^{33}R^{34}$; $-(CH_2)_m(CHR^{61})_sOCONR^{33}R^{75}$;
$-(CH_2)_m(CHR^{61})_sNR^{20}CONR^{33}R^{82}$; $-(CH_2)_o(CHR^{61})_sCOOR^{57}$;
$-(CH_2)_o(CHR^{61})_sCONR^{58}R^{59}$; $-(CH_2)_o(CHR^{61})_sPO(OR^{60})_2$;
$-(CH_2)_o(CHR^{61})_sSO_2R^{62}$; or $-(CH_2)_o(CHR^{61})_sC_6H_4R^8$;

$R^6$ is H; alkyl; alkenyl; $-(CH_2)_o(CHR^{61})_sOR^{65}$;
$(CH_2)_o(CHR^{61})_sSR^{56}$; $-(CH_2)_o(CHR^{61})_sNR^{33}R^{34}$;
$-(CH_2)_o(CHR^{61})_sOCONR^{33}R^{75}$; $-(CH_2)_o(CHR^{61})_sNR^{20}CONR^{33}R^{82}$;
$-(CH_2)_o(CHR^{61})_sCOOR^{57}$; $-(CH_2)_o(CHR^{61})_sCONR^{58}R^{59}$;
$(CH_2)_o(CHR^{61})_sPO(OR^{60})_2$;
$-(CH_2)_o(CHR^{61})_sSO_2R^{62}$; or $-(CH_2)_o(CHR^{61})_sC_6H_4R^8$;

$R^7$ is alkyl; alkenyl; $-(CH_2)_q(CHR^{61})_sOR^{55}$; $-(CH_2)_q(CHR^{61})_sNR^{33}R^{34}$;
$-(CH_2)_q(CHR^{61})_sOCONR^{33}R^{75}$; $-(CH_2)_q(CHR^{61})_sNR^{20}CONR^{33}R^{82}$;
$-(CH_2)_r(CHR^{61})_sCOOR^{57}$; $-(CH_2)_r(CHR^{61})_sCONR^{58}R^{59}$;
$-(CH_2)_r(CHR^{61})_sPO(OR^{60})_2$;
$-(CH_2)_r(CHR^{61})_sSO_2R^{62}$; or $-(CH_2)_r(CHR^{61})_sC_6H_4R^8$;

$R^8$ is H; Cl; F; $CF_3$; $NO_2$; lower alkyl; lower cycloalkyl; lower alkenyl; aryl; lower alkyl-aryl; aryl-lower alkyl; $-(CH_2)_o(CHR^{61})_sR^{77}$
$-(CH_2)_o(CHR^{61})_sOR^{55}$; $-(CH_2)_o(CHR^{61})_sSR^{56}$;
$-(CH_2)_o(CHR^{61})NR^{33}R^{34}$;
$-(CH_2)_o(CHR^{61})_sOCONR^{33}R^{75}$; $-(CH_2)_o(CHR^{61})_sNR^{20}CONR^{33}R^{82}$;
$-(CH_2)_o(CHR^{61})_sCOOR^{57}$; $-(CH_2)_o(CHR^{61})_sCONR^{58}R^{59}$;
$-(CH_2)_o(CHR^{61})_sPO(OR^{60})_2$;
$-(CH_2)_o(CHR^{61})_sSO_2R^{62}$; or $-(CH_2)_o(CHR^{61})_sCOR^{64}$;

$R^9$ is alkyl; alkenyl; $-(CH_2)_o(CHR^{61})_sOR^{55}$; $-(CH_2)_o(CHR^{61})_sSR^{56}$;
$-(CH_2)_o(CHR^{61})_sNR^{33}R^{34}$;
$-(CH_2)_o(CHR^{61})_sOCONR^{33}R^{75}$; $-(CH_2)_o(CHR^{61})_sNR^{20}CONR^{33}R^{82}$;
$-(CH_2)_o(CHR^{61})_sCOOR^{57}$; $-(CH_2)_o(CHR^{61})_sCONR^{58}R^{59}$;
$-(CH_2)_o(CHR^{61})_sPO(OR^{60})_2$;
$(CH_2)_o(CHR^{61})_sSO_2R^{62}$; or $-(CH_2)_o(CHR^{61})_sC_6H_4R^8$;

$R^{10}$ is alkyl; alkenyl; $-(CH_2)_o(CHR^{61})_sOR^{55}$; $-(CH_2)_o(CHR^{61})_sSR^{56}$;
$(CH_2)_o(CHR^{61})_sNR^{33}R^{34}$;

—(CH$_2$)$_o$(CHR$^{61}$)$_s$OCONR$^{33}$R$^{75}$;     —(CH$_2$)$_o$(CHR$^{61}$)$_s$NR$^{20}$CONR$^{33}$R$^{62}$;
—(CH$_2$)$_o$(CHR$^{61}$)$_s$COOR$^{57}$;     —(CH$_2$)$_o$(CHR$^{61}$)$_s$CONR$^{58}$R$^{59}$;
—(CH$_2$)$_o$(CHR$^{61}$)$_s$PO(OR$^{60}$)$_2$;
—(CH$_2$)$_o$(CHR$^{61}$)$_s$SO$_2$R$^{62}$; or —(CH$_2$)$_o$(CHR$^{61}$)$_s$C$_6$H$_4$R$^8$;

R$^{11}$ is H; alkyl; alkenyl; —(CH$_2$)$_m$(CHR$^{61}$)$_s$OR$^{55}$;
—(CH$_2$)$_m$(CHR$^{61}$)$_s$NR$^{33}$R$^{34}$;
—(CH$_2$)$_m$(CHR$^{61}$)$_s$OCONR$^{33}$R$^{75}$;     —(CH$_2$)$_m$(CHR$^{61}$)$_s$NR$^{20}$CONR$^{33}$R$^{82}$;
—(CH$_2$)$_o$(CHR$^{61}$)$_s$COOR$^{57}$;     —(CH$_2$)$_o$(CHR$^{61}$)$_s$CONR$^{58}$R$^{59}$;
—(CH$_2$)$_o$(CHR$^{61}$)$_s$PO(OR$^{60}$)$_2$;
—(CH$_2$)$_o$(CHR$^{61}$)$_s$SO$_2$R$^{62}$; or —(CH$_2$)$_o$(CHR$^{61}$)$_s$C$_6$H$_4$R$^8$;

R$^{12}$ is H; alkyl; alkenyl; —(CH$_2$)$_m$(CHR$^{61}$)$_s$OR$^{55}$;
—(CH$_2$)$_m$(CHR$^{61}$)$_s$SR$^{56}$;
—(CH$_2$)$_m$(CHR$^{61}$)$_s$NR$^{33}$R$^{34}$; —(CH$_2$)$_m$(CHR$^{61}$)$_s$OCONR$^{33}$R$^{75}$;
—(CH$_2$)$_m$(CHR$^{61}$)$_s$NR$^{20}$CONR$^{33}$R$^{82}$; —(CH$_2$)$_r$(CHR$^{61}$)$_s$COOR$^{57}$;
—(CH$_2$)$_r$(CHR$^{61}$)$_s$CONR$^{58}$R$^{59}$; —(CH$_2$)$_r$(CHR$^{61}$)$_s$PO(OR$^{60}$)$_2$;
—(CH$_2$)$_r$(CHR$^{61}$)$_s$SO$_2$R$^{62}$; or —(CH$_2$)$_r$(CHR$^{61}$)$_s$C$_6$H$_4$R$^8$;

R$^{13}$ is alkyl; alkenyl; —(CH$_2$)$_q$(CHR$^{61}$)$_s$OR$^{55}$; —(CH$_2$)$_q$(CHR$^{61}$)$_s$SR$^{56}$;
—(CH$_2$)$_q$(CHR$^{61}$)$_s$NR$^{33}$R$^{34}$;
—(CH$_2$)$_q$(CHR$^{61}$)$_s$OCONR$^{33}$R$^{75}$;     —(CH$_2$)$_q$(CHR$^{61}$)$_s$NR$^{20}$CONR$^{33}$R$^{82}$;
—(CH$_2$)$_q$(CHR$^{61}$)$_s$COOR$^{57}$;     —(CH$_2$)$_q$(CHR$^{61}$)$_s$CONR$^{58}$R$^{59}$;
—(CH$_2$)$_q$(CHR$^{61}$)$_s$PO(OR$^{60}$)$_2$;
—(CH$_2$)$_q$(CHR$^{61}$)$_s$SO$_2$R$^{62}$; or —(CH$_2$)$_q$(CHR$^{61}$)$_s$C$_6$H$_4$R$^8$;

R$^{14}$ is H; alkyl; alkenyl; —(CH$_2$)$_m$(CHR$^{61}$)$_s$OR$^{55}$;
—(CH$_2$)$_m$(CHR$^{61}$)$_s$NR$^{33}$R$^{34}$;
—(CH$_2$)$_m$(CHR$^{61}$)$_s$OCONR$^{33}$R$^{75}$;     —(CH$_2$)$_m$(CHR$^{61}$)$_s$NR$^{20}$CONR$^{33}$R$^{82}$;
—(CH$_2$)$_q$(CHR$^{61}$)$_s$COOR$^{57}$;     —(CH$_2$)$_q$(CHR$^{61}$)$_s$CONR$^{58}$R$^{59}$;
—(CH$_2$)$_q$(CHR$^{61}$)$_s$PO(OR$^{60}$)$_2$;
—(CH$_2$)$_q$(CHR$^{61}$)$_s$SOR$^{62}$; or —(CH$_2$)$_q$(CHR$^{61}$)$_s$C$_6$H$_4$R$^8$;

R$^{15}$ is alkyl; alkenyl; —(CH$_2$)$_o$(CHR$^{61}$)$_s$OR$^{55}$; (CH$_2$)$_o$(CHR$^{61}$)$_s$SR$^{56}$;
—(CH$_2$)$_o$(CHR$^{61}$)$_s$NR$^{33}$R$^{34}$;
—(CH$_2$)$_o$(CHR$^{61}$)$_s$OCONR$^{33}$R$^{75}$;     —(CH$_2$)$_o$(CHR$^{61}$)$_s$NR$^{20}$CONR$^{33}$R$^{82}$;
—(CH$_2$)$_o$(CHR$^{61}$)$_s$COOR$^{57}$;     —(CH$_2$)$_o$(CHR$^{61}$)$_s$CONR$^{58}$R$^{59}$;
—(CH$_2$)$_o$(CHR$^{61}$)$_s$PO(OR$^{60}$)$_2$;
—(CH$_2$)$_o$(CHR$^{61}$)$_s$SO$_2$R$^{62}$; or —(CH$_2$)$_o$(CHR$^{61}$)$_s$C$_6$H$_4$R$^8$;

R$^{16}$ is alkyl; alkenyl; —(CH$_2$)$_o$(CHR$^{61}$)$_s$OR$^{55}$; —(CH$_2$)$_o$(CHR$^{61}$)$_s$SR$^{56}$;
—(CH$_2$)$_o$(CHR$^{61}$)$_s$NR$^{33}$R$^{34}$;
—(CH$_2$)$_o$(CHR$^{61}$)$_s$OCONR$^{33}$R$^{75}$;     —(CH$_2$)$_o$(CHR$^{61}$)$_s$NR$^{26}$CONR$^{33}$R$^{82}$;
—(CH$_2$)$_o$(CHR$^{61}$)$_s$COOR$^{57}$;     —(CH$_2$)$_o$(CHR$^{61}$)$_s$CONR$^{58}$R$^{59}$;
—(CH$_2$)$_o$(CHR$^{61}$)$_s$PO(OR$^{60}$)$_2$;
—(CH$_2$)$_o$(CHR$^{61}$)$_s$SO$_2$R$^{62}$; or —(CH$_2$)$_o$(CHR$^{61}$)$_s$C$_6$H$_4$R$^8$;

R$^{17}$ is alkyl; alkenyl; —(CH$_2$)$_q$(CHR$^{61}$)$_s$OR$^{55}$; —(CH$_2$)$_q$(CHR$^{61}$)$_s$SR$^{56}$;
—(CH$_2$)$_q$(CHR$^{61}$)$_s$NR$^{33}$R$^{34}$;
—(CH$_2$)$_q$(CHR$^{61}$)$_s$OCONR$^{33}$R$^{75}$;     —(CH$_2$)$_q$(CHR$^{61}$)$_s$NR$^{20}$CONR$^{33}$R$^{82}$;
—(CH$_2$)$_q$(CHR$^{61}$)$_s$COOR$^{57}$;     —(CH$_2$)$_q$(CHR$^{61}$)$_s$CONR$^{58}$R$^{59}$;
(CH$_2$)$_q$(CHR$^{61}$)$_s$PO(OR$^{60}$)$_2$;
—(CH$_2$)$_q$(CHR$^{61}$)$_s$SO$_2$R$^{62}$; or —(CH$_2$)$_q$(CHR$^{61}$)$_s$C$_6$H$_4$R$^8$;

R$^{18}$ is alkyl; alkenyl; —(CH$_2$)$_p$(CHR$^{61}$)$_s$OR$^{55}$; —(CH$_2$)$_p$(CHR$^{61}$)$_s$SR$^{56}$;
—(CH$_2$)$_p$(CHR$^{61}$)$_s$NR$^{33}$R$^{34}$;
—(CH$_2$)$_p$(CHR$^{61}$)$_s$OCONR$^{33}$R$^{75}$;     —(CH$_2$)$_p$(CHR$^{61}$)$_s$NR$^{26}$CONR$^{33}$R$^{82}$;
—(CH$_2$)$_p$(CHR$^{61}$)$_s$COOR$^{57}$;     —(CH$_2$)$_p$(CHR$^{61}$)$_s$CONR$^{58}$R$^{59}$;
—(CH$_2$)$_p$(CHR$^{61}$)$_s$PO(OR$^{60}$)$_2$;
—(CH$_2$)$_p$(CHR$^{61}$)$_s$SO$_2$R$^{62}$; or —(CH$_2$)$_o$(CHR$^{61}$)$_s$C$_6$H$_4$R$^8$;

R$^{19}$ is lower alkyl; —(CH$_2$)$_p$(CHR$^{61}$)$_s$OR$^{55}$; —(CH$_2$)$_p$(CHR$^{61}$)$_s$SR$^{56}$;
—(CH$_2$)$_p$(CHR$^{61}$)$_s$NR$^{33}$R$^{34}$;
—(CH$_2$)$_p$(CHR$^{61}$)$_s$OCONR$^{33}$R$^{75}$;     —(CH$_2$)$_p$(CHR$^{61}$)$_s$NR$^{20}$CONR$^{33}$R$^{82}$;
—(CH$_2$)$_p$(CHR$^{61}$)$_s$COOR$^{57}$;     —(CH$_2$)$_p$(CHR$^{61}$)$_s$CONR$^{58}$R$^{59}$;
—(CH$_2$)$_p$(CHR$^{61}$)$_s$PO(OR$^{60}$)$_2$;
—(CH$_2$)$_p$(CHR$^{61}$)$_s$SO$_2$R$^{62}$; or —(CH$_2$)$_o$(CHR$^{61}$)$_s$C$_6$H$_4$R$^8$; or R$^{18}$ and R$^{19}$ taken together can form: —(CH$_2$)$_{2-6}$—;
—(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—;

R$^{20}$ is H; alkyl; lower cycloalkyl; alkenyl; lower alkyl-aryl; or aryl-lower alkyl;

R$^{21}$ is H; alkyl; alkenyl; —(CH$_2$)$_o$(CHR$^{61}$)$_s$OR$^{55}$;
—(CH$_2$)$_o$(CHR$^{61}$)$_s$SR$^{56}$; —(CH$_2$)$_o$(CHR$^{61}$)$_s$NR$^{33}$R$^{34}$;
—(CH$_2$)$_o$(CHR$^{61}$)$_s$OCONR$^{33}$R$^{75}$;     —(CH$_2$)$_o$(CHR$^{61}$)$_s$NR$^{20}$CONR$^{33}$R$^{82}$;
—(CH$_2$)$_o$(CHR$^{61}$)$_s$COOR$^{57}$;     —(CH$_2$)$_o$(CHR$^{61}$)$_s$CONR$^{58}$R$^{59}$;
—(CH$_2$)$_o$(CHR$^{61}$)$_s$PO(OR$^{60}$)$_2$;
—(CH$_2$)$_o$(CHR$^{61}$)$_s$SO$_2$R$^{62}$; or —(CH$_2$)$_o$(CHR$^{61}$)$_s$C$_6$H$_4$R$^8$;

R$^{22}$ is H; alkyl; alkenyl; —(CH$_2$)$_o$(CHR$^{61}$)$_s$OR$^{55}$;
—(CH$_2$)$_o$(CHR$^{61}$)$_s$SR$^{56}$; —(CH$_2$)$_o$(CHR$^{61}$)$_s$NR$^{33}$R$^{34}$;
—(CH$_2$)$_o$(CHR$^{61}$)$_s$OCONR$^{33}$R$^{75}$;     —(CH$_2$)$_o$(CHR$^{61}$)$_s$NR$^{20}$CONR$^{33}$R$^{82}$;
—(CH$_2$)$_o$(CHR$^{61}$)$_s$COOR$^{57}$;     —(CH$_2$)$_o$(CHR$^{61}$)$_s$CONR$^{58}$R$^{59}$;
—(CH$_2$)$_o$(CHR$^{61}$)$_s$PO(OR$^{60}$)$_2$;
—(CH$_2$)$_o$(CHR$^{61}$)$_s$SO$_2$R$^{62}$; or —(CH$_2$)$_o$(CHR$^{61}$)$_s$C$_6$H$_4$R$^8$;

R$^{23}$ is alkyl; alkenyl; —(CH$_2$)$_o$(CHR$^{61}$)$_s$OR$^{55}$; —(CH$_2$)$_o$(CHR$^{61}$)$_s$SR$^{56}$;
—(CH$_2$)$_o$(CHR$^{61}$)$_s$NR$^{33}$R$^{34}$;
—(CH$_2$)$_o$(CHR$^{61}$)$_s$OCONR$^{33}$R$^{75}$;     —(CH$_2$)$_o$(CHR$^{61}$)$_s$NR$^{20}$CONR$^{33}$R$^{82}$;
—(CH$_2$)$_o$(CHR$^{61}$)$_s$COOR$^{57}$;     —(CH$_2$)$_o$(CHR$^{61}$)$_s$CONR$^{58}$R$^{59}$;
—(CH$_2$)$_o$(CHR$^{61}$)$_s$PO(OR$^{60}$)$_2$;
—(CH$_2$)$_o$(CHR$^{61}$)$_s$SO$_2$R$^{62}$; or —(CH$_2$)$_o$(CHR$^{61}$)$_s$C$_6$H$_4$R$^8$;

R$^{24}$ is alkyl; alkenyl; —(CH$_2$)$_o$(CHR$^{61}$)$_s$OR$^{55}$; —(CH$_2$)$_o$(CHR$^{61}$)$_s$SR$^{56}$;
—(CH$_2$)$_o$(CHR$^{61}$)$_s$NR$^{33}$R$^{34}$;
—(CH$_2$)$_o$(CHR$^{61}$)$_s$OCONR$^{33}$R$^{75}$;     —(CH$_2$)$_o$(CHR$^{61}$)$_s$NR$^{20}$CONR$^{33}$R$^{82}$;
—(CH$_2$)$_o$(CHR$^{61}$)$_s$COOR$^{57}$;     —(CH$_2$)$_o$(CHR$^{61}$)$_s$CONR$^{58}$R$^{59}$;

$(CH_2)_o(CHR^{61})_sPO(OR^{60})_2$;
—$(CH_2)_o(CHR^{61})_sSO_2R^{62}$; or —$(CH_2)_o(CHR^{61})_sC_6H_4R^8$;

$R^{25}$ is H; alkyl; alkenyl; —$(CH_2)_m(CHR^{61})_sOR^{55}$;
—$(CH_2)_m(CHR^{61})_sSR^{56}$;
—$(CH_2)_m(CHR^{61})_sNR^{33}R^{34}$; —$(CH_2)_m(CHR^{61})_sOCONR^{33}R^{75}$;
—$(CH_2)_m(CHR^{61})_sNR^{20}CONR^{33}R^{82}$; —$(CH_2)_o(CHR^{61})_sCOOR^{57}$;
—$(CH_2)_o(CHR^{61})_sCONR^{58}R^{59}$; —$(CH_2)_o(CHR^{61})_sPO(OR^{60})_2$;
—$(CH_2)_o(CHR^{61})_sSO_2R^{62}$; or —$(CH_2)_o(CHR^{61})_sC_6H_4R^8$;

$R^{26}$ is H; alkyl; alkenyl; —$(CH_2)_m(CHR^{61})_sOR^{55}$;
—$(CH_2)_m(CHR^{61})_sSR^{56}$;
—$(CH_2)_m(CHR^{61})_sNR^{33}R^{34}$; —$(CH_2)_m(CHR^{61})_sOCONR^{33}R^{75}$;
—$(CH_2)_m(CHR^{61})_sNR^{20}CONR^{33}R^{82}$; —$(CH_2)_o(CHR^{61})_sCOOR^{57}$;
—$(CH_2)_o(CHR^{61})_sCONR^{58}R^{59}$; —$(CH_2)_o(CHR^{61})_sPO(OR^{60})_2$;
—$(CH_2)_o(CHR^{61})_sSO_2R^{62}$; or —$(CH_2)_o(CHR^{61})_sC_6H_4R^8$; or $R^{25}$ and $R^{26}$ taken together can form: —$(CH_2)_{2-6}$—;
—$(CH_2)_rO(CH_2)_r$;
—$(CH_2)_rS(CH_2)_r$—; or —$(CH_2)_rNR^{57}(CH_2)_r$—;

$R^{27}$ is H; alkyl; alkenyl; —$(CH_2)_o(CHR^{61})_sOR^{55}$;
—$(CH_2)_o(CHR^{61})_sSR^{56}$; —$(CH_2)_o(CHR^{61})_sNR^{33}R^{34}$;
—$(CH_2)_o(CHR^{61})_sCOOR^{57}$; —$(CH_2)_o(CHR^{61})_sCONR^{58}R^{59}$;
—$(CH_2)_o(CHR^{61})_sOCONR^{33}R^{75}$;
—$(CH_2)_o(CHR^{61})_sNR^{20}CONR^{33}R^{82}$; —$(CH_2)_o(CHR^{61})_sPO(OR^{60})_2$;
—$(CH_2)_o(CHR^{61})_sSO_2R^{62}$; or —$(CH_2)_o(CHR^{61})_sC_6H_4R^8$;

$R^{28}$ is alkyl; alkenyl; —$(CH_2)_o(CHR^{61})_s$—$OR^{55}$; —$(CH_2)_o(CHR^{61})_sSR^{56}$;
—$(CH_2)_o(CHR^{61})_sNR^{33}R^{34}$;
—$(CH_2)_o(CHR^{61})_sOCONR^{33}R^{75}$; —$(CH_2)_o(CHR^{61})_sNR^{20}CONR^{33}R^{82}$; —$(CH_2)_o(CHR^{61})_sCOOR^{57}$;
—$(CH_2)_o(CHR^{61})_sCONR^{58}R^{59}$;
—$(CH_2)_o(CHR^{61})_sPO(OR^{60})_2$;
—$(CH_2)_o(CHR^{61})_sSO_2R^{62}$; or —$(CH_2)_o(CHR^{61})_sC_6H_4R^8$;

$R^{29}$ is alkyl; alkenyl; —$(CH_2)_o(CHR^{61})_sOR^{55}$; $(CH_2)_o(CHR^{61})_sSR^{56}$;
—$(CH_2)_o(CHR^{61})_sNR^{33}R^{34}$;
—$(CH_2)_o(CHR^{61})_sOCONR^{33}R^{75}$; —$(CH_2)_o(CHR^{61})_sNR^{20}CONR^{33}R^{82}$;
—$(CH_2)_o(CHR^{61})_sCOOR^{57}$; —$(CH_2)_o(CHR^{61})_sCONR^{58}R^{59}$;
—$(CH_2)_o(CHR^{61})_sPO(OR^{60})_2$;
—$(CH_2)_o(CHR^{61})_sSO_2R^{62}$; or —$(CH_2)_o(CHR^{61})_sC_6H_4R^8$;

$R^{33}$ is H; alkyl, alkenyl; —$(CH_2)_m(CHR^{61})_sOR^{55}$;
—$(CH_2)_m(CHR^{61})_sNR^{34}R^{63}$;
—$(CH_2)_m(CHR^{61})_sOCONR^{75}R^{82}$; —$(CH_2)_m(CHR^{61})_sNR^{20}CONR^{78}R^{82}$;
—$(CH_2)_o(CHR^{61})_sCOR^{64}$; —$(CH_2)_o(CHR^{61})_s$—$CONR^{58}R^{59}$,
—$(CH_2)_o(CHR^{61})_sPO(OR^{60})_2$;
—$(CH_2)_o(CHR^{61})_sSO_2R^{62}$; or —$(CH_2)_o(CHR^{61})_sC_6H_4R^8$;

$R^{34}$ is H; lower alkyl; lower cycloalkyl; lower alkyl-aryl;
aryl or aryl-lower alkyl; or $R^{33}$ and $R^{34}$ taken together can form: —$(CH_2)_{2-6}$—;
—$(CH_2)_2O(CH_2)_2$—;
—$(CH_2)_2S(CH_2)_2$—; or —$(CH_2)_2NR^{57}(CH_2)_2$—;

$R^{50}$ is H; lower alkyl; lower cycloalkyl; lower alkyl-aryl; or aryl-lower alkyl;

$R^{55}$ is H; lower alkyl; lower alkenyl; lower cycloalkyl; lower alkyl-aryl; aryl-lower alkyl;
—$(CH_2)_m(CHR^{61})_sOR^{57}$;
—$(CH_2)_m(CHR^{61})_sNR^{34}R^{63}$; —$(CH_2)_m(CHR^{61})_sOCONR^{75}R^{82}$;
—$(CH_2)_m(CHR^{61})_sNR^{20}CONR^{78}R^{82}$; —$(CH_2)_o(CHR^{61})_s$—$COR^{64}$;
—$(CH_2)_o(CHR^{61})COOR^{57}$; or
—$(CH_2)_o(CHR^{61})_sCONR^{58}R^{59}$;

$R^{56}$ is H; lower alkyl; lower alkenyl; lower alkyl-aryl; aryl-lower alkyl;
—$(CH_2)_m(CHR^{61})_sOR^{57}$;
—$(CH_2)_m(CHR^{61})_sNR^{34}R^{63}$; —$(CH_2)_m(CHR^{61})_sOCONR^{75}R^{82}$;
—$(CH_2)_m(CHR^{61})_sNR^{20}CONR^{18}R^{82}$; —$(CH_2)_o(CHR^{61})_s$—$COR^{64}$; or
—$(CH_2)_o(CHR^{61})_sCONR^{58}R^{55}$;

$R^{57}$ is H; lower alkyl; lower alkenyl; lower cycloalkyl; lower alkyl-aryl; aryl-lower alkyl;
lower alkyl-heteroaryl; or heteroaryl-lower alkyl;

$R^{58}$ is H; lower alkyl; lower alkenyl; lower cycloalkyl; lower alkyl-aryl; aryl-lower alkyl;
lower alkyl-heteroaryl; or heteroaryl-lower alkyl;

$R^{59}$ is H; lower alkyl; lower alkenyl; lower cycloalkyl; lower alkyl-aryl; aryl-lower alkyl;
lower alkyl-heteroaryl; or heteroaryl-lower alkyl; or $R^{58}$ and $R^{59}$ taken together can form: —$(CH_2)_{2-6}$—;
—$(CH_2)_2O(CH_2)_2$—;
—$(CH_2)_2S(CH_2)_2$—; or
—$(CH_2)_2NR^{57}(CH_2)_2$—;

$R^{60}$ is H; lower alkyl; lower alkenyl; lower cycloalkyl; lower alkyl-aryl; aryl; or aryl-lower alkyl;

$R^{61}$ is alkyl; alkenyl; lower cycloalkyl; lower alkyl-aryl; lower alkyl-heteroaryl; aryl; heteroaryl;
aryl-lower alkyl; heteroaryl-lower alkyl; —$(CH_2)_pOR^{55}$;
—$(CH_2)_pNR^{33}R^{34}$; —$(CH_2)_pOCONR^{75}R^{82}$; —$(CH_2)_pNR^{20}CONR^{78}R^{82}$;
—$(CH_2)_oCOOR^{37}$; or —$(CH_2)_oPO(OR^{60})_2$;

$R^{62}$ is H; lower alkyl; lower alkenyl; lower cycloalkyl; lower alkyl-aryl; lower alkyl-heteroaryl; aryl;
heteroaryl; aryl-lower alkyl; or
heteroaryl-lower alkyl;

$R^{63}$ is H; lower alkyl; lower alkenyl; lower cycloalkyl; lower alkyl-aryl; lower alkyl-heteroaryl; aryl;
heteroaryl; aryl-lower alkyl; or
heteroaryl-lower alkyl;
—$COR^{64}$; —$COOR^{57}$; —$CONR^{58}R^{59}$; —$SO_2R^{62}$; or
—$PO(OR^{60})_2$; or $R^{34}$ and $R^{63}$ taken together can form: —$(CH_2)_{2-6}$—;
—$(CH_2)_2O(CH_2)_2$—;
—$(CH_2)_2S(CH_2)_2$—; or —$(CH_2)_2NR^{57}(CH_2)_2$—;

$R^{64}$ is H; lower alkyl; lower alkenyl; lower cycloalkyl; lower alkyl-aryl; lower alkyl-heteroaryl; aryl;
heteroaryl; aryl-lower alkyl; or heteroaryl-lower alkyl;
—$(CH_2)_p(CHR^{61})_sOR^{65}$; —$(CH_2)_p(CHR^{61})_sSR^{66}$;
—$(CH_2)_p(CHR^{61})_sNR^{34}R^{63}$;
—$(CH_2)_p(CHR^{61})_sOCONR^{75}R^{82}$; or —$(CH_2)_p(CHR^{61})_sNR^{20}CONR^{78}R^{82}$;

$R^{65}$ is H; lower alkyl; lower alkenyl; lower cycloalkyl; lower alkyl-aryl; lower alkyl-heteroaryl; aryl;
heteroaryl; aryl-lower alkyl; or
heteroaryl-lower alkyl; —$COR^{57}$;
—$COOR^{57}$; or —$CONR^{58}R^{59}$;

R$^{66}$ is H; lower alkyl; lower alkenyl; lower cycloalkyl; lower alkyl-aryl; lower alkyl-heteroaryl; aryl; heteroaryl; aryl-lower alkyl; or heteroaryl-lower alkyl; or —CONR$^{88}$R$^{88}$;

R$^{67}$ is H; Cl; Br; F; NO$_2$; —NR$^{34}$COR$^{57}$; —CF$_3$; CN; —OCF$_3$; —OCHF$_2$; —OR$^{57}$; —SR$^{62}$; lower alkyl; or lower alkenyl;

R$^{68}$ is H; Cl; Br; F; NO$_2$; —NR$^{34}$COR$^{57}$; —CF$_3$; CN; —OCF$_3$; —OCHF$_2$; —OR$^{57}$; —SR$^{62}$; lower alkyl; or lower alkenyl;

R$^{69}$ is H; Cl; Br; F; NO$_2$; —NR$^{34}$COR$^{57}$; —CF$_3$; CN; —OCF$_3$; —OCHF$_2$; —OR$^{57}$; —SR$^{62}$; lower alkyl; or lower alkenyl;

R$^{70}$ is H; Cl; Br; F; NO$_2$; —NR$^{34}$COR$^{57}$; —CF$_3$; CN; —OCF$_3$; —OCHF$_2$; —OR$^{57}$; —SR$^{62}$; lower alkyl; or lower alkenyl;

R$^{71}$ is lower alkyl; lower alkenyl; —(CH$_2$)$_p$(CHR$^{61}$)$_s$OR$^{75}$; —(CH$_2$)$_p$(CHR$^{61}$)$_s$SR$^{75}$; —(CH$_2$)$_p$(CHR$^{61}$)$_s$NR$^{33}$R$^{34}$; —(CH$_2$)$_p$(CHR$^{61}$)$_s$OCONR$^{33}$R$^{75}$; —(CH$_2$)$_p$(CHR$^{61}$)$_s$NR$^{20}$CONR$^{33}$R$^{82}$; —(CH$_2$)$_o$(CHR$^{61}$)$_s$COOR$^{75}$; —(CH$_2$)$_p$CONR$^{58}$R$^{59}$; —(CH$_2$)$_p$PO(OR$^{62}$)$_2$; —(CH$_2$)$_p$SO$_2$R$^{62}$; or —(CH$_2$)$_o$—C$_6$R$^{67}$R$^{68}$R$^{69}$R$^{70}$R$^{76}$;

R$^{72}$ is alkyl; alkenyl; lower cycloalkyl; —(CH$_2$)$_p$(CHR$^{61}$)$_s$OR$^{85}$; or —(CH$_2$)$_p$(CHR$^{61}$)$_s$SR$^{85}$;

R$^{73}$ is —(CH$_2$)$_o$R$^{77}$; —(CH$_2$)$_r$O(CH$_2$)$_o$R$^{77}$; —(CH$_2$)$_r$S(CH$_2$)$_o$R$^{77}$; or —(CH$_2$)$_r$NR$^{20}$(CH$_2$)$_o$R$^{77}$;

R$^{74}$ is —(CH$_2$)$_p$NR$^{78}$R$^{79}$; —(CH$_2$)$_p$NR$^{77}$R$^{80}$; —(CH$_2$)$_p$C(=NR$^{80}$)NR$^{78}$R$^{79}$; —(CH$_2$)$_p$C(=NOR$^{50}$)NR$^{78}$R$^{79}$; —(CH$_2$)$_p$C(=NNR$^{78}$R$^{79}$)NR$^{78}$R$^{79}$; —(CH$_2$)$_p$NR$^{80}$C(=NR)$^{80}$NR$^{78}$R$^{79}$; —(CH$_2$)$_p$N=C(NR$^{78}$R$^{80}$)NR$^{79}$R$^{80}$; —(CH$_2$)$_p$C$_6$H$_4$NR$^{78}$R$^{79}$; —(CH$_2$)$_p$C$_6$H$_4$NR$^{77}$R$^{80}$; —(CH$_2$)$_p$C$_6$H$_4$C(=NR$^{80}$)NR$^{78}$R$^{79}$; —(CH$_2$)$_p$C$_6$H$_4$C(=NOR$^{50}$)NR$^{78}$R$^{79}$; —(CH$_2$)$_p$C$_6$H$_4$C(=NNR$^{78}$R$^{79}$)NR$^{78}$R$^{79}$; —(CH$_2$)$_p$C$_6$H$_4$NR$^{80}$C(=NR$^{80}$)NR$^{78}$R$^{79}$; —(CH$_2$)$_p$C$_6$H$_4$N=C(NR$^{78}$R$^{80}$)NR$^{79}$R$^{80}$; —(CH$_2$)$_r$O(CH$_2$)$_m$NR$^{78}$R$^{79}$; —(CH$_2$)$_r$O(CH$_2$)$_m$NR$^{77}$R$^{80}$; —(CH$_2$)$_r$O(CH$_2$)$_p$C(=NR$^{80}$)NR$^{78}$R$^{79}$; —(CH$_2$)$_r$O(CH$_2$)$_p$C(=NOR$^{50}$)NR$^{78}$R$^{79}$; —(CH$_2$)$_r$O(CH$_2$)$_p$C(=NNR$^{78}$R$^{79}$)NR$^{78}$R$^{79}$; —(CH$_2$)$_r$O(CH$_2$)$_m$NR$^{80}$C(=NR$^{80}$)NR$^{78}$R$^{79}$; —(CH$_2$)$_r$O(CH$_2$)$_m$N=C(NR$^{78}$R$^{80}$)NR$^{79}$R$^{80}$; —(CH$_2$)$_r$O(CH$_2$)$_p$C$_6$H$_4$CNR$^{78}$R$^{79}$; —(CH$_2$)$_r$O(CH$_2$)$_p$C$_6$H$_4$C(=NR$^{80}$) NR$^{78}$R$^{79}$; —(CH$_2$)$_r$O(CH$_2$)$_p$C$_6$H$_4$C(=NOR$^{50}$)NR$^{78}$R$^{79}$; —(CH$_2$)$_r$O(CH$_2$)$_p$C$_6$H$_4$C(=NNR$^{78}$R$^{79}$)NR$^{78}$R$^{79}$; —(CH$_2$)$_r$O(CH$_2$)$_p$C$_6$H$_4$NR$^{80}$C(=NR$^{80}$)NR$^{78}$R$^{79}$; —(CH$_2$)$_r$S(CH$_2$)$_m$NR$^{78}$R$^{79}$; —(CH$_2$)$_r$S(CH$_2$)$_m$NR$^{77}$R$^{80}$; —(CH$_2$)$_r$S(CH$_2$)$_p$C(=NR$^{80}$)NR$^{78}$R$^{79}$; —(CH$_2$)$_r$S(CH$_2$)$_p$C(=NOR$^{50}$)NR$^{78}$R$^{79}$; —(CH$_2$)$_r$S(CH$_2$)$_p$C(=NNR$^{78}$R$^{79}$)NR$^{78}$R$^{79}$; —(CH$_2$)$_r$S(CH$_2$)$_m$NR$^{80}$C(=NR$^{80}$)NR$^{78}$R$^{79}$; —(CH$_2$)$_r$S(CH$_2$)$_m$N=C(NR$^{78}$R$^{80}$)NR$^{79}$R$^{80}$; —(CH$_2$)$_r$S(CH$_2$)$_p$C$_6$H$_4$CNR$^{78}$R$^{79}$; —(CH$_2$)$_r$S(CH$_2$)$_p$C$_6$H$_4$C(=NR$^{80}$)NR$^{78}$R$^{79}$; —(CH$_2$)$_r$S(CH$_2$)$_p$C$_6$H$_4$C(=NOR$^{50}$)NR$^{78}$R$^{79}$; —(CH$_2$)$_r$S(CH$_2$)$_p$C$_6$H$_4$C(=NNR$^{78}$R$^{79}$) NR$^{78}$R$^{79}$; —(CH$_2$)$_r$S(CH$_2$)$_p$C$_6$H$_4$NR$^{80}$C)(=NR$^{80}$NR$^{78}$R$^{79}$; —(CH$_2$)$_p$NR$^{80}$COR$^{64}$; —(CH$_2$)$_p$NR$^{80}$COR$^{77}$; —(CH$_2$)$_p$NR$^{80}$CONR$^{78}$R$^{79}$; or —(CH$_2$)$_p$C$_6$H$_4$NR$^{80}$CONR$^{78}$R$^{79}$;

R$^{75}$ is lower alkyl; lower alkenyl; lower cycloalkyl; lower-alkyl-aryl; or aryl-lower alkyl; or R$^{33}$ and R$^{75}$ taken together can form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—; or R$^{75}$ and R$^{82}$ taken together can form: —(CH$_2$)$_{2-6}$—; —(CH$_2$)$_2$O(CH$_2$)$_2$—; (CH$_2$)$_2$S(CH$_2$)$_2$—; or —(CH$_2$)$_2$NR$^{57}$(CH$_2$)$_2$—;

R$^{76}$ is H; lower alkyl; lower alkenyl; lower cycloalkyl; lower-alkyl-aryl; aryl-lower alkyl; —(CH$_2$)$_o$OR$^{72}$; —(CH$_2$)$_o$SR$^{72}$; —(CH$_2$)$_o$NR$^{33}$R$^{34}$; —(CH$_2$)$_o$OCONR$^{33}$R$^{75}$; —(CH$_2$)$_o$NR$^{20}$CONR$^{33}$R$^{81}$; —(CH$_2$)$_o$COOR$^{75}$; —(CH$_2$)$_o$CONR$^{58}$R$^{59}$; —(CH$_2$)$_o$PO(OR$^{60}$)$_2$; (CH$_2$)$_p$SO$_2$R$^{62}$; or —(CH$_2$)$_o$COR$^{64}$;

R$^{77}$ is —C$_6$R$^{67}$R$^{68}$R$^{69}$R$^{70}$R$^{76}$ with the proviso that at least two of R$^{67}$, R$^{68}$, R$^{69}$ and R$^{70}$ are H; or a heteroaryl group of one of the formulae

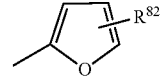
H1

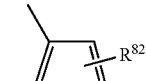
H2

H3

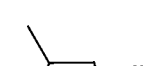
H4

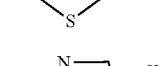
H5

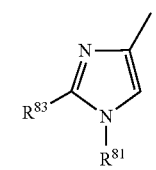
H6

-continued
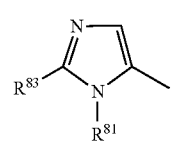 H7
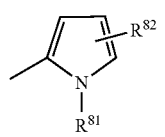 H8
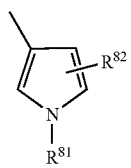 H9
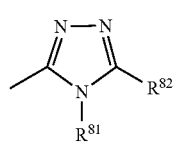 H10
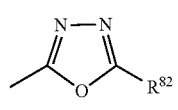 H11
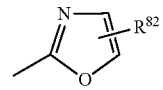 H12
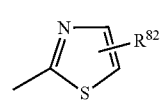 H13
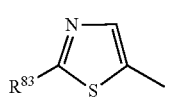 H14
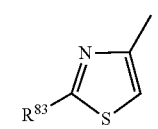 H15
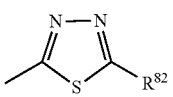 H16
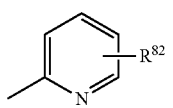 H17
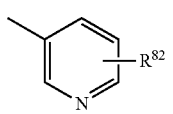 H18
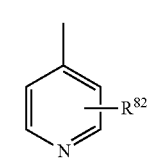 H19
-continued
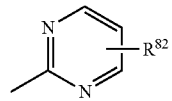 H20
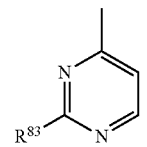 H21
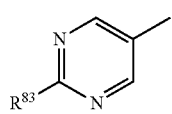 H22
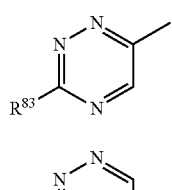 H23
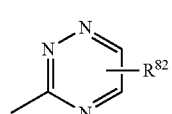 H24
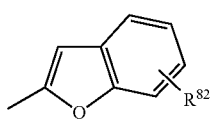 H25
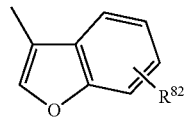 H26
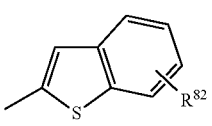 H27
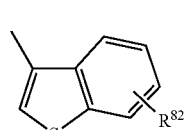 H28
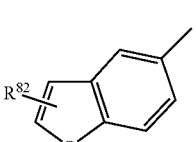 H29
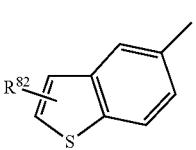 H30
H31

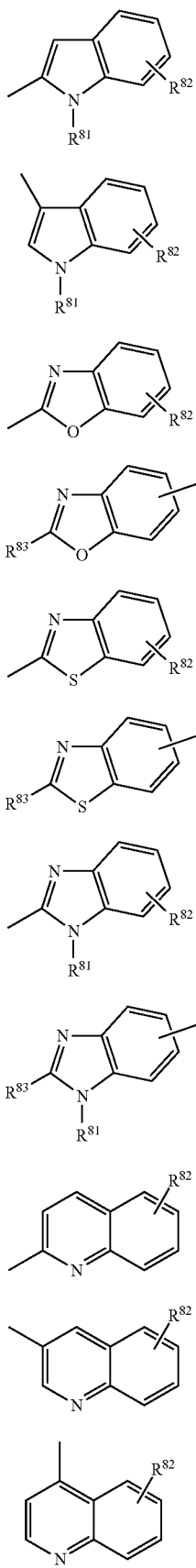
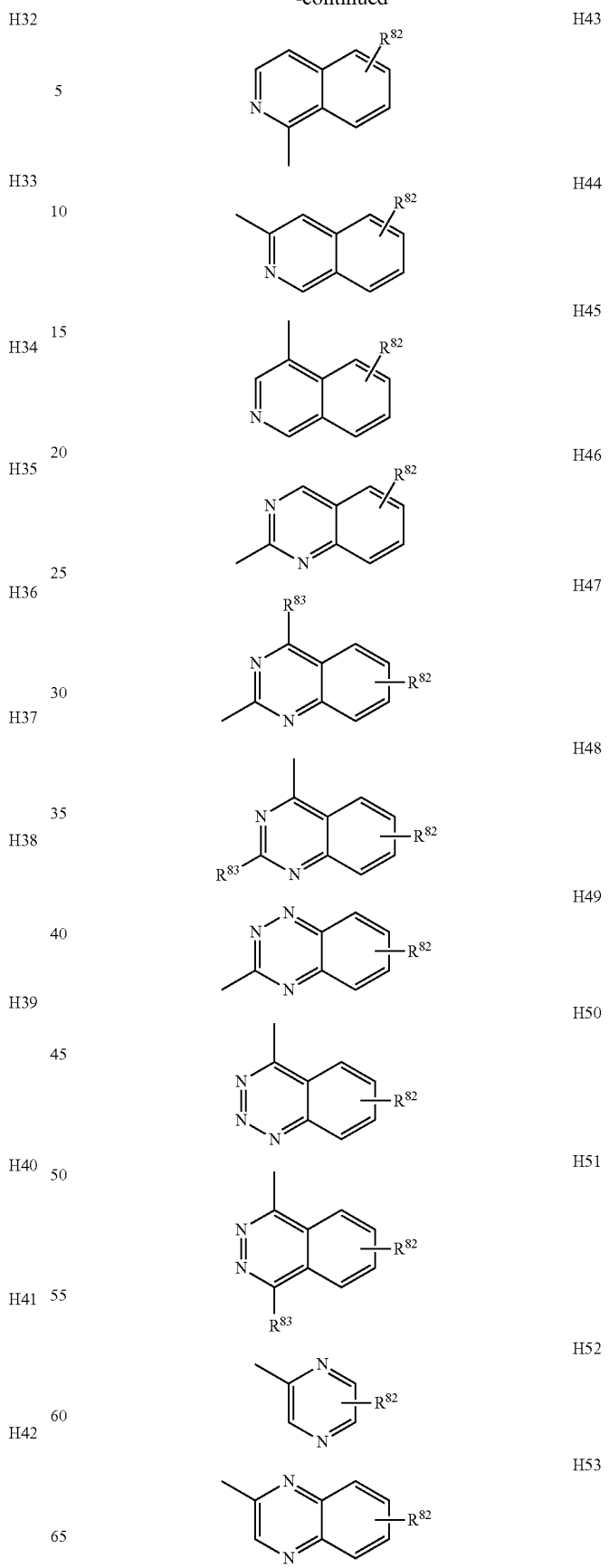

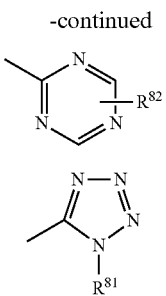

R⁷⁸ is H; lower alkyl; lower cycloalkyl; lower alkyl-aryl; aryl; or aryl-lower alkyl; or R⁷⁸ and R⁸² taken together can form: —(CH₂)₂₋₆—; (CH₂)₂O(CH₂)₂—; —(CH₂)₂S(CH₂)₂—; or —(CH₂)₂NR⁵⁷(CH₂)₂—;

R⁷⁹ is H; lower alkyl; lower alkyl-aryl; aryl; or aryl-lower alkyl; or

R⁷⁸ and R⁷⁹, taken together, can be —(CH₂)₂₋₇—; —(CH₂)₂O(CH₂)₂—; or —(CH₂)₂NR⁵⁷(CH₂)₂—;

R⁸⁰ is H; or lower alkyl;

R⁸¹ is H; lower alkyl; lower cycloalkyl; lower alkyl-aryl; or aryl-lower alkyl; or R³³ and R⁸¹ taken together can form: —(CH₂)₂₋₆—; —(CH₂)₂ O(CH₂)₂—; —(CH₂)₂S(CH₂)₂—; or —(CH₂)₂NR⁵⁷(CH₂)₂—;

R⁸² is H; —CF₃; —OCF₃; —OCHF₂; lower alkyl; aryl; heteroaryl; or aryl-lower alkyl;

R⁸³ is H; lower alkyl; aryl; or —NR⁷⁸R⁷⁹;

R⁸⁴ is —(CH₂)ₚ(CHR⁶¹)ₛOH; —(CH₂)ₚCOOR⁸⁰; —(CH₂)ₚ(CHR⁶¹)ₛSH; —(CH₂)ₚCONR⁷⁸R⁷⁹; —(CH₂)ₚNH⁸⁰CONR⁷⁸R⁷⁹; —(CH₂)ₚC₆H₄CONH⁷⁸H⁷⁹; or —(CH₂)ₚC₆H₄NR⁸⁰CONR⁷⁸R⁷⁹;

R⁸⁵ is lower alkyl; or lower alkenyl;

R⁸⁶ is R⁷⁴; —(CH₂)ₒR⁷⁷; —(CH₂)ₒ—CHR³³R⁷⁵; R⁸⁴;
—[(CH₂)ᵤ—X']ₜ—(CH₂)ᵥNR⁷⁸R⁷⁹;
—[(CH₂)ᵤ—X']ₜ—(CH₂)ᵥ—C(=NR⁸⁰)NR⁷⁸R⁷⁹;
—[(CH₂)ᵤ—X']ₜ—(CH₂)ᵥ—OR⁷⁸; —[(CH₂)ᵤ—X']ₜ—(CH₂)ᵥ—CONR⁷⁸R⁷⁹;
—[(CH₂)ᵤ—X']ₜ—(CH₂)ᵥ—NR⁸⁰CONR⁷⁸R⁷⁹;
—[(CH₂)ᵤ—X']ₜ—(CH₂)ᵥSR⁷⁸
where X' is —O—, —NR²⁰—, —S—; or —OCOO—, u is 1-3, t is 1-6, and v is 1-3;

m is 2-4; o is 0-4; p is 1-4; q is 0-2; r is 1 or 2; s is 0 or 1;

the amino acid residue of type C is a residue of formula —NR²⁰CH(R⁷²)CO—;

the amino acid residue of type D is a residue of formula —NR²⁰CH(R⁷³)CO—;

the amino acid residue of type E is a residue of the formula —NR²⁰CH(R⁷⁴)CO—;

the amino acid residue of type F is a residue of the formula —NR²⁸CH(R⁸⁴)CO—;

the amino acid residue of type H is a residue of the one of the formulae —NR²⁰—CH(CO—)-alkylene-CH(CO—)—NR²⁰—;
—NR²⁰—CH(CO—)-alkenylene-CH(CO—)—NR²⁰—;
—NR²⁰—CH(CO—)-alkynylene-CH(CO—)—NR²⁰—;
—NR²⁰—CH(CO—)—(CH₂)ₚSS(CH₂)ₚ—CH(CO—)—NR²⁰—;
—NR²⁰—CH(CO—)—(—(CH₂)ₚNR²⁰CO(CH₂)ₚ—CH(CO—)—NR²⁰—; and
—NR²⁰—CH(CO—)—(—(CH₂)ₚNR²⁰CONR²⁰(CH₂)ₚ—CH(CO—)—NR²⁰—;

non-canonical amino acid residues designate those amino acid residues being neither glycine nor the L- or D-isomers of alanine, arginine, aspartic acid, asparagine, cysteine, glutamic acid, glutamine, histidine, isoleucine, leucine, lysine, methionine, phenylalanine, proline, serine, threonine, tryptophan, tyrosine and valine;

and pharmaceutically acceptable salts thereof.

In accordance with the present invention these β-hairpin peptidomimetics can be prepared by a process which comprises (a) coupling an appropriately functionalized solid support with an appropriately N-protected derivative of that amino acid which in the desired end-product corresponds to Xaaⁿ, wherein n is 14, 13, 12, 7, 6 or 5, any functional group which may be present in said N-protected amino acid derivative being likewise appropriately protected;

(b) removing the N-protecting group from the product thus obtained;

(c) coupling the product thus obtained with an appropriately N-protected derivative of that amino acid which in the desired end-product corresponds to Xaaⁿ⁻¹, any functional group which may be present in said N-protected amino acid derivative being likewise appropriately protected;

(d) removing the N-protecting group from the product obtained in step (c);

(e) effecting steps substantially corresponding to steps (c) and (d) using appropriately N-protected derivatives of amino acids which in the desired end-product are in positions n−2 to 1, any functional group(s) which may be present in said N-protected amino acid derivatives being likewise appropriately protected;

(f) if n is not 14, further effecting steps substantially corresponding to steps (c) and (d) using appropriately N-protected derivatives of amino acids which in the desired end-product are in positions 14 to n+1, any functional group(s) which may be present in said N-protected amino acid derivatives being likewise appropriately protected;

(g) forming an interstrand linkage between side-chains of appropriate amino acid residues at P2 and P11; or alternatively, forming the aforesaid linkage subsequent to step (j), as described herein below;

(h) detaching the product thus obtained from the solid support;

(i) cyclizing the product cleaved from the solid support;

(j) removing any protecting groups present on functional groups of any members of the chain of amino acid residues and, if desired, any protecting group(s) which may in addition be present in the molecule; and (k) if desired, converting the product thus obtained into a pharmaceutically acceptable salt or converting a pharmaceutically acceptable, or unacceptable, salt thus obtained into the corresponding free compound or into a different, pharmaceutically acceptable, salt.

Enantiomers of the compounds defined herein before form also part of the present invention. These enantiomers can be prepared by a modification of the above process wherein enantiomers of all chiral starting materials are utilized.

As used in this description, the term "alkyl", taken alone or in combinations, designates saturated, straight-chain or branched hydrocarbon radicals having up to 24, preferably up to 12, carbon atoms. Similarly, the term "alkenyl", taken alone or in combinations, designates straight chain or branched hydrocarbon radicals having up to 24, preferably up to 12, carbon atoms and containing at least one or, depending on the chain length, up to four olefinic double bonds. The term "alkylene" designates a divalent "alkyl", e.g. —CH₂—CH₂—CH₂—, having 4 to 24, preferably 4 to 12, carbon atoms. Similarly, the term "alkenylene" designates a divalent "alkenyl", e.g. —CH₂—CH—CH—CH₂—, having 4 to 24, preferably 4 to 12, carbon atoms and containing at least one or, depending on the chain length, up to four olefinic double bonds. Likewise, the term "alkynylene" designates a divalent straight chain or branched hydrocarbon radical, having 4 to 24, preferably 4 to 12, carbon atoms and containing at least one or, depending on the chain length, up to four carbon-carbon triple bonds. The term "lower" designates radicals and compounds having up to 6 carbon atoms. Thus, for example, the term "lower alkyl" designates saturated, straight-chain, or branched hydrocarbon radicals having up to 6 carbon atoms, such as methyl, ethyl, n-propyl, isopropyl, n-butyl, sec.-butyl, isobutyl, tert.-butyl, and the like. Similarly, the term "lower cycloalkyl" designates saturated cyclic hydrocarbon radicals having up to 6 carbon atoms, such as cyclopentyl, cyclohexyl and the like. The term "aryl" designates aromatic carbocyclic hydrocarbon radicals containing one or two six-membered rings, such as phenyl or naphthyl, which may be substituted by up to three substituents such as Br, Cl, F, $CF_3$, $NO_2$, lower alkyl or lower alkenyl. The term "heteroaryl" designates aromatic heterocyclic radicals containing one or two five- and/or six-membered rings, at least one of them containing up to three heteroatoms selected from the group consisting of O, S and N and said ring(s) being optionally substituted; representative examples of such optionally substituted heteroaryl radicals are indicated hereinabove in connection with the definition of $R^{77}$.

The β-hairpin conformation of Cyclo(-$Xaa^1$-$Xaa^2$-$Xaa^3$-$Xaa^4$-$Xaa^5$-$Xaa^6$-$Xaa^7$-$Xaa^8$-$Xaa^9$-$Xaa^{10}$-$Xaa^{11}$-$Xaa^{12}$-$Xaa^{13}$-$Xaa^{14}$-) is highly relevant for the anti-infective activity of the β-hairpin peptidomimetics of the present invention and also for the synthesis process defined hereinabove, as incorporation of the residues $Xaa^6$, $Xaa^7$ and $Xaa^{13}$ near the beginning or near the middle of the linear protected peptide precursors enhances cyclization yields significantly.

Building blocks A1-A69 of the structural element -A-CO— belong to a class of amino acids wherein the N-terminus is a secondary amine forming part of a ring. Among the genetically encoded amino acids only proline falls into this class. The configuration of building block A1 through A69 is (D), and they can be combined with a building block —B—CO— of (L)-configuration. Thus, for example, $^D$Pro-$^L$Pro constitutes the prototype of such a combination.

It will be appreciated that building blocks -A1-CO— to -A69-CO— in which A has (D)-configuration, are carrying a group $R^1$ at the β-position to the N-terminus.

The preferred values for $R^1$ are H and lower alkyl with the most preferred values for $R^1$ being H and methyl. It will be recognized by those skilled in the art, that A1-A69 are shown in (D)-configuration which, for $R^1$ being H and methyl, corresponds to the (R)-configuration. Depending on the priority of other values for $R^1$ according to the Cahn, Ingold and Prelog rules, this configuration may also have to be expressed as (S).

In addition to $R^1$ building blocks -A1-CO— to -A69-CO— can carry an additional substituent designated as $R^2$ to $R^{17}$. This additional substituent can be H, and if it is other than H, it is preferably a small to medium-sized aliphatic or aromatic group. Examples of preferred values for $R^1$ to $R^{17}$ are:

$R^1$ is hydrogen or lower alkyl;
$R^2$ is H; lower alkyl; lower alkenyl;
  —$(CH_2)_pOR^5$ (where $R^{55}$: lower alkyl; or lower alkenyl);
  —$(CH_2)_sSR^{56}$ (where $R^{56}$: lower alkyl; or lower alkenyl);
  —$(CH_2)_pNR^{33}R^{34}$ (where $R^{33}$: lower alkyl; or lower alkenyl; $R^{34}$: H; or lower alkyl; or $R^{33}$ and $R^{34}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl);
  —$(CH_2)_pOCONR^{33}R^{75}$ (where $R^{33}$: H; lower alkyl; or lower alkenyl; $R^{75}$: lower alkyl; or $R^{33}$ and $R^{75}$ taken together form: —$(CH_2)_{2-6}$—); —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl);
  —$(CH_2)_pNR^{20}CONR^{33}R^{81}$ (where $R^{20}$: H; or lower alkyl; $R^{33}$: H; lower alkyl; or lower alkenyl; $R^{81}$: H; or lower alkyl; or $R^{33}$ and $R^{81}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl);
  —$(CH_2)_oN(R^{20})COR^{64}$ (where $R^{20}$: H; or lower alkyl; $R^{64}$: lower alkyl; or lower alkenyl);
  —$(CH_2)_oCOOR^{57}$ (where $R^{57}$: lower alkyl; or lower alkenyl);
  —$(CH_2)_oCONR^{58}R^{58}$ (where $R^{58}$: lower alkyl; or lower alkenyl; and $R^{59}$: H; or lower alkyl; or $R^{58}$ and $R^{59}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl);
  —$(CH_2)_oPO(OR^{60})_2$ (where $R^{60}$: H; lower alkyl; or lower alkenyl);
  —$(CH_2)_oSO_2R^{62}$ (where $R^{62}$: lower alkyl; or lower alkenyl);
  —$(CH_2)_qC_6H_4R^8$ (where $R^8$: H; F; Cl; $CF_3$; lower alkyl; lower alkenyl; or lower alkoxy); or
  —$(CH_2)_qCHN_4R^8$.

$R^3$ is H; lower alkyl; lower alkenyl;
  —$(CH_2)_oR^{55}$ (where $R^{55}$: lower alkyl; or lower alkenyl);
  —$(CH_2)_oSR^{56}$ (where $R^{56}$: lower alkyl; or lower alkenyl);
  —$(CH_2)_oNR^{33}R^{34}$ (where $R^{33}$: lower alkyl; or lower alkenyl; $R^{34}$: H; or lower alkyl; or $R^{33}$ and $R^{34}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl);
  —$(CH_2)_mOCONR^{33}R^{75}$ (where $R^{33}$: H; lower alkyl; or lower alkenyl; $R^{75}$: lower alkyl; or $R^{33}$ and $R^{75}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl);
  —$(CH_2)_mNR^{20}CONR^{33}R^{81}$ (where $R^{20}$: H; or lower alkyl; $R^{33}$: H; lower alkyl; or lower alkenyl; $R^{81}$: H; or lower alkyl; or $R^{33}$ and $R^{81}$ taken together form: —$(CH_2)_{2-6}$—;
  —$(CH_2)_2O(CH_2)_2$—; —$(CH_2)_2S(CH_2)_2$—; or —$(CH_2)_2$ $NR^{57}(CH_2)_2$— (where $R^{57}$: H; or lower alkyl);
  —$(CH_2)_oN(R^{20})COR^{64}$ (where $R^{20}$: H; or lower alkyl; $R^{64}$: lower alkyl; or lower alkenyl);
  —$(CH_2)_oCOOR^{57}$ (where $R^{57}$: lower alkyl; or lower alkenyl);
  —$(CH_2)_oCONR^{58}R^{59}$ (where $R^{58}$: lower alkyl; or lower alkenyl; and $R^{59}$: H; or lower alkyl; or $R^{58}$ and $R^{59}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl);
  —$(CH_2)_oPO(OR^{60})_2$ (where $R^{60}$: H; lower alkyl; or lower alkenyl);
  —$(CH_2)_oSO_2R^{62}$ (where $R^{62}$: lower alkyl; or lower alkenyl); or
  —$(CH_2)_qC_6H_4R^8$ (where $R^8$: H; F; Cl; $CF_3$; lower alkyl; lower alkenyl; or lower alkoxy).

$R^4$ is H; lower alkyl; lower alkenyl;
  —$(CH_2)_mOR^{55}$ (where $R^{55}$: lower alkyl; or lower alkenyl)

$-(CH_2)_mSR^{56}$ (where $R^{56}$: lower alkyl; or lower alkenyl);

$-(CH_2)_mNR^{33}R^{34}$ (where $R^{33}$: lower alkyl; or lower alkenyl; $R^{34}$: H; or lower alkyl; or $R^{33}$ and $R^{34}$ taken together form: $-(CH_2)_{2-6}-$; $-(CH_2)_2O(CH_2)_2-$; $-(CH_2)_2S(CH_2)_2-$; or $-(CH_2)_2NR^{57}(CH_2)_2-$ (where $R^{57}$: H; or lower alkyl);

$-(CH_2)_mOCONR^{33}R^{75}$ (where $R^{33}$: H; lower alkyl; or lower alkenyl; $R^{75}$: lower alkyl; or $R^{33}$ and $R^{75}$ taken together form: $-(CH_2)_{2-6}-$; $-(CH_2)_2O(CH_2)_2-$; $-(CH_2)_2S(CH_2)_2-$; or $-(CH_2)_2NR^{57}(CH_2)_2-$ (where $R^{57}$: H; or lower alkyl);

$-(CH_2)_mNR^{20}CONR^{33}R^{81}$ (where $R^{20}$: H; or lower alkyl; $R^{33}$: H; lower alkyl; or lower alkenyl; $R^{81}$: H; or lower alkyl; or $R^{33}$ and $R^{81}$ taken together form: $-(CH_2)_{2-6}-$; $-(CH_2)_2O(CH_2)_2-$; $-(CH_2)_2S(CH_2)_2-$; or $-(CH_2)_2NR^{57}(CH_2)_2-$ (where $R^{57}$: H; or lower alkyl);

$-(CH_2)_mN(R^{20})COR^{64}$ (where $R^{20}$: H; or lower alkyl; $R^{64}$: lower alkyl; or lower alkenyl);

$-(CH_2)_oCOOR^{57}$ (where $R^{57}$: lower alkyl; or lower alkenyl);

$-(CH_2)_oCONR^{58}R^{59}$ (where $R^{58}$: lower alkyl; or lower alkenyl; and $R^{59}$: H; or lower alkyl; or $R^{58}$ and $R^{59}$ taken together form: $-(CH_2)_{2-6}-$; $-(CH_2)_2O(CH_2)_2-$; $-(CH_2)_2S(CH_2)_2-$; or $-(CH_2)_2NR^{57}(CH_2)_2-$ (where $R^{57}$: H; or lower alkyl);

$-(CH_2)_oPO(OR^{60})_2$ (where $R^{60}$: lower alkyl; or lower alkenyl);

$-(CH_2)_oSO_2R^{62}$ (where $R^{62}$: lower alkyl; or lower alkenyl); or $-(CH_2)_qC_6H_4R^8$ (where $R^8$: H; F; Cl; CF$_3$; lower alkyl; lower alkenyl; or lower alkoxy).

$R^5$ is lower alkyl; lower alkenyl;

$-(CH_2)_mOR^{55}$ (where $R^{55}$: lower alkyl; or lower alkenyl);

$-(CH_2)_mSR^{56}$ (where $R^{56}$: lower alkyl; or lower alkenyl);

$-(CH_2)_mNR^{33}R^{34}$ (where $R^{33}$: lower alkyl; or lower alkenyl; $R^{34}$: H; or lower alkyl; or $R^{33}$ and $R^{34}$ taken together form: $-(CH_2)_{2-6}-$; $-(CH_2)_2O(CH_2)_2-$; $-(CH_2)_2S(CH_2)_2-$; or $-(CH_2)_2NR^{57}(CH_2)_2-$ (where $R^{57}$: H; or lower alkyl);

$-(CH_2)_mOCONR^{33}R^{75}$ (where $R^{33}$: H; lower alkyl; or lower alkenyl; $R^{75}$: lower alkyl; or $R^{33}$ and $R^{75}$ taken together form: $-(CH_2)_{2-6}$; $-(CH_2)_2O(CH_2)_2-$; $-(CH_2)_2S(CH_2)_2-$; or $-(CH_2)_2NR^{57}(CH_2)_2-$ (where $R^{57}$: H; or lower alkyl);

$-(CH_2)_mNR^{20}CONR^{33}R^{81}$ (where $R^{20}$: H; or lower alkyl; $R^{33}$: H; lower alkyl; or lower alkenyl; $R^{81}$: H; or lower alkyl; or $R^{33}$ and $R^{81}$ taken together form: $-(CH_2)_{2-6}-$; $-(CH_2)_2O(CH_2)_2-$; $-(CH_2)_2S(CH_2)_2-$; or $-(CH_2)_2NR^{57}(CH_2)_2-$ (where $R^{57}$: H; or lower alkyl);

$-(CH_2)_mN(R^{20})COR^{64}$ (where $R^{20}$: H; or lower alkyl; $R^{64}$: alkyl; alkenyl; aryl; aryl-lower alkyl; or heteroaryl-lower alkyl);

$-(CH_2)_oCOOR^{57}$ (where $R^{57}$: lower alkyl; or lower alkenyl);

$-(CH_2)_oCONR^{59}R^{59}$ (where $R^{58}$: lower alkyl; or lower alkenyl; and $R^{59}$: H; or lower alkyl; or $R^{58}$ and $R^{59}$ taken together form: $-(CH_2)_{2-6}-$; $-(CH_2)_2O(CH_2)_2-$; $-(CH_2)_2S(CH_2)_2-$; or $-(CH_2)_2NR^{57}(CH_2)_2-$ (where $R^{57}$: H; or lower alkyl);

$-(CH_2)_oPO(OR^{60})_2$ (where $R^{60}$: lower alkyl; or lower alkenyl);

$-(CH_2)_oSO_2R^{62}$ (where $R^{62}$: lower alkyl; or lower alkenyl); or $-(CH_2)_qC_6H_4R^8$ (where $R^8$: H; F; Cl; CF$_3$; lower alkyl; lower alkenyl; or lower alkoxy).

$R^6$ is H; lower alkyl; lower alkenyl;

$-(CH_2)_oOR^{55}$ (where $R^{55}$: lower alkyl; or lower alkenyl);

$-(CH_2)_oSR^{56}$ (where $R^{56}$: lower alkyl; or lower alkenyl);

$-(CH_2)_oNR^{33}R^{34}$ (where $R^{33}$: lower alkyl; or lower alkenyl; $R^{34}$: H; or lower alkyl; or $R^{33}$ and $R^{34}$ taken together form: $-(CH_2)_{2-6}-$; $(CH_2)_2O(CH_2)_2-$; $-(CH_2)_2S(CH_2)_2-$; or $-(CH_2)_2NR^{57}(CH_2)_2-$ (where $R^{57}$: H; or lower alkyl);

$-(CH_2)_oOCONR^{33}R^{75}$ (where $R^{33}$: H; lower alkyl; or lower alkenyl; $R^{75}$: lower alkyl; or $R^{33}$ and $R^{75}$ taken together form: $-(CH_2)_{2-6}-$: $-(CH_2)_2O(CH_2)_2-$; $-(CH_2)_2S(CH_2)_2-$; or $-(CH_2)_2NR^{57}(CH_2)_2-$ (where $R^{57}$: H; or lower alkyl);

$-(CH_2)_oNR^{20}CONR^{33}R^{81}$ (where $R^{29}$: H; or lower alkyl; $R^{33}$: H; lower alkyl; or lower alkenyl; $R^{81}$: H; or lower alkyl; or $R^{33}$ and $R^{81}$ taken together form: $-(CH_2)_{2-6}-$; $-(CH_2)_2O(CH_2)_2-$; $-(CH_2)_2S(CH_2)_2-$; or $-(CH_2)_2NR^{57}(CH_2)_2-$ (where $R^{57}$: H; or lower alkyl);

$-(CH_2)_oN(R^{20})COR^{64}$ (where $R^{20}$: H; or lower alkyl; $R^{64}$: lower alkyl; or lower alkenyl);

$-(CH_2)_oCOOR^{57}$ (where $R^{57}$: lower alkyl; or lower alkenyl);

$-(CH_2)_oCONR^{58}R^{59}$ (where $R^{58}$: lower alkyl; or lower alkenyl; and $R^{59}$: H; or lower alkyl; or $R^{58}$ and $R^{59}$ taken together form: $-(CH_2)_{2-6}-$; $-(CH_2)_2O(CH_2)_2-$; $-(CH_2)_2S(CH_2)_2-$; or $-(CH_2)_2NR^{57}(CH_2)_2-$ (where $R^{57}$: H; or lower alkyl);

$-(CH_2)_oPO(OR^{60})_2$ (where $R^{60}$: lower alkyl; or lower alkenyl);

$-(CH_2)_oSO_2R^{62}$ (where $R^{62}$: lower alkyl; or lower alkenyl); or $-(CH_2)_qC_6H_4R^8$ (where $R^8$: H; F; Cl; CF$_3$; lower alkyl; lower alkenyl; or lower alkoxy).

$R^7$ is lower alkyl; lower alkenyl;

$-(CH_2)_qOR^{55}$ (where $R^{55}$: lower alkyl; or lower alkenyl);

$-(CH_2)_qSR^{56}$ (where $R^{56}$: lower alkyl; or lower alkenyl);

$-(CH_2)_qNR^{33}R^{34}$ (where $R^{33}$: lower alkyl; or lower alkenyl; $R^{34}$: H; or lower alkyl; or $R^{33}$ and $R^{34}$ taken together form: $-(CH_2)_{2-6}-$; $-(CH_2)_2O(CH_2)_2-$; $-(CH_2)_2S(CH_2)_2-$; or $-(CH_2)_2NR^{57}(CH_2)_2-$ (where $R^{57}$: H; or lower alkyl);

$-(CH_2)_qOCONR^{33}R^{75}$ (where $R^{33}$: H; lower alkyl; or lower alkenyl; $R^{75}$: lower alkyl; or $R^{33}$ and $R^{75}$ taken together form: $-(CH_2)_{2-6}-$; $-(CH_2)_2O(CH_2)_2-$; $-(CH_2)_2S(CH_2)_2-$; or $-(CH_2)_2NR^{57}(CH_2)_2-$ (where $R^{57}$: H; or lower alkyl);

$-(CH_2)_qNR^{20}CONR^{33}R^{81}$ (where $R^{20}$: H; or lower alkyl; $R^{33}$: H; lower alkyl; or lower alkenyl; $R^{81}$: H; or lower alkyl; or $R^{33}$ and $R^{81}$ taken together form: $-(CH_2)_{2-6}-$; $-(CH_2)_2O(CH_2)_2-$; $-(CH_2)_2S(CH_2)_2-$; or $-(CH_2)_2NR^{57}(CH_2)_2-$ (where $R^{57}$: H; or lower alkyl);

$-(CH_2)_qN(R^{20})COR^{64}$ (where $R^{20}$: H; or lower alkyl; $R^{64}$: lower alkyl; or lower alkenyl);

$-(CH_2)_rCOOR^{57}$ (where $R^{57}$: lower alkyl; or lower alkenyl);

$-(CH_2)_qCONR^{58}R^{59}$ (where $R^{58}$: lower alkyl; or lower alkenyl; and $R^{59}$: H; or lower alkyl; or $R^{58}$ and $R^{59}$ taken together form: $-(CH_2)_{2-6}-$; $-(CH_2)_2O$ $(CH_2)_2$—; —$(CH_2)_2S(CH_2)_2$—; or —$(CH_2)_2NR^{57}$ $(CH_2)_2$— (where $R^{57}$: H; or lower alkyl);
—$(CH_2)_rPO(OR^{60})_2$ (where $R^{60}$: lower alkyl; or lower alkenyl);
—$(CH_2)_rSO_2R^{62}$ (where $R^{62}$: lower alkyl; or lower alkenyl); or
$(CH_2)_qC_6H_4R^8$ (where $R^8$: H; F; Cl; $CF_3$; lower alkyl; lower alkenyl; or lower alkoxy).

$R^8$ is H; F; Cl; $CF_3$; lower alkyl; lower alkenyl;
—$(CH_2)_oOR^{55}$ (where $R^{55}$: lower alkyl; or lower alkenyl);
—$(CH_2)_oSR^{56}$ (where $R^{56}$: lower alkyl; or lower alkenyl);
—$(CH_2)_oNR^{33}R^{34}$ (where $R^{33}$: lower alkyl; or lower alkenyl; $R^{34}$: H; or lower alkyl; or $R^{33}$ and $R^{34}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl);
—$(CH_2)_oOCONR^{33}R^{75}$ (where $R^{33}$: H; lower alkyl; or lower alkenyl; $R^{75}$: lower alkyl; or $R^{33}$ and $R^{75}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl);
—$(CH_2)_oNR^{20}CONR^{33}R^{81}$ (where $R^{20}$: H; or lower alkyl; $R^{33}$: H; lower alkyl; or lower alkenyl; $R^{81}$: H; or lower alkyl; or $R^{33}$ and $R^{81}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl);
—$(CH_2)_oN(R^{20})COR^{64}$ (where $R^{20}$: H; or lower alkyl; $R^{64}$: lower alkyl; or lower alkenyl);
—$(CH_2)_oCOOR^{57}$ (where $R^{57}$: lower alkyl; or lower alkenyl);
—$(CH_2)_oCONR^{58}R^{59}$ (where $R^{58}$: lower alkyl; or lower alkenyl; and $R^{59}$: H; or lower alkyl; or $R^{58}$ and $R^{59}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl);
—$(CH_2)_oPO(OR^{60})_2$ (where $R^{60}$: lower alkyl; or lower alkenyl);
—$(CH_2)_oSO_2R^{62}$ (where $R^{62}$: lower alkyl; or lower alkenyl); or
—$(CH_2)_qC_6H_4R^8$ (where $R^8$: H; F; Cl; $CF_3$; lower alkyl; lower alkenyl; or lower alkoxy).

$R^9$ is lower alkyl; lower alkenyl;
—$(CH_2)_oOR^{55}$ (where $R^{55}$: lower alkyl; or lower alkenyl);
—$(CH_2)_oSR^{56}$ (where $R^{56}$: lower alkyl; or lower alkenyl);
—$(CH_2)_oNR^{33}R^{34}$ (where $R^{33}$: lower alkyl; or lower alkenyl; $R^{34}$: H; or lower alkyl; or $R^{33}$ and $R^{34}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl);
—$(CH_2)_oOCONR^{33}R^{75}$ (where $R^{33}$: H; lower alkyl; or lower alkenyl; $R^{75}$: lower alkyl; or $R^{33}$ and $R^{75}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl);
—$(CH_2)_mNR^{20}CONR^{33}R^{81}$ (where $R^{20}$: H; or lower alkyl; $R^{33}$: H; lower alkyl; or lower alkenyl; $R^{81}$: H; or lower alkyl; or $R^{33}$ and $R^{81}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl); —$(CH_2)_oN(R^{20})COR^{64}$ (where $R^{20}$: H; or lower alkyl; $R^{64}$: lower alkyl; or lower alkenyl);

—$(CH_2)_oCOOR^{57}$ (where $R^{57}$: lower alkyl; or lower alkenyl);
—$(CH_2)_oCONR^{58}R^{59}$ (where $R^{58}$: lower alkyl; or lower alkenyl; and $R^{59}$: H; or lower alkyl; or $R^{58}$ and $R^{59}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl);
—$(CH_2)_oPO(OR^{60})_2$ (where $R^{60}$: lower alkyl; or lower alkenyl);
—$(CH_2)_oSO_2R^{62}$ (where $R^{62}$: lower alkyl; or lower alkenyl); or
—$(CH_2)_qC_6H_4R^8$ (where $R^8$: H; F; Cl; $CF_3$; lower alkyl; lower alkenyl; or lower alkoxy).

$R^{10}$ is lower alkyl; lower alkenyl;
—$(CH_2)_oOR^{55}$ (where $R^{55}$: lower alkyl; or lower alkenyl);
—$(CH_2)_oSR^{56}$ (where $R^{56}$: lower alkyl; or lower alkenyl);
—$(CH_2)_oNR^{33}R^{34}$ (where $R^{33}$: lower alkyl; or lower alkenyl; $R^{34}$: H; or lower alkyl; or $R^{33}$ and $R^{34}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl);
—$(CH_2)_oOCONR^{33}R^{75}$ (where $R^{33}$: H; lower alkyl; or lower alkenyl; $R^{75}$: lower alkyl; or $R^{33}$ and $R^{75}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl);
—$(CH_2)_oNR^{20}CONR^{33}R^{81}$ (where $R^{20}$: H; or lower alkyl; $R^{33}$: H; lower alkyl; or lower alkenyl; $R^{81}$: H; or lower alkyl; or $R^{33}$ and $R^{81}$ taken together form: —$(CH_2)_{2-6}$—; —$(CH_2)_2O(CH_2)_2$—; —$(CH_2)_2S(CH_2)_2$—; or—$(CH_2)_2NR^{57}(CH_2)_2$—(where $R^{57}$: H; or lower alkyl);
—$(CH_2)_oN(R^{20})COR^{64}$ (where $R^{20}$: H; or lower alkyl; $R^{64}$: lower alkyl; or lower alkenyl);
—$(CH_2)_oCOOR^{57}$ (where $R^{57}$: lower alkyl; or lower alkenyl);
—$(CH_2)_oCONR^{58}R^{59}$ (where $R^{58}$: lower alkyl; or lower alkenyl; and $R^{59}$: H; or lower alkyl; or $R^{58}$ and $R^{59}$ taken together form: —$(CH_2)_{2-6}$—; —$(CH_2)_2O(CH_2)_2$—;
—$(CH_2)_2S(CH_2)_2$—; or —$(CH_2)_2NR^{57}(CH_2)_2$— (where $R^{57}$: H; or lower alkyl);
—$(CH_2)_oPO(OR^{60})_2$ (where $R^{60}$: lower alkyl; or lower alkenyl);
—$(CH_2)_oSO_2R^{62}$ (where $R^{62}$: lower alkyl; or lower alkenyl); or
—$(CH_2)_qC_6H_4R^8$ (where $R^8$: H; F; Cl; $CF_3$; lower alkyl; lower alkenyl; or lower alkoxy).

$R^{11}$ is H; lower alkyl; lower alkenyl;
—$(CH_2)_mOR^{55}$ (where $R^{55}$: lower alkyl; or lower alkenyl);
—$(CH_2)_mSR^{56}$ (where $R^{56}$: lower alkyl; or lower alkenyl);
$(CH_2)_mNR^{33}R^{34}$ (where $R^{33}$: lower alkyl; or lower alkenyl; $R^{34}$: H; or lower alkyl; or $R^{33}$ and $R^{34}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl);
—$(CH_2)_mOCONR^{33}R^{75}$ (where $R^{33}$: H; lower alkyl; or lower alkenyl; $R^{75}$: lower alkyl; or $R^{33}$ and $R^{75}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl);
—$(CH_2)_mNR^{20}CONR^{33}R^{81}$ (where $R^{25}$: H; or lower alkyl; $R^{33}$: H; lower alkyl; or lower alkenyl; $R^{81}$: H; or lower alkyl; or $R^{33}$ and $R^{81}$ taken together form: $-(CH_2)_{2-6}-$; $-(CH_2)_2O(CH_2)_2-$; $-(CH_2)_2S(CH_2)_2-$; or $-(CH_2)_2NR^{57}(CH_2)_2-$ (where $R^{57}$: H; or lower alkyl);

—$(CH_2)_mN(R^{20})COR^{64}$ (where $R^{20}$: H; or lower alkyl; $R^{64}$: lower alkyl; or lower alkenyl);

—$(CH_2)_oCOOR^{57}$ (where $R^{57}$: lower alkyl; or lower alkenyl);

—$(CH_2)_oCONR^{58}R^{59}$ (where $R^{58}$: lower alkyl; or lower alkenyl; and $R^{59}$: H; or lower alkyl; or $R^{58}$ and $R^{59}$ taken together form: $-(CH_2)_{2-6}-$; $-(CH_2)_2O(CH_2)_2-$;

—$(CH_2)_2S(CH_2)_2-$; or $-(CH_2)_2NR^{57}(CH_2)_2-$ (where $R^{57}$: H; or lower alkyl);

—$(CH_2)_oPO(OR^{60})_2$ (where $R^{60}$: lower alkyl; or lower alkenyl);

—$(CH_2)_oSO_2R^{62}$ (where $R^{62}$: lower alkyl; or lower alkenyl); or $(CH_2)_qC_6H_4R^8$ (where $R^8$: H; F; Cl; $CF_3$; lower alkyl; lower alkenyl; or lower alkoxy).

$R^{12}$ is H; lower alkyl; lower alkenyl;

—$(CH_2)_mOR^{55}$ (where $R^{55}$: lower alkyl; or lower alkenyl);

—$(CH_2)_mSR^{56}$ (where $R^{56}$: lower alkyl; or lower alkenyl);

—$(CH_2)_mNR^{33}R^{34}$ (where $R^{33}$: lower alkyl; or lower alkenyl; $R^{34}$: H; or lower alkyl; or $R^{33}$ and $R^{34}$ taken together form: $-(CH_2)_{2-6}-$; $-(CH_2)_2O(CH_2)_2-$; $-(CH_2)_2S(CH_2)_2-$; or $-(CH_2)_2NR^{57}(CH_2)_2-$ (where $R^{57}$: H; or lower alkyl);

—$(CH_2)_mOCONR^{33}R^{75}$ (where $R^{33}$: H; lower alkyl; or lower alkenyl; $R^{75}$: lower alkyl; or $R^{33}$ and $R^{75}$ taken together form: $-(CH_2)_{2-6}-$; $-(CH_2)_2O(CH_2)_2-$; $-(CH_2)_2S(CH_2)_2-$; or $-(CH_2)_2NR^{57}(CH_2)_2-$ (where $R^{57}$: H; or lower alkyl);

—$(CH_2)_mNR^{20}CONR^{33}R^{81}$ (where $R^{20}$: H; or lower alkyl; $R^{33}$: H; lower alkyl; or lower alkenyl; $R^{81}$: H; or lower alkyl; or $R^{33}$ and $R^{81}$ taken together form: $-(CH_2)_{2-6}-$;

—$(CH_2)_2O(CH_2)_2-$: $-(CH_2)_2S(CH_2)_2-$; or $-(CH_2)_2NR^{57}(CH_2)_2-$ (where $R^{57}$: H; or lower alkyl);

—$(CH_2)_mN(R^{20})COR^{64}$ (where $R^{20}$: H; or lower alkyl; $R^{64}$: lower alkyl; or lower alkenyl);

—$(CH_2)_rCOOR^{57}$ (where $R^{57}$: lower alkyl; or lower alkenyl);

—$(CH_2)_rCONR^{58}R^{59}$ (where $R^{58}$: lower alkyl; or lower alkenyl; and $R^{59}$: H; or lower alkyl; or $R^{58}$ and $R^{59}$ taken together form: $-(CH_2)_{2-6}-$; $-(CH_2)_2O(CH_2)_2-$; $-(CH_2)_2S(CH_2)_2-$; or $-(CH_2)_2NR^{57}(CH_2)_2-$ (where $R^{57}$: H; or lower alkyl);

—$(CH_2)_rPO(OR^{60})_2$ (where $R^{60}$: lower alkyl; or lower alkenyl);

—$(CH_2)_oSO_2R^{62}$ (where $R^{62}$: lower alkyl; or lower alkenyl); or

—$(CH_2)_oC_6H_4R^8$ (where $R^8$: H; F; Cl; $CF_3$; lower alkyl; lower alkenyl; or lower alkoxy).

$R^{13}$ is lower alkyl; lower alkenyl;

—$(CH_2)_qOR^{55}$ (where $R^{55}$: lower alkyl; or lower alkenyl);

—$(CH_2)_qSR^{56}$ (where $R^{56}$: lower alkyl; or lower alkenyl);

—$(CH_2)_qNR^{33}R^{34}$ (where $R^{33}$: lower alkyl; or lower alkenyl; $R^{34}$: H; or lower alkyl; or $R^{33}$ and $R^{34}$ taken together form: $-(CH_2)_{2-6}-$; $-(CH_2)_2O(CH_2)_2-$; $-(CH_2)_2S(CH_2)_2-$; or $-(CH_2)_2NR^{57}(CH_2)_2-$ (where $R^{57}$: H; or lower alkyl);

—$(CH_2)_qOCONR^{33}R^{75}$ (where $R^{33}$: H; lower alkyl; or lower alkenyl; $R^{75}$: lower alkyl; or $R^{33}$ and $R^{75}$ taken together form: $-(CH_2)_{2-6}-$: $-(CH_2)_2O(CH_2)_2-$; $-(CH_2)_2S(CH_2)_2-$; or $-(CH_2)_2NR^{57}(CH_2)_2-$ (where $R^{57}$: H; or lower alkyl);

—$(CH_2)_qNR^{20}CONR^{33}R^{81}$ (where $R^{20}$: H; or lower alkyl; $R^{33}$: H; lower alkyl; or lower alkenyl; $R^{81}$: H; or lower alkyl; or $R^{33}$ and $R^{81}$ taken together form: $-(CH_2)_{2-6}-$; $-(CH_2)_2O(CH_2)_2-$; $-(CH_2)_2S(CH_2)_2-$; or $-(CH_2)_2NR^{57}(CH_2)_2-$ (where $R^{57}$: H; or lower alkyl);

—$(CH_2)_qN(R^{20})COR^{64}$ (where $R^{20}$: H; or lower alkyl; $R^{64}$: lower alkyl; or lower alkenyl);

—$(CH_2)_rCOO^{57}$ (where $R^{57}$: lower alkyl; or lower alkenyl);

—$(CH_2)_qCONR^{58}R^{59}$ (where $R^{58}$: lower alkyl; or lower alkenyl; and $R^{59}$: H; or lower alkyl; or $R^{58}$ and $R^{59}$ taken together form: $-(CH_2)_{2-6}-$; $-(CH_2)_2O(CH_2)_2-$; $-(CH_2)_2S(CH_2)_2-$; or $-(CH_2)_2NR^{57}(CH_2)_2-$ (where $R^{57}$: H; or lower alkyl);

—$(CH_2)_rPO(OR^{60})_2$ (where $R^{60}$: lower alkyl; or lower alkenyl);

—$(CH_2)_rSO_2R^{62}$ (where $R^{62}$: lower alkyl; or lower alkenyl); or

—$(CH_2)_qC_6H_4R^8$ (where $R^8$: H; F; Cl; $CF_3$; lower alkyl; lower alkenyl; or lower alkoxy).

$R^{14}$ is H; lower alkyl; lower alkenyl;

—$(CH_2)_mOR^{55}$ (where $R^{55}$: lower alkyl; or lower alkenyl);

—$(CH_2)_mSR^{56}$ (where $R^{56}$: lower alkyl; or lower alkenyl);

—$(CH_2)_mNR^{33}R^{34}$ (where $R^{33}$: lower alkyl; or lower alkenyl; $R^{34}$: H; or lower alkyl; or $R^{33}$ and $R^{34}$ taken together form: $-(CH_2)_{2-6}-$; $-(CH_2)_2O(CH_2)_2-$; $-(CH_2)_2S(CH_2)_2-$; or $-(CH_2)_2NR^{57}(CH_2)_2-$ (where $R^{57}$: H; or lower alkyl);

—$(CH_2)_mOCONR^{33}R^{75}$ (where $R^{33}$: H; lower alkyl; or lower alkenyl; $R^{75}$: lower alkyl; or $R^{33}$ and $R^{75}$ taken together form: $-(CH_2)_{2-6}-$; $-(CH_2)_2O(CH_2)_2-$; $-(CH_2)_2S(CH_2)_2-$; or $-(CH_2)_2NR^{57}(CH_2)_2-$ (where $R^{57}$: H; or lower alkyl);

—$(CH_2)_mNR^{20}CONR^{33}R^{81}$ (where $R^{20}$: H; or lower alkyl; $R^{33}$: H; lower alkyl; or lower alkenyl; $R^{81}$: H; or lower alkyl; or $R^{33}$ and $R^{81}$ taken together form: $(CH_2)_{2-6}-$; $-(CH_2)_2O(CH_2)_2-$; $-(CH_2)_2S(CH_2)_2-$; or $-(CH_2)_2NR^{57}(CH_2)_2-$ (where $R^{57}$: H; or lower alkyl);

—$(CH_2)_mN(R^{20})COR^{64}$ (where $R^{20}$: H; lower alkyl; $R^{64}$: lower alkyl; or lower alkenyl);

—$(CH_2)_oCOOR^{57}$ (where $R^{57}$: lower alkyl; or lower alkenyl);

—$(CH_2)_oCONR^{58}R^{59}$ (where $R^{58}$: lower alkyl; or lower alkenyl; and $R^{59}$: H; or lower alkyl; or $R^{58}$ and $R^{59}$ taken together form: $-(CH_2)_{2-6}-$; $-(CH_2)_2O(CH_2)_2-$; $-(CH_2)_2S(CH_2)_2-$; or $-(CH_2)_2NR^{57}(CH_2)_2-$ (where $R^{57}$: H; or lower alkyl);

—$(CH_2)_oPO(OR^{60})_2$ (where $R^{60}$: lower alkyl; or lower alkenyl);

—$(CH_2)_oSO_2R^{62}$ (where $R^{62}$: lower alkyl; or lower alkenyl);

—$(CH_2)_qC_6H_4R^8$ (where $R^8$: H; F; Cl; $CF_3$; lower alkyl; lower alkenyl; or lower alkoxy).

$R^{15}$ is lower alkyl; lower alkenyl;

—$(CH_2)_oOR^{55}$ (where $R^{55}$: lower alkyl; or lower alkenyl);

—$(CH_2)_oSR^{56}$ (where $R^{56}$: lower alkyl; or lower alkenyl);

—(CH$_2$)$_o$NR$^{33}$R$^{34}$ (where R$^{33}$: lower alkyl; or lower alkenyl; R$^{34}$: H; or lower alkyl; or R$^{33}$ and R$^{34}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$— (where R$^{57}$: H; or lower alkyl);

—(CH$_2$)$_o$OCONR$^{33}$R$^{75}$ (where R$^{33}$: H; lower alkyl; or lower alkenyl; R$^{75}$: lower alkyl; or R$^{33}$ and R$^{75}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$— (where R$^{57}$: H; or lower alkyl);

—(CH$_2$)$_o$NR$^{20}$CONR$^{33}$R$^{81}$ (where R$^{20}$: H; or lower alkyl; R$^{33}$: H; lower alkyl; or lower alkenyl; R$^{81}$: H; or lower alkyl; or R$^{33}$ and R$^{81}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$— (where R$^{57}$: H; or lower alkyl);

—(CH$_2$)$_o$N(R$^{20}$)COR$^{64}$ (where R$^{20}$: H; or lower alkyl; R$^{64}$: lower alkyl; or lower alkenyl); particularly favoured being —NR$^{20}$CO-lower alkyl (where R$^{20}$: H; or lower alkyl);

—(CH$_2$)$_o$COOR$^{57}$ (where R$^{57}$: lower alkyl; or lower alkenyl);

—(CH$_2$)$_o$CONR$^{58}$R$^{59}$ (where R$^{58}$: lower alkyl, or lower alkenyl; and R$^{59}$: H; or lower alkyl; or R$^{58}$ and R$^{59}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$— (where R$^{57}$: H; or lower alkyl);

—(CH$_2$)$_o$PO(OR$^{60}$)$_2$ (where R$^{60}$: lower alkyl; or lower alkenyl);

—(CH$_2$)$_o$SO$_2$R$^{62}$ (where R$^{62}$: lower alkyl; or lower alkenyl); or

—(CH$_2$)$_q$C$_6$H$_4$R$^8$ (where R$^8$: H; F; Cl; CF$_3$; lower alkyl; lower alkenyl; or lower alkoxy).

R$^{16}$ is lower alkyl; lower alkenyl;

—(CH$_2$)$_q$OR$^{55}$ (where R$^{55}$: lower alkyl; or lower alkenyl);

—(CH$_2$)$_q$SR$^{56}$ (where R$^{56}$: lower alkyl; or lower alkenyl);

—(CH$_2$)$_q$NR$^{33}$R$^{34}$ (where R$^{33}$: lower alkyl; or lower alkenyl; R$^{34}$: H; or lower alkyl; or R$^{33}$ and R$^{34}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$— (where R$^{57}$: H; or lower alkyl);

—(CH$_2$)$_o$OCONR$^{33}$R$^{75}$ (where R$^{33}$: H; lower alkyl; or lower alkenyl; R$^{75}$: lower alkyl; or R$^{33}$ and R$^{75}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$— (where R$^{57}$: H; or lower alkyl);

—(CH$_2$)$_o$NR$^{20}$CONR$^{33}$R$^{81}$ (where R$^{20}$: H; or lower alkyl; R$^{33}$: H; lower alkyl; or lower alkenyl; R$^{81}$: H; or lower alkyl; or R$^{33}$ and R$^{81}$ taken together form: —(CH$_2$)$_{2-6}$—;

—(CH$_2$)$_2$—; (CH$_2$)$_2$—; —(CH$_2$)$_2$S(CH$_2$)$_2$—; or —(CH$_2$)$_2$NR$^{57}$(CH$_2$)$_2$—(where R$^{57}$: H; or lower alkyl);

—(CH$_2$)$_o$N(R$^{20}$)COR$^{64}$ (where R$^{20}$: H; or lower alkyl; R$^{64}$: lower alkyl; or lower alkenyl);

—(CH$_2$)$_o$COOR$^{57}$ (where R$^{57}$: lower alkyl; or lower alkenyl);

—(CH$_2$)$_o$CONR$^{58}$R$^{59}$ (where R$^{58}$: lower alkyl; or lower alkenyl; and R$^{59}$: H; or lower alkyl; or R$^{58}$ and R$^{59}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$— (where R$^{57}$: H; or lower alkyl);

—(CH$_2$)$_o$PO(OR$^{60}$)$_2$ (where R$^{60}$: lower alkyl; or lower alkenyl);

—(CH$_2$)$_o$SO$_2$R$^{62}$ (where R$^{62}$: lower alkyl; or lower alkenyl); or

—(CH$_2$)$_q$C$_6$H$_4$R$^8$ (where R$^8$: H; F; Cl; CF$_3$; lower alkyl; lower alkenyl; or lower alkoxy).

R$^{17}$ is lower alkyl; lower alkenyl;

—(CH$_2$)$_q$OR$^{55}$ (where R$^{55}$: lower alkyl; or lower alkenyl);

—(CH$_2$)$_q$SR$^{56}$ (where R$^{56}$: lower alkyl; or lower alkenyl);

—(CH$_2$)$_q$NR$^{33}$R$^{34}$ (where R$^{33}$: lower alkyl; or lower alkenyl; R$^{34}$: H; or lower alkyl; or R$^{33}$ and R$^{34}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$— (where R$^{57}$: H; or lower alkyl);

—(CH$_2$)$_q$OCONR$^{33}$R$^{75}$ (where R$^{33}$: H; lower alkyl; or lower alkenyl; R$^{75}$: lower alkyl; or R$^{33}$ and R$^{75}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$— (where R$^{57}$: H; or lower alkyl);

—(CH$_2$)$_q$NR$^{20}$CONR$^{33}$R$^{81}$ (where R$^{20}$: H; or lower alkyl; R$^{33}$: H; lower alkyl; or lower alkenyl; R$^{81}$: H; or lower alkyl; or R$^{33}$ and R$^{81}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$— (where R$^{57}$: H; or lower alkyl);

—(CH$_2$)$_q$N(R$^{20}$)COR$^{64}$ (where R$^{20}$: H; or lower alkyl; R$^{64}$: lower alkyl; or lower alkenyl);

—(CH$_2$)$_r$COOR$^{57}$ (where R$^{57}$: lower alkyl; or lower alkenyl);

—(CH$_2$)$_q$CONR$^{58}$R$^{59}$ (where R$^{58}$: lower alkyl; or lower alkenyl; and R$^{59}$: H; or lower alkyl; or R$^{58}$ and R$^{59}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$— (where R$^{57}$: H; or lower alkyl);

—(CH$_2$)$_r$PO(OR$^{60}$)$_2$ (where R$^{60}$: lower alkyl; or lower alkenyl);

—(CH$_2$)$_r$SO$_2$R$^{62}$ (where R$^{62}$: lower alkyl; or lower alkenyl); or

—(CH$_2$)$_q$C$_6$H$_4$R$^8$ (where R$^8$: H; F; Cl; CF$_3$; lower alkyl; lower alkenyl; or lower alkoxy).

Among the building blocks A1 to A69 the following are preferred: A5 with R$^2$ being H, A8, A22, A25, A38 with R$^2$ being H, A42, A47, and A50. Also, and particularly, preferred are building blocks of type A8':

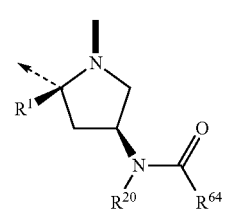

A8' wherein R$^{20}$ is H or lower alkyl; and R$^{64}$ is alkyl; alkenyl; aryl; aryl-lower alkyl; or heteroaryl-lower alkyl; especially those wherein R$^{64}$ is n-hexyl (A8'-1); n-heptyl (A8'-2); 4-(phenyl) benzyl (A8'-3); diphenylmethyl (A8'-4); 3-amino-propyl (A8'-5); 5-amino-pentyl (A8'-6); methyl (A8'-7); ethyl (A8'-8); isopropyl (A8'-9); isobutyl (A8'-10); n-propyl (A8'-11); cyclohexyl (A8'-12); cyclohexylmethyl (A8'-13); n-butyl (A8'-14); phenyl (A8'-15); benzyl (A8'-16); (3-indolyl)methyl (A8'-17); 2-(3-indolyl)ethyl (A8'-18); (4-phenyl) phenyl (A8'-19); and n-nonyl (A8'-20).

Building block A70 belongs to the class of open-chain α-substituted α-amino acids, building blocks A71 and A72 to the corresponding β-amino acid analogues and building blocks A73-A104 to the cyclic analogues of A70. Such amino acid derivatives have been shown to constrain small peptides in well defined reverse turn or U-shaped conformations (C. M. Venkatachalam, Biopolymers 1968, 6, 1425-1434; W. Kabsch, C. Sander, *Biopolymers* 1983, 22, 2577). Such building blocks are ideally suited for the stabilization of β-hairpin conformations in peptide loops (D. Obrecht, M. Altorfer, J. A. Robinson, "Novel Peptide Mimetic Building Blocks and Straties for Efficient Lead Finding", *Adv. Med. Chem.* 1999, Vol. 4, 1-68; P. Balaram, "Non-standard amino acids in peptide design and protein engineering", *Curr. Opin. Struct. Biol.* 1992, 2, 845-851; M. Crisma, G. Valle, C. Toniolo, S. Prasad, R. B. Rao, P. Balaram, "β-turn conformations in crystal structures of model peptides containing α.α-disubstituted amino acids", *Biopolymers* 1995, 35, 1-9; V. J. Hruby, F. Al-Obeidi, W. Kazmierski, *Biochem. J.* 1990, 268, 249-262).

It has been shown that both enantiomers of building blocks -A70-CO— to A104-CO— in combination with a building block —B—CO— being an α-amino acid with L-configuration can efficiently stabilize and induce β-hairpin conformations (D. Obrecht, M. Altorfer, J. A. Robinson, "Novel Peptide Mimetic Building Blocks and Strategies for Efficient Lead Finding", *Adv. Med. Chem.* 1999, Vol. 4, 1-68; D. Obrecht, C. Spiegler, P. Schönholzer, K. Müller, H. Heimgartner, F. Stierli, *Helv. Chico. Acta* 1992, 75, 1666-1696; D. Obrecht, U. Bohdal, J. Daly, C. Lehmann, P. Schönholzer, K. Müller, *Tetrahedron* 1995, 51, 10883-10900; D. Obrecht, C. Lehmann, C. Ruffieux, P. Schönholzer, K. Müller, *Helv. Chim. Acta* 1995, 78, 1567-1587; D. Obrecht, U. Bohdal, C. Broger, D. Bur, C. Lehmann, R. Ruffieux, P. Schönholzer, C. Spiegler, *Helv. Chim. Acta* 1995, 78, 563-580; D. Obrecht, H. Karajiannis, C. Lehmann, P. Schönholzer, C. Spiegler, *Helv. Chim. Acta* 1995, 78, 703-714).

Preferred values for $R^{29}$ in A70 to A104 are H or lower alkyl with methyl being most preferred. Preferred values for $R^{18}$, $R^{19}$ and $R^{21}$-$R^{29}$ in building blocks A70 to A104 are the following:

$R^{18}$ is lower alkyl.

$R^{19}$ is lower alkyl; lower alkenyl;
- —$(CH_2)_pOR^{55}$ (where $R^{55}$: lower alkyl; or lower alkenyl);
- —$(CH_2)_pSR^{56}$ (where $R^{56}$: lower alkyl; or lower alkenyl); —$(CH_2)_pNR^{33}R^{34}$ (where $R^{33}$: lower alkyl; or lower alkenyl; $R^{39}$: H; or lower alkyl; or $R^{33}$ and $R^{34}$ taken together form: —$(CH_2)_{2-6}$—; —$(CH_2)_2O(CH_2)_2$—;
- —$(CH_2)_2S(CH_2)_2$—; or —$(CH_2)_2NR^{57}(CH_2)_2$— (where $R^{57}$: H; or lower alkyl);
- —$(CH_2)_pOCONR^{33}R^{75}$ (where $R^{33}$: H; lower alkyl; or lower alkenyl; $R^{75}$: lower alkyl; or $R^{33}$ and $R^{75}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl);
- —$(CH_2)_pNR^{20}CONR^{33}R^{81}$ (where $R^{20}$: H; or lower alkyl; $R^{33}$: H; lower alkyl; or lower alkenyl; $R^{81}$: H; or lower alkyl; or $R^{33}$ and $R^{81}$ taken together form: —$(CH_2)_{2-6}$—;
- —$(CH_2)_2O(CH_2)_2$—; —$(CH_2)_2S(CH_2)_2$—; or —$(CH_2)_2 NR^{57}(CH_2)_2$— (where $R^{57}$: H; or lower alkyl);
- —$(CH_2)_pN(R^{29})COR^{64}$ (where $R^{20}$: H; or lower alkyl; $R^{64}$: lower alkyl; or lower alkenyl);
- —$(CH_2)_pCOOR^{57}$ (where $R^{57}$: lower alkyl; or lower alkenyl);
- —$(CH_2)_pCONR^{58}R^{59}$ (where $R^{58}$: lower alkyl; or lower alkenyl; and $R^{59}$: H; or lower alkyl; or $R^{58}$ and $R^{59}$ taken together form: —$(CH_2)_{2-6}$—; —$(CH_2)_2O(CH_2)_2$—;
- —$(CH_2)_2S(CH_2)_2$—; or —$(CH_2)_2NR^{57}(CH_2)_2$— (where $R^{57}$: H; or lower alkyl);
- —$(CH_2)_oPO(OR^{60})_2$ (where $R^{60}$: lower alkyl; or lower alkenyl);
- —$(CH_2)_pSO_2R^{62}$ (where $R^{62}$: lower alkyl; or lower alkenyl); or
- —$(CH_2)_oC_6H_4R^8$ (where $R^8$: H; F; Cl; $CF_3$; lower alkyl; lower alkenyl; or lower alkoxy).

$R^{21}$ is H; lower alkyl; lower alkenyl;
- —$(CH_2)_oOR^{55}$ (where $R^{55}$: lower alkyl; or lower alkenyl);
- —$(CH_2)_oSR^{56}$ (where $R^{56}$: lower alkyl; or lower alkenyl);
- —$(CH_2)_oNR^{33}R^{34}$ (where $R^{33}$: lower alkyl; or lower alkenyl; $R^{34}$: H; or lower alkyl; or $R^{33}$ and $R^{34}$ taken together form: —$(CH_2)_{2-6}$—; —$(CH_2)_2O(CH_2)_2$—;
- —$(CH_2)_2S(CH_2)_2$—; or —$(CH_2)_2NR^{57}(CH_2)_2$— (where $R^{57}$: H; or lower alkyl);
- —$(CH_2)_oCONR^{33}R^{75}$ (where $R^{33}$: H; lower alkyl; or lower alkenyl; $R^{75}$: lower alkyl; or $R^{33}$ and $R^{75}$ taken together form: —$(CH_2)_{2-6}$—; —$(CH_2)_2O(CH_2)_2$—;
- —$(CH_2)_2S(CH_2)_2$—; or —$(CH_2)_2NR^{57}(CH_2)_2$— (where $R^{57}$: H; or lower alkyl);
- —$(CH_2)_oNR^{20}CONR^{33}R^{81}$ (where $R^{20}$: H; or lower alkyl; $R^{33}$: H; lower alkyl; or lower alkenyl; $R^{81}$: H; or lower alkyl; or $R^{33}$ and $R^{81}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl);
- —$(CH_2)_oN(R^{20})COR^{64}$ (where $R^{20}$: H; or lower alkyl; $R^{64}$: lower alkyl; or lower alkenyl);
- —$(CH_2)_oCOOR^{57}$ (where $R^{57}$: lower alkyl; or lower alkenyl);
- —$(CH_2)_oCONR^{58}R^{59}$ (where $R^{58}$: lower alkyl, or lower alkenyl; and $R^{59}$: H; or lower alkyl; or $R^{58}$ and $R^{59}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl);
- —$(CH_2)_oPO(OR^{60})_2$ (where $R^{60}$: lower alkyl; or lower alkenyl);
- —$(CH_2)_oSO_2R^{62}$ (where $R^{62}$: lower alkyl; or lower alkenyl); or
- —$(CH_2)_qC_6H_4R^8$ (where $R^8$: H; F; Cl; $CF_3$; lower alkyl; lower alkenyl; or lower alkoxy).

$R^{22}$ is lower alkyl; lower alkenyl;
- —$(CH_2)_oOR^{55}$ (where $R^{55}$: lower alkyl; or lower alkenyl);
- —$(CH_2)_oSR^{56}$ (where $R^{56}$: lower alkyl; or lower alkenyl);
- —$(CH_2)_oNR^{33}R^{34}$ (where $R^{33}$: lower alkyl; or lower alkenyl; $R^{34}$: H; or lower alkyl; or $R^{33}$ and $R^{34}$ taken together form: —$(CH_2)_{2-6}$—; —$(CH_2)_2O(CH_2)_2$—;
- —$(CH_2)_2S(CH_2)_2$—; or —$(CH_2)_2NR^{57}(CH_2)_2$— (where $R^{57}$: H; or lower alkyl);
- —$(CH_2)_oOCONR^{33}R^{75}$ (where $R^{33}$: H; lower alkyl; or lower alkenyl; $R^{75}$: lower alkyl; or $R^{33}$ and $R^{75}$ taken together form: —$(CH_2)_{2-6}$—; —$(CH_2)_2O(CH_2)_2$—;
- —$(CH_2)_2S(CH_2)_2$—; or —$(CH_2)_2NR^{57}(CH_2)_2$— (where $R^{57}$: H; or lower alkyl);
- —$(CH_2)_oNR^{20}CONR^{33}R^{81}$ (where $R^{20}$: H; or lower alkyl; $R^{33}$: H; lower alkyl; or lower alkenyl; $R^{81}$: H; or lower alkyl; or $R^{33}$ and $R^{81}$ taken together form:

—$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl);

—$(CH_2)_oN(R^{20})COR^{64}$ (where $R^{20}$: H; or lower alkyl; $R^{64}$: lower alkyl; or lower alkenyl);

—$(CH_2)_oCOOR^{57}$ (where $R^{57}$: lower alkyl; or lower alkenyl);

—$(CH_2)_oCONR^{58}R^{58}$ (where $R^{58}$: lower alkyl, or lower alkenyl; and $R^{59}$: H; or lower alkyl; or $R^{58}$ and $R^{59}$ taken together form: —$(CH_2)_{2-6}$—; —$(CH_2)_2O(CH_2)_2$—;

—$(CH_2)_2S(CH_2)_2$—; or —$(CH_2)_2NR^{57}(CH_2)_2$— (where $R^{57}$: H; or lower alkyl);

—$(CH_2)_oPO(OR^{60})_2$ (where $R^{60}$: lower alkyl; or lower alkenyl);

—$(CH_2)_oSO_2R^{62}$ (where $R^{62}$: lower alkyl; or lower alkenyl); or

—$(CH_2)_qC_6H_4R^8$ (where $R^8$: H; F; Cl; CF; lower alkyl; lower alkenyl; or lower alkoxy).

$R^{23}$ is H; lower alkyl; lower alkenyl;

—$(CH_2)_oOR^{55}$ (where $R^{55}$: lower alkyl; or lower alkenyl);

—$(CH_2)_oSR^{56}$ (where $R^{56}$: lower alkyl; or lower alkenyl);

—$(CH_2)_oNR^{33}R^{34}$ (where $R^{33}$: lower alkyl; or lower alkenyl; $R^{34}$: H; or lower alkyl; or $R^{33}$ and $R^{34}$ taken together form: —$(CH_2)_{2-6}$—: —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl);

—$(CH_2)_oOCONR^{33}R^{75}$ (where $R^{33}$: H; lower alkyl; or lower alkenyl; $R^{75}$: lower alkyl; or $R^{33}$ and $R^{75}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl);

—$(CH_2)_oNR^{20}CONR^{33}R^{81}$ (where $R^{20}$: H; or lower alkyl; $R^{33}$: H; lower alkyl; or lower alkenyl; $R^{81}$: H; or lower alkyl; or $R^{33}$ and $R^{81}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl);

—$(CH_2)_oN(R^{20})COR^{64}$ (where $R^{20}$: H; or lower alkyl; $R^{64}$: lower alkyl; or lower alkenyl); particularly favoured are $NR^{20}CO$-lower alkyl (where $R^{20}$: H; or lower alkyl);

—$(CH_2)_oCOOR^{57}$ (where $R^{57}$: lower alkyl; or lower alkenyl);

—$(CH_2)_oCONR^{58}R^{59}$ (where $R^{58}$: lower alkyl, or lower alkenyl; and $R^{59}$: H; or lower alkyl; or $R^{58}$ and $R^{59}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl);

—$(CH_2)_oPO(OR^{60})_2$ (where $R^{60}$: lower alkyl; or lower alkenyl);

—$(CH_2)_oSO_2R^{62}$ (where $R^{62}$: lower alkyl; or lower alkenyl); or

—$(CH_2)_qC_6H_4R^8$ (where $R^8$: H; F; Cl; CF$_3$; lower alkyl; lower alkenyl; or lower alkoxy).

$R^{24}$ is lower alkyl; lower alkenyl;

—$(CH_2)_oOR^{55}$ (where $R^{55}$: lower alkyl; or lower alkenyl);

—$(CH_2)_oSR^{56}$ (where $R^{56}$: lower alkyl; or lower alkenyl);

—$(CH_2)_oNR^{33}R^{34}$ (where $R^{33}$: lower alkyl; or lower alkenyl; $R^{34}$: H; or lower alkyl; or $R^{33}$ and $R^{34}$ taken together form: —$(CH_2)_{2-6}$—; —$(CH_2)_2O(CH_2)_2$—;

—$(CH_2)_2S(CH_2)_2$—; or —$(CH_2)_2NR^{57}(CH_2)_2$— (where $R^{57}$: H; or lower alkyl);

—$(CH_2)_oOCONR^{33}R^{75}$ (where $R^{33}$: H; lower alkyl; or lower alkenyl; $R^{75}$: lower alkyl; or $R^{33}$ and $R^{75}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl);

—$(CH_2)_oNR^{20}CONR^{33}R^{81}$ (where $R^{20}$: H; or lower alkyl; $R^{33}$: H; lower alkyl; or lower alkenyl; $R^{81}$: H; or lower alkyl; or $R^{33}$ and $R^{81}$ taken together form: —$(CH_2)_{2-6}$—; —$(CH_2)_2O(CH_2)_2$—; —$(CH_2)_2S(CH_2)_2$—; or —$(CH_2)_2 NR^{57}(CH_2)_2$— (where $R^{57}$: H; or lower alkyl);

—$(CH_2)_oN(R^{20})COR^{64}$ (where $R^{20}$: H; or lower alkyl; $R^{64}$: lower alkyl; or lower alkenyl); particularly favoured are $NR^{20}CO$-lower alkyl (where $R^{20}$: H; or lower alkyl);

—$(CH_2)_oCOOR^{57}$ (where $R^{57}$: lower alkyl; or lower alkenyl);

—$(CH_2)_oCONR^{58}R^{59}$ (where $R^{58}$: lower alkyl, or lower alkenyl; and $R^{59}$: H; or lower alkyl; or $R^{58}$ and $R^{59}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl);

—$(CH_2)_oPO(OR^{60})_2$ (where $R^{60}$: lower alkyl; or lower alkenyl);

—$(CH_2)_oSO_2R^{62}$ (where $R^{62}$: lower alkyl; or lower alkenyl); or

—$(CH_2)_qC_6H_4R^8$ (where $R^8$: H; F; Cl; CF$_3$; lower alkyl; lower alkenyl; or lower alkoxy).

$R^{25}$ is H; lower alkyl; lower alkenyl;

—$(CH_2)_mOR^{55}$ (where $R^{55}$: lower alkyl; or lower alkenyl);

—$(CH_2)_mNR^{33}R^{34}$ (where $R^{33}$: lower alkyl; or lower alkenyl; $R^{34}$: H; or lower alkyl; or $R^{33}$ and $R^{34}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl);

—$(CH_2)_mOCONR^{33}R^{75}$ (where $R^{33}$: H; lower alkyl; or lower alkenyl; $R^{75}$: lower alkyl; or $R^{33}$ and $R^{75}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl);

—$(CH_2)_mNR^{20}CONR^{33}R^{81}$ (where $R^{20}$: H; or lower alkyl; $R^{33}$: H; lower alkyl; or lower alkenyl; $R^{81}$: H; or lower alkyl; or $R^{33}$ and $R^{81}$ taken together form: —$(CH_2)_{2-6}$—; —$(CH_2)_2O(CH_2)_2$—; —$(CH_2)_2S(CH_2)_2$—; or —$(CH_2)_2 NR^{57}(CH_2)_2$— (where $R^{57}$: H; or lower alkyl);

—$(CH_2)_mN)(R^{20})COR^{64}$ (where $R^{20}$: H; or lower alkyl; $R^{64}$: lower alkyl; or lower alkenyl);

—$(CH_2)_oCOOR^{57}$ (where $R^{57}$: lower alkyl; or lower alkenyl);

—$(CH_2)_oCONR^{58}R^{59}$ (where $R^{58}$: lower alkyl; or lower alkenyl; and $R^{59}$: H; or lower alkyl; or $R^{58}$ and $R^{59}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl);

—$(CH_2)_oPO(OR^{60})_2$ (where $R^{60}$: lower alkyl; or lower alkenyl);

—$(CH_2)_oSO_2R^{62}$ (where $R^{62}$: lower alkyl; or lower alkenyl); or

—$(CH_2)_qC_6H_4R^8$ (where $R^8$: H; F; Cl; CF$_3$; lower alkyl; lower alkenyl; or lower alkoxy).

$R^{26}$ is H; lower alkyl; lower alkenyl;

—$(CH_2)_mOR^{55}$ (where $R^{55}$: lower alkyl; or lower alkenyl); —$(CH_2)_mNR^{33}R^{34}$ (where $R^{33}$: lower alkyl; or lower alkenyl; $R^{34}$: H; or lower alkyl; or $R^{33}$ and $R^{34}$ taken together form: $-(CH_2)_{2-6}-$; $-(CH_2)_2O(CH_2)_2-$; $-(CH_2)_2S(CH_2)_2-$; or $-(CH_2)_2NR^{57}(CH_2)_2-$ (where $R^{57}$: H; or lower alkyl);

$-(CH_2)_mOCONR^{33}R^{75}$ (where $R^{33}$: H; lower alkyl; or lower alkenyl; $R^{75}$: lower alkyl; or $R^{33}$ and $R^{75}$ taken together form: $-(CH_2)_{2-6}-$; $-(CH_2)_2O(CH_2)_2-$; $-(CH_2)_2S(CH_2)_2-$; or $-(CH_2)_2NR^{57}(CH_2)_2-$ (where $R^{57}$: H; or lower alkyl);

$-(CH_2)_mNR^{20}CONR^{33}R^{81}$ (where $R^{20}$: H; or lower alkyl; $R^{33}$: H; lower alkyl; or lower alkenyl; $R^{81}$: H; or lower alkyl; or $R^{33}$ and $R^{81}$ taken together form: $-(CH_2)_{2-6}-$;

$-(CH_2)_2O(CH_2)_2-$; $-(CH_2)_2S(CH_2)_2-$; or $-(CH_2)_2NR^{57}(CH_2)_2-$ (where $R^{57}$: H; or lower alkyl);

$-(CH_2)_mN(R^{20})COR^{64}$ (where $R^{20}$: H; or lower alkyl; $R^{64}$: lower alkyl; or lower alkenyl);

$-(CH_2)_oCOOR^{57}$ (where $R^{57}$: lower alkyl; or lower alkenyl);

$-(CH_2)_oCONR^{58}R^{59}$ (where $R^{58}$: lower alkyl; or lower alkenyl; and $R^{59}$: H; or lower alkyl; or $R^{58}$ and $R^{59}$ taken together form: $-(CH_2)_{2-6}-$; $(CH_2)_2O(CH_2)_2-$;

$-(CH_2)_2S(CH_2)_2-$; or $-(CH_2)_2NR^{57}(CH_2)_2-$ (where $R^{57}$: H; or lower alkyl);

$-(CH_2)_oPO(OR^{60})_2$ (where $R^{60}$: lower alkyl; or lower alkenyl);

$-(CH_2)_oSO_2R^{62}$ (where $R^{62}$: lower alkyl; or lower alkenyl); or $-(CH_2)_qC_6H_4R^8$ (where $R^8$: H; F; Cl; $CF_3$; lower alkyl; lower alkenyl; or lower alkoxy); or, alternatively, $R^{25}$ and $R^{26}$ taken together can be
$(CH_2)_{2-6}-$; $-(CH_2)_2O(CH_2)_2-$; $-(CH_2)_2S(CH_2)_2-$; or $(CH_2)_2NR^{57}(CH_2)_2-$ (where $R^{57}$: H; or lower alkyl).

$R^{27}$ is H; lower alkyl; lower alkenyl;

$-(CH_2)_oOR^{55}$ (where $R^{55}$: lower alkyl; or lower alkenyl);

$-(CH_2)_oSR^{56}$ (where $R^{56}$: lower alkyl; or lower alkenyl);

$-(CH_2)_oNR^{33}R^{34}$ (where $R^{33}$: lower alkyl; or lower alkenyl; $R^{34}$: H; or lower alkyl; or $R^{33}$ and $R^{34}$ taken together form: $-(CH_2)_{2-6}-$; $-(CH_2)_2O(CH_2)_2-$; $-(CH_2)_2S(CH_2)_2-$; or $-(CH_2)_2NR^{57}(CH_2)_2-$ (where $R^{57}$: H; or lower alkyl);

$-(CH_2)_oOCONR^{33}R^{75}$ (where $R^{33}$: H; lower alkyl; or lower alkenyl; $R^{75}$: lower alkyl; or $R^{33}$ and $R^{75}$ taken together form: $-(CH_2)_{2-6}-$; $-(CH_2)_2O(CH_2)_2-$; $-(CH_2)_2S(CH_2)_2-$; or $-(CH_2)_2NR^{57}(CH_2)_2-$ (where $R^{57}$: H; or lower alkyl);

$-(CH_2)_oNR^{20}CONR^{33}R^{81}$ (where $R^{20}$: H; or lower alkyl; $R^{33}$: H; lower alkyl; or lower alkenyl; $R^{81}$: H; or lower alkyl; or $R^{33}$ and $R^{81}$ taken together form: $-(CH_2)_{2-6}-$; $-(CH_2)_2O(CH_2)_2-$; $-(CH_2)_2S(CH_2)_2-$; or $-(CH_2)_2NR^{57}(CH_2)_2-$ (where $R^{57}$: H; or lower alkyl);

$-(CH_2)_oN(R^{20})COR^{64}$ (where $R^{20}$: H; or lower alkyl; $R^{64}$: lower alkyl; or lower alkenyl);

$-(CH_2)_oCOOR^{57}$ (where $R^{57}$: lower alkyl; or lower alkenyl);

$-(CH_2)_oCONR^{58}R^{59}$ (where $R^{58}$: lower alkyl, or lower alkenyl; and $R^{59}$: H; or lower alkyl; or $R^{58}$ and $R^{59}$ taken together form: $-(CH_2)_{2-6}-$; $-(CH_2)_2O(CH_2)_2-$; $-(CH_2)_2S(CH_2)-$; or $-(CH_2)_2NR^{57}(CH_2)_2-$ (where $R^{57}$: H; or lower alkyl);

$-(CH_2)_oPO(OR^{60})_2$ (where $R^{60}$: lower alkyl; or lower alkenyl);

$-(CH_2)_oSO_2R^{62}$ (where $R^{62}$: lower alkyl; or lower alkenyl); or $-(CH_2)_qC_6H_4R^8$ (where $R^8$: H; F; Cl; $CF_3$; lower alkyl; lower alkenyl; or lower alkoxy).

$R^{28}$ is lower alkyl; lower alkenyl;

$-(CH_2)_oR^{55}$ (where $R^{55}$: lower alkyl; or lower alkenyl);

$-(CH_2)_oSR^{56}$ (where $R^{56}$: lower alkyl; or lower alkenyl);

$-(CH_2)_oNR^{33}R^{34}$ (where $R^{33}$: lower alkyl; or lower alkenyl; $R^{34}$: H; or lower alkyl; or $R^{33}$ and $R^{34}$ taken together form: $-(CH_2)_{2-6}-$; $-(CH_2)_2O(CH_2)_2-$; $-(CH_2)_2S(CH_2)_2-$; or $-(CH_2)_2NR^{57}(CH_2)_2-$ (where $R^{57}$: H; or lower alkyl);

$-(CH_2)_oOCONR^{33}R^{75}$ (where $R^{33}$: H; lower alkyl; or lower alkenyl; $R^{75}$: lower alkyl; or $R^{33}$ and $R^{75}$ taken together form: $-(CH_2)_{2-6}-$; $-(CH_2)_2O(CH_2)_2-$; $-(CH_2)_2S(CH_2)_2-$; or $-(CH_2)_2NR^{57}(CH_2)_2-$ (where $R^{57}$: H; or lower alkyl);

$-(CH_2)_oNR^{20}CONR^{33}R^{81}$ (where $R^{20}$: H; or lower alkyl; $R^{33}$: H; lower alkyl; or lower alkenyl; $R^{81}$: H; or lower alkyl; or $R^{33}$ and $R^{81}$ taken together form: $-(CH_2)_{2-6}-$; $-(CH_2)_2O(CH_2)_2-$; $-(CH_2)_2S(CH_2)_2-$; or $-(CH_2)_2NR^{57}(CH_2)_2-$ (where $R^{57}$: H; or lower alkyl);

$-(CH_2)_oN(R^{20})COR^{64}$ (where $R^{20}$: H; or lower alkyl; $R^{64}$: lower alkyl; or lower alkenyl);

$-(CH_2)_oCOOR^{57}$ (where $R^{57}$: lower alkyl; or lower alkenyl);

$-(CH_2)_oCONR^{58}R^{59}$ (where $R^{58}$: lower alkyl, or lower alkenyl; and $R^{59}$: H; or lower alkyl; or $R^{58}$ and $R^{59}$ taken together form: $-(CH_2)_{2-6}-$: $-(CH_2)_2O(CH_2)_2-$;

$-(CH_2)_2S(CH_2)_2-$; or $-(CH_2)_2NR^{57}(CH_2)_2-$ (where $R^{57}$: H; or lower alkyl);

$-(CH_2)_oPO(OR^{60})_2$ (where $R^{60}$: lower alkyl; or lower alkenyl);

$-(CH_2)_oSO_2R^{62}$ (where $R^{62}$: lower alkyl; or lower alkenyl); or $-(CH_2)_qC_6H_4R^8$ (where $R^8$: H; F; Cl; $CF_3$; lower alkyl; lower alkenyl; or lower alkoxy).

$R^{29}$ is lower alkyl; lower alkenyl;

$-(CH_2)_oOR^{55}$ (where $R^{55}$: lower alkyl; or lower alkenyl); $-(CH_2)_oSR^{56}$ (where $R^{56}$: lower alkyl; or lower alkenyl); $-(CH_2)_oNR^{33}R^{34}$ (where $R^{33}$: lower alkyl; or lower alkenyl; $R^{34}$: H; or lower alkyl; or $R^{33}$ and $R^{34}$ taken together form: $-(CH_2)_{2-6}-$; $-(CH_2)_2O(CH_2)_2-$; $-(CH_2)_2S(CH_2)_2-$; or $-(CH_2)_2NR^{57}(CH_2)_2-$ (where $R^{57}$: H; or lower alkyl);

$-(CH_2)_oOCONR^{33}R^{75}$ (where $R^{33}$: H; lower alkyl; or lower alkenyl; $R^{75}$: lower alkyl; or $R^{33}$ and $R^{75}$ taken together form: $-(CH_2)_{2-6}-$; $-(CH_2)_2O(CH_2)_2-$; $-(CH_2)_2S(CH_2)_2-$; or $-(CH_2)_2NR^{57}(CH_2)_2-$ (where $R^{57}$: H; or lower alkyl);

$-(CH_2)_oNR^{20}CONR^{33}R^{81}$ (where $R^{20}$: H; or lower alkyl; $R^{33}$: H; lower alkyl; or lower alkenyl; $R^{81}$: H; or lower alkyl; or $R^{33}$ and $R^{81}$ taken together form: $-(CH_2)_{2-6}-$; $-(CH_2)^2O(CH_2)_2-$; $-(CH_2)_2S(CH_2)_2-$; or $-(CH_2)_2NR^{57}(CH_2)_2-$ (where $R^{57}$: H; or lower alkyl);

$-(CH_2)_oN(R^{20})COR^{64}$ (where $R^{20}$: H; or lower alkyl; $R^{64}$: lower alkyl; or lower alkenyl); particularly favored are $NR^{20}CO$-lower-alkyl (where $R^{20}$: H; or lower alkyl); $-(CH_2)_oCOOR^{57}$ (where $R^{57}$: lower alkyl; or lower alkenyl);

$-(CH_2)_oCONR^{58}R^{58}$ (where $R^{58}$: lower alkyl, or lower alkenyl; and $R^{59}$: H; or lower alkyl; or $R^{58}$ and $R^{59}$ taken together form: $-(CH_2)_{2-6}-$; $-(CH_2)_2O(CH_2)_2-$;

—(CH$_2$)$_2$S(CH$_2$)$_2$—; or —(CH$_2$)$_2$NR$^{57}$(CH$_2$)$_2$— (where R$^{57}$: H; or lower alkyl);
—(CH$_2$)$_o$PO(OR$^{60}$)$_2$ (where R$^{60}$: lower alkyl; or lower alkenyl);
—(CH$_2$)$_o$SO$_2$R$^{62}$ (where R$^{62}$: lower alkyl; or lower alkenyl); or
—(CH$_2$)$_q$C$_6$H$_4$R$^8$ (where R$^8$: H; F; Cl; CF$_3$; lower alkyl; lower alkenyl; or lower alkoxy).

Among the building blocks A70 to A104 the following are preferred: A74 with R$^{22}$ being H, A75, A76, A77 with R$^{22}$ being H, A78 and A79.

The building block —B—CO— designates an L-amino acid residue. Preferred values for B are: —NR$^{20}$CH(R$^{71}$)—, or —NR$^{20}$CH(R$^{72}$)— or, —NR$^{20}$CH(R$^{73}$)—, or —NR$^{20}$CH(R$^{74}$)—, or —NR$^{20}$CH(R$^{84}$)—, or enantiomers of groups A5 with R$^2$ being H, A8, A22, A25, A38 with R$^2$ being H, A42, A47, and A50. Most preferred building blocks —B—CO— are Ala L-Alanine
Arg L-Arginine
Asn L-Asparagine
Asp L-Aspartic acid
Cys L-Cysteine
Gln L-Glutamine
Glu L-Glutamic acid
Gly Glycine
His L-Histidine
Ile L-Isoleucine
Leu L-Leucine
Lys L-Lysine
Met L-Methionine
Phe L-Phenylalanine
Pro L-Proline
Ser L-Serine
Thr L-Threonine
Trp L-Tryptophan
Tyr L-Tyrosine
Val L-Valine
Cit L-Citrulline
Orn L-Ornithine
tBuA L-t-Butylalanine
Sar Sarcosine
t-BuG L-tert.-Butylglycine
4AmPhe L-para-Aminophenylalanine
3AmPhe L-meta-Aminophenylalanine
2AmPhe L-ortho-Aminophenylalanine
Phe (mC(NH$_2$)=NH) L-meta-Amidinophenylalanine
Phe(pC(NH$_2$)=NH) L-para-Amidinophenylalanine
Phe(mNHC(NH$_2$)=NH) L-meta-Guanidinophenylalanine
Phe(pNHC(NH$_2$)=NH) L-para-Guanidinophenylalanine
Phg L-Phenylglycine
Cha L-Cyclohexylalanine
C$_4$al L-3-Cyclobutylalanine
C$_5$al L-3-Cyclopentylalanine
Nle L-Norleucine
2-Nal L-2-Naphthylalanine
1-Nal L-1-Naphthylalanine
4Cl-Phe L-4-Chlorophenylalanine
3Cl-Phe L-3-Chlorophenylalanine
2Cl-Phe L-2-Chlorophenylalanine
3,4Cl$_2$-Phe L-3,4-Dichlorophenylalanine
4F-Phe L-4-Fluorophenylalanine
3F-Phe L-3-Fluorophenylalanine
2F-Phe L-2-Fluorophenylalanine
Tic L-1,2,3,4-Tetrahydroisoquinoline-3-carboxylic acid
Thi L-β-2-Thienylalanine
Tza L-2-Thiazolylalanine
Mso L-Methionine sulfoxide
AcLys L-N-Acetyllysine
Dpr L-2,3-Diaminopropionic acid
Dab L-2,4-Diaminobutyric acid
Dbu (2S,3S)-2,3-Diaminobutyric acid
Abu γ-Aminobutyric acid (GABA)
Aha ε-Aminohexanoic acid
Aib α-Aminoisobutyric acid
Y(Bzl) L-O-Benzyltyrosine
Bip L-Biphenylalanine
S(Bzl) L-O-Benzylserine
T(Bzl) L-O-Benzylthreonine
hCha L-Homo-cyclohexylalanine
hCys L-Homo-cysteine
hSer L-Homo-serine
hArg L-Homo-arginine
hPhe L-Homo-phenylalanine
Bpa L-4-Benzoylphenylalanine
Pip L-Pipecolic acid
MePhe L-N-Methylphenylalanine
MeNle L-N-Methylnorleucine
MeAla L-N-Methylalanine
MeIle L-N-Methylisoleucine
MeVal L-N-Methyaline
MeLeu L-N-Methylleucine
4Hyp1(4S)-L-Hydroxyproline
4Hyp2 (4R)-L-Hydroxyproline
4Mp1 (4S)-L-Mercaptoproline
4Mp2 (4R)-L-Mercaptoproline In addition, the most preferred values for B also include groups of type A8" of (L)-configuration:

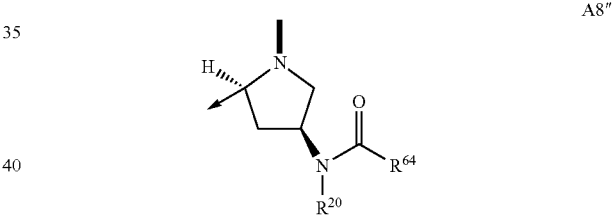

A8"

wherein R$^{20}$ is H or lower alkyl and R$^{64}$ is alkyl; alkenyl; —[(CH$_2$)$_u$—X]$_t$—CH$_3$ (where X is —O—; —NR$^{20}$—, or —S—; u=1-3, and t=1-6), aryl; aryl-lower alkyl; or heteroaryl-lower alkyl; especially those wherein R$^{64}$ is n-hexyl (A8"-21); n-heptyl (A8"-22); 4-(phenyl)benzyl (A8"-23); diphenylmethyl (A8"-24); 3-amino-propyl (A8"-25); 5-amino-pentyl (A8"-26); methyl (A8"-27); ethyl (A8"-28); isopropyl (A8"-29); isobutyl (A8"-30); n-propyl (A8"-31); cyclohexyl (A8"-32); cyclohexyl-methyl (A8"-33); n-butyl (A8"-34); phenyl (A8"-35); benzyl (A8"-36); (3-indolyl)methyl (A8"-37); 2-(3-indolyl)ethyl (A8"-38); (4-phenyl)-phenyl (A8"-39); n-nonyl (A8"-40); CH$_3$—OCH$_2$CH$_2$—OCH$_2$— (A8"-41) and CH$_3$—(OCH$_2$CH$_2$)$_2$—OCH$_2$— (A8"-42).

Besides the structural element —B—CO— the β-hairpin peptidomimetics of the present invention can comprise the structural element -A-CO— and amino acid residues belonging to one of the following groups:

Group C —NR$^{20}$CH(R$^{72}$)CO—; "hydrophobic: small to medium-sized"
Group D —NR$^{20}$CH(R$^{73}$)CO—; "hydrophobic: large aromatic or heteroaromatic"
Group E —NR$^{20}$CH(R$^{74}$)CO—; "polar-cationic" and "urea-derived"

Group F —NR$^{20}$CH(R$^{84}$)CO—; "polar-non-charged or anionic"

Group H —NR$^{20}$—CH(CO—)-alkylene-CH(CO—)—NR$^{20}$—;

—NR$^{20}$—CH(CO—)-alkenylene-CH(CO—)—NR$^{20}$—;

—NR$^{20}$—CH(CO—)-alkynylene-CH(CO—)—NR$^{20}$—;

—NR$^{20}$—CH(CO—)—(CH$_2$)$_p$SS(CH$_2$)$_p$—CH(CO—)—NR$^{20}$—;

—NR$^{20}$—CH(CO—)—(CH$_2$)$_p$NR$^{20}$CO(CH$_2$)$_p$—CH(CO—)—NR$^{20}$—;

—NR$^{20}$—CH(CO—)—(CH$_2$)$_p$NR$^{20}$CONR$^{20}$(CH$_2$)$_p$—CH(CO—)—NR$^{20}$—; "interstrand linkage"

Group C comprises amino acid residues with small to medium-sized hydrophobic side chain groups according to the general definition for substituent R$^{72}$. A hydrophobic residue refers to an amino acid side chain that is uncharged at physiological pH and that is repelled by aqueous solution. Furthermore these side chains generally do not contain hydrogen bond donor groups, such as (but not limited to) primary and secondary amides, primary and secondary amines and the corresponding protonated salts thereof, thiols, alcohols, phosphonates, phosphates, ureas or thioureas. However, they may contain hydrogen bond acceptor groups such as ethers, thioethers, esters, tertiary amides, alkyl- or aryl phosphonates and phosphates or tertiary amines. Genetically encoded small-to-medium-sized hydrophobic amino acids include alanine, isoleucine, leucine, methionine and valine.

Group D comprises amino acid residues with aromatic and heteroaromatic side chain groups according to the general definition for substituent R$^{73}$. An aromatic amino acid residue refers to a hydrophobic amino acid having a side chain containing at least one ring having a conjugated π-electron system (aromatic group). In addition they may contain hydrogen bond donor groups such as (but not limited to) primary and secondary amides, primary and secondary amines and the corresponding protonated salts thereof, thiols, alcohols, phosphonates, phosphates, ureas or thioureas, and hydrogen bond acceptor groups such as (but not limited to) ethers, thioethers, esters, tetriary amides, alkyl- or aryl phosphonates- and phosphates or tertiary amines. Genetically encoded aromatic amino acids include phenylalanine and tyrosine.

A heteroaromatic amino acid residue refers to a hydrophobic amino acid having a side chain containing at least one ring having a conjugated π-system incorporating at least one heteroatom such as (but not limited to) O, S and N according to the general definition for substituent R$^{77}$. In addition such residues may contain hydrogen bond donor groups such as (but not limited to) primary and secondary amides, primary and secondary amines and the corresponding protonated salts thereof, thiols, alcohols, phosphonates, phosphates, ureas or thioureas, and hydrogen bond acceptor groups such as (but not limited to) ethers, thioethers, esters, tetriary amides, alkyl- or aryl phosphonates- and phosphates or tertiary amines. Genetically encoded heteroaromatic amino acids include tryptophan and histidine.

Group E comprises amino acids containing side chains with polar-cationic, acylamino- and urea-derived residues according to the general definition for substituent R$^{74}$. Polar-cationic refers to a basic side chain which is protonated at physiological pH. Genetically encoded polar-cationic amino acids include arginine, lysine and histidine. Citrulline is an example for an urea derived amino acid residue.

Group F comprises amino acids containing side chains with polar-non-charged or anionic residues according to the general definition for substituent R$^{84}$. A polar-non-charged or anionic residue refers to a hydrophilic side chain that is uncharged and, respectively anionic at physiological pH (carboxylic acids being included), but that is not repelled by aqueous solutions. Such side chains typically contain hydrogen bond donor groups such as (but not limited to) primary and secondary amides, carboxyclic acids and esters, primary and secondary amines, thiols, alcohols, phosphonates, phosphates, ureas or thioureas. These groups can form hydrogen bond networks with water molecules. In addition they may also contain hydrogen bond acceptor groups such as (but not limited to) ethers, thioethers, esters, tetriary amides, carboxylic acids and carboxylates, alkyl- or aryl phosphonates- and phosphates or tertiary amines. Genetically encoded polar-non-charged amino acids include asparagine, cysteine, glutamine, serine and threonine, but also aspartic acid and glutamic acid.

Group H comprises side chains of preferably (L)-amino acids at opposite positions of the β-strand region that can form an interstrand linkage. Various methods are known to form interstrand linkages including those described by: J. P. Tam et al., *Synthesis* 1979, 955-957; Stewart et al., *Solid Phase Peptide Synthesis,* 2d Ed., Pierce Chemical Company, Rockford, Ill, 1984; Ahmed et al. *J. Biol. Chem.* 1975, 250, 8477-8482; and Pennington et al., *Peptides*, pages 164-166, Giralt and Andreu, Eds., ESCOM Leiden, The Netherlands, 1990; C. E. Schafineister et al., *J. Am. Chem. Soc.* 2000, 122, 5891. The most widely known linkage is the disulfide bridge formed by cysteines and homo-cysteines positioned at opposite positions of the β-strand. Preferably, for the scope of the present invention, disulfide linkages can be prepared using acetamidomethyl (Acm)- or trityl (Trt)-protective groups for cysteine. Another well established interstrand linkage consists in linking ornithines and lysines, respectively, with glutamic and aspartic acid residues located at opposite β-strand positions by means of an amide bond formation. Preferred protective groups for the side chain amino-groups of ornithine and lysine are allyloxycarbonyl (Alloc) and ally-lesters for aspartic and glutamic acid. Finally, interstrand linkages can also be established by linking the amino groups of lysine and ornithine located at opposite β-strand positions with reagents such as N,N-carbonylimidazole to form cyclic ureas.

As mentioned earlier, Xaa$^2$ and Xaa$^{11}$ of Cyclo(-Xaa$^1$-Xaa$^2$-Xaa$^3$-Xaa$^4$-Xaa$^5$-Xaa$^6$-Xaa$^7$-Xaa$^8$-Xaa$^9$-Xaa$^{10}$-Xaa$^{11}$-Xaa$^{12}$-Xaa$^{13}$-Xaa$^{14}$-) are amino acid residues which, taken together, can form an interstrand linkage. Such an interstrand linkage is known to stabilize the β-hairpin conformations and thus constitute an important structural element for the design of β-hairpin mimetics.

Most preferred amino acid residues in Cyclo(-Xaa$^1$-Xaa$^2$-Xaa$^3$-Xaa$^4$-Xaa$^5$-Xaa$^6$-Xaa$^7$-Xaa$^8$-Xaa$^9$-Xaa$^{10}$-Xaa$^{11}$-Xaa$^{12}$-Xaa$^{13}$-Xaa$^{14}$-), are those derived from natural α-amino acids. Hereinafter follows a list of amino acids which, or the residues of which, are suitable for the purposes of the present invention, the abbreviations corresponding to generally adopted usual practice:

| three letter code | | one letter code |
|---|---|---|
| Ala | L-Alanine | A |
| Arg | L-Arginine | R |
| $^D$Arg | D-Arginine | $^D$R |
| Asn | L-Asparagine | N |

-continued

| three letter code | | one letter code |
|---|---|---|
| Asp | L-Aspartic acid | D |
| Cys | L-Cysteine | C |
| Glu | L-Glutamic acid | E |
| Gln | L-Glutamine | Q |
| Gly | Glycine | G |
| His | L-Histidine | H |
| Ile | L-Isoleucine | I |
| Leu | L-Leucine | L |
| Lys | L-Lysine | K |
| $^D$Lys | D-Lysine | $^D$K |
| Met | L-Methionine | M |
| Phe | L-Phenylalanine | F |
| Pro | L-Proline | P |
| $^D$Pro | D-Proline | $^D$P |
| Ser | L-Serine | S |
| Thr | L-Threonine | T |
| Trp | L-Tryptophan | W |
| Tyr | L-Tyrosine | Y |
| Val | L-Valine | V |

Other α-amino acids which, or the residues of which, are suitable for the purposes of the present invention include:
Cit L-Citrulline
$^D$Cit D-Citrulline
Orn L-Ornithine
$^D$Orn D-Ornithine
tBuA L-t-Butylalanine
Pen L-Penicillamine
tBuG L-tert.-Butylglycine
$^D$tBuG D-tert.-Butylglycine
4AmPhe L-para-Aminophenylalanine
$^D$4AmPhe D-para-Aminophenylalanine
3AmPhe L-meta-Aminophenylalanine
$^D$3AmPhe D-meta-Aminophenylalanine
2AmPhe L-ortho-Aminophenylalanine
$^D$2AmPhe D-ortho-Aminophenylalanine
Phe(mC(NH$_2$)=NH) L-meta-Amidinophenylalanine
$^D$Phe(mC(NH$_2$)=NH) D-meta-Amidinophenylalanine
Phe (pC(NH$_2$)=NH) L-para-Amidinophenylalanine
$^D$Phe (pC(NH$_2$)=NH) D-para-Amidinophenylalanine
Phe(mNHC(NH$_2$)=NH) L-meta-Guanidinophenylalanine
$^D$Phe(mNHC(NH$_2$)=NH) D-meta-Guanidinophenylalanine
Phe(pNHC(NH$_2$)=NH) L-para-Guanidinophenylalanine
$^D$Phe(pNHC(NH$_2$)=NH) D-para-Guanidinophenylalanine
Agp (2S)-2-Amino-3-guanidino-propionic acid
Agb (2S)-2-Amino-4-guanidino-butanoic acid
2Pal (2S)-2-Amino-3-(pyridine-2'-yl)-propionic acid
4Pal (2S)-2-Amino-3-(pyridine-4'-yl)-propionic acid
Phg L-Phenylglycine
C$_3$al L-3-Cycloproylalanine
C$_4$al L-3-Cyclobutylalanine
C$_5$al L-3-Cyclopentylalanine
Cha L-Cyclohexylalanine
C$_3$g L-Cyclopoylglycine
C$_4$g L-Cyclobutylglycine
C$_5$g L-Cyclopentylglycine
Nle L-Norleucine
2-Nal L-2-Naphthylalanine
1-Nal L-1-Naphthylalanine
4ClPhe L-4-Chlorophenylalanine
3ClPhe L-3-Chlorophenylalanine
2ClPhe L-2-Chlorophenylalanine
3,4Cl$_2$Phe L-3,4-Dichlorophenylalanine
4FPhe L-4-Fluorophenylalanine
3FPhe L-3-Fluorophenylalanine
2FPhe L-2-Fluorophenylalanine
Thi L-β-2-Thienylalanine
Tza L-2-Thiazolylalanine
Mso L-Methionine sulfoxide
AcLys N-Acetyllysine
$^D$AcLys N-Acetyl-D-lysine
Dpr 2,3-Diaminopropionic acid
$^D$Dpr D-2,3-Diaminopropionic acid
Dab 2,4-Diaminobutyric acid
$^D$Dab (2R)-2,4-Diaminobutyric acid
Dbu (2S)-2,3-Diamino-butyric acid
$^D$Dbu (2R)-2,3-Diamino-butyric acid
Abu γ-Aminobutyric acid (GABA)
Aha ε-Aminohexanoic acid
Aib α-Aminoisobutyric acid
Cyp 1-Aminocyclopentane carboxylic acid
Y(Bzl) L-O-Benzyltyrosine
H(Bzl) (3S)-2-Amino-3-(1'-benzylimidazole-4'-yl)-propionic acid
Bip L-(4-phenyl)phenylalanine
S(Bzl) L-O-Benzylserine
T(Bzl) L-O-Benzylthreonine
alloT (2S,3S)-2-Amino-3-hydroxy-butyric acid
Leu3OH (2S,3R)-2-Amino-3-hydroxy-4-methyl-pentanoic acid
hAla L-Homo-alanine
hArg L-Homo-arginine
$^D$hArg D-Homo-arginine
hCys L-Homo-cysteine
hGlu L-Homo-glutamic acid
hGln L-Homo-glutamine
hHis L-Homo-histidine
hIle L-Homo-isoleucine
hLeu L-Homo-leucine
hNle L-Homo-norleucine
hLys L-Homo-lysine
$^D$hLys D-Homo-lysine
hMet L-Homo-methionine
hPhe L-Homo-phenylalanine
hSer L-Homo-serine
hThr L-Homo-threonine
hTrp L-Homo-tryptophan
hTyr L-Homo-tyrosine
hVal L-Homo-valine
hCha L-Homo-cyclohexylalanine
Bpa L-4-Benzoylphenylalanine
Tic (3S)-1,2,3,4-Tetrahydroisoquinoline-3-carboxylic acid
$^D$Tic (3R)-1,2,3,4-Tetrahydroisoquinoline-3-carboxylic acid
Tiq (1S)-1,2,3,4-Tetrahydroisoquinoline-1-carboxylic acid
$^D$Tiq (1R)-1,2,3,4-Tetrahydroisoquinoline-1-carboxylic acid
4AmPyrr1 (2S,4S)-4-Amino-pyrrolidine-2-carboxylic acid
$^D$4AmPyrr1 (2R,4S)-4-Amino-pyrrolidine-2-carboxylic acid
4AmPyrr2 (2S,4R)-4-Amino-pyrrolidine-2-carboxylic acid
$^D$4AmPyrr2 (2R,4R)-4-Amino-pyrrolidine-2-carboxylic acid
4PhePyrr1 (2S,4R)-4-Phenyl-pyrrolidine-2-carboxylic acid
$^D$4PhePyrr1 (2R,4R)-4-Phenyl-pyrrolidine-2-carboxylic acid
4PhePyrr2 (2S,4S)-4-Phenyl-pyrrolidine-2-carboxylic acid
$^D$4PhePyrr2 (2R,4S)-4-Phenyl-pyrrolidine-2-carboxylic acid
5PhePyrr1 (2S,5R)-5-Phenyl-pyrrolidine-2-carboxylic acid
$^D$5PhePyrr1 (2R,5R)-5-Phenyl-pyrrolidine-2-carboxylic acid
5PhePyrr2 (2S,5S)-5-Phenyl-pyrrolidine-2-carboxylic acid
$^D$5PhePyrr2 (2R,5S)-5-Phenyl-pyrrolidine-2-carboxylic acid
4Hyp1 (4S)-L-Hydroxyproline
$^D$4Hyp1 (4S)-D-Hydroxyproline
4Hyp2 (4R)-L-Hydroxyproline ᴰ4Hyp2 (4R)-D-Hydroxyproline
4Mp1 (4S)-L-Mercaptoproline
ᴰ4Mp1 (4S)-D-Mercaptoproline
4Mp2 (4R)-L-Mercaptoproline
ᴰ4Mp2 (4R)-D-Mercaptoproline
Pip L-Pipecolic acid
ᴰPip D-Pipecolic acid
NMeAla L-N-Methylalanine
NMeVal L-N-Methylvaline
NMeIle L-N-Methylisoleucine
NMeLeu L-N-Methylleucine
NMeNle L-N-Methylnorleucine
NMeMet L-N-Methylmethionine
NMeTyr L-N-Methyltyrosine
NMeHis L-N-Methylhistidine
NMePhe L-N-Methylphenylalanine
NMeTrp L-N-Methyltryptophane
NMeSer L-N-Methylserine
NMeAsp L-N-Methylaspartic acid
NMeGlu L-N-Methylglutamic acid
NMeLys L-N-Methyllysine
NMeᴰLys D-N-Methyllysine
NMeArg L-N-Methylarginine
NMeᴰArg D-N-Methylarginine
NMeDab L-N-Methyl-2,4-diamino butyric acid
NMeᴰDab D-N-Methyl-2,4-diamino butyric acid
NMeCys L-N-Methylcysteine
NMeAsn L-N-Methylasparagine
NMeGln L-N-Methylglutamine
NMeThr L-N-Methylthreonine In a preferred embodiment of the present invention, $Xaa^{13}$ is ᴰPro, ᴰCha, NMeᴰIle, ᴰTyr, ᴰHis, ᴰHis(Bzl), ᴰ4Pal, NMeᴰTyr, NMeᴰLys, (ABu)G, ᴰIle, NMeᴰAla, ᴰLys, or ᴰDab; $Xaa^{14}$ is ᴸPro; the aforesaid Pro moiety and/or the aforesaid ᴸPro moiety being optionally substituted as shown in formulae A8' and, respectively, A8", as defined above.

Particularly preferred residues for group C are:
Ala L-Alanine
Ile L-Isoleucine
Leu L-Leucine
Met L-Methionine
Val L-Valine
tBuA L-t-Butylalanine
tBuG L-tert.-Butylglycine
$C_3$al L-3-Cycloproylalanine
$C_4$al L-3-Cyclobutylalanine
$C_5$al L-3-Cyclopentylalanine
Cha L-Cyclohexylalanine
$C_3$g L-Cycloproylglycine
$C_4$g L-Cyclobutylglycine
$C_5$g L-Cyclopentylglycine
Nle L-Norleucine
hAla L-Homo-alanine
hIle L-Homo-isoleucine
hLeu L-Homo-leucine
hMet L-Homo-methionine
hVal L-Homo-valine
hCha L-Homo-cyclohexylalanine
NMeAla L-N-Methylalanine
NMeVal L-N-Methylvaline
NMeIle L-N-Methylisoleucine
NMeLeu L-N-Methylleucine
NMeNle L-N-Methylnorleucine
NMeNle L-N-Methylnorleucine
NMeMet L-N-Methylmethionine Particularly preferred residues for group D are:
His L-Histidine
Phe L-Phenylalanine
Trp L-Tryptophan
Tyr L-Tyrosine
2Pal (2S)-2-Amino-3-(pyridine-2'-yl)-propionic acid
4Pal (2S)-2-Amino-3-(pyridine-4'-yl)-propionic acid
Phg L-Phenylglycine
2Nal L-2-Naphthylalanine
1-Nal L-1-Naphthylalanine
4ClPhe L-4-Chlorophenylalanine
3ClPhe L-3-Chlorophenylalanine
2ClPhe L-2-Chlorophenylalanine
3,4Cl$_2$Phe L-3,4-Dichlorophenylalanine
4FPhe L-4-Fluorophenylalanine
3FPhe L-3-Fluorophenylalanine
2FPhe L-2-Fluorophenylalanine
Thi L-β-2-Thienylalanine
Tza L-2-Thiazolylalanine
Y(Bzl) L-O-Benzyltyrosine
H(Bzl) (3S)-2-Amino-3-(1'-benzylimidazole-4'-yl)-propionic acid
Bip L-(4-phenyl)phenylalanine
S(Bzl) L-O-Benzylserine
T(Bzl) L-O-Benzylthreonine
hPhe L-Homo-phenylalanine
hTrp L-Homo-tryptophan
hTyr L-Homo-tyrosine
hHis L-Homo-histidine
Bpa L-4-Benzoylphenylalanine
NMePhe L-N-Methylphenylalanine
NMeTyr L-N-Methyltyrosine
NMeHis L-N-Methylhistidine
NMeTrp L-N-Methyltryptophane Particularly preferred residues for group E are
Arg L-Arginine
ᴰArg D-Arginine
Lys L-Lysine
ᴰLys D-Lysine
Orn L-Ornithine
ᴰOrn D-Ornithine
Dpr L-2,3-Diaminopropionic acid
ᴰDpr D-2,3-Diaminopropionic acid
Dab L-2,4-Diaminobutyric acid
ᴰDab (2R)-2,4-Diaminobutyric acid
Dbu (2S,3S)-2,3-Diaminobutyric acid
ᴰDbu (2R)-2,3-Diamino-butyric acid
Cit L-Citrulline
ᴰCit D-Citrulline
4AmPhe L-para-Aminophenylalanine
ᴰ4AmPhe D-para-Aminophenylalanine
3AmPhe L-meta-Aminophenylalanine
ᴰ3AmPne D-meta-Aminophenylalanine
2AmPhe L-ortho-Aminophenylalanine
ᴰ2AmPhe D-ortho-Aminophenylalanine
Phe(mC(NH$_2$)=NH) L-meta-Amidinophenylalanine
ᴰPhe(mC(NH$_2$)=NH) D-meta-Amidinophenylalanine
Phe(pC(NH$_2$)=NH) L-para-Amidinophenylalanine
ᴰPhe(pC(NH$_2$)=NH) D-para-Amidinophenylalanine
Phe(mNHC(NH$_2$)=NH) L-meta-Guanidinophenylalanine
ᴰPhe(mNHC(NH$_2$)=NH) D-meta-Guanidinophenylalanine
Phe(pNHC(NH$_2$)=NH) L-para-Guanidinophenylalanine
ᴰPhe(pNHC(NH$_2$)=NH) D-para-Guanidinophenylalanine
Agp (2S)-2-Amino-3-guanidino-propionic acid
Agb (2S)-2-Amino-4-guanidino-butanoic acid
hArg L-Homo-arginine
ᴰhArg D-Homo-arginine
hLys L-Homo-lysine
ᴰhLys D-Homo-lysine NMeLys L-N-Methyllysine
NMe$^D$Lys D-N-Methyllysine
NMeArg L-N-Methylarginine
NMe$^D$Arg D-N-Methylarginine
NMeDab L-N-Methyl-2,4-diamino butyric acid
NMe$^D$Dab D-N-Methyl-2,4-diamino butyric acid
  Particularly preferred residues for group F are
Asn L-Asparagine
Asp L-Aspartic acid
Cys L-Cysteine
Gln L-Glutamine
Glu L-Glutamic acid
Ser L-Serine
Thr L-Threonine
Pen L-Penicillamine
AcLys L-N'-Acetyllysine
alloT (2S,3S)-2-Amino-3-hydroxy-butyric acid
Leu3OH (2S,3R)-2-Amino-3-hydroxy-4-methyl-pentanoic acid
hCys L-Homo-cysteine
hSer L-Homo-serine
hGlu L-Homo-glutamic acid
hGln L-Homo-glutamine
hThr L-Homo-threonine
NMeSer L-N-Methylserine
NMeAsp L-N-Methylaspartic acid
NMeGlu L-N-Methylglutamic acid
NMeCys L-N-Methylcysteine
NMeAsn L-N-Methylasparagine
NMeGln L-N-Methylglutamine
NMeThr L-N-Methylthreonine In a preferred embodiment of the invention the amino acid residues in Cyclo(-Xaa$^1$-Xaa$^2$-Xaa$^3$-Xaa$^4$-Xaa$^5$-Xaa$^6$-Xaa$^7$-Xaa$^8$-Xaa$^9$-Xaa$^{10}$-Xaa$^{11}$-Xaa$^{12}$-Xaa$^{13}$-Xaa$^{14}$-) are:

Xaa$^1$: Trp;
Xaa$^2$: Arg, Dab or Orn;
Xaa$^3$: Ile;
Xaa$^4$: Arg, Dab or Orn;
Xaa$^5$: Ile;
Xaa$^6$: $^D$Arg, Dab, $^D$Dab, Orn;
Xaa$^7$: Asn, Gln, Thr, Leu or Tyr;
Xaa$^8$: Lys, Gln, Trp or His;
Xaa$^8$: Arg or Dab;
Xaa$^{10}$: Asn, Leu, Cha, Tyr or Trp;
Xaa$^{11}$: Arg or Gln;
Xaa$^{12}$: Arg, Dab, Ala or Gln;
Xaa$^{13}$: DPro;
Xaa$^{14}$: LPro;

Particularly preferred β-peptidomimetics of the invention include those described in Examples 2, 5, 16, and 17.

The process of the invention can advantageously be carried out as parallel array synthesis to yield libraries of β-hairpin peptidomimetics of the invention. Such parallel syntheses allow one to obtain arrays of numerous (normally 12 to 192, typically 96) compounds as described above in moderate to high yields and defined purities, minimizing the formation of dimeric and polymeric by-products. The proper choice of the functionalized solid-support (i.e. solid support plus linker molecule) and site of cyclization play thereby key roles.

The functionalized solid support is conveniently derived from polystyrene crosslinked with, preferably 1-5%, divinylbenzene; polystyrene coated with polyethyleneglycol spacers (Tentagel™); and polyacrylamide resins (see also D. Obrecht, J.-M. Villalgordo, "Solid-Supported Combinatorial and Parallel Synthesis of Small-Molecular-Weight Compound Libraries", Tetrahedron Organic Chemistry Series, Vol. 17, Pergamon, Elsevier Science, 1998).

The solid support is functionalized by means of a linker, i.e. a bifunctional spacer molecule which contains on one end an anchoring group for attachment to the solid support and on the other end a selectively cleavable functional group used for the subsequent chemical transformations and cleavage procedures. For the purposes of the present invention two types of linkers are used:

Type 1 linkers are designed to release the amide group under acid conditions (H. Rink, Tetrahedron Lett. 1987, 28, 3783-3790). Linkers of this kind form amides of the carboxyl group of the amino acids; examples of resins functionalized by such linker structures include 4-[(((2,4-dimethoxy-phenyl)Fmoc-aminomethyl)phenoxyacetamido)aminomethyl] PS resin, 4-[(((2,4-dimethoxyphenyl)Fmoc-aminomethyl) phenoxy-acetamido)aminomethyl]-4-methyl-benzydrylamine PS resin (Rink amide MBHA PS Resin), and 4-[(((2, 4-dimethoxy-phenyl)Fmoc-aminomethyl) phenoxyacetamido)aminomethyl]benzhydrylamine PS-resin (Rink amide BHA PS resin). Preferably, the support is derived from polystyrene crosslinked with, most preferably 1-5%, divinylbenzene and functionalized by means of the 4-(((2,4-dimethoxy-phenyl)Fmoc-aminomethyl)phenoxyacetamido) linker.

Type 2 linkers are designed to eventually release the carboxyl group under acidic conditions. Linkers of this kind form acid-labile esters with the carboxyl group of the amino acids, usually acid-labile benzyl, benzhydryl and trityl esters; examples of such linker structures include 2-methoxy-4-hydroxymethylphenoxy (Sasrin™ linker), 4-(2,4-dimethoxyphenyl-hydroxymethyl)-phenoxy (Rink linker), 4-(4-hydroxymethyl-3-methoxyphenoxy)butyric acid (HMPB linker), trityl and 2-chlorotrityl. Preferably, the support is derived from polystyrene crosslinked with, most preferably 1-5%, divinylbenzene and functionalized by means of the 2-chlorotrityl linker.

When carried out as parallel array synthesis the process of the invention can be advantageously carried out as described herein below but it will be immediately apparent to those skilled in the art how these procedures will have to be modified in case it is desired to synthesize one single compound of the invention.

A number of reaction vessels (normally 12 to 192, typically 96) equal to the total number of compounds to be synthesized by the parallel method are loaded with 25 to 1000 mg, preferably 60 mg, of the appropriate functionalized solid support, preferably 1 to 3% cross-linked polystyrene or Tentagel resin.

The solvent to be used must be capable of swelling the resin and includes, but is not limited to, dichloromethane (DCM), dimethylformamide (DMF), N-methylpyrrolidone (NMP), dioxane, toluene, tetrahydrofuran (THF), ethanol (EtOH), trifluoroethanol (TFE), isopropylalcohol and the like. Solvent mixtures containing as at least one component a polar solvent (e.g. 20% TFE/DCM, 35% THF/NMP) are beneficial for ensuring high reactivity and solvation of the resin-bound peptide chains (G. B. Fields, C. G. Fields, J. Am. Chem. Soc. 1991, 113, 4202-4207).

With the development of various linkers that release the C-terminal carboxylic acid group under mild acidic conditions, not affecting acid-labile groups protecting functional groups in the side chain(s), considerable progresses have been made in the synthesis of protected peptide fragments. The 2-methoxy-4-hydroxybenzylalcohol-derived linker (Sasrin™ linker, Mergler et al., Tetrahedron Lett. 1988, 29 4005-4008) is cleavable with diluted trifluoroacetic acid (0.5-1% TFA in DCM) and is stable to Fmoc deprotection conditions during the peptide synthesis, Boc/tBu-based additional protecting groups being compatible with this protection scheme. Other linkers which are suitable for the process of the invention include the super acid labile 4-(2,4-dimethoxyphenyl-hydroxymethyl)-phenoxy linker (Rink linker, H. Rink, *Tetrahedron Lett.* 1987, 28, 3787-3790), where the removal of the peptide requires 10% acetic acid in DCM or 0.2% trifluoroacetic acid in DCM; the 4-(4-hydroxymethyl-3-methoxyphenoxy)butyric acid-derived linker (HMPB-linker, Flörsheimer & Riniker, 1991, Peptides 1990: Proceedings of the Twenty-First European Peptide Symposium, 131) which is also cleaved with 1% TFA/DCM in order to yield a peptide fragment containing all acid labile side-chain protective groups; and, in addition, the 2-chlorotritylchloride linker (Barlos et al., *Tetrahedron Lett.* 1989, 30, 3943-3946), which allows the peptide detachment using a mixture of glacial acetic acid/trifluoroethanol/DCM (1:2:7) for 30 min.

Suitable protecting groups for amino acids and, respectively, for their residues are, for example, for the amino group (as is present e.g. also in the side-chain of lysine)
Cbz benzyloxycarbonyl
Boc tert.-butyloxycarbonyl
Fmoc 9-fluorenylmethoxycarbonyl
Alloc allyloxycarbonyl
Teoc trimethylsilylethoxycarbonyl
Tcc trichloroethoxycarbonyl
Nps o-nitrophenylsulfonyl;
Trt triphenymethyl or trityl
for the carboxyl group (as is present e.g. also in the side-chain of aspartic and glutamic acid) by conversion into esters with the alcohol components
tBu tert.-butyl
Bn benzyl
Me methyl
Ph phenyl
Pac phenacyl
allyl
Tse trimethylsilylethyl
Tce trichloroethyl;
for the guanidino group (as is present e.g. in the side-chain of arginine)
Pmc 2,2,5,7,8-pentamethylchroman-6-sulfonyl
Ts tosyl (i.e. p-toluenesulfonyl)
Cbz benzyloxycarbonyl
Pbf pentamethyldihydrobenzofuran-5-sulfonyl
for the hydroxy group (as is present e.g. in the side-chain of threonine and serine)
tBu tert.-butyl
Bn benzyl
Trt trityl
Alloc allyloxycarbonyl
and for the mercapto group (as is present e.g. in the side-chain of cysteine)
Acm acetamidomethyl
tBu tert.-butyl
Bn benzyl
Trt trityl
Mtr 4-methoxytrityl.

The 9-fluorenylmethoxycarbonyl-(Fmoc)-protected amino acid derivatives are preferably used as the building blocks for the construction of the β-hairpin loop mimetics of the invention. For the deprotection, i.e. cleaving off of the Fmoc group, 20% piperidine in DMF or 2% DBU/2% piperidine in DMF can be used.

The quantity of the reactant, i.e. of the amino acid derivative, is usually 1 to 20 equivalents based on the milliequivalents per gram (meq/g) loading of the functionalized solid support (typically 0.1 to 2.85 meq/g for polystyrene resins) originally weighed into the reaction tube. Additional equivalents of reactants can be used, if required, to drive the reaction to completion in a reasonable time. The preferred workstations (without, however, being limited thereto) are Labsource's Combi-chem station, Protein Technologies' Symphony and MultiSyn Tech's-Syro synthesizer, the latter additionally equipped with a transfer unit and a reservoir box during the process of detachment of the fully protected linear peptide from the solid support. All synthesizers are able to provide a controlled environment, for example, reactions can be accomplished at temperatures different from room temperature as well as under inert gas atmosphere, if desired.

Amide bond formation requires the activation of the α-carboxyl group for the acylation step. When this activation is being carried out by means of the commonly used carbodiimides such as dicyclohexylcarbodiimide (DCC, Sheehan & Hess, *J. Am. Chem. Soc.* 1955, 77, 1067-1068) or diisopropylcarbodiimide (DIC, Sarantakis et al *Biochem. Biophys. Res. Commun.* 1976, 73, 336-342), the resulting dicyclohexylurea and, respectively, diisopropylurea is insoluble and, respectively, soluble in the solvents generally used. In a variation of the carbodiimide method 1-hydroxybenzotriazole (HOBt, König & Geiger, *Chem. Ber.* 1970, 103, 788-798) is included as an additive to the coupling mixture. HOBt prevents dehydration, suppresses racemization of the activated amino acids and acts as a catalyst to improve the sluggish coupling reactions. Certain phosphonium reagents have been used as direct coupling reagents, such as benzotriazol-1-yl-oxy-tris-(dimethyl-amino)-phosphonium hexafluorophosphate (BOP, Castro et al., *Tetrahedron Lett.* 1975, 14, 1219-1222; *Synthesis* 1976, 751-752), or benzotriazol-1-yl-oxy-tris-pyrrolidino-phosphonium hexafluorophoshate (Py-BOP, Coste et al., *Tetrahedron Lett.* 1990, 31, 205-208), or 2-(1H-benzotriazol-1-yl-)1,1,3,3-tetramethyluronium tetrafluoroborate (TBTU), or hexafluorophosphate (HBTU, Knorr et al., *Tetrahedron Lett.* 1989, 30, 1927-1930); these phosphonium reagents are also suitable for in situ formation of HOBt esters with the protected amino acid derivatives. More recently diphenoxyphosphoryl azide (DPPA) or O-(7-aza-benzotriazol-1-yl)-N,N,N',N'-tetramethyluronium tetrafluoroborate (TATU) or O-(7-aza-benzotriazol-1-yl)-N,N,N',N'-tetramethyluronium hexafluorophosphate (HATU)/7-aza-1-hydroxy benzotriazole (HOAt, Carpino et al., *Tetrahedron Lett.* 1994, 35, 2279-2281) or -(6-Chloro-1H-benzotriazol-1-yl-)-N,N,N',N'-1,1,3,3-tetramethyluronium tetrafluoroborate (TCTU), or hexafluorophosphate (HCTU, Marder, Shivo and Albericio: HCTU and TCTU: New Coupling Reagents: Development and Industrial Applications, Poster Presentation, Gordon Conference February 2002) have also been used as coupling reagents as well as 1,1,3,3-Bis(tetramethylene) chlorouronium hexafluoro-phosphate (PyClU) especially for coupling N-methylated amino acids (J. Coste, E. Frérot, P. Jouin, B. Castro, *Tetrahedron Lett.* 1991, 32, 1967).

Due to the fact that near-quantitative coupling reactions are essential, it is desirable to have experimental evidence for completion of the reactions. The ninhydrin test (Kaiser et al., *Anal. Biochemistry* 1970, 34, 595), where a positive colorimetric response to an aliquot of resin-bound peptide or peptide indicates qualitatively the presence of the primary amine, can easily and quickly be performed after each coupling step. Fmoc chemistry allows the spectrophotometric detection of the Fmoc chromophore when it is released with the base (Meienhofer et al., *Int. J. Peptide Protein Res.* 1979, 13, 35-42).

The resin-bound intermediate within each reaction vessel is washed free of excess of retained reagents, of solvents, and of by-products by repetitive exposure to pure solvent(s) by one of the two following methods:

1) The reaction vessels are filled with solvent (preferably 5 mL), agitated for 5 to 300 minutes, preferably 15 minutes, and drained to expel the solvent;

2) The reaction vessels are filled with solvent (preferably 5 mL) and drained into a receiving vessel such as a test tube or vial.

Both of the above washing procedures are repeated up to about 50 times (preferably about 10 times), monitoring the efficiency of reagent, solvent, and by-product removal by methods such as TLC, GC, or inspection of the washings.

The above described procedure of reacting the resin-bound compound with reagents within the reaction tubes followed by removal of excess reagents, by-products, and solvents is repeated with each successive transformation until the final resin-bound fully protected linear peptide has been obtained.

Before this fully protected linear peptide is detached from the solid support, an interstrand linkage between $Xaa^2$ and $Xaa^{11}$ of $-Xaa^1-Xaa^2-Xaa^3-Xaa^4-Xaa^5-Xaa^6-Xaa^7-Xaa^8-Xaa^9-Xaa^{10}-Xaa^{11}-Xaa^{12}-Xaa^{13}-Xaa^{14}-$ can be formed.

Interstrand linkages and their formation have been discussed above, in connection with the explanations made regarding groups of the type H which can, for example, be disulfide bridges formed by cysteine and homocysteine residues at opposite positions of the β-strand; or lactam bridges formed by glutamic and aspartic acid residues linking ornithine and, respectively, lysine residues, or by glutamic acid residues linking 2,4-diaminobutyric acid residues located at opposite β-strand positions by amide bond formation. The formation of such interstrand linkages can be effected by methods well known in the art.

For the formation of a disulfide bridge preferably a solution of 10 equivalents of iodine solution is applied in DMF or in a mixture of $CH_2Cl_2$/MeOH for 1.5 h which is repeated for another 3 h with a fresh iodine solution after filtering of the iodine solution, or in a mixture of DMSO and acetic acid solution, buffered with 5% $NaHCO_3$ to pH 5-6 for 4 h, or in water after adjusting to pH 8 with ammonium hydroxide solution by stirring for 24 h, or in a solution of NMP and tri-n-butylphosphine (preferably 50 eq.).

Alternatively, the formation of the disulfide bridge between $Xaa^2$ and $Xaa^{11}$ of $-Xaa^1-Xaa^2-Xaa^3-Xaa^4-Xaa^5-Xaa^6-Xaa^7-Xaa^8-Xaa^9-Xaa^{10}-Xaa^{11}-Xaa^{12}-Xaa^{13}-Xaa^{14}-$ can be carried out subsequent to the work-up method 2), as described herein below, by stirring the crude fully deprotected and cyclized peptide for 24 h in water containing DMSO up to 15% by volume, buffered with 5% $NaHCO_3$ to pH 5-6, or buffered with ammonium acetate to pH 7-8, or adjusted with ammonium hydroxide to pH 8. Following evaporation to dryness Cyclo(-$Xaa^1-Xaa^2-Xaa^3-Xaa^4-Xaa^5-Xaa^6-Xaa^7-Xaa^8-Xaa^9-Xaa^{10}-Xaa^{11}-Xaa^{12}-Xaa^{13}-Xaa^{14}-$), disulfide bond between $Cys^2$ and $Cys^{11}$ is obtained as end-product.

Detachment of the fully protected linear peptide from the solid support is achieved by exposing the loaded resin with a solution of the reagent used for cleavage (preferably 3 to 5 mL). Temperature control, agitation, and reaction monitoring are implemented as described above. Via a transfer-unit the reaction vessels are connected with a reservoir box containing reservoir tubes to efficiently collect the cleaved product solutions. The resins remaining in the reaction vessels are then washed 2 to 5 times as above with 3 to 5 mL of an appropriate solvent to extract (wash out) as much of the detached products as possible. The product solutions thus obtained are combined, taking care to avoid cross-mixing. The individual solutions/extracts are then manipulated as needed to isolate the final compounds. Typical manipulations include, but are not limited to, evaporation, concentration, liquid/liquid extraction, acidification, basification, neutralization or additional reactions in solution.

The solutions containing fully protected linear peptide derivatives which have been cleaved off from the solid support and neutralized with a base, are evaporated. Cyclization is then effected in solution using solvents such as DCM, DMF, dioxane, THF and the like. Various coupling reagents which were mentioned earlier can be used for the cyclization. The duration of the cyclization is about 6-48 hours, preferably about 16 hours. The progress of the reaction is followed, e.g. by RP-HPLC (Reverse Phase High Performance Liquid Chromatography). Then the solvent is removed by evaporation, the fully protected cyclic peptide derivative is dissolved in a solvent which is not miscible with water, such as DCM, and the solution is extracted with water or a mixture of water-miscible solvents, in order to remove any excess of the coupling reagent.

Finally, the fully protected peptide derivative is treated with 95% TFA, 2.5% $H_2O$, 2.5% TIS or another combination of scavengers for effecting the cleavage of protecting groups. The cleavage reaction time is commonly 30 minutes to 12 hours, preferably about 2.5 hours.

Alternatively, the detachment and complete deprotection of the fully protected peptide from the solid support can be achieved manually in glass vessels.

After full deprotection one of the following methods can be used for further work-up:

1) The volatiles are evaporated to dryness and the crude peptide is dissolved in 20% AcOH in water and extracted with isopropyl ether or other solvents which are suitable therefor. The aqueous layer is collected and evaporated to dryness, and the fully deprotected peptide, Cyclo(-$Xaa^1-Xaa^2-Xaa^3-Xaa^4-Xaa^5-Xaa^6-Xaa^7-Xaa^8-Xaa^9-Xaa^{10}-Xaa^{11}-Xaa^{12}-Xaa^{13}-Xaa^{14}-$), is obtained as final product;

2) The deprotection mixture is concentrated under vacuum. Following precipitation of the fully deprotected peptide in diethylether at preferably 0° C. the solid is washed up to about 10 times, preferably 3 times, dried, and the fully deprotected peptide, Cyclo(-$Xaa^1-Xaa^2-Xaa^3-Xaa^4-Xaa^5-Xaa^6-Xaa^7-Xaa^8-Xaa^9-Xaa^{10}-Xaa^{11}-Xaa^{12}-Xaa^{13}-Xaa^{14}-$) is obtained as final product, if a disulfide bond between $Xaa^2$ and $Xaa^{11}$ has been formed on solid support as described herein above.

As mentioned earlier, it is thereafter possible, if desired, to convert the fully deprotected product of Cyclo(-$Xaa^1-Xaa^2-Xaa^3-Xaa^4-Xaa^5-Xaa^6-Xaa^7-Xaa^s-Xaa^9-Xaa^{10}-Xaa^{11}-Xaa^{12}-Xaa^{13}-Xaa^{14}-$), thus obtained into a pharmaceutically acceptable salt or to convert a pharmaceutically acceptable, or unacceptable, salt thus obtained into the corresponding free compound of Cyclo(-$Xaa^1-Xaa^2-Xaa^3-Xaa^4-Xaa^5-Xaa^6-Xaa^7-Xaa^8-Xaa^9-Xaa^{10}-Xaa^{11}-Xaa^{12}-Xaa^{13}-Xaa^{14}-$), or into a different, pharmaceutically acceptable, salt. Any of these operations can be carried out by methods well known in the art.

The β-hairpin peptidomimetics of the invention can be used in a wide range of applications in order to inhibit the growth of or to kill microorganisms. In particular they can be used to selectively inhibit the growth of or to kill microorganisms such as *Bacillus subtilis* and/or *Shigella boydii* and/or to inhibit the development of viral pathogens as, for example, human immunodeficiency viruses (HIV).

They can be used for example as disinfectants or as preservatives for materials such as foodstuffs, cosmetics, medicaments and other nutrient-containing materials.

The β-hairpin peptidomimetics of the invention can also be used to treat or prevent diseases related to microbial infection in plants and animals.

For use as disinfectants or preservatives the β-hairpin peptidomimetics can be added to the desired material singly, as mixtures of several β-hairpin peptidomimetics or in combination with other anti-infective agents. The β-hairpin peptidomimetics may be administered per se or may be applied as an appropriate formulation together with carriers, diluents or excipients well known in the art.

When used to treat or prevent infections or diseases related to such infections, particularly infections related to respiratory diseases such as cystic fibrosis, emphysema, asthma or pneumonia; infections related to skin or soft tissue diseases such as surgical wounds, traumatic wounds, burn wounds or herpes, smallpox, rubella or measles; infections related to gastrointestinal diseases such as epidemic diarrhea, necrotizing enterocolitis, typhlitis or gastroenteritis or pancreatitis; infections related to eye diseases such as keratitis and endophthalmitis; infections related to ear diseases such as otitis; infections related to CNS diseases such as brain abscess and meningitis or encephalitis; infections related to bone diseases such as osteochondritis and osteomyelitis; infections related to cardiovascular diseases such as endocartitis and pericarditis; or infections related to gastrourinal diseases such as epididymitis, prostatitis and urethritis; infections related to liver diseases such as hepatitis; infections related to sexually transmitted diseases such as AIDS; infections related to diseases such as common cold, influenza, parotitis or gingivostomatitis; the β-hairpin peptidomimetics can be administered singly, as mixtures of several β-hairpin peptidomimetics, in combination with other antimicrobial or antibiotic agents, or anti cancer agents, or antiviral (e.g. anti-HIV) agents, or in combination with other pharmaceutically active agents. The β-hairpin peptidomimetics can be administered per se or as pharmaceutical compositions.

The β-hairpin peptidomimetics of the invention can be used in a wide range of applications in order to prevent HIV infections in healthy individuals and slow or halt viral progression in infected patients.

The β-hairpin peptidomimetics of the invention may be administered per se or may be applied as an appropriate formulation together with carriers, diluents or excipients well known in the art.

Pharmaceutical compositions comprising β-hairpin peptidomimetics of the invention may be manufactured by means of conventional mixing, dissolving, granulating, coated tablet-making, levigating, emulsifying, encapsulating, entrapping or lyophilizing processes. Pharmaceutical compositions may be formulated in conventional manner using one or more physiologically acceptable carriers, diluents, excipients or auxilliaries which facilitate processing of the active β-hairpin peptidomimetics into preparations which can be used pharmaceutically. Proper formulation depends upon the method of administration chosen.

For topical administration the β-hairpin peptidomimetics of the invention may be formulated as solutions, gels, ointments, creams, suspensions, etc. as are well-known in the art.

Systemic formulations include those designed for administration by injection, e.g. subcutaneous, intravenous, intramuscular, intrathecal or intraperitoneal injection, as well as those designed for transdermal, transmucosal, oral or pulmonary administration.

For injections, the β-hairpin peptidomimetics of the invention may be formulated in adequate solutions, preferably in physiologically compatible buffers such as Hink's solution, Ringer's solution, or physiological saline buffer. The solutions may contain formulatory agents such as suspending, stabilizing and/or dispersing agents. Alternatively, the β-hairpin peptidomimetics of the invention may be in powder form for combination with a suitable vehicle, e.g., sterile pyrogen-free water, before use.

For transmucosal administration, penetrants appropriate to the barrier to be permeated are used in the formulation as known in the art.

For oral administration, the compounds can be readily formulated by combining the active β-hairpin peptidomimetics of the invention with pharmaceutically acceptable carriers well known in the art. Such carriers enable the β-hairpin peptidomimetics of the invention to be formulated as tablets, pills, dragees, capsules, liquids, gels, syrups, slurries, suspensions etc., for oral ingestion by a patient to be treated. For oral formulations such as, for example, powders, capsules and tablets, suitable excipients include fillers such as sugars, such as lactose, sucrose, mannitol and sorbitol; cellulose preparations such as maize starch, wheat starch, rice starch, potato starch, gelatin, gum tragacanth, methyl cellulose, hydroxypropylmethyl cellulose, sodium carboxymethylcellulose, and/or polyvinylpyrrolidone (PVP); granulating agents; and binding agents. If desired, desintegrating agents may be added, such as cross-linked polyvinylpyrrolidones, agar, or alginic acid or a salt thereof, such as sodium alginate. If desired, solid dosage forms may be sugar-coated or enteric-coated using standard techniques.

For oral liquid preparations such as, for example, suspensions, elixirs and solutions, suitable carriers, excipients or diluents include water, glycols, oils, alcohols, etc. In addition, flavoring agents, preservatives, coloring agents and the like may be added.

For buccal administration, the composition may take the form of tablets, lozenges, etc. formulated as usual.

For administration by inhalation, the β-hairpin peptidomimetics of the invention are conveniently delivered in form of an aeorosol spray from pressurized packs or a nebulizer, with the use of a suitable propellant, e.g. dichlorodifluoromethane, trichlorofluoromethane, carbon dioxide or another suitable gas. In the case of a pressurized aerosol the dose unit may be determined by providing a valve to deliver a metered amount. Capsules and cartridges of e.g. gelatin for use in an inhaler or insufflator may be formulated containing a powder mix of the β-hairpin peptidomimetics of the invention and a suitable powder base such as lactose or starch.

The compounds may also be formulated in rectal or vaginal compositions such as suppositories together with appropriate suppository bases such as cocoa butter or other glycerides.

In addition to the formulations described above, the β-hairpin peptidomimetics of the invention may also be formulated as depot preparations. Such long acting formulations may be administered by implantation (e.g. subcutaneously or intramuscularly) or by intramuscular injection. For the manufacture of such depot preparations the β-hairpin peptidomimetics of the invention may be formulated with suitable polymeric or hydrophobic materials (e.g. as an emulsion in an acceptable oil) or ion exchange resins, or as sparingly soluble salts.

In addition, other pharmaceutical delivery systems may be employed such as liposomes and emulsions well known in the art. Certain organic solvents such as dimethylsulfoxide may also be employed. Additionally, the β-hairpin peptidomimetics of the invention may be delivered using a sustained-release system, such as semipermeable matrices of solid polymers containing the therapeutic agent (e.g. for coated stents). Various sustained-release materials have been established and are well known by those skilled in the art. Sustained-release capsules may, depending on their chemical nature, release the compounds for a few weeks up to over 100 days.

Depending on the chemical nature and the biological stability of the therapeutic agent, additional strategies for protein stabilization may be employed.

As the β-hairpin pepdidomimetics of the invention may contain charged residues, they may be included in any of the above-described formulations as such or as pharmaceutically acceptable salts. Pharmaceutically acceptable salts tend to be more soluble in aqueous and other protic solvents than are the corresponding free forms.

The β-hairpin peptidomimetics of the invention, or compositions thereof, will generally be used in an amount effective to achieve the intended purpose. It is to be understood that the amount used will depend on a particular application.

For example, for use as a desinfectant or preservative, an antimicrobially effective amount of a β-hairpin peptidomimetic of the invention, or a composition thereof, is applied or added to the material to be desinfected or preserved. By antimicrobially effective amount is meant an amount of a β-hairpin peptidomimetic of the invention, or a composition thereof, that inhibits the growth of, or is lethal to, a target microbe population. While the antimicrobially effective amount will depend on a particular application, for use as desinfectants or preservatives the β-hairpin peptidomimetics of the invention, or compositions thereof, are usually added or applied to the material to be desinfected or preserved in relatively low amounts. Typically, the β-hairpin peptidomimetics of the invention comprise less than about 5% by weight of a desinfectant solution or material to be preserved, preferably less than 1% by weight and more preferably less than 0.1% by weight. An ordinary skilled expert will be able to determine antimicrobially effective amounts of particular β-hairpin pepdidomimetics of the invention for particular applications without undue experimentation using, for example, the results of the in vitro assays provided in the examples.

For use to treat or prevent microbial infections or diseases related to such infections, the β-hairpin pepdidomimetics of the invention, or compositions thereof, are administered or applied in a therapeutically effective amount. By therapeutically effective amount is meant an amount effective in ameliorating the symptoms of, or in ameliorating, treating or preventing microbial infections or diseases related thereto. Determination of a therapeutically effective amount is well within the capacities of those skilled in the art, especially in view of the detailed disclosure provided herein.

As in the case of desinfectants and preservatives, for topical administration to treat or prevent bacterial infections and/or viral infections a therapeutically effective dose can be determined using, for example, the results of the in vitro assays provided in the examples. The treatment may be applied while the infection is visible, or even when it is not visible. An ordinary skilled expert will be able to determine therapeutically effective amounts to treat topical infections without undue experimentation.

For systemic administration, a therapeutically effective dose can be estimated initially from in vitro assays. For example, a dose can be formulated in animal models to achieve a circulating β-hairpin peptidomimetic concentration range that includes the $IC_{50}$ as determined in the cell culture (i.e. the concentration of a test compound that is lethal to 50% of a cell culture). Such information can be used to more accurately determine useful doses in humans.

Initial dosages can also be determined from in vivo data, e.g. animal models, using techniques that are well known in the art. One having ordinary skill in the art could readily optimize administration to humans based on animal data.

Dosage amounts for applications as anti-infective agents may be adjusted individually to provide plasma levels of the β-hairpin peptidomimetics of the invention which are sufficient to maintain the therapeutic effect. Therapeutically effective serum levels may be achieved by administering multiple doses each day.

In cases of local administration or selective uptake, the effective local concentration of the β-hairpin peptidomimetics of the invention may not be related to plasma concentration. One having the ordinary skill in the art will be able to optimize therapeutically effective local dosages without undue experimentation.

The amount of β-hairpin peptidomimetics administered will, of course, be dependent on the subject being treated, on the subject's weight, the severity of the affliction, the manner of administration and the judgement of the prescribing physician.

The anti-infective therapy may be repeated intermittently while infections are detectable or even when they are not detectable. The therapy may be provided alone or in combination with other drugs, such as for example other anti-HIV agents or anti-cancer agents, or other antimicrobial agents.

Normally, a therapeutically effective dose of the β-hairpin peptidomimetics described herein will provide therapeutic benefit without causing substantial toxicity.

Toxicity of the β-hairpin peptidomimetics of the invention can be determined by standard pharmaceutical procedures in cell cultures or experimental animals, e.g., by determining the $LD_{50}$ (the dose lethal to 50% of the population) or the $LD_{100}$ (the dose lethal to 100% of the population). The dose ratio between toxic and therapeutic effect is the therapeutic index. Compounds which exhibit high therapeutic indices are preferred. The data obtained from these cell culture assays and animal studies can be used in formulating a dosage range that is not toxic for use in humans. The dosage of the β-hairpin peptidomimetics of the invention lies preferably within a range of circulating concentrations that include the effective dose with little or no toxicity. The dosage may vary within the range depending upon the dosage form employed and the route of administration utilized. The exact formulation, route of administration and dose can be chosen by the individual physician in view of the patient's condition (see, e.g. Fingl et al. 1975, In: *The Pharmacological Basis of Therapeutics*, Ch. 1, p. 1).

The present invention may also include compounds, which are identical to the compounds of the general formula Cyclo (-Xaa$^1$-Xaa$^2$-Xaa$^3$-Xaa$^4$-Xaa$^5$-Xaa$^6$-Xaa$^7$-Xaa$^8$-Xaa$^9$-Xaa$^{10}$-Xaa$^{11}$-Xaa$^{12}$-Xaa$^{13}$-Xaa$^{14}$-), except that one or more atoms are replaced by an atom having an atomic mass number or mass different from the atomic mass number or mass usually found in nature, e.g. compounds enriched in 2H (D), 3H, 11C, 14C, 127I etc. These isotopic analogs and their pharmaceutical salts and formulations are considered useful agents in the therapy and/or diagnostic, for example, but not limited to, where a fine-tuning of in vivo half-life time could lead to an optimized dosage regimen.

The following Examples illustrate the present invention but are not to be construed as limiting its scope in any way.

EXAMPLES

1. Peptide Synthesis

Coupling of the First Protected Amino Acid Residue to the Resin 1 g (1.4 mMol) 2-chlorotritylchloride resin (1.4 mMol/g; Barlos et al. *Tetrahedron Lett.* 1989, 30, 3943-3946) was filled into a dried flask. The resin was suspended in CH$_2$Cl$_2$ (5 mL) and allowed to swell at room temperature under constant shaking for 30 min. A solution of 0.98 mMol (0.7 eq) of the first suitably protected amino acid residue (see below) in CH$_2$Cl$_2$ (5 mL) mixed with 960 µl (4 eq) of diisopropylethylamine (DIEA) was added. After shaking the reaction mixture for 4 hours at 25° C., the resin was filtered off and washed successively with CH$_2$Cl$_2$ (1×), DMF (1×) and CH$_2$Cl$_2$ (1×). A solution of CH$_2$Cl$_2$/MeOH/DIEA (17/2/1, mL) was added to the resin and the suspension was shaken for 30 min. After filtration the resin was washed in the following order with CH$_2$Cl$_2$ (1×), DMF (1×), CH$_2$Cl$_2$ (1×), MeOH (1×), CH$_2$Cl$_2$ (1×), MeOH (1×), CH$_2$Cl$_2$ (2×), Et$_2$O (2×) and dried under vacuum for 6 hours.

Loading was typically 0.6-0.7 mMol/g.

Fmoc-Pro-O-chlorotrityl resin was prepared as a preloaded resin and used in the synthesis.

The synthesis was carried out employing a Syro-peptide synthesizer (MultiSynTech) using 24-96 reaction vessels. In each vessel 0.04 mMol of the above resin was placed and the resin was swollen in CH$_2$Cl$_2$ and DMF for 15 min, respectively. The following reaction cycles were programmed and carried out:

| Step | Reagent | Time |
|---|---|---|
| 1 | DMF, wash | 2 × 1 min |
| 2 | 20% piperidine/DMF | 1 × 5 min, 1 × 15 min |
| 3 | DMF, wash | 5 × 1 min |
| 4a | 5 eq Fmoc amino acid/DMF + 5 eq HCTU/DMF, 10 eq DIEA/DMF | 1 × 60 min |
| 5 | DMF, wash | 3 × 1 min |

Step 4a was repeated once.

Unless indicated otherwise, the final coupling of an amino acid was followed by a Fmoc deprotection by applying steps 1-3 of the above described reaction cycle.

Cyclization and Work Up of Backbone Cyclized Peptides

Cleavage of the Fully Protected Peptide Fragment

After completion of the synthesis, the resin (0.04 mMol) was suspended in 1 mL (0.13 mMol, 3.4 eq) of 1% TFA in CH$_2$Cl$_2$ (v/v) for 3 minutes, filtered, and the filtrate was neutralized with 1 mL (0.58 mMol, 14.6 eq) of 10% DIEA in CH$_2$Cl$_2$ (v/v). This procedure was repeated three times to ensure completion of the cleavage. The filtrate was evaporated to dryness and a sample of the product was fully deprotected by using a cleavage mixture containing 95% trifluoroacetic acid (TFA), 2.5% water and 2.5% triisopropylsilane (TIS) to be analyzed by reverse phase-HPLC (C$_{18}$ column) and ESI-MS to monitor the efficiency of the linear peptide synthesis.

Cyclization of the Linear Peptide

The fully protected linear peptide (0.04 mMol) was dissolved in DMF (4 µMol/mL). Then 30.4 mg (0.08 mMol, 2 eq) of HATU, 10.9 mg (0.08 mMol, 2 eq) of HOAt and 28 µl (0.16 mMol, 4 eq) DIEA were added, and the mixture was vortexed at 25° C. for 16 hours and subsequently concentrated under high vacuum. The residue was partitioned between CH$_2$Cl$_2$ and H$_2$O/CH$_3$CN (90/10: v/v). The CH$_2$Cl$_2$ phase was evaporated to yield the fully protected cyclic peptide.

Full Deprotection of the Cyclic Peptide

The cyclic peptide obtained was dissolved in 3 mL of the cleavage mixture containing 82.5% trifluoroacetic acid (TFA), 5% water, 5% thioanisole, 5% phenol and 2.5% ethanedithiole (EDT). The mixture was allowed to stand at ° C. for 2.5 hours and thereafter concentrated under vacuum. After precipitation of the cyclic fully deprotected peptide in diethylether (Et$_2$O) at 0° C. the solid was washed twice with Et$_2$O and dried.

Analytical Method 1:

Analytical HPLC retention times (RT, in minutes) were determined using a GeminiNX C18 3 µm column with the following solvents A (H$_2$O+0.1% TFA) and B (CH$_3$CN+0.09% TFA) and the gradient: 0-0.1 min: 97% A, 3% B; 2.7 min: 3% A, 97% B; 2.71-3 min: 3% A, 97% B; 3.05 min: 97% A, 3% B; 3.06-3.3 min: 97% A, 3% B.

Analytical Method 2:

Analytical HPLC retention times (RT, in minutes) were determined using a Xbridge C18 2.5 µm column with the following solvents A (H$_2$O+0.1% TFA) and B (CH$_3$CN+0.09% TFA) and the gradient: 0-0.05 min: 97% A, 3% B; 3.0 min: 3% A, 97% B; 3.01-3.6 min: 3% A, 97% B; 3.6 min: 97% A, 3% B; 3.61-4.3 min: 97% A, 3% B.

Examples 1-18 as shown in Table 1 were synthesized starting with the amino acid Pro (Xaa$^{14}$), which was grafted to the resin. Starting resin was Fmoc-Pro-O-chlorotrityl resin, which was prepared as described above. The linear peptide was synthesized on solid support according to the procedure described above in the following sequence: Resin-Pro$^{14}$-Xaa$^{13}$-Xaa$^{12}$-Xaa$^{11}$-Xaa$^{10}$-Xaa$^9$-Xaa$^8$-Xaa$^7$-Xaa$^6$-Xaa$^5$-Xaa$^4$-Xaa$^3$-Xaa$^2$-Xaa$^1$-. Following a final Fmoc deprotection as described above, the peptide was cleaved from the resin, cyclized, deprotected and purified as indicated above.

The HPLC-retention times (minutes, see Table 2) for Ex. 1, 2 and 4-16 were determined using the analytical method 1, as described above, whereas the HPLC-retention times (minutes, see Table 2) for Ex. 3, 17 and 18 were determined using the analytical method 2, as described above.

TABLE 1

Examples (Ex.)

| Ex. | Seq ID | Xaa$^1$ | Xaa$^2$ | Xaa$^3$ | Xaa$^4$ | Xaa$^5$ | Xaa$^6$ | Xaa$^7$ | Xaa$^8$ | Xaa$^9$ | Xaa$^{10}$ | Xaa$^{11}$ | Xaa$^{12}$ | Xaa$^{13}$ | Xaa$^{14}$ |
|---|---|---|---|---|---|---|---|---|---|---|---|---|---|---|---|
| 1. | Seq ID No: 1 | Trp | Arg | Ile | Arg | Ile | $^D$Arg | Asn | Lys | Dab | Leu | Arg | Arg | $^D$Pro | Pro |
| 2. | Seq ID No: 2 | Trp | Arg | Ile | Arg | Ile | $^D$Arg | Asn | Lys | Arg | Leu | Arg | Gln | $^D$Pro | Pro |
| 3. | Seq ID No: 3 | Trp | Arg | Ile | Arg | Ile | $^D$Arg | Asn | Lys | Arg | Asn | Arg | Ala | $^D$Pro | Pro |
| 4. | Seq ID No: 4 | Trp | Arg | Ile | Arg | Ile | $^D$Arg | Asn | Gln | Arg | Cha | Gln | Ala | $^D$Pro | Pro |
| 5. | Seq ID No: 5 | Trp | Dab | Ile | Arg | Ile | $^D$Arg | Asn | Gln | Arg | Leu | Gln | Ala | $^D$Pro | Pro |
| 6. | Seq ID No: 6 | Trp | Orn | Ile | Arg | Ile | $^D$Arg | Asn | Gln | Arg | Leu | Gln | Ala | $^D$Pro | Pro |

TABLE 1-continued

Examples (Ex.)

| Ex. Seq ID | Xaa¹ | Xaa² | Xaa³ | Xaa⁴ | Xaa⁵ | Xaa⁶ | Xaa⁷ | Xaa⁸ | Xaa⁹ | Xaa¹⁰ | Xaa¹¹ | Xaa¹² | Xaa¹³ | Xaa¹⁴ |
|---|---|---|---|---|---|---|---|---|---|---|---|---|---|---|
| 7. Seq ID No: 7 | Trp | Arg | Ile | Dab | Ile | $^D$Arg | Asn | Gln | Arg | Leu | Gln | Ala | $^D$Pro | Pro |
| 8. Seq ID No: 8 | Trp | Arg | Ile | Orn | Ile | $^D$Arg | Asn | Gln | Arg | Leu | Gln | Ala | $^D$Pro | Pro |
| 9. Seq ID No: 9 | Trp | Arg | Ile | Arg | Ile | Orn | Asn | Gln | Arg | Leu | Gln | Ala | $^D$Pro | Pro |
| 10. Seq ID No: 10 | Trp | Arg | Ile | Arg | Ile | Dab | Asn | Gln | Arg | Leu | Gln | Ala | $^D$Pro | Pro |
| 11. Seq ID No: 11 | Trp | Arg | Ile | Arg | Ile | $^D$Arg | Gln | Gln | Arg | Leu | Gln | Ala | $^D$Pro | Pro |
| 12. Seq ID No: 12 | Trp | Arg | Ile | Arg | Ile | $^D$Arg | Thr | Gln | Arg | Leu | Gln | Ala | $^D$Pro | Pro |
| 13. Seq ID No: 13 | Trp | Arg | Ile | Arg | Ile | $^D$Arg | Leu | Gln | Arg | Leu | Gln | Ala | $^D$Pro | Pro |
| 14. Seq ID No: 14 | Trp | Arg | Ile | Arg | Ile | $^D$Arg | Tyr | Gln | Arg | Leu | Gln | Ala | $^D$Pro | Pro |
| 15. Seq ID No: 15 | Trp | Arg | Ile | Arg | Ile | $^D$Arg | Asn | Gln | Arg | Tyr | Gln | Ala | $^D$Pro | Pro |
| 16. Seq ID No: 16 | Trp | Arg | Ile | Arg | Ile | $^D$Arg | Asn | Gln | Arg | Trp | Gln | Ala | $^D$Pro | Pro |
| 17. Seq ID No: 17 | Trp | Arg | Ile | Arg | Ile | $^D$Dab | Asn | Trp | Dab | Asn | Arg | Dab | $^D$Pro | Pro |
| 18. Seq ID No: 18 | Trp | Arg | Ile | Arg | Ile | $^D$Arg | Asn | His | Arg | Asn | Arg | Arg | $^D$Pro | Pro |

TABLE 2

| Ex. | Purity [%]$^{a)}$ | (M + 3H)/3 | RT [min] |
|---|---|---|---|
| 1 | 94 | 615.2 | 1.38 |
| 2 | 90 | 624.5 | 1.44 |
| 3 | 95 | 605.8 | 1.86 |
| 4 | 92 | 609.5 | 1.76 |
| 5 | 97 | 577.5 | 1.68 |
| 6 | 97 | 582.1 | 1.69 |
| 7 | 97 | 577.4 | 1.69 |
| 8 | 97 | 582.1 | 1.69 |
| 9 | 95 | 582.1 | 1.68 |
| 10 | 92 | 577.5 | 1.67 |
| 11 | 97 | 600.8 | 1.69 |
| 12 | 94 | 591.8 | 1.69 |
| 13 | 97 | 595.8 | 1.71 |
| 14 | 97 | 612.5 | 1.7 |
| 15 | 94 | 612.7 | 1.66 |
| 16 | 94 | 620.5 | 1.70 |
| 17 | 95 | 597.5 | 1.79 |
| 18 | 94 | 637.2 | 1.71 |

$^{a)}$%-purity of compounds after prep. HPLC.

2. Biological Methods 2.1. Preparation of the Peptides

Lyophilized peptides were weighed on a Microbalance (Mettler MT5) and dissolved in sterile water to a final concentration of 1 mg/ml. Stock solutions were kept at +4° C., light protected.

2.2. Antimicrobial Activity of the Peptides

The selective antimicrobial activities of the peptides were determined in 96-well plates (Greiner, polypropylene) by the standard NCCLS broth microdilution method (National Committee for Clinical Laboratory Standards 1993. Methods for dilution antimicrobial susceptibility tests for bacteria that grow aerobically, 3rd ed. Approved standard M7-A6. National Committee for Clinical laboratory standards, Wayne, Pa.) with slight modifications. Inocula of the microorganisms were diluted into Mueller-Hinton II (MH, cation adjusted) broth+0.02% BSA and compared with a 0.5 McFarland standard to give appr. 106 colony forming units (CFU)/mL. Aliquots (50 µl) of inoculate were added to 50 µl of MH broth+0.02% BSA containing the peptide in serial two-fold dilutions. The following microorganisms were used to determine antibiotic selectivity of the peptides: *Bacillus subtilis* DSM 10 and *Shigella boydii* DSM 7532. Antimicrobial activities of the peptides were expressed as the minimal inhibitory concentration (MIC) in µg/mL at which no visible growth was observed after 18-20 hours of incubation at 37° C.

2.3. Cytotoxicity Assay

The cytotoxicity of the peptides to HELA cells (Acc57) and COS-7 cells (CRL-1651) was determined using the MTT reduction assay (T. Mossman, *J. Immunol. Meth.* 1983, 65, 55-63; M. V. Berridge, A. S. Tan, *Arch. Biochem. Biophys.* 1993, 303, 474-482). Briefly, the method was as follows: 4000 HELA cells/well and 3400 COS-7 cells/well were seeded and grown in 96-well microtiter plates for 24 h at 37° C. at 5% $CO_2$. Thereafter, time zero (Tz) was determined by MTT reduction (see below). The supernatant of the remaining wells was discarded, and fresh medium and compounds in serial dilutions (12.5, 25 and 50 µg/mL, triplicates) were pipetted into the wells. After incubation of the cells for 48 h at 37° C. at 5% $CO_2$ the supernatant was discarded again and 100 µL MTT reagent (0.5 mg/mL in RPMI1640 and DMEM, respectively)/well was added. Following incubation at 37° C. for 2-4 h the media were aspirated and the cells were spiked (100 µL isopropanol/well). The absorbance of the solubilized formazan was measured at 595 nm ($OD_{595}$peptide). For each concentration averages were calculated from triplicates. The percentage of growth was calculated as follows: ($OD_{595}$peptide-$OD_{595}$Tz-$OD_{595}$Empty well)/($OD_{595}$Tz-$OD_{595}$Empty well)×100%. The $GI_{50}$ (Growth Inhibition) concentrations were calculated for each peptide by using a trend line function for the concentrations (50, 25, 12.5 and 0 µg/mL), the corresponding percentages and the value 50, (=TREND ($C_{50}$:$C_0$%$_{50}$:%$_0$,50).

2.4. Hemolysis

The peptides were tested for their hemolytic activity against human red blood cells (hRBC). Fresh hRBC were washed three times with phosphate buffered saline (PBS) and centrifuged for 10 min at 2000×g. Compounds (100 µg/mL) were incubated with 20% hRBC (v/v) for 1 h at 37° C. and shaking at 300 rpm. The final erythrocyte concentration was approximately 0.9×10⁹ cells/mL. A value of 0% and 100% cell lyses, respectively, was determined by incubation of hRBC in the presence of PBS containing 0.001% acetic acid and 2.5% Triton X-100 in $H_2O$, respectively. The samples were centrifuged, the supernatants were 8-fold diluted in PBS buffer and the optical densities (OD) were measured at 540 nm. The 100% lyses value ($OD_{540}H_2O$) gave an $OD_{50}$ of approximately 0.5-1.0.

Percent hemolysis was calculated as follows: ($OD_{540}$peptide/$OD_{540}H_2O$)×100%.

The results of the experiments described in 2.2-2.4 are indicated in Table 3 herein below.

TABLE 3

Minimal inhibitory concentrations (MIC) in Mueller-Hinton broth, cytotoxicity and hemolysis

| Ex. | Bactillus subtilis DSM 10 MIC [μg/mL] | Shigella boydii DSM 7532 MIC [μg/mL] | Cytotoxicity Hela Cells $GI_{50}$ [μg/mL] | Cos-7 Cells $GI_{50}$ [μg/mL] | Hemolysis at 100 μg/mL [%] |
|---|---|---|---|---|---|
| 1 | 4 | 8 | >50 | >50 | 0.0 |
| 2 | 2 | 4 | >50 | >50 | 0.0 |
| 3 | 4 | 16 | >50 | >50 | 0.1 |
| 4 | 4 | >16 | >50 | >50 | 0.8 |
| 5 | 2 | 16 | >50 | >50 | 0.0 |
| 6 | 4 | >16 | >50 | >50 | 0.0 |
| 7 | 4 | >16 | >50 | >50 | 0.0 |
| 8 | 2 | 16 | >50 | >50 | 0.0 |
| 9 | 2 | >16 | >50 | >50 | 0.0 |
| 10 | 4 | >16 | >50 | >50 | 0.4 |
| 11 | 4 | >16 | >50 | >50 | 0.0 |
| 12 | 4 | >16 | >50 | >50 | 0.7 |
| 13 | 4 | 16 | >50 | >50 | 0.0 |
| 14 | 4 | 16 | >50 | >50 | 0.0 |
| 15 | 4 | 16 | >50 | >50 | 0.0 |
| 16 | 2 | 16 | >50 | >50 | 0.5 |
| 17 | 2 | 4 | 38 | 44 | 0.2 |
| 18 | 16 | 4 | 39 | >50 | 0.3 |

The invention claimed is:

1. Compounds of the general formula Cyclo(-$Xaa^1$-$Xaa^2$-$Xaa^3$-$Xaa^4$-$Xaa^5$-$Xaa^6$-$Xaa^7$-$Xaa^8$-$Xaa^9$-$Xaa^{10}$-$Xaa^{11}$-$Xaa^{12}$-$Xaa^{13}$-$Xaa^{14}$-), wherein the amino acid residues $Xaa^1$ to $Xaa^{14}$ are:

$Xaa^1$: amino acid residue of type C, or of type D, as described herein below;

$Xaa^2$: amino acid residue of type E, as described herein below;

$Xaa^3$: amino acid residue of type C, or of type F, as described herein below;

$Xaa^4$: amino acid residue of type C, or of type E, as described herein below;

$Xaa^5$: amino acid residue of type C, as described herein below;

$Xaa^6$: amino acid residue of type E, as described herein below; or the D-isomer of an amino acid residue of type E, as described herein below;

$Xaa^7$: amino acid residue of type F, as described herein below, or Gly;

$Xaa^8$: amino acid residue of type E, as described herein below;

$Xaa^9$: amino acid residue of type E, as described herein below;

$Xaa^{10}$: amino acid residue of type C, or of type F, as described herein below;

$Xaa^{11}$: amino acid residue of type E, or of type F, as described herein below;

$Xaa^{12}$: amino acid residue of type C, or of type E, or of type F, as described herein below;

$Xaa^{13}$: amino acid residue of formula -A-CO—, as described herein below;

$Xaa^{14}$: amino acid residue of formula —B—CO—, as described herein below;

with the proviso that if
$Xaa^9$ is an amino acid residue of type E, as described herein below,
then $Xaa^9$ is Dab; and/or if
$Xaa^{12}$ is an amino acid residue of type F, as described herein below,
then $Xaa^{12}$ is Gln; and/or
at least two of the amino acid residues of Cyclo(-$Xaa^1$-$Xaa^2$-$Xaa^3$-$Xaa^4$-$Xaa^5$-$Xaa^6$-$Xaa^7$-$Xaa^8$-$Xaa^9$-$Xaa^{10}$-$Xaa^{11}$-$Xaa^{12}$-$Xaa^{13}$-$Xaa^{14}$-) are non-canonical amino acid residues, as described herein below;

or compounds of the general formula Cyclo(-Xaa$^1$-Xaa$^2$-Xaa$^3$-Xaa$^4$-Xaa$^5$-Xaa$^6$-Xaa$^7$-Xaa$^8$-Xaa$^9$-Xaa$^{10}$-Xaa$^{11}$-Xaa$^{12}$-Xaa$^{13}$-Xaa$^{14}$-), wherein the amino acid residues Xaa$^1$ to Xaa$^{14}$ are:
    Xaa$^1$: amino acid residue of type D,
        as described herein below;
    Xaa$^2$: amino acid residue of type E,
        as described herein below;
    Xaa$^3$: amino acid residue of type C, or of type F,
        as described herein below;
    Xaa$^4$: amino acid residue of type E,
        as described herein below;
    Xaa$^5$: amino acid residue of type C,
        as described herein below;
    Xaa$^6$: amino acid residue of type E, or the D-isomer of an amino acid residue of type E,
        as described herein below;
    Xaa$^7$: amino acid residue of type C, or of type D, or of type E, or of type F,
        as described herein below, or Gly;
    Xaa$^8$: amino acid residue of type F,
        as described herein below;
    Xaa$^9$: amino acid residue of type E,
        as described herein below;
    Xaa$^{10}$: amino acid residue of type C, or of type D, or of type F, as described herein below;
    Xaa$^{11}$: amino acid residue of type E, or or type F,
        as described herein below;
    Xaa$^{12}$: amino acid residue of type C or of type E,
        as described herein below;
    Xaa$^{13}$: amino acid residue of formula -A-CO—,
        as described herein below;
    Xaa$^{14}$: amino acid residue of formula —B—CO—,
        as described herein below;
with the proviso that if
    Xaa$^7$ is an amino acid residue of type F,
    as described herein below,
then Xaa$^7$ is Gln or Thr; and/or if
    Xaa$^{10}$ is an amino acid residue of type F,
    as described herein below,
then Xaa$^{10}$ is Ser; and/or
at least one of the amino acid residues of Cyclo(-Xaa$^1$-Xaa$^2$-Xaa$^3$-Xaa$^4$-Xaa$^5$-Xaa$^6$-Xaa$^7$-Xaa$^8$-Xaa$^9$-Xaa$^{10}$-Xaa$^{11}$-Xaa$^{12}$-Xaa$^{13}$-Xaa$^{14}$-) is a non-canonical amino acid residue, as described herein below;
or
compounds of the general formula Cyclo(-Xaa$^1$-Xaa$^2$-Xaa$^3$-Xaa$^4$-Xaa$^5$-Xaa$^6$-Xaa$^7$-Xaa$^8$-Xaa$^9$-Xaa$^{10}$-Xaa$^{11}$-Xaa$^{12}$-Xaa$^{13}$-Xaa$^{14}$-), wherein the amino acid residues Xaa$^1$ to Xaa$^{14}$ are:
    Xaa$^1$: amino acid residue of type D,
        as described herein below;
    Xaa$^2$: amino acid residue of type E,
        as described herein below;
    Xaa$^3$: amino acid residue of type C,
        as described herein below;
    Xaa$^4$: amino acid residue of type E,
        as described herein below;
    Xaa$^5$: amino acid residue of type C,
        as described herein below;
    Xaa$^6$: amino acid residue of type E, as described herein below, or the D-isomer of an amino acid residue of type E, as described herein below;
    Xaa$^7$: amino acid residue of type F,
        as described herein below;
    Xaa$^8$: amino acid residue of type D,
        as described herein below;
    Xaa$^9$: amino acid residue of type E,
        as described herein below;
    Xaa$^{10}$: amino acid residue of type F,
        as described herein below;
    Xaa$^{11}$: amino acid residue of type E,
        as described herein below;
    Xaa$^{12}$: amino acid residue of type E,
        as described herein below;
    Xaa$^{13}$: amino acid residue of formula -A-CO—,
        as described herein below;
    Xaa$^{14}$: amino acid residue of formula —B—CO—,
        as described herein below;
or
compounds of the general formula Cyclo(-Xaa$^1$-Xaa$^2$-Xaa$^3$-Xaa$^4$-Xaa$^5$-Xaa$^6$-Xaa$^7$-Xaa$^8$-Xaa$^9$-Xaa$^{10}$-Xaa$^{11}$-Xaa$^{12}$-Xaa$^{13}$-Xaa$^{14}$- wherein the amino acid residues Xaa$^1$ to Xaa$^{14}$ are:
    Xaa$^1$: amino acid residue of type D,
        as described herein below;
    Xaa$^2$: amino acid residue of type E,
        as described herein below;
    Xaa$^3$: amino acid residue of type E,
        as described herein below;
    Xaa$^4$: amino acid residue of type E,
        as described herein below;
    Xaa$^5$: amino acid residue of type C,
        as described herein below, or Gly;
    Xaa$^6$: amino acid residue of type E, or of type F,
        as described herein below, or the D-isomer of an amino acid residue of type E, as described herein below, or —B—CO—, as described herein below or Gly;
    Xaa$^7$: amino acid residue of type E, as described herein below, or the D-isomer of an amino acid residue of type E, as described herein below, or Gly;
    Xaa$^8$: amino acid residue of type F,
        as described herein below, or Gly;
    Xaa$^9$: amino acid residue of type E,
        as described herein below;
    Xaa$^{10}$: amino acid residue of type F,
        as described herein below;
    Xaa$^{11}$: amino acid residue of type E,
        as described herein below;
    Xaa$^{12}$: amino acid residue of type E,
        as described herein below;
    Xaa$^{13}$: amino acid residue of formula -A-CO—,
        as described herein below;
    Xaa$^{14}$: amino acid residue of formula —B—CO—,
        as described herein below;
with the proviso that at least one of the amino acid residues of Cyclo(-Xaa$^1$-Xaa$^2$-Xaa$^3$-Xaa$^4$-Xaa$^5$-Xaa$^6$-Xaa$^7$-Xaa$^8$-Xaa$^9$-Xaa$^{10}$-Xaa$^{11}$-Xaa$^{12}$-Xaa$^{13}$-Xaa$^{14}$-) is a non-canonical amino acid residue, as described herein below;
or
compounds of the general formula Cyclo(-Xaa$^1$-Xaa$^2$-Xaa$^3$-Xaa$^4$-Xaa$^5$-Xaa$^6$-Xaa$^7$-Xaa$^8$-Xaa$^9$-Xaa$^{10}$-Xaa$^{11}$-Xaa$^{12}$-Xaa$^{13}$-Xaa$^{14}$-), wherein the amino acid residues Xaa$^1$ to Xaa$^{14}$ are:
    Xaa$^1$: amino acid residue of type E,
        as described herein below;
    Xaa$^2$: amino acid residue of type E,
        as described herein below;
    Xaa$^3$: amino acid residue of type C, or of type F,
        as described herein below;
    Xaa$^4$: amino acid residue of type E,
        as described herein below;
    Xaa$^5$: amino acid residue of type C, or of type F,
        as described herein below;

Xaa⁶: amino acid residue of type E, as described herein below, or the D-isomer of an amino acid residue of type E, as described herein below;
Xaa⁷: Gly;
Xaa⁸: amino acid residue of type E, or of type F, as described herein below;
Xaa⁹: amino acid residue of type E, as described herein below;
Xaa¹⁰: amino acid residue of type C, or of type F, as described herein below;
Xaa¹¹: amino acid residue of type E, as described herein below;
Xaa¹²: amino acid residue of type E, as described herein below;
Xaa¹³: amino acid residue of formula -A-CO—, as described herein below;
Xaa¹⁴: amino acid residue of formula —B—CO—, as described herein below;
with the proviso that at least two of the amino acid residues of Cyclo(-Xaa¹-Xaa²-Xaa³-Xaa⁴-Xaa⁵-Xaa⁶-Xaa⁷-Xaa⁸-Xaa⁹-Xaa¹⁰-Xaa¹¹-Xaa¹²-Xaa¹³-Xaa¹⁴-) are non-canonical amino acid residues;
or
compounds of the general formula Cyclo(-Xaa¹-Xaa²-Xaa³-Xaa⁴-Xaa⁵-Xaa⁶-Xaa⁷-Xaa⁸-Xaa⁹-Xaa¹⁰-Xaa¹¹-Xaa¹²-Xaa¹³-Xaa¹⁴-), wherein the amino acid residues Xaa¹ to Xaa¹⁴ are:
Xaa¹: amino acid residue of type E, as described herein below;
Xaa²: amino acid residue of type C, or of type F, as described herein below;
Xaa³: amino acid residue of type E, as described herein below;
Xaa⁴: amino acid residue of type E, as described herein below;
Xaa⁵: amino acid residue of type C, as described herein below;
Xaa⁶: amino acid residue of type E, as described herein below;
Xaa⁷: Gly;
Xaa⁸: amino acid residue of type F, as described herein below;
Xaa⁹: amino acid residue of type E, as described herein below;
Xaa¹⁰: amino acid residue of type E, or of type F, as described herein below;
Xaa¹¹: amino acid residue of type E, or of type F, as described herein below;
Xaa¹²: amino acid residue of type E, as described herein below;
Xaa¹³: amino acid residue of formula -A-CO—, as described herein below;
Xaa¹⁴: amino acid residue of formula —B—CO—, as described herein below;
the amino acid residues Xaa² and Xaa¹¹, taken together, can form an amino acid residue of type H, as described herein below;
with the proviso that at least one of the amino acid residues of Cyclo(-Xaa¹-Xaa²-Xaa³-Xaa⁴-Xaa⁵-Xaa⁶-Xaa⁷-Xaa⁸-Xaa⁹-Xaa¹⁰-Xaa¹¹-Xaa¹²-Xaa¹³-Xaa¹⁴-) are non-canonical amino acid residues;
or
compounds of the general formula Cyclo(-Xaa¹-Xaa²-Xaa³-Xaa⁴-Xaa⁵-Xaa⁶-Xaa⁷-Xaa⁸-Xaa⁹-Xaa¹⁰-Xaa¹¹-Xaa¹²-Xaa¹³-Xaa¹⁴-), wherein the amino acid residues Xaa¹ to Xaa¹⁴ are:

Xaa¹: amino acid residue of type, E or of type F, as described herein below;
Xaa²: amino acid residue of type C, or of type D, or of type E, or of type F, as described herein below;
Xaa³: amino acid residue of type E, as described herein below, or the D-isomer of an amino acid residue of type E, as described herein below, or Gly;
Xaa⁴: amino acid residue of type C, or of type D, or of type E, or of type F, as described herein below;
Xaa⁵: amino acid residue of type E, as described herein below;
Xaa⁶: amino acid residue of type E, or of type F, as described herein below, or Gly;
Xaa⁷: amino acid residue of type D, or of type E, or of type F, as described herein below, or Gly;
Xaa⁸: amino acid residue of type E, as described herein below;
Xaa⁹: amino acid residue of type D, or of type E, as described herein below;
Xaa¹⁰: amino acid residue of type C, or of type D, or of type E, or of type F, as described herein below;
Xaa¹¹: amino acid residue of type D, or of type E, or of type F, as described herein below, or Gly;
Xaa¹²: amino acid residue of type C, or of type D, or of type E, or of type F, as described herein below;
Xaa¹³: amino acid residue of formula -A-CO—, as described herein below;
Xaa¹⁴: amino acid residue of formula —B—CO—, as described herein below;
the amino acid residues Xaa² and Xaa¹¹, taken together, can form an amino acid residue of type H, as described herein below;
with the proviso that at least two of the amino acid residues of Cyclo(-Xaa¹-Xaa²-Xaa³-Xaa⁴-Xaa⁵-Xaa⁶-Xaa⁷-Xaa⁸-Xaa⁹-Xaa¹⁰-Xaa¹¹-Xaa¹²-Xaa¹³-Xaa¹⁴-) are non-canonical amino acid residues;
—B—CO— is Gly, NMeGly or the residue of an L-α-amino acid with B being a residue of formula —NR²⁰CH(R⁷¹)—, or —NR²⁰CH(R⁷²)—, or —NR²⁰CH(R⁷³)—, or —NR²⁰CH(R⁷⁴)—, or —NR²⁰CH(R⁸⁴)—, or the enantiomer of one of the groups A1 to A69 as defined hereinafter;
A of -A-CO— is a group of one of the formulae

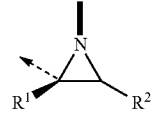

A1

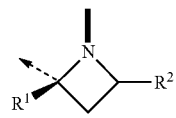

A2

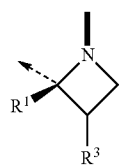

A3

-continued
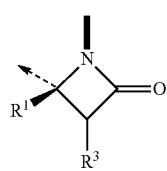   A4
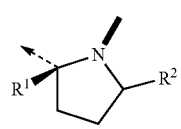   A5
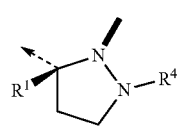   A6
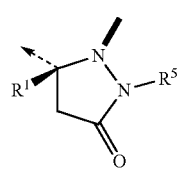   A7
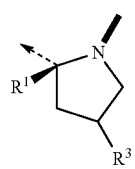   A8
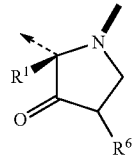   A9
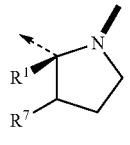   A10
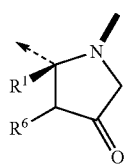   A11
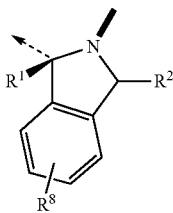   A12
-continued
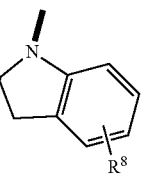   A13
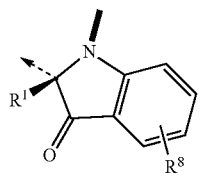   A14
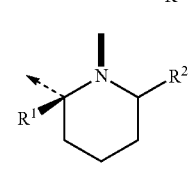   A15
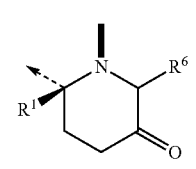   A16
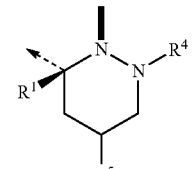   A17
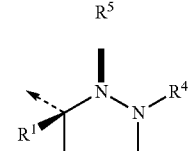   A18
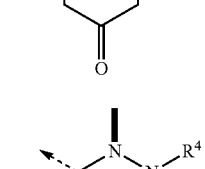   A19
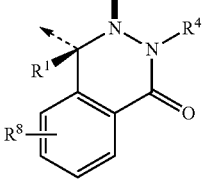   A20
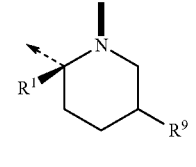   A21
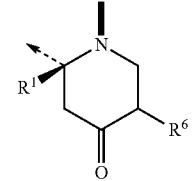

-continued
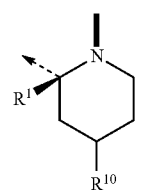 A22
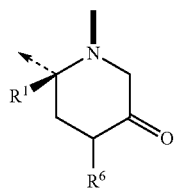 A23
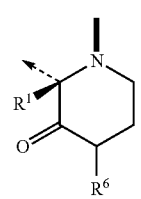 A24
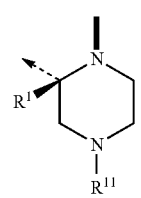 A25
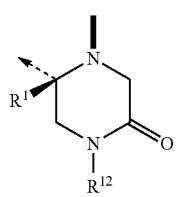 A26
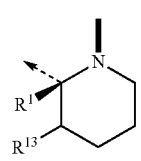 A27
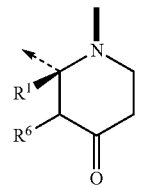 A28
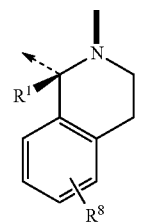 A29
-continued
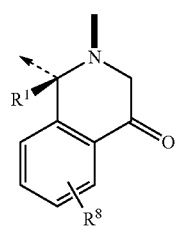 A30
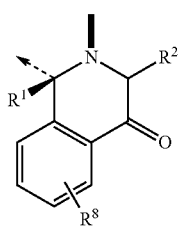 A31
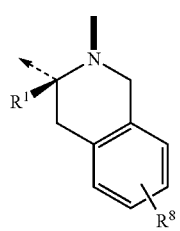 A32
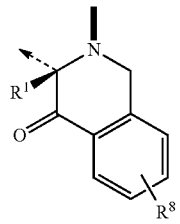 A33
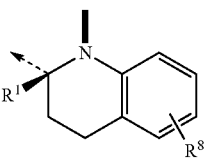 A34
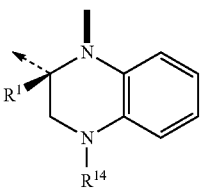 A35
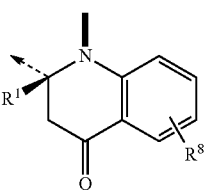 A36

-continued
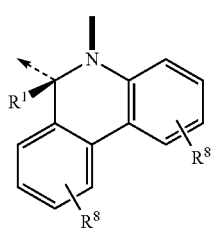
A37
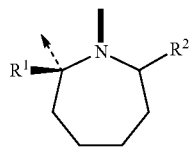
A38
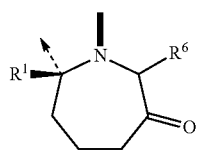
A39
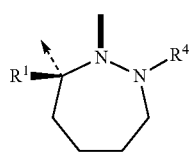
A40
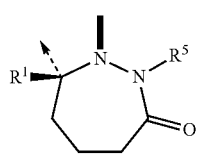
A41
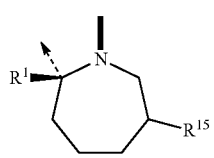
A42
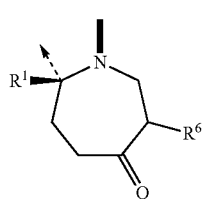
A43
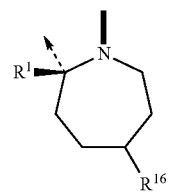
A44
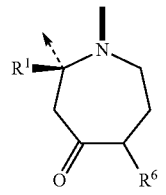
A45
-continued
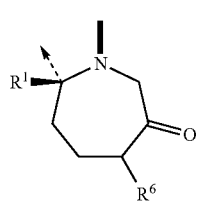
A46
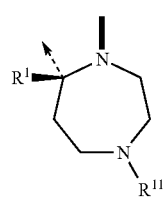
A47
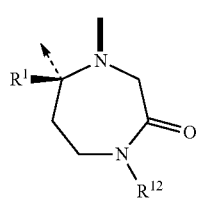
A48
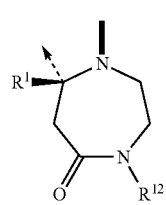
A49
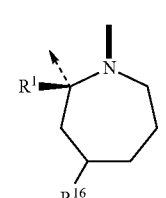
A50
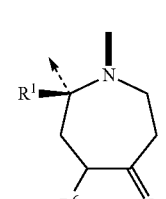
A51
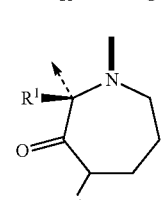
A52
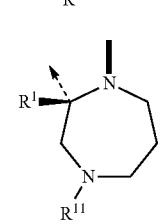
A53

-continued
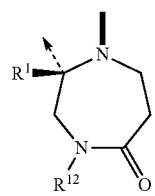
A54
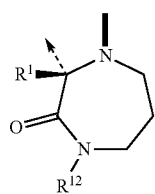
A55
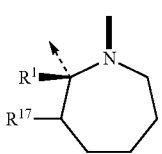
A56
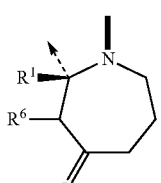
A57
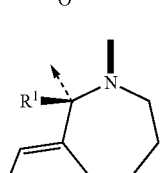
A58
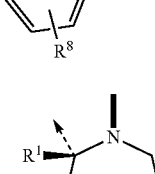
A59
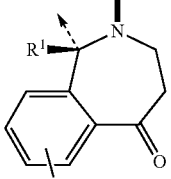
A60
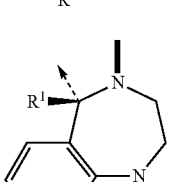
A61
-continued
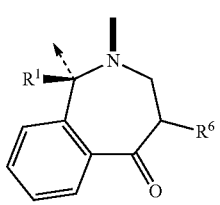
A62
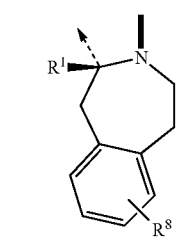
A63
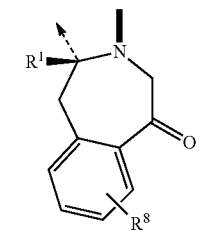
A64
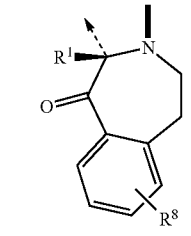
A65
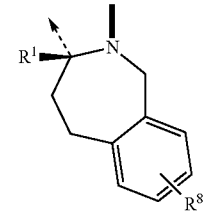
A66
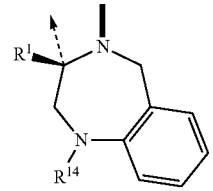
A67
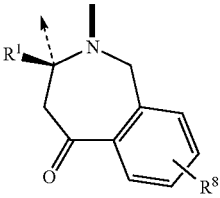
A68

95
-continued
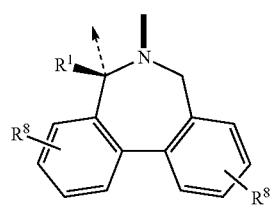
A69
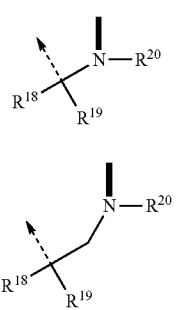
A70
A71
A72
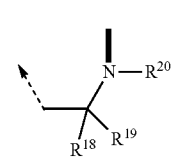
A73
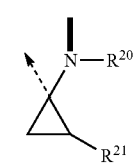
A74
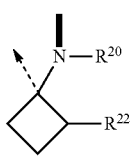
A75
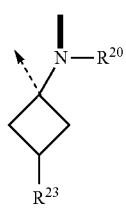
A76
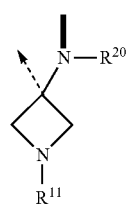
A77
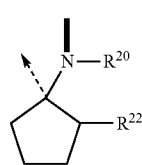
96
-continued
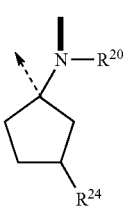
A78
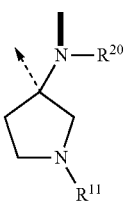
A79
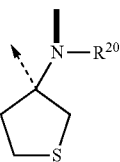
A80
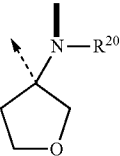
A81
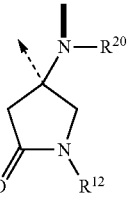
A82
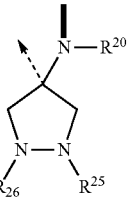
A83
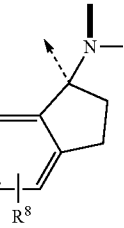
A84

-continued
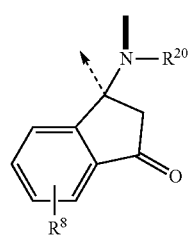
A85
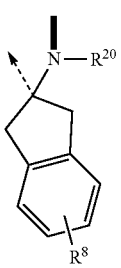
A86
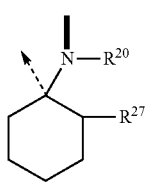
A87
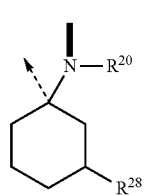
A88
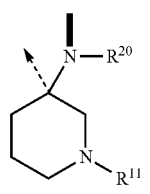
A89
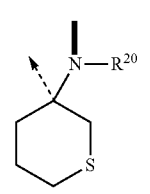
A90
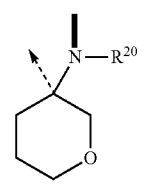
A91
-continued
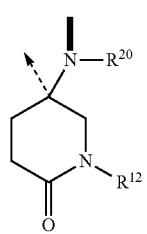
A92
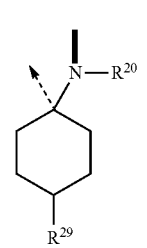
A93
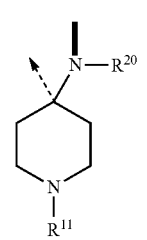
A94
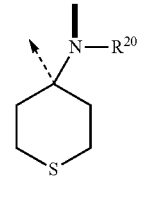
A95
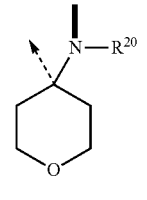
A96
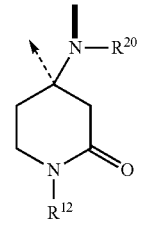
A97
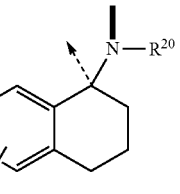
A98

-continued

A99

A100

A101

A102

A103

A104

$R^1$ is H; lower alkyl; lower cycloalkyl; lower alkyl-aryl or aryl-lower alkyl;
$R^2$ is H; alkyl; alkenyl; —$(CH_2)_p(CHR^{61})_sOR^{55}$;
—$(CH_2)_p(CHR^{61})_sSR^5$;
—$(CH_2)_p(CHR^{61})_sNR^{33}R^{34}$; —$(CH_2)_p(CHR^{61})_sOCONR^{33}R^{75}$;
—$(CH_2)_p(CHR^{61})_sNR^{20}CONR^{33}R^{82}$; —$(CH_2)_o(CHR^{61})_sCOO^{57}$;
—$(CH_2)_o(CHR^{61})_sCONR^{58}R^{59}$; —$(CH_2)_o(CHR^{61})_sPO(OR^{60})_2$;
—$(CH_2)_o(CHR^{61})_sSO_2R^{62}$; or —$(CH_2)_o(CHR^{61})_sSR^{77}$;
$R^3$ is alkyl; alkenyl; —$(CH_2)_o(CHR^{61})_sOR^{55}$; —$(CH_2)_o(CHR^{61})_sSR^{56}$;
—$(CH_2)_o(CHR^{61})_sNR^{33}R^{34}$;
—$(CH_2)_o(CHR^{61})_sOCONR^{33}R^{75}$; —$(CH_2)_o(CHR^{61})_sNR^{20}CONR^{33}R^{82}$;
—$(CH_2)_o(CHR^{61})_sCOOR^{57}$; —$(CH_2)_o(CHR^{61})_sCONR^{58}R^{59}$;
—$(CH_2)_o(CHR^{61})_sPO(OR^{60})_2$;
—$(CH_2)_o(CHR^{61})_sSO_2R^{62}$; or —$(CH_2)_o(CHR^{61})_sC_6H_4R^8$;
$R^4$ is H; alkyl; alkenyl; —$(CH_2)_m(CHR^{61})_sOR^{55}$;
—$(CH_2)_m(CHR^{61})_sSR^{56}$; —$(CH_2)_m(CHR^{61})_sR^{33}R^{34}$;
—$(CH_2)_m(CHR^{61})_sOCONR^{33}R^{75}$; —$(CH_2)_m(CHR^{61})_sNR^{20}CONR^{33}R^{82}$;
—$(CH_2)_p(CHR^{61})_sCOOR^{57}$; —$(CH_2)_p(CHR^{61})_sCONR^{58}R^{59}$;
—$(CH_2)_p(CHR^{61})_sPO(OR^{60})_2$;
—$(CH_2)_p(CHR^{61})_sSO_2R^{62}$; or —$(CH_2)_o(CHR^{61})_sC_6H_4R^8$;
$R^5$ is H; alkyl; alkenyl; —$(CH_2)_m(CHR^{61})_sOR^{55}$;
—$(CH_2)_m(CHR^{61})_sSR^{56}$;
—$(CH_2)_m(CHR^{61})_sNR^{33}R^{34}$; —$(CH_2)_m(CHR^{61})_sOCONR^{33}R^{75}$;
—$(CH_2)_m(CHR^{61})_sNR^{20}CONR^{33}R^{82}$; —$(CH_2)_o(CHR^{61})COOR^{57}$;
—$(CH_2)_o(CHR^{61})_sCONR^{58}R^{59}$; —$(CH_2)_o(CHR^{61})_sPO(OR^{60})_2$;
—$(CH_2)_o(CHR^{61})_sSO_2R^{62}$; or —$(CH_2)_o(CHR^{61})_sC_6H_4^8$;
$R^6$ is H; alkyl; alkenyl; —$(CH_2)_o(CHR^{61})_sOR^{55}$; —$(CH_2)_o(CHR^{61})_sSR^{56}$; —$(CH_2)_o(CHR^{61})_sNR^{33}R^{34}$;
—$(CH_2)_o(CHR^{61})_sOCONR^{33}R^{75}$; —$(CH_2)_o(CHR^{61})_sNR^{20}CONR^{33}R^{82}$;
—$(CH_2)_o(CHR^{61})_sCOOR^{57}$; —$(CH_2)_o(CHR^{61})_sCONR^{58}R^{59}$;
—$(CH_2)_o(CHR^{61})_sPO(OR^{60})_2$;
—$(CH_2)_o(CHR^{61})_sSO_2R^{62}$; or —$(CH_2)_o(CHR^{61})_6C_6H_4^8$;
$R^7$ is alkyl; alkenyl; —$(CH_2)_q(CHR^{61})_sOR^{55}$; —$(CH_2)_q(CHR^{61})_sNR^{33}R^{34}$;
—$(CH_2)_q(CHR^{61})_sOCONR^{33}R^{75}$; —$(CH_2)_q(CHR^{61})_sNR^{20}CONR^{33}R^{82}$;
—$(CH_2)_r(CHR^{61})_sCOOR^{57}$; —$(CH_2)_r(CHR^{61})_sCONR^{58}R^{59}$;
—$(CH_2)_r(CHR^{61})_sO(OR^{60})_2$;
—$(CH_2)_r(CHR^{61})_sSO_2R^{62}$; or —$(CH_2)_r(CHR^{61})_sC_6H_4R^8$;
$R^8$ is H; Cl; F; $CF_3$; $NO_2$; lower alkyl; lower cycloalkyl; lower alkenyl; aryl; lower alkyl-aryl; aryl-lower alkyl;
—$(CH_2)_o(CHR^{61})_sR^{77}$
—$(CH_2)_o(CHR^{61})_sOR^{55}$; —$(CH_2)_o(CHR^{61})_sSR^{56}$;
—$(CH_2)_o(CHR^{61})NR^{33}R^{34}$;
—$(CH_2)_o(CHR^{61})_sOCONR^{33}R^{75}$; —$(CH_2)_o(CHR^{61})_sNR^{20}CONR^{33}R^{82}$;
—$(CH_2)_o(CHR^{61})_sCOOR^{57}$; —$(CH_2)_o(CHR^{61})_sCONR^{58}R^{59}$;
—$(CH_2)_o(CHR^{61})_sPO(OR^{60})_2$;
—$(CH_2)_o(CHR^{61})_sSO_2R^{62}$; or —$(CH_2)_o(CHR^{61})COR^{64}$;
$R^9$ is alkyl; alkenyl; —$(CH_2)_o(CHR^{61})_sOR^{55}$; —$(CH_2)_o(CHR^{61})_sSR^{56}$;

—(CH$_2$)$_o$(CHR$^{61}$)$_s$NR$^{33}$R$^{34}$;
—(CH$_2$)$_o$(CHR$^{61}$)$_s$OCONR$^{33}$R$^{75}$; —(CH$_2$)$_o$(CHR$^{61}$)$_s$NR$^{20}$CONR$^{33}$R$^{82}$;
—(CH$_2$)$_o$(CHR$^{61}$)$_s$COOR$^{57}$; —(CH$_2$)$_o$(CHR$^{61}$)$_s$CONR$^{58}$R$^{59}$;
—(CH$_2$)$_o$(CHR$^{61}$)$_s$PO(OR$^{60}$)$_2$;
—(CH$_2$)$_o$(CHR$^{61}$)$_s$SO$_2$R$^{62}$; or —(CH$_2$)$_o$(CHR$^{61}$)$_s$C$_6$H$_4$R$^8$;

R$^{10}$ is alkyl; alkenyl; —(CH$_2$)$_o$(CHR$^{61}$)$_s$OR$^{55}$; —(CH$_2$)$_o$(CHR$^{61}$)$_s$SR$^{56}$;
—(CH$_2$)$_o$(CHR$^{61}$)$_s$NR$^{33}$R$^{34}$;
—(CH$_2$)$_o$(CHR$^{61}$)$_s$OCONR$^{33}$R$^{75}$; —(CH$_2$)$_o$(CHR$^{61}$)$_s$NR$^{20}$CONR$^{33}$R$^{82}$;
—(CH$_2$)$_o$(CHR$^{61}$)$_s$COOR$^{57}$; —(CH$_2$)$_o$(CHR$^{61}$)$_s$CONR$^{58}$R$^{59}$;
—(CH$_2$)$_o$(CHR$^{61}$)$_s$PO(OR$^{60}$)$_2$;
—(CH$_2$)$_o$(CHR$^{61}$)$_s$SO$_2$R$^{62}$; or —(CH$_2$)$_o$(CHR$^{61}$)$_s$C$_6$H$_4$R$^8$;

R$^{11}$ is H; alkyl; alkenyl; —(CH$_2$)$_m$(CHR$^{61}$)$_s$OR$^{55}$;
—(CH$_2$)$_m$(CHR$^{61}$)$_s$NR$^{33}$R$^{34}$;
—(CH$_2$)$_m$(CHR$^{61}$)$_s$OCONR$^{33}$R$^{75}$; —(CH$_2$)$_m$(CHR$^{61}$)$_s$NR$^{20}$CONR$^{33}$R$^{82}$;
—(CH$_2$)$_o$(CHR$^{61}$)$_s$COOR$^{57}$; —(CH$_2$)$_o$(CHR$^{61}$)$_s$CONR$^{58}$R$^{59}$;
—(CH$_2$)$_o$(CHR$^{61}$)$_s$PO(OR$^{60}$)$_2$;
—(CH$_2$)$_o$(CHR$^{61}$)$_s$SO$_2$R$^{62}$; or —(CH$_2$)$_o$(CHR$^{61}$)$_s$C$_6$H$_4$R$^8$;

R$^{12}$ is H; alkyl; alkenyl; —(CH$_2$)$_m$(CHR$^{61}$)$_s$OR$^{55}$;
—(CH$_2$)$_m$(CHR$^{61}$)$_s$SR$^{56}$;
—(CH$_2$)$_m$(CHR$^{61}$)$_s$NR$^{33}$R$^{34}$; —(CH$_2$)$_m$(CHR$^{61}$)$_s$OCONR$^{33}$R$^{75}$;
—(CH$_2$)$_m$(CHR$^{61}$)$_s$NR$^{20}$CONR$^{33}$R$^{82}$; —(CH$_2$)$_r$(CHR$^{6}$)$_s$COOR$^{57}$;
—(CH$_2$)$_r$(CHR$^{61}$)$_s$CONR$^{58}$R$^{59}$; —(CH$_2$)$_r$(CHR$^{61}$)$_s$PO(OR$^{60}$)$_2$;
—(CH$_2$)$_r$(CHR$^{61}$)$_s$SO$_2$R$^{62}$; or —(CH$_2$)$_r$(CHR$^{61}$)$_s$C$_6$H$_4$R$^8$;

R$^{13}$ is alkyl; alkenyl; —(CH$_2$)$_q$(CHR$^{61}$)$_s$OR$^{55}$; —(CH$_2$)$_q$(CHR$^{61}$)$_s$SR$^{56}$;
—(CH$_2$)$_q$(CHR$^{61}$)$_s$NR$^{33}$R$^{34}$;
—(CH$_2$)$_q$(CHR$^{61}$)$_s$OCONR$^{33}$R$^{75}$; —(CH$_2$)$_q$(CHR$^{61}$)$_s$NR$^{20}$CONR$^{33}$R$^{82}$;
—(CH$_2$)$_q$(CHR$^{61}$)$_s$COOR$^{57}$; —(CH$_2$)$_q$(CHR$^{61}$)$_s$CONR$^{58}$R$^{59}$;
—(CH$_2$)$_q$(CHR$^{61}$)$_s$PO(OR$^{60}$)$_2$;
—(CH$_2$)$_q$(CHR$^{61}$)$_s$SO$_2$R$^{62}$; or —(CH$_2$)$_q$(CHR$^{61}$)$_s$C$_6$H$_4$R$^8$;

R$^{14}$ is H; alkyl; alkenyl; —(CH$_2$)$_m$(CHR$^{61}$)$_s$OR$^{55}$;
—(CH$_2$)$_m$(CHR$^{61}$)$_s$NR$^{33}$R$^{34}$;
—(CH$_2$)$_m$(CHR$^{61}$)$_s$OCONR$^{33}$R$^{75}$; —(CH$_2$)$_m$(CHR$^{61}$)$_s$NR$^{20}$CONR$^{33}$R$^{82}$;
—(CH$_2$)$_q$(CHR$^{61}$)$_s$COOR$^{57}$; —(CH$_2$)$_q$(CHR$^{61}$)$_s$CONR$^{58}$R$^{59}$;
—(CH$_2$)$_q$(CHR$^{61}$)$_s$PO(OR$^{60}$)$_2$;
—(CH$_2$)$_q$(CHR$^{61}$)$_s$SOR$^{62}$; or —(CH$_2$)$_q$(CHR$^{61}$)$_s$C$_6$H$_4$R$^8$;

R$^{15}$ is alkyl; alkenyl; —(CH$_2$)$_o$(CHR$^{61}$)$_s$OR$^{55}$; —(CH$_2$)$_o$(CHR$^{61}$)$_s$SR$^{56}$;
—(CH$_2$)$_o$(CHR$^{61}$)$_s$NR$^{33}$R$^{34}$;
—(CH$_2$)$_o$(CHR$^{61}$)$_s$OCONR$^{33}$R$^{75}$; —(CH$_2$)$_o$(CHR$^{61}$)$_s$NR$^{20}$CONR$^{33}$R$^{82}$;
—(CH$_2$)$_o$(CHR$^{61}$)$_s$COOR$^{57}$; —(CH$_2$)$_o$(CHR$^{61}$)$_s$CONR$^{58}$R$^{59}$;
—(CH$_2$)$_o$(CHR$^{61}$)$_s$PO(OR$^{60}$)$_2$;
—(CH$_2$)$_o$(CHR$^{61}$)$_s$SO$_2$R$^{62}$; or —(CH$_2$)$_o$(CHR$^{61}$)$_s$C$_6$H$_4$R$^8$;

R$^{16}$ is alkyl; alkenyl; —(CH$_2$)$_o$(CHR$^{61}$)$_s$OR$^{55}$; —(CH$_2$)$_o$(CHR$^{61}$)$_s$SR$^{56}$;
—(CH$_2$)$_o$(CHR$^{61}$)$_s$NR$^{33}$R$^{34}$;
—(CH$_2$)$_o$(CHR$^{61}$)$_s$OCONR$^{33}$R$^{75}$; —(CH$_2$)$_o$(CHR$^{61}$)$_s$NR$^{20}$CONR$^{33}$R$^{82}$;
—(CH$_2$)$_o$(CHR$^{61}$)$_s$COOR$^{57}$; —(CH$_2$)$_o$(CHR$^{61}$)$_s$CONR$^{58}$R$^{59}$;
—(CH$_2$)$_o$(CHR$^{61}$)$_s$PO(OR$^{60}$)$_2$;
—(CH$_2$)$_o$(CHR$^{61}$)$_s$SO$_2$R$^{62}$; or —(CH$_2$)$_o$(CHR$^{61}$)$_s$C$_6$H$_4$R$^8$;

R$^{17}$ is alkyl; alkenyl; —(CH$_2$)$_q$(CHR$^{61}$)$_s$OR$^{55}$; —(CH$_2$)$_q$(CHR$^{61}$)$_s$SR$^{16}$;
—(CH$_2$)$_q$(CHR$^{61}$)$_s$NR$^{33}$R$^{34}$;
—(CH$_2$)$_q$(CHR$^{61}$)$_s$OCONR$^{33}$R$^{75}$; —(CH$_2$)$_q$(CHR$^{61}$)$_s$NR$^{20}$CONR$^{33}$R$^{82}$;
—(CH$_2$)$_q$(CHR$^{61}$)$_s$COR$^{57}$; —(CH$_2$)$_q$(CHR$^{61}$)$_s$CONR$^{58}$R$^{59}$;
—(CH$_2$)$_q$(CHR$^{61}$)$_s$PO(OR$^{60}$)$_2$;
—(CH$_2$)$_q$(CHR$^{61}$)$_s$SO$_2$R$^{62}$; or —(CH$_2$)$_q$(CHR$^{61}$)$_s$C$_6$H$_4$R$^8$;

R$^{18}$ is alkyl; alkenyl; —(CH$_2$)$_p$(CHR$^{61}$)$_s$OR$^{55}$; —(CH$_2$)$_p$(CHR$^{61}$)$_s$SR$^{56}$;
—(CH$_2$)$_p$(CHR$^{61}$)$_s$NR$^{33}$R$^{34}$;
—(CH$_2$)$_p$(CHR$^{61}$)$_s$OCONR$^{33}$R$^{75}$; (CH$_2$)$_p$(CHR$^{61}$)$_s$NR$^{20}$CONR$^{33}$R$^{82}$;
—(CH$_2$)$_p$(CHR$^{61}$)$_s$COOR$^{57}$; —(CH$_2$)$_p$(CHR$^{61}$)$_s$CONR$^{58}$R$^{59}$;
—(CH$_2$)$_p$(CHR$^{61}$)$_s$PO(OR$^{60}$)$_2$;
—(CH$_2$)$_p$(CHR$^{61}$)$_s$SO$_2$R$^{62}$; or —(CH$_2$)$_o$(CHR$^{61}$)$_s$C$_6$H$_4$R$^8$;

R$^{19}$ is lower alkyl; —(CH$_2$)$_p$(CHR$^{61}$)$_s$OR$^{55}$; —(CH$_2$)$_p$(CHR$^{61}$)$_s$SR$^{56}$;
—(CH$_2$)$_p$(CHR$^{61}$)$_s$NR$^{33}$R$^{34}$;
—(CH$_2$)$_p$(CHR$^{61}$)$_s$OCONR$^{33}$R$^{75}$; —(CH$_2$)$_p$(CHR$^{61}$)$_s$NR$^{20}$CONR$^{33}$R$^{82}$;
—(CH$_2$)$_p$(CHR$^{61}$)$_s$COOR$^{57}$; —(CH$_2$)$_p$(CHR$^{61}$)$_s$CONR$^{58}$R$^{59}$;
—(CH$_2$)$_p$(CHR$^{61}$)$_s$PO(OR$^{60}$)$_2$;
—(CH$_2$)$_p$(CHR$^{61}$)$_s$SO$_2$R$^{62}$; or —(CH$_2$)$_o$(CHR$^{61}$)$_s$C$_6$H$_4$R$^8$; or R$^{18}$ and R$^{19}$ taken together can form: —(CH$_2$)$_{2-6}$—;
—(CH$_2$)$_2$O(CH$_2$)$_2$—; —(CH$_2$)$_2$S(CH$_2$)$_2$—; or —(CH$_2$)$_2$ NR$^{57}$(CH$_2$)$_2$—;

R$^{20}$ is H; alkyl; lower cycloalkyl; alkenyl; lower alkyl-aryl; or aryl-lower alkyl;

R$^{21}$ is H; alkyl; alkenyl; —(CH$_2$)$_o$(CHR$^{61}$)$_s$OR$^{55}$;
—(CH$_2$)$_o$(CHR$^{61}$)$_s$SR$^{56}$; —(CH$_2$)$_o$(CHR$^{61}$)$_s$NR$^{33}$R$^{34}$;
—(CH$_2$)$_o$(CHR$^{61}$)$_s$OCONR$^{33}$R$^{75}$; —(CH$_2$)$_o$(CHR$^{61}$)$_s$NR$^{20}$CONR$^{33}$R$^{82}$;
—(CH$_2$)$_o$(CHR$^{61}$)$_s$COOR$^{57}$; —(CH$_2$)$_o$(CHR$^{61}$)$_s$CONR$^{58}$R$^{59}$;
—(CH$_2$)$_o$(CHR$^{61}$)$_s$PO(OR$^{60}$)$_2$;
—(CH$_2$)$_o$(CHR$^{61}$)$_s$SO$_2$R$^{62}$; or —(CH$_2$)$_o$(CHR$^{61}$)$_s$C$_6$H$_4$R$^8$;

R$^{22}$ is H; alkyl; alkenyl; —(CH$_2$)$_o$(CHR$^{61}$)$_s$OR$^{55}$;
—(CH$_2$)$_o$(CHR$^{61}$)$_s$SR$^{56}$; —(CH$_2$)$_o$(CHR$^{61}$)$_s$NR$^{33}$R$^{34}$;
—(CH$_2$)$_o$(CHR$^{61}$)$_s$OCONR$^{33}$R$^{75}$; —(CH$_2$)$_o$(CHR$^{61}$)$_s$NR$^{20}$CONR$^{33}$R$^{82}$;
—(CH$_2$)$_o$(CHR$^{61}$)$_s$COOR$^{57}$; —(CH$_2$)$_o$(CHR$^{61}$)$_s$CONR$^{58}$R$^{59}$;
—(CH$_2$)$_o$(CHR$^{61}$)$_s$PO(OR$^{60}$)$_2$;
—(CH$_2$)$_o$(CHR$^{61}$)$_s$SO$_2$R$^{62}$; or —(CH$_2$)$_o$(CHR$^{61}$)$_s$C$_6$H$_4$R$^8$;

R$^{23}$ is alkyl; alkenyl; —(CH$_2$)$_o$(CHR$^{61}$)$_s$OR$^{55}$; —(CH$_2$)$_o$(CHR$^{61}$)$_s$SR$^{56}$;
—(CH$_2$)$_o$(CHR$^{61}$)$_s$NR$^{33}$R$^{34}$;

—(CH$_2$)$_o$(CHR$^{61}$)$_s$OCONR$^{33}$R$^{75}$; —(CH$_2$)$_o$(CHR$^{61}$)$_s$NR$^{20}$CONR$^{33}$R$^{82}$;
—(CH$_2$)$_o$(CHR$^{61}$)$_s$COOR$^{57}$; —(CH$_2$)$_o$(CHR$^{61}$)$_s$CONR$^{58}$R$^{59}$;
—(CH$_2$)$_o$(CHR$^{61}$)$_s$PO(OR$^{60}$)$_2$;
—(CH$_2$)$_o$(CHR$^{61}$)$_s$SO$_2$R$^{62}$; or —(CH$_2$)$_o$(CHR$^{61}$)$_s$C$_6$H$_4$R$^8$;

R$^{24}$ is alkyl; alkenyl; —(CH$_2$)$_o$(CHR$^{61}$)$_s$OR$^{55}$; —(CH$_2$)$_o$(CHR$^{61}$)$_s$SR$^{56}$;
—(CH$_2$)$_o$(CHR$^{61}$)$_s$NR$^{33}$R$^{34}$;
—(CH$_2$)$_o$(CHR$^{61}$)$_s$OCONR$^{33}$R$^{75}$; —(CH$_2$)$_o$(CHR$^{61}$)$_s$NR$^{20}$CONR$^{33}$R$^{82}$;
—(CH$_2$)$_o$(CHR$^{61}$)$_s$COOR$^{57}$; —(CH$_2$)$_o$(CHR$^{61}$)$_s$CONR$^{58}$R$^{59}$;
—(CH$_2$)$_o$(CHR$^{61}$)$_s$PO(OR$^{60}$)$_2$;
—(CH$_2$)$_o$(CHR$^{61}$)$_s$SO$_2$R$^{62}$; or —(CH$_2$)$_o$(CHR$^{61}$)$_s$C$_6$H$_4$R$^8$;

R$^{25}$ is H; alkyl; alkenyl; —(CH$_2$)$_m$(CHR$^{61}$)$_s$OR$^{55}$;
—(CH$_2$)$_m$(CHR$^{61}$)$_s$SR$^{56}$;
—(CH$_2$)$_m$(CHR$^{61}$)$_s$NR$^{33}$R$^{34}$; —(CH$_2$)$_m$(CHR$^{61}$)$_s$OCONR$^{33}$R$^{75}$;
—(CH$_2$)$_m$(CHR$^{61}$)$_s$NR$^{20}$CONR$^{33}$R$^{82}$; —(CH$_2$)$_o$(CHR$^{61}$)$_s$COOR$^{57}$;
—(CH$_2$)$_o$(CHR$^{61}$)$_s$CONR$^{58}$R$^{59}$; —(CH$_2$)$_o$(CHR$^{61}$)$_s$PO(OR$^{60}$)$_2$;
—(CH$_2$)$_o$(CHR$^{61}$)$_s$SO$_2$R$^{62}$; or —(CH$_2$)$_o$(CHR$^{61}$)$_s$C$_6$H$_4$R$^8$;

R$^{26}$ is H; alkyl; alkenyl; —(CH$_2$)$_m$(CHR$^{61}$)$_s$OR$^{55}$;
—(CH$_2$)$_m$(CHR$^{61}$)$_s$SR$^{56}$;
—(CH$_2$)$_m$(CHR$^{61}$)$_s$NR$^{33}$R$^{34}$; —(CH$_2$)$_m$(CHR$^{61}$)$_s$OCONR$^{33}$R$^{75}$;
—(CH$_2$)$_m$(CHR$^{61}$)$_s$NR$^{20}$CONR$^{33}$R$^{82}$; —(CH$_2$)$_o$(CHR$^{61}$)$_s$COOR$^{57}$;
—(CH$_2$)$_o$(CHR$^{61}$):CONR$^{58}$R$^{59}$; —(CH$_2$)$_o$(CHR$^{61}$)$_s$PO(OR$^{60}$)$_2$;
—(CH$_2$)$_o$(CHR$^{61}$)$_s$SO$_2$R$^{62}$; or —(CH$_2$)$_o$(CHR$^{61}$)$_s$C$_6$H$_4$R$^8$; or R$^{25}$ and R$^{26}$ taken together can form: —(CH$_2$)$_{2-6}$—;
—(CH$_2$)$_r$O(CH$_2$)$_r$—;
—(CH$_2$)$_r$S(CH$_2$)$_r$—; or —(CH$_2$)$_r$NR$^{57}$(CH$_2$)$_r$—;

R$^{27}$ is H; alkyl; alkenyl; —(CH$_2$)$_o$(CHR$^{61}$)$_s$OR$^{55}$;
—(CH$_2$)$_o$(CHR$^{61}$)$_s$SR$^{56}$; —(CH$_2$)$_o$(CHR$^{61}$)$_s$NR$^{33}$R$^{34}$;
—(CH$_2$)$_o$(CHR$^{61}$)$_s$COOR$^{57}$; —(CH$_2$)$_o$(CHR$^{61}$)$_s$CONR$^{58}$R$^{59}$;
—(CH$_2$)$_o$(CHR$^{61}$)$_s$OCONR$^{33}$R$^{75}$;
—(CH$_2$)$_o$(CHR$^{61}$)$_s$NR$^{20}$CONR$^{33}$R$^{82}$; —(CH$_2$)$_o$(CHR$^{61}$)$_s$PO(OR$^{60}$)$_2$;
—(CH$_2$)$_o$(CHR$^{61}$)$_s$ SO$_2$R$^{62}$; or —(CH$_2$)$_o$(CHR$^{61}$)$_s$C$_6$H$_4$R$^8$;

R$^{28}$ is alkyl; alkenyl; —(CH$_2$)$_o$(CHR$^{61}$)$_s$—OR$^{55}$;
—(CH$_2$)$_o$(CHR$^{61}$)$_s$SR$^{56}$; —(CH$_2$)$_o$(CHR$^{61}$)$_s$NR$^{33}$R$^{34}$;
—(CH$_2$)$_o$(CHR$^{61}$)$_s$OCONR$^{33}$R$^{75}$; —(CH$_2$)$_o$(CHR$^{61}$)$_s$NR$^{20}$CONR$^{33}$R$^{82}$;
—(CH$_2$)$_o$(CHR$^{61}$)$_s$COOR$^{57}$; —(CH$_2$)$_o$(CHR$^{61}$)$_s$CONR$^{58}$R$^{59}$;
—(CH$_2$)$_o$(CHR$^{61}$)$_s$PO(OR$^{60}$)$_2$;
—(CH$_2$)$_o$(CHR$^{61}$)$_s$SO$_2$R$^{62}$; or —(CH$_2$)$_o$(CHR$^{61}$)$_s$C$_6$H$_4$R$^8$;

R$^{29}$ is alkyl; alkenyl; —(CH$_2$)$_o$(CHR$^{61}$)$_s$OR$^{55}$; —(CH$_2$)$_o$(CHR$^{61}$)$_s$SR$^{56}$;
—(CH$_2$)$_o$(CHR$^{61}$)$_s$NR$^{33}$R$^{34}$;
—(CH$_2$)$_o$(CHR$^{61}$)$_s$OCONR$^{33}$R$^{75}$; —(CH$_2$)$_o$(CHR$^{61}$)$_s$NR$^{20}$CONR$^{33}$R$^{82}$;
—(CH$_2$)$_o$(CHR$^{61}$)$_s$COOR$^{57}$; —(CH$_2$)$_o$(CHR$^{61}$)$_s$CONR$^{58}$R$^{59}$;
—(CH$_2$)$_o$(CHR$^{61}$)$_s$PO(OR$^{60}$)$_2$;
—(CH$_2$)$_o$(CHR$^{61}$)$_s$SO$_2$R$^{62}$; or —(CH$_2$)$_o$(CHR$^{61}$)$_s$C$_6$H$_4$R$^8$;

R$^{33}$ is H; alkyl, alkenyl; —(CH$_2$)$_m$(CHR$^{61}$)$_s$OR$^{55}$;
—(CH$_2$)$_m$(CHR$^{61}$)$_s$NR$^{34}$R$^{63}$;
—(CH$_2$)$_m$(CHR$^{61}$)$_s$OCONR$^{75}$R$^{82}$; —(CH$_2$)$_m$(CHR$^{61}$)$_s$NR$^{20}$CONR$^{78}$R$^{82}$;
—(CH$_2$)$_o$(CHR$^{61}$)$_s$COR$^{64}$; —(CH$_2$)$_o$(CHR$^{61}$)$_6$—CONR$^{58}$R$^{59}$,
—(CH$_2$)$_o$(CHR$^{61}$)$_s$PO(OR$^{60}$)$_2$;
—(CH$_2$)$_o$(CHR$^{61}$)$_s$SO$_2$R$^{62}$; or —(CH$_2$)$_o$(CHR$^{61}$)$_s$C$_6$H$_4$R$^8$;

R$^{34}$ is H; lower alkyl; lower cycloalkyl; lower alkyl-aryl; aryl or aryl-lower alkyl; or R$^{33}$ and R$^{34}$ taken together can form: —(CH$_2$)$_{2-6}$—;
—(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—;

R$^{50}$ is H; lower alkyl; lower cycloalkyl; lower alkyl-aryl; or aryl-lower alkyl;

R$^{55}$ is H; lower alkyl; lower alkenyl; lower cycloalkyl; lower alkyl-aryl; aryl-lower alkyl;
—(CH$_2$)$_m$(CHR$^{61}$)$_s$OR$^{57}$;
—(CH$_2$)$_m$(CHR$^{61}$)$_s$NR$^{34}$R$^{63}$; —(CH$_2$)$_m$(CHR$^{61}$)$_s$OCONR$^{75}$R$^{82}$;
—(CH$_2$)$_m$(CHR$^{61}$)$_s$NR$^{20}$CONR$^{78}$R$^{82}$; —(CH$_2$)$_o$(CHR$^{61}$)$_s$—COR$^{64}$;
—(CH$_2$)$_o$(CHR$^{61}$)COOR$^{57}$; or
—(CH$_2$)$_o$(CHR$^{61}$)$_s$CONR$^{58}$R$^{59}$;

R$^{56}$ is H; lower alkyl; lower alkenyl; lower alkyl-aryl; aryl-lower alkyl;
—(CH$_2$)$_m$(CHR$^{61}$)$_s$OR$^{57}$;
—(CH$_2$)$_m$(CHR$^{61}$)$_s$R$^{34}$R$^{63}$; —(CH$_2$)$_m$(CHR$^{61}$)$_s$OCONR$^{75}$R$^{82}$;
—(CH$_2$)$_m$(CHR$^{61}$)$_s$NR$^{20}$CONR$^{78}$R$^{82}$; —(CH$_2$)$_o$(CHR$^{61}$)$_s$—COR$^{64}$; or
—(CH$_2$)$_o$(CHR$^{61}$)$_s$CONR$^{58}$R$^{59}$;

R$^{57}$ is H; lower alkyl; lower alkenyl; lower cycloalkyl; lower alkyl-aryl; aryl-lower alkyl;
lower alkyl-heteroaryl; or heteroaryl-lower alkyl;

R$^{58}$ is H; lower alkyl; lower alkenyl; lower cycloalkyl; lower alkyl-aryl; aryl-lower alkyl;
lower alkyl-heteroaryl; or heteroaryl-lower alkyl;

R$^{59}$ is H; lower alkyl; lower alkenyl; lower cycloalkyl; lower alkyl-aryl; aryl-lower alkyl;
lower alkyl-heteroaryl; or heteroaryl-lower alkyl; or R$^{58}$ and R$^{59}$ taken together can form: —(CH$_2$)$_{2-6}$—;
—(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—;

R$^{60}$ is H; lower alkyl; lower alkenyl; lower cycloalkyl; lower alkyl-aryl; aryl; or aryl-lower alkyl;

R$^{61}$ is alkyl; alkenyl; lower cycloalkyl; lower alkyl-aryl; lower alkyl-heteroaryl; aryl; heteroaryl;
aryl-lower alkyl; heteroaryl-lower alkyl; —(CH$_2$)$_p$OR$^{55}$;
—(CH$_2$)$_p$NR$^{33}$R$^{34}$; —(CH$_2$)$_p$OCONR$^{75}$R$^{82}$; —(CH$_2$)$_p$NR$^{20}$CONR$^{78}$R$^{82}$;
—(CH$_2$)$_o$COOR$^{37}$; or —(CH$_2$)$_o$PO(OR$^{60}$)$_2$;

R$^{62}$ is H; lower alkyl; lower alkenyl; lower cycloalkyl; lower alkyl-aryl; lower alkyl-heteroaryl; aryl;
heteroaryl; aryl-lower alkyl; or heteroaryl-lower alkyl;

R$^{63}$ is H; lower alkyl; lower alkenyl; lower cycloalkyl; lower alkyl-aryl; lower alkyl-heteroaryl; aryl; heteroaryl; aryl-lower alkyl; or heteroaryl-lower alkyl;
—COR$^{64}$; —COOR$^{57}$; —CONR$^{58}$R$^{59}$; —SO$_2$R$^{62}$; or —PO(OR$^{60}$)$_2$; or $R^{34}$ and $R^{63}$ taken together can form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—;

$R^{64}$ is H; lower alkyl; lower alkenyl; lower cycloalkyl; lower alkyl-aryl; lower alkyl-heteroaryl; aryl; heteroaryl; aryl-lower alkyl; or heteroaryl-lower alkyl;
—$(CH_2)_p(CHR^{61})_sOR^{65}$; —$(CH_2)_p(CHR^{61})_sSR^{66}$;
—$(CH_2)_p(CHR^{61})_sNR^{34}R^{63}$;
—$(CH_2)_p(CHR^{61})OCONR^{75}R^{82}$; or —$(CH_2)_p(CHR^{61})_sNR^{20}CONR^{78}R^{82}$;

$R^{65}$ is H; lower alkyl; lower alkenyl; lower cycloalkyl; lower alkyl-aryl; lower alkyl-heteroaryl; aryl; heteroaryl; aryl-lower alkyl; or heteroaryl-lower alkyl; —$COR^{57}$; —$COOR^{57}$; or —$CONR^{58}R^{59}$;

$R^{66}$ is H; lower alkyl; lower alkenyl; lower cycloalkyl; lower alkyl-aryl; lower alkyl-heteroaryl; aryl; heteroaryl; aryl-lower alkyl; or heteroaryl-lower alkyl; or —$CONR^{58}R^{59}$;

$R^{67}$ is H; Cl; Br; F; $NO_2$; —$NR^{34}COR^{57}$; —$CF_3$; CN; —$OCF_3$; —$OCHF_2$; —$OR^{57}$; —$SR^{62}$; lower alkyl; or lower alkenyl;

$R^{68}$ is H; Cl; Br; F; $NO_2$; —$NR^{34}COR^{57}$; —$CF_3$; CN; —$OCF_3$; —$OCHF_2$; —$OR^{57}$; —$SR^{62}$; lower alkyl; or lower alkenyl;

$R^{69}$ is H; Cl; Br; F; $NO_2$; —$NR^{34}COR^{57}$; —$CF_3$; CN; —$OCF_3$; —$OCHF_2$; —$OR^{57}$; —$SR^{62}$; lower alkyl; or lower alkenyl;

$R^{70}$ is H; Cl; Br; F; $NO_2$; —$NR^{34}COR^{57}$; —$CF_3$; CN; —$OCF_3$; —$OCHF_2$; —$OR^{57}$; —$SR^{62}$; lower alkyl; or lower alkenyl;

$R^{71}$ is lower alkyl; lower alkenyl; —$(CH_2)_p(CHR^{61})_sOR^{75}$;
—$(CH_2)_p(CHR^{61})_sSR^{75}$;
—$(CH_2)_p(CHR^{61})_sNR^{33}R^{34}$; —$(CH_2)_p(CHR^{61})_sOCONR^{33}R^{75}$;
—$(CH_2)_p(CHR^{61})_sNR^{20}CONR^{33}R^{82}$;
—$(CH_2)_o(CHR^{61})_sCOOR^{75}$; —$(CH_2)_pCONR^{58}R^{59}$;
—$(CH_2)_pPO(OR^{62})_2$;
—$(CH_2)_pSO_2R^{62}$; or
—$(CH_2)_o$—$C_6R^{67}R^{68}R^{69}R^{70}R^{76}$;

$R^{72}$ is alkyl; alkenyl; lower cycloalkcyl; —$(CH_2)_p(CHR^{61})_sOR^{85}$; or —$(CH_2)_p(CHR^{61})_sSR^{85}$;

$R^{73}$ is —$(CH_2)_rOR^{77}$; —$(CH_2)_rO(CH_2)OR^{77}$; —$(CH_2)_rS(CH_2)_rR^{77}$; or —$(CH_2)_rNR^{20}(CH_2)OR^{77}$;

$R^{74}$ is —$(CH_2)_pNR^{78}R^{79}$; —$(CH_2)_pNR^{77}R^{80}$; —$(CH_2)_pC(=NR^{80})NR^{78}R^{79}$;
—$(CH_2)_pC(=NOR^{50})NR^{78}R^{79}$;
—$(CH_2)_pC(=NNR^{78}R^{79})NR^{78}R^{79}$; —$(CH_2)_pNR^{80}C(=NR^{80})NR^{78}R^{79}$;
—$(CH_2)_pN=C(NR^{78}R^{80})NR^{79}R^{80}$; —$(CH_2)_pC_6H_4NR^{78}R^{79}$;
—$(CH_2)_pC_6H_4NR^{77}R^{80}$;
—$(CH_2)_pC_6H_4C(=NR^{80})NR^{78}R^{79}$; —$(CH_2)_pC_6H_4C(=NOR^{50})NR^{78}R^{79}$;
—$(CH_2)_pC_6H_4C(=NNR^{78}R^{79})NR^{78}R^{79}$; —$(CH_2)_pC_6H_4NR^{80}C(=NR^{80})NR^{78}R^{79}$;
—$(CH_2)_pC_6H_4C(=NR^{78}R^{80})NR^{79}R^{80}$; —$(CH_2)_rO(CH_2)_mNR^{78}R^{79}$;
—$(CH_2)_rO(CH_2)_mNR^{77}R^{80}$;
—$(CH_2)_rO(CH_2)_pC(=NR^{80})NR^{78}R^{79}$; —$(CH_2)_rO(CH_2)_pC(=NOR^{50})NR^{78}R^{79}$;
—$(CH_2)_rO(CH_2)_p(=NNR^{78}R^{79})NR^{78}R^{79}$;
—$(CH_2)_rO(CH_2)_mNR^{80}C(=NR^{80})NR^{78}R^{79}$;
—$(CH_2)_rO(CH_2)_mN=C(NR^{78}R^{80})NR^{79}R^{80}$;
—$(CH_2)_rO(CH_2)_pC_6H_4CNR^{78}R^{79}$;
—$(CH_2)_rO(CH_2)_pC_6H_4C(=NR^{80})NR^{78}R^{79}$;
—$(CH_2)_rO(CH_2)_pC_6H_4C(=NOR^{50})NR^{78}R^{79}$;
—$(CH_2)_rO(CH_2)_pC_6H_4C(=NNR^{78}R^{79})NR^{78}R^{79}$;
—$(CH_2)_rO(CH_2)_pC_6H_4NR^{80}(=NR^{80})NR^{78}R^{79}$;
—$(CH_2)_rS(CH_2)_mNR^{78}R^{79}$;
—$(CH_2)_rS(CH_2)_mNR^{77}R^{80}$; —$(CH_2)_rS(CH_2)_pC(=NR^{80})NR^{78}R^{79}$;
—$(CH_2)_rS(CH_2)_pC(=NOR^{50})NR^{78}R^{79}$;
—$(CH_2)_rS(CH_2)_pC(=NNR^{78}R^{79})NR^{78}R^{79}$;
—$(CH_2)_rS(CH_2)_mNR^{80}C(=NR^{80})NR^{78}R^{79}$;
—$(CH_2)_rS(CH_2)_mN=C(NR^{78}R^{80})NR^{79}R^{80}$;
—$(CH_2)_rS(CH_2)_pC_6H_4CNR^{78}R^{79}$; —$(CH_2)_rS(CH_2)_pC_6H_4C(=NR^{80})NR^{78}R^{79}$;
—$(CH_2)_rS(CH_2)_pC_6H_4C(=NOR^{50})NR^{78}R^{79}$;
—$(CH_2)_rS(CH_2)_pC_6H_4C(=NNR^{78}R^{79})NR^{78}R^{79}$;
—$(CH_2)_rS(CH_2)_pC_6H_4NR^{80}C(=NR^{80})NR^{78}R^{79}$;
—$(CH_2)_pNR^{80}COR^{64}$;
—$(CH_2)_pNR^{80}COR^{77}$;
—$(CH_2)_pNR^{80}CONR^{78}R^{79}$; or —$(CH_2)_pC_6H_4NR^{80}CONR^{78}R^{79}$;

$R^{75}$ is lower alkyl; lower alkenyl; lower cycloalkyl; lower-alkyl-aryl; or aryl-lower alkyl; or $R^{33}$ and $R^{75}$ taken together can form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; or $R^{75}$ and $R^{82}$ taken together can form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—;

$R^{76}$ is H; lower alkyl; lower alkenyl; lower cycloalkyl; lower-alkyl-aryl; aryl-lower alkyl;
—$(CH_2)_oOR^{72}$; —$(CH_2)_oSR^{72}$;
—$(CH_2)_oNR^{33}R^{34}$; —$(CH_2)_oOCONR^{33}R^{75}$; —$(CH_2)_oNR^{20}CONR^{33}R^{81}$;
—$(CH_2)_oCOOR^{75}$; —$(CH_2)_oCONR^{58}R^{59}$; —$(CH_2)_oPO(OR^{60})_2$;
—$(CH_2)_pSO_2R^{62}$; or
—$(CH_2)_oCOR^{64}$;

$R^{77}$ is —$C_6R^{67}R^{68}R^{69}R^{70}R^{76}$ with the proviso that at least two of $R^{67}$, $R^{68}$, $R^{69}$ and $R^{70}$ are H; or a heteroaryl group of one of the formulae

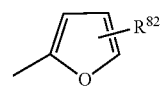

H1

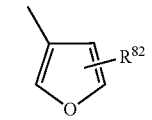

H2

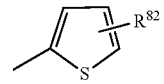

H3

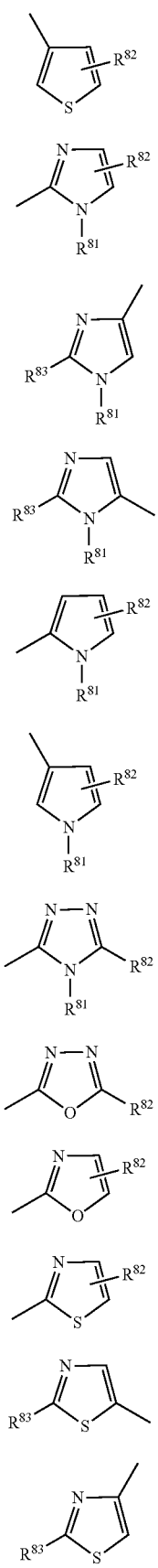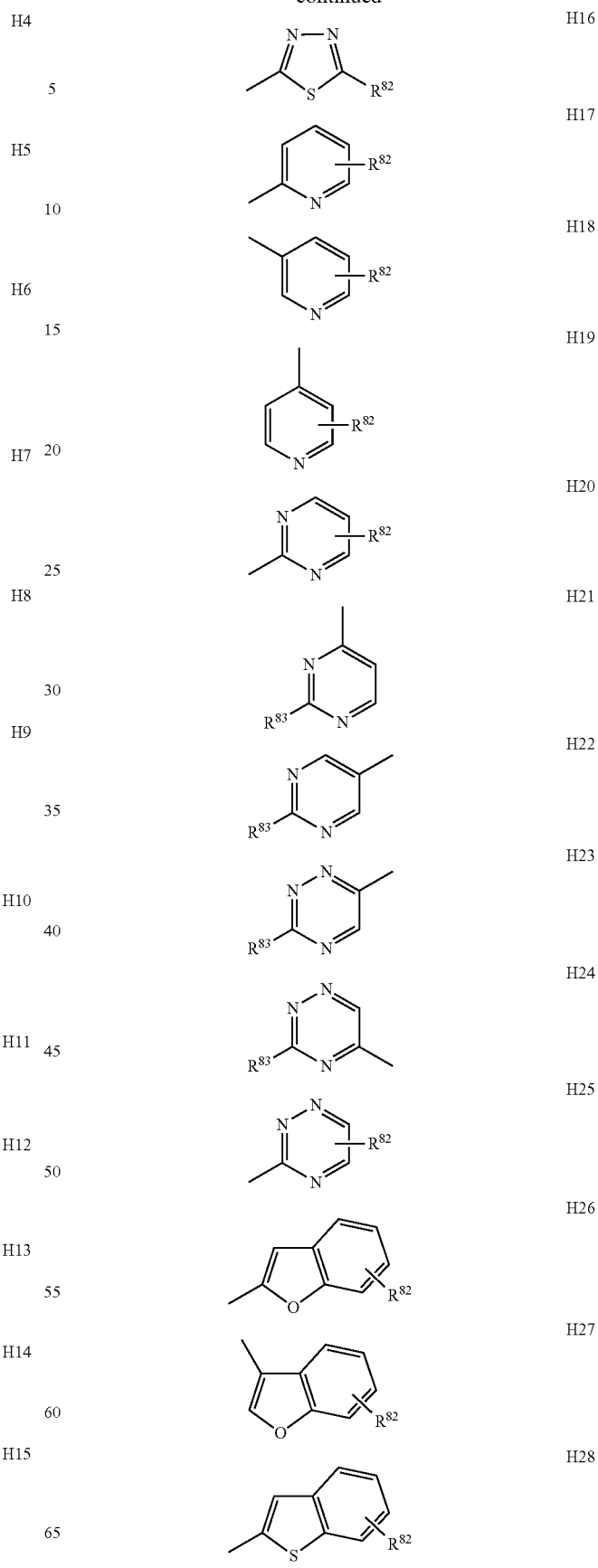

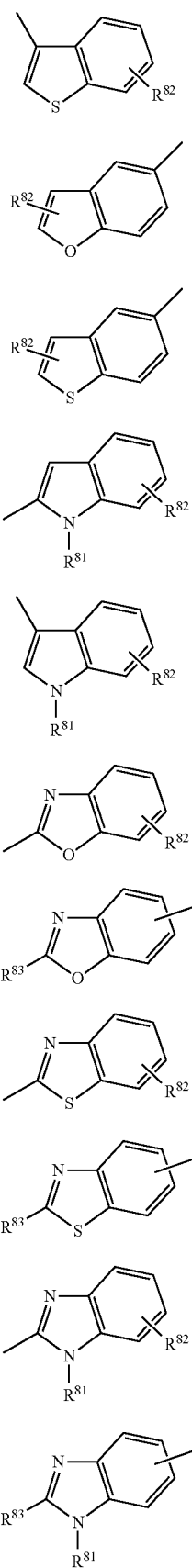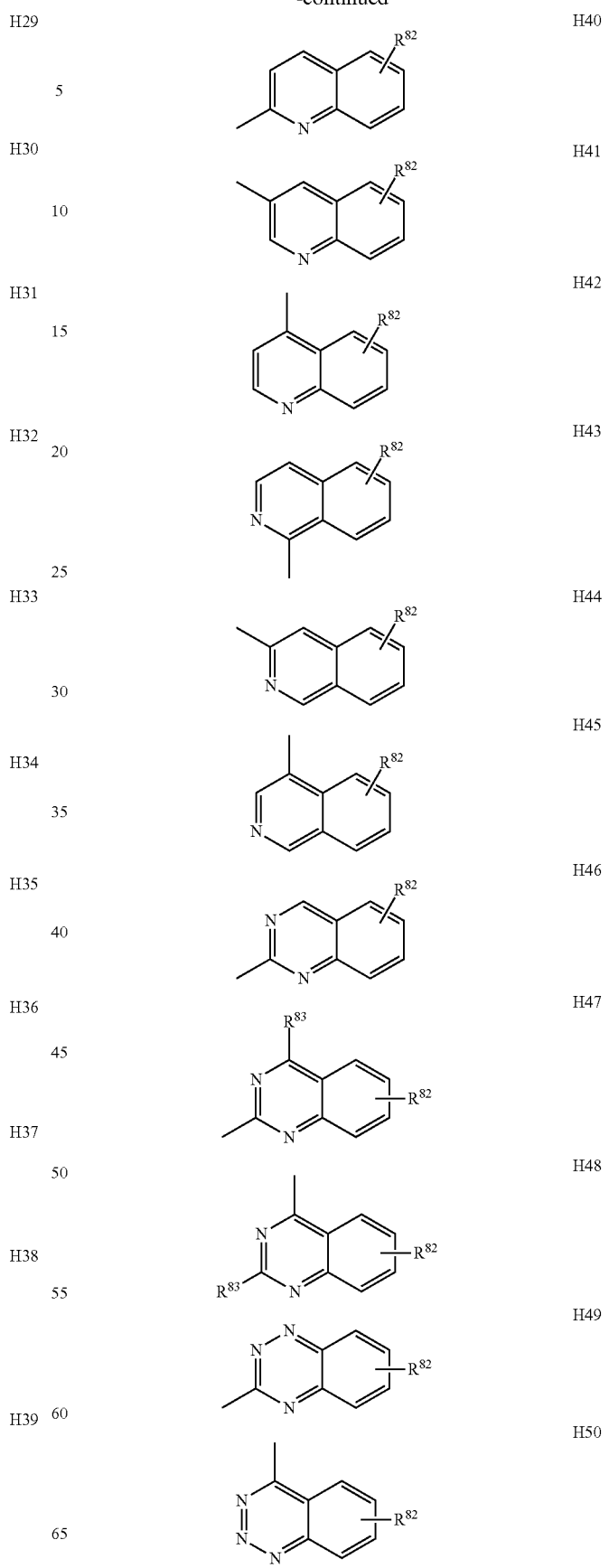

-continued

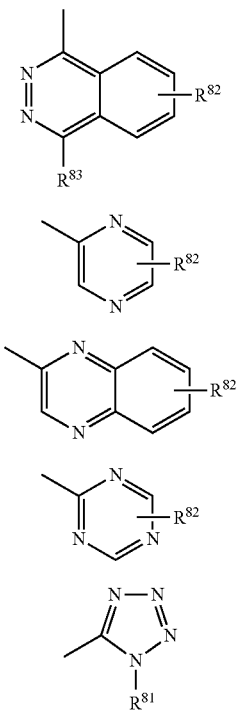

H51

H52

H53

H54

H55

R[78] is H; lower alkyl; lower cycloalkyl; lower alkyl-aryl; aryl; or aryl-lower alkyl; or R[78] and R[82] taken together can form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—;

R[79] is H; lower alkyl; lower alkyl-aryl; aryl; or aryl-lower alkyl; or

R[78] and R[79], taken together, can be —$(CH_2)_{2-7}$—; —$(CH_2)_2O(CH_2)_2$—; or —$(CH_2)_2NR^{57}(CH_2)_2$—;

R[80] is H; or lower alkyl;

R[81] is H; lower alkyl; lower cycloalkyl; lower alkyl-aryl; or aryl-lower alkyl; or R[33] and R[81] taken together can form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—;

R[82] is H; —$CF_3$; —$OCF_3$; —$OCHF_2$; lower alkyl; aryl; heteroaryl; or aryl-lower alkyl;

R[83] is H; lower alkyl; aryl; or —$NR^{78}R^{79}$;

R[84] is —$(CH_2)_p(CHR^{61})_sOH$; —$(CH_2)_pCOOR^{80}$; —$(CH_2)_p(CHR^{61})_sSH$; —$(CH_2)_pCONR^{78}R^{79}$; —$(CH_2)_pNR^{80}CONR^{78}R^{79}$; —$(CH_2)_pC_6H_4CONR^{78}R^{79}$; or —$(CH_2)_pC_6H_4NR^{80}CONR^{78}R^{79}$;

R[85] is lower alkyl; or lower alkenyl;

R[86] is R[74]; —$(CH_2)OR^{77}$; —$(CH_2)_o$—$CHR^{33}R^{75}$; R[84]; —$[(CH_2)_u$—$X']_t$—$(CH_2)_vNR^{78}R^{79}$; —$[(CH_2)_u$—$X']_t$—$(CH_2)_v$—$C(=NR^{80})NR^{78}R^{79}$; —$[(CH_2)_u$—$X']_t$—$(CH_2)_vOR^{78}$; —$[(CH_2)_u$—$X']_t$—$(CH_2)_v$—$CONR^{78}R^{79}$; —$[(CH_2)_u$—$X']_t$—$(CH_2)_v$—$NR^{80}CONR^{78}R^{79}$; —$[(CH_2)_u$—$X']_t$—$(CH_2)_vSR^{78}$ where X' is —O—, —$NR^{20}$—, —S—; or —OCOO—, u is 1-3, t is 1-6, and v is 1-3;

m is 2-4; o is 0-2; p is 1-4; q is 0-2; r is 1 or 2; s is 0 or 1;

the amino acid residue of type C is a residue of formula —$NR^{20}CH(R^{72})CO$—;

the amino acid residue of type D is a residue of formula —$NR^{20}CH(R^{73})CO$—;

the amino acid residue of type E is a residue of the formula —$NR^{20}CH(R^{74})CO$—;

the amino acid residue of type F is a residue of the formula —$NR^{20}CH(R^{84})CO$—;

the amino acid residue of type H is a residue of the one of the formulae —$NR^{20}$—$CH(CO$—$)$-alkylene-CH(CO—)—$NR^{20}$—;

—$NR^{20}$—$CH(CO$—$)$-alkenylene-CH(CO—)—$NR^{20}$—;

—$NR^{20}$—$CH(CO$—$)$-alkynylene-CH(CO—)—$NR^{20}$—;

—$NR^{20}$—$CH(CO$—$)$—$(CH_2)_pSS(CH_2)_p$—$CH(CO$—$)$—$NR^{20}$—;

—$NR^{20}$—$CH(CO$—$)$—$($—$(CH_2)_pNR^{20}CO(CH_2)_p$—$CH(CO$—$)$—$NR^{20}$—; and —$NR^{20}$—$CH(CO$—$)$—$($—$(CH_2)_pNR^{20}CONR^{20}(CH_2)_p$—$CH(CO$—$)$—$NR^{20}$—;

non-canonical amino acid residues designate those amino acid residues being neither glycine nor the L- or D-isomers of alanine, arginine, aspartic acid, asparagine, cysteine, glutamic acid, glutamine, histidine, isoleucine, leucine, lysine, methionine, phenylalanine, proline, serine, threonine, tryptophan, tyrosine and valine;

and pharmaceutically acceptable salts thereof.

2. Compounds according to claim 1 wherein A is a group of one of the formulae A1-A69;

R[1] is hydrogen or lower alkyl;

R[2] is H; lower alkyl; lower alkenyl;

—$(CH_2)_pOR^{55}$ (where R[55]: lower alkyl; or lower alkenyl); —$(CH_2)_pSR^{56}$ (where R[56]: lower alkyl; or lower alkenyl); —$(CH_2)_pNR^{33}R^{34}$ (where R[33]: lower alkyl; or lower alkenyl; R[34]: H; or lower alkyl; or R[33] and R[34] taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where R[57]: H; or lower alkyl);

—$(CH_2)_pOCONR^{33}R^{75}$ (where R[33]: H; lower alkyl; or lower alkenyl; R[75]: lower alkyl; or R[33] and R[75] taken together form: —$(CH_2)_{2-6}$—); —$(CH_2)_2O(CH_2)_2$—; —$(CH_2)_2S(CH_2)_2$—; or —$(CH_2)_2NR^{57}(CH_2)_2$— (where R[57]: H; or lower alkyl);

—$(CH_2)_pNR^{20}CONR^{33}R^{81}$ (where R[20]: H; or lower alkyl; R[33]: H; lower alkyl; or lower alkenyl; R[81]: H; or lower alkyl; or R[33] and R[81] taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where R[57]: H; or lower alkyl);

—$(CH_2)_oN(R^{20})COR^{64}$ (where R[20]: H; or lower alkyl; R[64]: lower alkyl; or lower alkenyl);

—$(CH_2)_oCOOR^{57}$ (where R[57]: lower alkyl; or lower alkenyl);

—$(CH_2)_oCONR^{58}R^{59}$ (where R[58]: lower alkyl; or lower alkenyl; and R[59]: H; or lower alkyl; or R[58] and R[59] taken together form: —$(CH_2)_{2-6}$—; —$(CH_2)_2O(CH_2)_2$—;

—$(CH_2)_2S(CH_2)_2$—; or —$(CH_2)_2NR^{57}(CH_2)_2$— (where R[57]: H; or lower alkyl);

—$(CH_2)_oPO(OR^{60})_2$ (where R[60]: H; lower alkyl; or lower alkenyl);

—$(CH_2)_oSO_2R^{62}$ (where R[62]: lower alkyl; or lower alkenyl);

—$(CH_2)_qC_6H_4R^8$ (where R[8]: H; F; Cl; $CF_3$; lower alkyl; lower alkenyl; or lower alkoxy); or —$(CH_2)_qCHN_4R^8$ R[3] is H; lower alkyl; lower alkenyl;

—$(CH_2)_oOR^{55}$ (where R[55]: lower alkyl; or lower alkenyl);

—$(CH_2)_oSR^{56}$ (where R[56]: lower alkyl; or lower alkenyl);

—$(CH_2)_oNR^{33}R^{34}$ (where $R^{33}$: lower alkyl; or lower alkenyl; $R^{34}$: H; or lower alkyl; or $R^{33}$ and $R^{34}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl);

—$(CH_2)_mOCONR^{33}R^{75}$ (where $R^{33}$: H; lower alkyl; or lower alkenyl; $R^{75}$: lower alkyl; or $R^{33}$ and $R^{75}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl);

—$(CH_2)_mNR^{20}CONR^{33}R^{81}$ (where $R^{20}$: H; or lower alkyl; $R^{33}$: H; lower alkyl; or lower alkenyl; $R^{81}$: H; or lower alkyl; or $R^{33}$ and $R^{81}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl);

—$(CH_2)_oN(R^{20})COR^{64}$ (where $R^{20}$: H; or lower alkyl; $R^{64}$: lower alkyl; or lower alkenyl);

—$(CH_2)_oCOOR^{57}$ (where $R^{57}$: lower alkyl; or lower alkenyl);

—$(CH_2)_oCONR^{58}R^{59}$ (where $R^{58}$: lower alkyl; or lower alkenyl; and $R^{59}$: H; or lower alkyl; or $R^{58}$ and $R^{59}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl);

—$(CH_2)_oPO(OR^{60})_2$ (where $R^{60}$: lower alkyl; or lower alkenyl);

—$(CH_2)_oSO_2R^{62}$ (where $R^{62}$: lower alkyl; or lower alkenyl); or

—$(CH_2)_qC_6H_4R^8$ (where $R^8$: H; F; Cl; $CF_3$; lower alkyl; lower alkenyl; or lower alkoxy)

$R^4$ is H; lower alkyl; lower alkenyl;

—$(CH_2)_mOR^{55}$ (where $R^{55}$: lower alkyl; or lower alkenyl);

—$(CH_2)_mSR^{56}$ (where $R^{56}$: lower alkyl; or lower alkenyl);

—$(CH_2)_mNR^{33}R^{34}$ (where $R^{33}$: lower alkyl; or lower alkenyl; $R^{34}$: H; or lower alkyl; or $R^{33}$ and $R^{34}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl);

—$(CH_2)_mOCONR^{33}R^{75}$ (where $R^{33}$: H; lower alkyl; or lower alkenyl; $R^{75}$: lower alkyl;

or $R^{33}$ and $R^{75}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl);

—$(CH_2)_mNR^{20}CONR^{33}R^{81}$ (where $R^{20}$: H; or lower alkyl; $R^{33}$: H; lower alkyl; or lower alkenyl; $R^{81}$: H; or lower alkyl; or $R^{33}$ and $R^{81}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl);

—$(CH_2)_mN(R^{20})COR^{64}$ (where $R^{20}$: H; or lower alkyl; $R^{64}$: lower alkyl; or lower alkenyl);

—$(CH_2)_oCOOR^{57}$ (where $R^{57}$: lower alkyl; or lower alkenyl);

—$(CH_2)_oCONR^{58}R^{59}$ (where $R^{58}$: lower alkyl; or lower alkenyl; and $R^{59}$: H; or lower alkyl; or $R^{58}$ and $R^{59}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl);

—$(CH_2)_oPO(OR^{60})_2$ (where $R^{60}$: lower alkyl; or lower alkenyl);

—$(CH_2)_oSO_2R^{62}$ (where $R^{62}$: lower alkyl; or lower alkenyl); or

—$(CH_2)_qC_6H_4R^8$ (where $R^8$: H; F; Cl; $CF_3$; lower alkyl; lower alkenyl; or lower alkoxy)

$R^5$ is lower alkyl; lower alkenyl;

—$(CH_2)_mOR^{55}$ (where $R^{55}$: lower alkyl; or lower alkenyl);

—$(CH_2)_mSR^{56}$ (where $R^{56}$: lower alkyl; or lower alkenyl);

—$(CH_2)_mNR^{33}R^{34}$ (where $R^{33}$: lower alkyl; or lower alkenyl; $R^{34}$: H; or lower alkyl; or $R^{33}$ and $R^{34}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl);

—$(CH_2)_mOCONR^{33}R^{75}$ (where $R^{33}$: H; lower alkyl; or lower alkenyl; $R^{75}$: lower alkyl; or $R^{33}$ and $R^{75}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl);

—$(CH_2)_mNR^{20}CONR^{33}R^{81}$ (where $R^{20}$: H; or lower alkyl; $R^{33}$: H; lower alkyl; or lower alkenyl; $R^{81}$: H; or lower alkyl; or $R^{33}$ and $R^{81}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl);

—$(CH_2)_mN(R^{20})COR^{64}$ (where $R^{20}$: H; or lower alkyl; $R^{64}$: alkyl; alkenyl; aryl; aryl-lower alkyl; or heteroaryl-lower alkyl);

—$(CH_2)_oCOOR^{57}$ (where $R^{57}$: lower alkyl; or lower alkenyl);

—$(CH_2)_oCONR^{58}R^{59}$ (where $R^{58}$: lower alkyl; or lower alkenyl; and $R^{59}$: H; or lower alkyl; or $R^{58}$ and $R^{59}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl);

—$(CH_2)_oPO(OR^{60})_2$ (where $R^{60}$: lower alkyl; or lower alkenyl);

—$(CH_2)_oSO_2R^{62}$ (where $R^{62}$: lower alkyl; or lower alkenyl); or

—$(CH_2)_qC_6H_4R^8$ (where $R^8$: H; F; Cl; $CF_3$; lower alkyl; lower alkenyl; or lower alkoxy)

$R^6$ is H; lower alkyl; lower alkenyl;

—$(CH_2)_oOR^{55}$ (where $R^{55}$: lower alkyl; or lower alkenyl);

—$(CH_2)_oSR^{56}$ (where $R^{56}$: lower alkyl; or lower alkenyl);

—$(CH_2)_oNR^{33}R^{34}$ (where $R^{33}$: lower alkyl; or lower alkenyl; $R^{34}$: H; or lower alkyl; or $R^{33}$ and $R^{34}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl);

—$(CH_2)_oOCONR^{33}R^{75}$ (where $R^{33}$: H; lower alkyl; or lower alkenyl; $R^{75}$: lower alkyl; or $R^{33}$ and $R^{75}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl);

—$(CH_2)_oNR^{20}CONR^{33}R^{81}$ (where $R^{20}$: H; or lower alkyl; $R^{33}$: H; lower alkyl; or lower alkenyl; $R^{81}$: H; or lower alkyl; or $R^{33}$ and $R^{81}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl);

—$(CH_2)_oN(R^{20})COR^{64}$ (where $R^{20}$: H; or lower alkyl; $R^{64}$: lower alkyl; or lower alkenyl);

—$(CH_2)_oCOOR^{57}$ (where $R^{57}$: lower alkyl; or lower alkenyl);

—(CH$_2$)$_o$CONR$^{58}$R$^{59}$ (where R$^{58}$: lower alkyl; or lower alkenyl; and R$^{59}$: H; or lower alkyl; or R$^{58}$ and R$^{59}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$— (where R$^{57}$: H; or lower alkyl);
—(CH$_2$)$_o$PO(OR$^{60}$)$_2$ (where R$^{60}$: lower alkyl; or lower alkenyl);
—(CH$_2$)$_o$SO$_2$R$^{62}$ (where R$^{62}$: lower alkyl; or lower alkenyl); or
—(CH$_2$)$_q$C$_6$H$_4$R$^8$ (where R$^8$: H; F; Cl; CF$_3$; lower alkyl; lower alkenyl; or lower alkoxy)

R$^7$ is lower alkyl; lower alkenyl;
—(CH$_2$)$_q$OR$^{55}$ (where R$^{55}$: lower alkyl; or lower alkenyl);
—(CH$_2$)$_q$SR$^{56}$ (where R$^{56}$: lower alkyl; or lower alkenyl);
—(CH$_2$)$_q$NR$^{33}$R$^{34}$ (where R$^{33}$: lower alkyl; or lower alkenyl; R$^{34}$: H; or lower alkyl; or R$^{33}$ and R$^{34}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$— (where R$^{57}$: H; or lower alkyl);
—(CH$_2$)$_q$OCONR$^{33}$R$^{75}$ (where R$^{33}$: H; lower alkyl; or lower alkenyl; R$^{75}$: lower alkyl; or R$^{33}$ and R$^{75}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$— (where R$^{57}$: H; or lower alkyl);
—(CH$_2$)$_q$NR$^{20}$CONR$^{33}$R (where R$^{20}$: H; or lower alkyl; R$^{33}$: H; lower alkyl; or lower alkenyl; R$^{81}$: H; or lower alkyl; or R$^{33}$ and R$^{81}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$— (where R$^{57}$: H; or lower alkyl);
—(CH$_2$)$_q$N(R$^{20}$)COR$^{64}$ (where R$^{20}$: H; or lower alkyl; R$^{64}$: lower alkyl; or lower alkenyl);
—(CH$_2$)$_r$COOR$^{57}$ (where R$^{57}$: lower alkyl; or lower alkenyl);
—(CH$_2$)$_q$CONR$^{58}$R$^{59}$ (where R$^{58}$: lower alkyl; or lower alkenyl; and R$^{59}$: H; or lower alkyl; or R$^{58}$ and R$^{59}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$— (where R$^{57}$: H; or lower alkyl);
—(CH$_2$)$_r$PO(OR$^{60}$)$_2$ (where R$^{60}$: lower alkyl; or lower alkenyl);
—(CH$_2$)$_r$SO$_2$R$^{62}$ (where R$^{62}$: lower alkyl; or lower alkenyl); or
—(CH$_2$)$_q$C$_6$H$_4$R$^8$ (where R$^8$: H; F; Cl; CF$_3$; lower alkyl; lower alkenyl; or lower alkoxy)

R$^8$ is H; F; Cl; CF$_3$; lower alkyl; lower alkenyl;
—(CH$_2$)$_o$OR$^{55}$ (where R$^{55}$: lower alkyl; or lower alkenyl);
—(CH$_2$)$_o$SR$^{56}$ (where R$^{56}$: lower alkyl; or lower alkenyl);
—(CH$_2$)$_o$NR$^{33}$R$^{34}$ (where R$^{33}$: lower alkyl; or lower alkenyl; R$^{34}$: H; or lower alkyl; or R$^{33}$ and R$^{34}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$— (where R$^{57}$: H; or lower alkyl);
—(CH$_2$)$_o$OCONR$^{33}$R$^{75}$ (where R$^{33}$: H; or lower alkyl; or lower alkenyl; R$^{75}$: lower alkyl; or R$^{33}$ and R$^{75}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$— (where R$^{57}$: H; or lower alkyl);
—(CH$_2$)$_o$NR$^{20}$CONR$^{33}$R$^{81}$ (where R$^{20}$: H; or lower alkyl; R$^{33}$: H; lower alkyl; or lower alkenyl; R$^{81}$: H; or lower alkyl; or R$^{33}$ and R$^{81}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$— (where R$^{57}$: H; or lower alkyl);
—(CH$_2$)$_o$N(R$^{20}$)COR$^{64}$ (where R$^{20}$: H; or lower alkyl; R$^{64}$: lower alkyl; or lower alkenyl);
—(CH$_2$)$_o$COOR$^{57}$ (where R$^{57}$: lower alkyl; or lower alkenyl);
—(CH$_2$)$_o$CONR$^{58}$R$^{59}$ (where R$^{58}$: lower alkyl; or lower alkenyl; and R$^{59}$: H; or lower alkyl; or R$^{58}$ and R$^{59}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$— (where R$^{57}$: H; or lower alkyl);
—(CH$_2$)$_o$PO(OR$^{60}$)$_2$ (where R$^{60}$: lower alkyl; or lower alkenyl);
—(CH$_2$)$_o$SO$_2$R$^{62}$ (where R$^{62}$: lower alkyl; or lower alkenyl); or
(CH$_2$)$_q$C$_6$H$_4$R$^8$ (where R$^8$: H; F; Cl; CF$_3$; lower alkyl; lower alkenyl; or lower alkoxy)

R$^9$ is lower alkyl; lower alkenyl;
—(CH$_2$)$_o$OR$^{55}$ (where R$^{55}$: lower alkyl; or lower alkenyl);
—(CH$_2$)$_o$SR$^{56}$ (where R$^{56}$: lower alkyl; or lower alkenyl);
—(CH$_2$)$_o$NR$^{33}$R$^{34}$ (where R$^{33}$: lower alkyl; or lower alkenyl; R$^{34}$: H; or lower alkyl; or R$^{33}$ and R$^{34}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$— (where R$^{57}$: H; or lower alkyl);
—(CH$_2$)$_o$OCONR$^{33}$R$^{75}$ (where R$^{33}$: H; lower alkyl; or lower alkenyl; R$^{75}$: lower alkyl; or R$^{33}$ and R$^{75}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$— (where R$^{57}$: H; or lower alkyl);
—(CH$_2$)$_m$NR$^{20}$CONR$^{33}$R$^{81}$ (where R$^{20}$: H; or lower alkyl; R$^{33}$: H; lower alkyl; or lower alkenyl; R$^{81}$: H; or lower alkyl; or R$^{33}$ and R$^{81}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$— (where R$^{57}$: H; or lower alkyl);
—(CH$_2$)$_o$N(R$^{20}$)COR$^{64}$ (where R$^{20}$: H; or lower alkyl; R$^{64}$: lower alkyl; or lower alkenyl);
—(CH$_2$)$_o$COOR$^{57}$ (where R$^{57}$: lower alkyl; or lower alkenyl);
—(CH$_2$)$_o$CONR$^{58}$R$^{59}$ (where R$^{58}$: lower alkyl; or lower alkenyl; and R$^{59}$: H; or lower alkyl; or R$^{58}$ and R$^{59}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$— (where R$^{57}$: H; or lower alkyl);
—(CH$_2$)$_o$PO(OR$^{60}$)$_2$ (where R$^{60}$: lower alkyl; or lower alkenyl);
—(CH$_2$)$_o$SO$_2$R$^{62}$ (where R$^{62}$: lower alkyl; or lower alkenyl); or
—(CH$_2$)$_q$C$_6$H$_4$R$^8$ (where R$^8$: H; F; Cl; CF$_3$; lower alkyl; lower alkenyl; or lower alkoxy)

R$^{10}$ is lower alkyl; lower alkenyl;
—(CH$_2$)$_o$OR$^{55}$ (where R$^{55}$: lower alkyl; or lower alkenyl);
—(CH$_2$)$_o$SR$^{56}$ (where R$^{56}$: lower alkyl; or lower alkenyl);
—(CH$_2$)$_o$NR$^{33}$R$^{34}$ (where R$^{33}$: lower alkyl; or lower alkenyl; R$^{34}$: H; or lower alkyl; or R$^{33}$ and R$^{34}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$— (where R$^{57}$: H; or lower alkyl);
—(CH$_2$)$_o$OCONR$^{33}$R$^{75}$ (where R$^{33}$: H; lower alkyl; or lower alkenyl; R$^{75}$: lower alkyl; or R$^{33}$ and R$^{75}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$— (where R$^{57}$: H; or lower alkyl);

—(CH$_2$)$_o$NR$^{20}$CONR$^{33}$R$^{81}$ (where R$^{20}$: H; or lower alkyl; R$^{33}$: H; lower alkyl; or lower alkenyl; R$^{81}$: H; or lower alkyl; or R$^{33}$ and R$^{81}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$— (where R$^{57}$: H; or lower alkyl);

—(CH$_2$)$_o$N(R$^{20}$)COR$^{64}$ (where R$^{20}$: H; or lower alkyl; R$^{64}$: lower alkyl; or lower alkenyl);

—(CH$_2$)$_o$COOR$^{57}$ (where R$^{57}$: lower alkyl; or lower alkenyl);

—(CH$_2$)$_o$CONR$^{58}$R$^{59}$ (where R$^{58}$: lower alkyl; or lower alkenyl; and R$^{59}$: H; or lower alkyl; or R$^{58}$ and R$^{59}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$— (where R$^{57}$: H; or lower alkyl);

—(CH$_2$)$_o$PO(OR$^{60}$)$_2$ (where R$^{60}$: lower alkyl; or lower alkenyl);

—(CH$_2$)$_o$SO$_2$R$^{62}$ (where R$^{62}$: lower alkyl; or lower alkenyl); or

—(CH$_2$)$_q$C$_6$H$_4$R$^8$ (where R$^8$: H; F; Cl; CF$_3$; lower alkyl; lower alkenyl; or lower alkoxy)

R$^{11}$ is H; lower alkyl; lower alkenyl;

—(CH$_2$)$_m$OR$^{55}$ (where R$^{55}$: lower alkyl; or lower alkenyl);

—(CH$_2$)$_m$SR$^{56}$ (where R$^{56}$: lower alkyl; or lower alkenyl);

—(CH$_2$)$_m$NR$^{33}$R$^{34}$ (where R$^{33}$: lower alkyl; or lower alkenyl; R$^{34}$: H; or lower alkyl; or R$^{33}$ and R$^{34}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$— (where R$^{57}$: H; or lower alkyl);

—(CH$_2$)$_m$OCONR$^{33}$R$^{75}$ (where R$^{33}$: H; lower alkyl; or lower alkenyl; R$^{75}$: lower alkyl; or R$^{33}$ and R$^{75}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$— (where R$^{57}$: H; or lower alkyl);

—(CH$_2$)$_m$NR$^{20}$CONR$^{33}$R$^{81}$ (where R$^{20}$: H; or lower alkyl; R$^{33}$: H; lower alkyl; or lower alkenyl; R$^{81}$: H; or lower alkyl; or R$^{33}$ and R$^{81}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$— (where R$^{57}$: H; or lower alkyl);

—(CH$_2$)$_m$N(R$^{20}$)COR$^{64}$ (where R$^{20}$: H; or lower alkyl; R$^{64}$: lower alkyl; or lower alkenyl);

—(CH$_2$)$_o$COOR$^{57}$ (where R$^{57}$: lower alkyl; or lower alkenyl);

—(CH$_2$)$_o$CONR$^{58}$R$^{59}$ (where R$^{58}$: lower alkyl; or lower alkenyl; and R$^{59}$: H; or lower alkyl; or R$^{58}$ and R$^{59}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$— (where R$^{57}$: H; or lower alkyl);

—(CH$_2$)$_o$PO(OR$^{60}$)$_2$ (where R$^{60}$: lower alkyl; or lower alkenyl);

—(CH$_2$)$_o$SO$_2$R$^{62}$ (where R$^{62}$: lower alkyl; or lower alkenyl); or

—(CH$_2$)$_q$C$_6$H$_4$R$^8$ (where R$^8$: H; F; Cl; CF$_3$; lower alkyl; lower alkenyl; or lower alkoxy)

R$^{12}$ is H; lower alkyl; lower alkenyl;

—(CH$_2$)$_m$OR$^{55}$ (where R$^{55}$: lower alkyl; or lower alkenyl);

—(CH$_2$)$_m$SR$^{56}$ (where R$^{56}$: lower alkyl; or lower alkenyl);

—(CH$_2$)$_m$NR$^{33}$R$^{34}$ (where R$^{33}$: lower alkyl; or lower alkenyl; R$^{34}$: H; or lower alkyl; or R$^{33}$ and R$^{34}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$— (where R$^{57}$: H; or lower alkyl);

—(CH$_2$)$_m$OCONR$^{33}$R$^{75}$ (where R$^{33}$: H; lower alkyl; or lower alkenyl; R$^{75}$: lower alkyl; or R$^{33}$ and R$^{75}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$— (where R$^{57}$: H; or lower alkyl);

—(CH$_2$)$_m$NR$^{20}$CONR$^{33}$R$^{81}$ (where R$^{20}$: H; or lower alkyl; R$^{33}$: H; lower alkyl; or lower alkenyl; R$^{81}$: H; or lower alkyl; or R$^{33}$ and R$^{81}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$— (where R$^{57}$: H; or lower alkyl);

—(CH$_2$)$_m$N(R$^{20}$)COR$^{64}$ (where R$^{20}$: H; or lower alkyl; R$^{64}$: lower alkyl; or lower alkenyl);

—(CH$_2$)$_r$COOR$^{57}$ (where R$^{57}$: lower alkyl; or lower alkenyl);

—(CH$_2$)$_r$CONR$^{58}$R$^{59}$ (where R$^{58}$: lower alkyl; or lower alkenyl; and R$^{59}$: H; or lower alkyl; or R$^{58}$ and R$^{59}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$— (where R$^{57}$: H; or lower alkyl);

—(CH$_2$)$_r$PO(OR$^{60}$)$_2$ (where R$^{60}$: lower alkyl; or lower alkenyl);

—(CH$_2$)$_o$SO$_2$R$^{62}$ (where R$^{62}$: lower alkyl; or lower alkenyl); or

—(CH$_2$)$_q$C$_6$H$_4$R$^8$ (where R$^8$: H; F; Cl; CF$_3$; lower alkyl; lower alkenyl; or lower alkoxy)

R$^{13}$ is lower alkyl; lower alkenyl;

—(CH$_2$)$_q$OR$^{55}$ (where R$^{55}$: lower alkyl; or lower alkenyl);

—(CH$_2$)$_q$SR$^{56}$ (where R$^{56}$: lower alkyl; or lower alkenyl);

—(CH$_2$)$_q$NR$^{33}$R$^{34}$ (where R$^{33}$: lower alkyl; or lower alkenyl; R$^{34}$: H; or lower alkyl; or R$^{33}$ and R$^{34}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$— (where R$^{57}$: H; or lower alkyl);

—(CH$_2$)$_q$OCONR$^{33}$R$^{75}$ (where R$^{33}$: H; lower alkyl; or lower alkenyl; R$^{75}$: lower alkyl; or R$^{33}$ and R$^{75}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$— (where R$^{57}$: H; or lower alkyl);

—(CH$_2$)$_q$NR$^{20}$CONR$^{33}$R$^{81}$ (where R$^{20}$: H; or lower alkyl; R$^{33}$: H; lower alkyl; or lower alkenyl; R$^{81}$: H; or lower alkyl; or R$^{33}$ and R$^{81}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$— (where R$^{57}$: H; or lower alkyl);

—(CH$_2$)$_q$N(R$^{20}$)COR$^{64}$ (where R$^{20}$: H; or lower alkyl; R$^{64}$: lower alkyl; or lower alkenyl);

—(CH$_2$)$_r$COO$^{57}$ (where R$^{57}$: lower alkyl; or lower alkenyl);

—(CH$_2$)$_q$CONR$^{58}$R$^{59}$ (where R$^{58}$: lower alkyl; or lower alkenyl; and R$^{59}$: H; or lower alkyl; or R$^{58}$ and R$^{59}$ taken together form: —(CH$_2$)$_{2-6}$—; —(CH$_2$)$_2$O (CH$_2$)$_2$—;

—(CH$_2$)$_2$S(CH$_2$)$_2$—; or —(CH$_2$)$_2$NR$^{57}$(CH$_2$)$_2$— (where R$^{57}$: H; or lower alkyl);

—(CH$_2$)$_r$PO(OR$^{60}$)$_2$ (where R$^{60}$: lower alkyl; or lower alkenyl);

—(CH$_2$)$_r$SO$_2$R$^{62}$ (where R$^{62}$: lower alkyl; or lower alkenyl); or

—$(CH_2)_qC_6H_4R^8$ (where $R^8$: H; F; Cl; $CF_3$; lower alkyl; lower alkenyl; or lower alkoxy)

$R^{14}$ is H; lower alkyl; lower alkenyl;
- —$(CH_2)_mOR^{55}$ (where $R^{55}$: lower alkyl; or lower alkenyl);
- —$(CH_2)_mSR^{56}$ (where $R^{56}$: lower alkyl; or lower alkenyl);
- —$(CH_2)_mNR^{33}R^{34}$ (where $R^{33}$: lower alkyl; or lower alkenyl; $R^{34}$: H; or lower alkyl; or $R^{33}$ and $R^{34}$ taken together form: —$(CH_2)_{2-6}$—; —$(CH_2)_2O(CH_2)_2$—; —$(CH_2)_2S(CH_2)_2$—; or
- —$(CH_2)_2NR^{57}(CH_2)_2$— (where $R^{57}$: H; or lower alkyl);
- —$(CH_2)_mOCONR^{33}R^{75}$ (where $R^{33}$: H; lower alkyl; or lower alkenyl; $R^{75}$: lower alkyl; or $R^{33}$ and $R^{75}$ taken together form: —$(CH_2)_{2-6}$—; —$(CH_2)_2O(CH_2)_2$—; —$(CH_2)_2S(CH_2)_2$—; or
- —$(CH_2)_2NR^{57}(CH_2)_2$— (where $R^{57}$: H; or lower alkyl);
- —$(CH_2)_mNR^{20}CONR^{33}R^{81}$ (where $R^{20}$: H; or lower alkyl; $R^{33}$: H; lower alkyl; or lower alkenyl; $R^{81}$: H; or lower alkyl; or $R^{33}$ and $R^{81}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl);
- —$(CH_2)_mN(R^{20})COR^{64}$ (where $R^{20}$: H; lower alkyl; $R^{64}$: lower alkyl; or lower alkenyl);
- —$(CH_2)_oCOOR^{57}$ (where $R^{57}$: lower alkyl; or lower alkenyl);
- —$(CH_2)_oCONR^{58}R^{59}$ (where $R^{58}$: lower alkyl; or lower alkenyl; and $R^{59}$: H; or lower alkyl; or $R^{58}$ and $R^{59}$ taken together form: —$(CH_2)_{2-6}$—; —$(CH_2)_2O(CH_2)_2$—;
- —$(CH_2)_2S(CH_2)_2$—; or —$(CH_2)_2NR^{57}(CH_2)_2$— (where $R^{57}$: H; or lower alkyl);
- —$(CH_2)_oPO(OR^{60})_2$ (where $R^{60}$: lower alkyl; or lower alkenyl);
- —$(CH_2)_oSO_2R^{62}$ (where $R^{62}$: lower alkyl; or lower alkenyl);
- —$(CH_2)_qC_6H_4R^8$ (where $R^8$: H; F; Cl; $CF_3$; lower alkyl; lower alkenyl; or lower alkoxy)

$R^{15}$ is lower alkyl; lower alkenyl;
- —$(CH_2)_oOR^{55}$ (where $R^{55}$: lower alkyl; or lower alkenyl);
- —$(CH_2)_oSR^{56}$ (where $R^{56}$: lower alkyl; or lower alkenyl);
- —$(CH_2)_oNR^{33}R^{34}$ (where $R^{33}$: lower alkyl; or lower alkenyl; $R^{34}$: H; or lower alkyl; or $R^{33}$ and $R^{34}$ taken together form: —$(CH_2)_{2-6}$—; —$(CH_2)_2O(CH_2)_2$—; —$(CH_2)_2S(CH_2)_2$—; or
- —$(CH_2)_2NR^{57}(CH_2)_2$— (where $R^{57}$: H; or lower alkyl);
- —$(CH_2)_oOCONR^{33}R^{75}$ (where $R^{33}$: H; lower alkyl; or lower alkenyl; $R^{75}$: lower alkyl; or $R^{33}$ and $R^{75}$ taken together form: —$(CH_2)_{2-6}$—; —$(CH_2)_2O(CH_2)_2$—; —$(CH_2)_2S(CH_2)_2$—; or
- —$(CH_2)_2NR^{57}(CH_2)_2$— (where $R^{57}$: H; or lower alkyl);
- —$(CH_2)_oNR^{20}CONR^{33}R^{81}$ (where $R^{20}$: H; or lower alkyl; $R^{33}$: H; lower alkyl; or lower alkenyl; $R^{81}$: H; or lower alkyl; or $R^{33}$ and $R^{81}$ taken together form: —$(CH_2)_{2-6}$—;
- —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl);
- —$(CH_2)_oN(R^{20})COR^{64}$ (where $R^{20}$: H; or lower alkyl; $R^{64}$: lower alkyl; or lower alkenyl); particularly favoured being —$NR^{20}CO$-lower alkyl (where $R^{20}$: H; or lower alkyl);
- —$(CH_2)_oCOOR^{57}$ (where $R^{57}$: lower alkyl; or lower alkenyl);
- —$(CH_2)_oCONR^{58}R^{59}$ (where $R^{58}$: lower alkyl; or lower alkenyl; and $R^{59}$: H; or lower alkyl; or $R^{58}$ and $R^{59}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl);
- —$(CH_2)_oPO(OR^{60})_2$ (where $R^{60}$: lower alkyl; or lower alkenyl);
- —$(CH_2)_oSO_2R^{62}$ (where $R^{62}$: lower alkyl; or lower alkenyl); or
- —$(CH_2)_qC_6H_4R^8$ (where $R^8$: H; F; Cl; $CF_3$; lower alkyl; lower alkenyl; or lower alkoxy)

$R^{16}$ is lower alkyl; lower alkenyl;
- —$(CH_2)_oOR^{55}$ (where $R^{55}$: lower alkyl; or lower alkenyl);
- —$(CH_2)_oSR^{56}$ (where $R^{56}$: lower alkyl; or lower alkenyl);
- —$(CH_2)_oNR^{33}R^{34}$ (where $R^{33}$: lower alkyl; or lower alkenyl; $R^{34}$: H; or lower alkyl; or $R^{33}$ and $R^{34}$ taken together form: —$(CH_2)_{2-6}$—; —$(CH_2)_2O(CH_2)_2$—; —$(CH_2)_2S(CH_2)_2$—; or
- —$(CH_2)_2NR^{57}(CH_2)_2$— (where $R^{57}$: H; or lower alkyl);
- —$(CH_2)_oOCONR^{33}R^{75}$ (where $R^{33}$: H; lower alkyl; or lower alkenyl; $R^{75}$: lower alkyl; or $R^{33}$ and $R^{75}$ taken together form: —$(CH_2)_{2-6}$—; —$(CH_2)_2O(CH_2)_2$—; —$(CH_2)_2S(CH_2)_2$—; or
- —$(CH_2)_2NR^{57}(CH_2)_2$— (where $R^{57}$: H; or lower alkyl);
- —$(CH_2)_oNR^{20}CONR^{33}R^{81}$ (where $R^{20}$: H; or lower alkyl; $R^{33}$: H; lower alkyl; or lower alkenyl; $R^{81}$: H; or lower alkyl; or $R^{33}$ and $R^{81}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl);
- —$(CH_2)_oN(R^{20})COR^{64}$ (where $R^{20}$: H; or lower alkyl; $R^{64}$: lower alkyl; or lower alkenyl);
- —$(CH_2)_oCOOR^{57}$ (where $R^{57}$: lower alkyl; or lower alkenyl);
- —$(CH_2)_oCONR^{58}R^{59}$ (where $R^{58}$: lower alkyl; or lower alkenyl; and $R^{59}$: H; or lower alkyl; or $R^{58}$ and $R^{59}$ taken together form: —$(CH_2)_{2-6}$—; —$(CH_2)_2O(CH_2)_2$—;
- —$(CH_2)_2S(CH_2)_2$—; or —$(CH_2)_2NR^{57}(CH_2)_2$— (where $R^{57}$: H; or lower alkyl);
- —$(CH_2)_oPO(OR^{60})_2$ (where $R^{60}$: lower alkyl; or lower alkenyl);
- —$(CH_2)_oSO_2R^{62}$ (where $R^{62}$: lower alkyl; or lower alkenyl); or
- —$(CH_2)_qC_6H_4R^8$ (where $R^8$: H; F; Cl; $CF_3$; lower alkyl; lower alkenyl; or lower alkoxy)

$R^{17}$ is lower alkyl; lower alkenyl;
- —$(CH_2)_qOR^{55}$ (where $R^{55}$: lower alkyl; or lower alkenyl);
- —$(CH_2)_qSR^{56}$ (where $R^{56}$: lower alkyl; or lower alkenyl);
- —$(CH_2)_qNR^{33}R^{34}$ (where $R^{33}$: lower alkyl; or lower alkenyl; $R^{34}$: H; or lower alkyl; or $R^{33}$ and $R^{34}$ taken together form: —$(CH_2)_{2-6}$—; —$(CH_2)_2O(CH_2)_2$—; —$(CH_2)_2S(CH_2)_2$—; or
- —$(CH_2)_2NR^{57}(CH_2)_2$— (where $R^{57}$: H; or lower alkyl);
- —$(CH_2)_qOCONR^{33}R^{75}$ (where $R^{33}$: H; lower alkyl; or lower alkenyl; $R^{75}$: lower alkyl; or $R^{33}$ and $R^{75}$ taken together form: —$(CH_2)_{2-6}$—; —$(CH_2)_2O(CH_2)_2$—; —$(CH_2)_2S(CH_2)_2$—; or
- —$(CH_2)_2NR^{57}(CH_2)_2$— (where $R^{57}$: H; or lower alkyl);
- —$(CH_2)_qNR^{20}CONR^{33}R^{81}$ (where $R^{20}$: H; or lower alkyl; $R^{33}$: H; lower alkyl; or lower alkenyl; $R^{81}$: H; or lower alkyl; or $R^{33}$ and $R^{81}$ taken together form: —$(CH_2)_{2-6}$—;

—(CH$_2$)$_2$O(CH$_2$)$_2$—; —(CH$_2$)$_2$S(CH$_2$)$_2$—; or —(CH$_2$)$_2$NR$^{57}$(CH$_2$)$_2$— (where R$^{57}$: H; or lower alkyl);

—(CH$_2$)$_q$N(R$^{20}$)COR$^{64}$ (where R$^{20}$: H; or lower alkyl; R$^{64}$: lower alkyl; or lower alkenyl);

—(CH$_2$)$_r$COOR$^{57}$ (where R$^{57}$: lower alkyl; or lower alkenyl);

—(CH$_2$)$_q$CONR$^{58}$R$^{59}$ (where R$^{58}$: lower alkyl; or lower alkenyl; and R$^{59}$: H; or lower alkyl; or R$^{58}$ and R$^{59}$ taken together form: —(CH$_2$)$_{2-6}$—; —(CH$_2$)$_2$O(CH$_2$)$_2$—;

—(CH$_2$)$_2$S(CH$_2$)$_2$—; or —(CH$_2$)$_2$NR$^{57}$(CH$_2$)$_2$— (where R$^{57}$: H; or lower alkyl);

—(CH$_2$)$_r$PO(OR$^{60}$)$_2$ (where R$^{60}$: lower alkyl; or lower alkenyl);

—(CH$_2$)$_r$SO$_2$R$^{62}$ (where R$^{62}$: lower alkyl; or lower alkenyl); or

—(CH$_2$)$_q$C$_6$H$_4$R$^8$ (where R$^8$: H; F; Cl; CF$_3$; lower alkyl; lower alkenyl; or lower alkoxy).

3. Compounds according to claim 1 wherein A is a group of formula

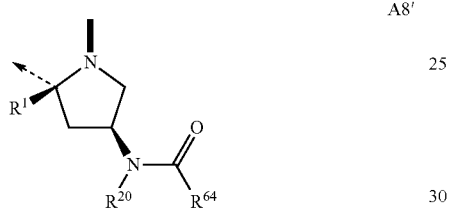

A8' wherein R$^{20}$ is H or lower alkyl; and R$^{64}$ is alkyl; alkenyl; aryl; aryl-lower alkyl; or heteroaryl-lower alkyl; especially those wherein R$^{64}$ is n-hexyl (A8'-1); n-heptyl (A8'-2); 4-(phenyl)benzyl (A8'-3); diphenylmethyl (A8'-4); 3-amino-propyl (A8'-5); 5-amino-pentyl (A8'-6); methyl (A8'-7); ethyl (A8'-8); isopropyl (A8'-9); isobutyl (A8'-10); n-propyl (A8'-11); cyclohexyl (A8'-12); cyclohexylmethyl (A8'-13); n-butyl (A8'-14); phenyl (A8'-15); benzyl (A8'-16); (3-indolyl)methyl (A8'-17); 2-(3-indolyl)ethyl (A8'-18); (4-phenyl)phenyl (A8'-19); and n-nonyl (A8'-20).

4. Compounds according to claim 1 wherein A is a group of one of the formulae A70 to A104;

R$^{18}$ is lower alkyl

R$^{19}$ is lower alkyl; lower alkenyl;

—(CH$_2$)$_p$OR$^{55}$ (where R$^{55}$: lower alkyl; or lower alkenyl);

—(CH$_2$)$_p$SR$^{56}$ (where R$^{56}$: lower alkyl; or lower alkenyl);

—(CH$_2$)$_p$NR$^{33}$R$^{34}$ (where R$^{33}$: lower alkyl; or lower alkenyl; R$^{34}$: H; or lower alkyl; or R$^{33}$ and R$^{34}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$— (where R$^{57}$: H; or lower alkyl);

—(CH$_2$)$_p$OCONR$^{33}$R$^{75}$ (where R$^{33}$: H; lower alkyl; or lower alkenyl; R$^{75}$: lower alkyl; or R$^{33}$ and R$^{75}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$— (where R$^{57}$: H; or lower alkyl);

—(CH$_2$)$_p$NR$^{20}$CONR$^{33}$R$^{81}$ (where R$^{20}$: H; or lower alkyl; R$^{33}$: H; lower alkyl; or lower alkenyl; R$^{81}$: H; or lower alkyl; or R$^{33}$ and R$^{81}$ taken together form: —(CH$_2$)$_{2-6}$—;

—(CH$_2$)$_2$O(CH$_2$)$_2$—; —(CH$_2$)$_2$S(CH$_2$)$_2$—; or —(CH$_2$)$_2$NR$^{57}$(CH$_2$)$_2$— (where R$^{57}$: H; or lower alkyl);

—(CH$_2$)$_p$N(R$^{20}$)COR$^{64}$ (where R$^{20}$: H; or lower alkyl; R$^{64}$: lower alkyl; or lower alkenyl);

—(CH$_2$)$_p$COOR$^{57}$ (where R$^{57}$: lower alkyl; or lower alkenyl);

—(CH$_2$)$_p$CONR$^{58}$R$^{59}$ (where R$^{58}$: lower alkyl; or lower alkenyl; and R$^{59}$: H; or lower alkyl; or R$^{58}$ and R$^{59}$ taken together form: —(CH$_2$)$_{2-6}$—; —(CH$_2$)$_2$O(CH$_2$)$_2$—;

—(CH$_2$)$_2$S(CH$_2$)$_2$—; or —(CH$_2$)$_2$NR$^{57}$(CH$_2$)$_2$— (where R$^{57}$: H; or lower alkyl);

—(CH$_2$)$_o$PO(OR$^{60}$)$_2$ (where R$^{60}$: lower alkyl; or lower alkenyl);

—(CH$_2$)$_p$SO$_2$R$^{62}$ (where R$^{62}$: lower alkyl; or lower alkenyl); or

—(CH$_2$)$_o$C$_6$H$_4$R$^8$ (where R$^8$: H; F; Cl; CF$_3$; lower alkyl; lower alkenyl; or lower alkoxy)

R$^{21}$ is H; lower alkyl; lower alkenyl;

—(CH$_2$)$_o$OR$^{55}$ (where R$^{55}$: lower alkyl; or lower alkenyl);

—(CH$_2$)$_o$SR$^{56}$ (where R$^{56}$: lower alkyl; or lower alkenyl);

—(CH$_2$)$_o$NR$^{33}$R$^{34}$ (where R$^{33}$: lower alkyl; or lower alkenyl; R$^{34}$: H; or lower alkyl; or R$^{33}$ and R$^{34}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$— (where R$^{57}$: H; or lower alkyl);

—(CH$_2$)$_o$OCONR$^{33}$R$^{75}$ (where R$^{33}$: H; lower alkyl; or lower alkenyl; R$^{75}$: lower alkyl; or R$^{33}$ and R$^{75}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$— (where R$^{57}$: H; or lower alkyl);

—(CH$_2$)$_o$NR$^{20}$CONR$^{33}$R$^{81}$ (where R$^{20}$: H; or lower alkyl; R$^{33}$: H; lower alkyl; or lower alkenyl; R$^{81}$: H; or lower alkyl; or R$^{33}$ and R$^{81}$ taken together form: —(CH$_2$)$_{2-6}$—;

—(CH$_2$)$_2$O(CH$_2$)$_2$—; —(CH$_2$)$_2$S(CH$_2$)$_2$—; or —(CH$_2$)$_2$NR$^{57}$(CH$_2$)$_2$— (where R$^{57}$: H; or lower alkyl);

—(CH$_2$)$_o$N(R$^{20}$)COR$^{64}$ (where R$^{20}$: H; or lower alkyl; R$^{64}$: lower alkyl; or lower alkenyl);

—(CH$_2$)$_o$COOR$^{57}$ (where R$^{57}$: lower alkyl; or lower alkenyl);

—(CH$_2$)$_o$CONR$^{58}$R$^{59}$ (where R$^{58}$: lower alkyl, or lower alkenyl; and R$^{59}$: H; or lower alkyl; or R$^{58}$ and R$^{59}$ taken together form: —(CH$_2$)$_{2-6}$—; —(CH$_2$)$_2$O(CH$_2$)$_2$—;

—(CH$_2$)$_2$S(CH$_2$)$_2$—; or —(CH$_2$)$_2$NR$^{57}$(CH$_2$)$_2$— (where R$^{57}$: H; or lower alkyl);

—(CH$_2$)$_o$PO(OR$^{60}$)$_2$ (where R$^{60}$: lower alkyl; or lower alkenyl);

—(CH$_2$)$_o$SO$_2$R$^{62}$ (where R$^{62}$: lower alkyl; or lower alkenyl); or

—(CH$_2$)$_q$C$_6$H$_4$R$^8$ (where R$^8$: H; F; Cl; CF$_3$; lower alkyl; lower alkenyl; or lower alkoxy)

R$^{22}$ is lower alkyl; lower alkenyl;

—(CH$_2$)$_o$OR$^{55}$ (where R$^{55}$: lower alkyl; or lower alkenyl);

—(CH$_2$)$_o$SR$^{56}$ (where R$^{56}$: lower alkyl; or lower alkenyl);

—(CH$_2$)$_o$NR$^{33}$R$^{34}$ (where R$^{33}$: lower alkyl; or lower alkenyl; R$^{34}$: H; or lower alkyl; or R$^{33}$ and R$^{34}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$— (where R$^{57}$: H; or lower alkyl);

—(CH$_2$)$_o$OCONR$^{33}$R$^{75}$ (where R$^{33}$: H; lower alkyl; or lower alkenyl; R$^{75}$: lower alkyl; or R$^{33}$ and R$^{75}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$— (where R$^{57}$: H; or lower alkyl);
—(CH$_2$)$_o$NR$^{20}$CONR$^{33}$R$^{81}$ (where R$^{20}$: H; or lower alkyl; R$^{33}$: H; lower alkyl; or lower alkenyl; R$^{81}$: H; or lower alkyl; or R$^{33}$ and R$^{81}$ taken together form: —(CH$_2$)$_{2-6}$—;
—(CH$_2$)$_2$O(CH$_2$)$_2$—; —(CH$_2$)$_2$S(CH$_2$)$_2$—; or —(CH$_2$)$_2$NR$^{57}$(CH$_2$)$_2$— (where R$^{57}$: H; or lower alkyl);
—(CH$_2$)$_o$N(R$^{20}$)COR$^{64}$ (where R$^{20}$: H; or lower alkyl; R$^{64}$: lower alkyl; or lower alkenyl);
—(CH$_2$)$_o$COOR$^{57}$ (where R$^{57}$: lower alkyl; or lower alkenyl);
—(CH$_2$)$_o$CONR$^{58}$R$^{59}$ (where R$^{58}$: lower alkyl, or lower alkenyl; and R$^{59}$: H; or lower alkyl; or R$^{58}$ and R$^{59}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$— (where R$^{57}$: H; or lower alkyl);
—(CH$_2$)$_o$PO(OR$^{60}$)$_2$ (where R$^{60}$: lower alkyl; or lower alkenyl);
—(CH$_2$)$_o$SO$_2$R$^{62}$ (where R$^{62}$: lower alkyl; or lower alkenyl); or
—(CH$_2$)$_q$C$_6$H$_4$R$^8$ (where R$^8$: H; F; Cl; CF; lower alkyl; lower alkenyl; or lower alkoxy)

R$^{23}$ is H; lower alkyl; lower alkenyl;
—(CH$_2$)$_o$OR$^{55}$ (where R$^{55}$: lower alkyl; or lower alkenyl);
—(CH$_2$)$_o$SR$^{56}$ (where R$^{56}$: lower alkyl; or lower alkenyl);
—(CH$_2$)$_o$NR$^{33}$R$^{34}$ (where R$^{33}$: lower alkyl; or lower alkenyl; R$^{34}$: H; or lower alkyl; or R$^{33}$ and R$^{34}$ taken together form: —(CH$_2$)$_{2-6}$—; —(CH$_2$)$_2$O(CH$_2$)$_2$—; —(CH$_2$)$_2$S(CH$_2$)$_2$—; or
—(CH$_2$)$_2$NR$^{57}$(CH$_2$)$_2$— (where R$^{57}$: H; or lower alkyl);
—(CH$_2$)$_o$OCONR$^{33}$R$^{75}$ (where R$^{33}$: H; lower alkyl; or lower alkenyl; R$^{75}$: lower alkyl; or R$^{33}$ and R$^{75}$ taken together form: —(CH$_2$)$_{2-6}$—; —(CH$_2$)$_2$O(CH$_2$)$_2$—; —(CH$_2$)$_2$S(CH$_2$)$_2$—; or
—(CH$_2$)$_2$NR$^{57}$(CH$_2$)$_2$— (where R$^{57}$: H; or lower alkyl);
—(CH$_2$)$_o$NR$^{20}$CONR$^{33}$R$^{81}$ (where R$^{20}$: H; or lower alkyl; R$^{33}$: H; lower alkyl; or lower alkenyl; R$^{81}$: H; or lower alkyl; or R$^{33}$ and R$^{81}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$— (where R$^{57}$: H; or lower alkyl);
—(CH$_2$)$_o$N(R$^{20}$)COR$^{64}$ (where R$^{20}$: H; or lower alkyl; R$^{64}$: lower alkyl; or lower alkenyl); particularly favoured are NR$^{20}$CO-lower alkyl (where R$^{20}$: H; or lower alkyl);
—(CH$_2$)$_o$COOR$^{57}$ (where R$^{57}$: lower alkyl; or lower alkenyl);
—(CH$_2$)$_o$CONR$^{58}$R$^{59}$ (where R$^{58}$: lower alkyl, or lower alkenyl; and R$^{59}$: H; or lower alkyl; or R$^{58}$ and R$^{59}$ taken together form: —(CH$_2$)$_{2-6}$—; —(CH$_2$)$_2$O(CH$_2$)$_2$—;
—(CH$_2$)$_2$S(CH$_2$)$_2$—; or —(CH$_2$)$_2$NR$^{57}$(CH$_2$)$_2$— (where R$^{57}$: H; or lower alkyl);
—(CH$_2$)$_o$PO(OR$^{60}$)$_2$ (where R$^{60}$: lower alkyl; or lower alkenyl);
—(CH$_2$)$_o$SO$_2$R$^{62}$ (where R$^{62}$: lower alkyl; or lower alkenyl); or
—(CH$_2$)$_q$C$_6$H$_4$R$^8$ (where R$^8$: H; F; Cl; CF$_3$; lower alkyl; lower alkenyl; or lower alkoxy)

R$^{24}$ is lower alkyl; lower alkenyl;
—(CH$_2$)$_o$OR$^{55}$ (where R$^{55}$: lower alkyl; or lower alkenyl);
—(CH$_2$)$_o$SR$^{56}$ (where R$^{56}$: lower alkyl; or lower alkenyl);

—(CH$_2$)$_o$NR$^{33}$R$^{34}$ (where R$^{33}$: lower alkyl; or lower alkenyl; R$^{34}$: H; or lower alkyl; or R$^{33}$ and R$^{34}$ taken together form: —(CH$_2$)$_{2-6}$—; —(CH$_2$)$_2$O(CH$_2$)$_2$—; —(CH$_2$)$_2$S(CH$_2$)$_2$—; or
—(CH$_2$)$_2$NR$^{57}$(CH$_2$)$_2$— (where R$^{57}$: H; or lower alkyl);
—(CH$_2$)$_o$OCONR$^{33}$R$^{75}$ (where R$^{33}$: H; lower alkyl; or lower alkenyl; R$^{75}$: lower alkyl; or R$^{33}$ and R$^{75}$ taken together form: —(CH$_2$)$_{2-6}$—; —(CH$_2$)$_2$O(CH$_2$)$_2$—; —(CH$_2$)$_2$S(CH$_2$)$_2$—; or
—(CH$_2$)$_2$NR$^{57}$(CH$_2$)$_2$— (where R$^{57}$: H; or lower alkyl);
—(CH$_2$)$_o$NR$^{20}$CONR$^{33}$R$^{81}$ (where R$^{20}$: H; or lower alkyl; R$^{33}$: H; lower alkyl; or lower alkenyl; R$^{81}$: H; or lower alkyl; or R$^{33}$ and R$^{81}$ taken together form: —(CH$_2$)$_{2-6}$—;
—(CH$_2$)$_2$O(CH$_2$)$_2$—; —(CH$_2$)$_2$S(CH$_2$)$_2$—; or —(CH$_2$)$_2$NR$^{57}$(CH$_2$)$_2$— (where R$^{57}$: H; or lower alkyl);
—(CH$_2$)$_o$N(R$^{20}$)COR$^{64}$ (where R$^{20}$: H; or lower alkyl; R$^{64}$: lower alkyl; or lower alkenyl); particularly favoured are NR$^{20}$CO-lower alkyl (where R$^{20}$: H; or lower alkyl);
—(CH$_2$)$_o$COOR$^{57}$ (where R$^{57}$: lower alkyl; or lower alkenyl);
—(CH$_2$)$_o$CONR$^{58}$R$^{59}$ (where R$^{58}$: lower alkyl, or lower alkenyl; and R$^{59}$: H; or lower alkyl; or R$^{58}$ and R$^{59}$ taken together form: —(CH$_2$)$_{2-6}$—; —(CH$_2$)$_2$O(CH$_2$)$_2$—;
—(CH$_2$)$_2$S(CH$_2$)$_2$—; or —(CH$_2$)$_2$NR$^{57}$(CH$_2$)$_2$— (where R$^{57}$: H; or lower alkyl);
—(CH$_2$)$_o$PO(OR$^{60}$)$_2$ (where R$^{60}$: lower alkyl; or lower alkenyl);
—(CH$_2$)$_o$SO$_2$R$^{62}$ (where R$^{62}$: lower alkyl; or lower alkenyl); or
—(CH$_2$)$_q$C$_6$H$_4$R$^8$ (where R$^8$: H; F; Cl; CF$_3$; lower alkyl; lower alkenyl; or lower alkoxy)

R$^{25}$ is H; lower alkyl; lower alkenyl;
—(CH$_2$)$_m$OR$^{55}$ (where R$^{55}$: lower alkyl; or lower alkenyl);
—(CH$_2$)$_m$NR$^{33}$R$^{34}$ (where R$^{33}$: lower alkyl; or lower alkenyl; R$^{34}$: H; or lower alkyl; or
R$^{33}$ and R$^{34}$ taken together form: —(CH$_2$)$_{2-6}$—;
—(CH$_2$)$_2$O(CH$_2$)$_2$—; —(CH$_2$)$_2$S(CH$_2$)$_2$—; or
—(CH$_2$)$_2$NR$^{57}$(CH$_2$)$_2$— (where R$^{57}$: H; or lower alkyl);
—(CH$_2$)$_m$OCONR$^{33}$R$^{75}$ (where R$^{33}$: H; lower alkyl; or lower alkenyl; R$^{75}$: lower alkyl; or R$^{33}$ and R$^{75}$ taken together form: —(CH$_2$)$_{2-6}$—; —(CH$_2$)$_2$O(CH$_2$)$_2$—; —(CH$_2$)$_2$S(CH$_2$)$_2$—; or
—(CH$_2$)$_2$NR$^{57}$(CH$_2$)$_2$— (where R$^{57}$: H; or lower alkyl);
—(CH$_2$)$_m$NR$^{20}$CONR$^{33}$R$^{81}$ (where R$^{20}$: H; or lower alkyl; R$^{33}$: H; lower alkyl; or lower alkenyl; R$^{81}$: H; or lower alkyl; or R$^{33}$ and R$^{81}$ taken together form: —(CH$_2$)$_{2-6}$—;
—(CH$_2$)$_2$O(CH$_2$)$_2$—; —(CH$_2$)$_2$S(CH$_2$)$_2$—; or —(CH$_2$)$_2$NR$^{57}$(CH$_2$)$_2$— (where R$^{57}$: H; or lower alkyl);
—(CH$_2$)$_m$N(R$^{20}$)COR$^{64}$ (where R$^{20}$: H; or lower alkyl; R$^{64}$: lower alkyl; or lower alkenyl);
—(CH$_2$)$_o$COOR$^{57}$ (where R$^{57}$: lower alkyl; or lower alkenyl);
—(CH$_2$)$_o$CONR$^{58}$R$^{59}$ (where R$^{58}$: lower alkyl; or lower alkenyl; and R$^{59}$: H; or lower alkyl; or R$^{58}$ and R$^{59}$ taken together form: —(CH$_2$)$_{2-6}$—; —(CH$_2$)$_2$O (CH$_2$)$_2$—;
—(CH$_2$)$_2$S(CH$_2$)$_2$—; or —(CH$_2$)$_2$NR$^{57}$(CH$_2$)$_2$— (where R$^{57}$: H; or lower alkyl);
—(CH$_2$)$_o$PO(OR$^{60}$)$_2$ (where R$^{60}$: lower alkyl; or lower alkenyl);
—(CH$_2$)$_o$SO$_2$R$^{62}$ (where R$^{62}$: lower alkyl; or lower alkenyl); or —$(CH_2)_qC_6H_4R^8$ (where $R^8$: H; F; Cl; $CF_3$; lower alkyl; lower alkenyl; or lower alkoxy)

$R^{26}$ is H; lower alkyl; lower alkenyl;
—$(CH_2)_mOR^{55}$ (where $R^{55}$: lower alkyl; or lower alkenyl);
—$(CH_2)_mNR^{33}R^{34}$ (where $R^{33}$: lower alkyl; or lower alkenyl; $R^{34}$: H; or lower alkyl; or $R^{33}$ and $R^{34}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl);
—$(CH_2)_mOCONR^{33}R^{75}$ (where $R^{33}$: H; lower alkyl; or lower alkenyl; $R^{75}$: lower alkyl; or $R^{33}$ and $R^{75}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl);
—$(CH_2)_mNR^{20}CONR^{33}R^{81}$ (where $R^{20}$: H; or lower alkyl; $R^{33}$: H; lower alkyl; or lower alkenyl; $R^{81}$: H; or lower alkyl; or $R^{33}$ and $R^{81}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl);
—$(CH_2)_mN(R^{20})COR^{64}$ (where $R^{20}$: H; or lower alkyl; $R^{64}$: lower alkyl; or lower alkenyl);
—$(CH_2)_oCOOR^{57}$ (where $R^{57}$: lower alkyl; or lower alkenyl);
—$(CH_2)_oCONR^{58}R^{59}$ (where $R^{58}$: lower alkyl; or lower alkenyl; and $R^{59}$: H; or lower alkyl; or $R^{58}$ and $R^{59}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl);
—$(CH_2)_oPO(OR^{60})_2$ (where $R^{60}$: lower alkyl; or lower alkenyl);
—$(CH_2)_oSO_2R^{62}$ (where $R^{62}$: lower alkyl; or lower alkenyl); or
—$(CH_2)_qC_6H_4R^8$ (where $R^8$: H; F; Cl; $CF_3$; lower alkyl; lower alkenyl; or lower alkoxy); or, alternatively, $R^{25}$ and $R^{26}$ taken together can be
—$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl)

$R^{27}$ is H; lower alkyl; lower alkenyl;
—$(CH_2)_oOR^{55}$ (where $R^{55}$: lower alkyl; or lower alkenyl);
—$(CH_2)_oSR^{56}$ (where $R^{56}$: lower alkyl; or lower alkenyl);
—$(CH_2)_oNR^{33}R^{34}$ (where $R^{33}$: lower alkyl; or lower alkenyl; $R^{34}$: H; or lower alkyl; or $R^{33}$ and $R^{34}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl);
—$(CH_2)_oOCONR^{33}R^{75}$ (where $R^{33}$: H; lower alkyl; or lower alkenyl; $R^{75}$: lower alkyl; or $R^{33}$ and $R^{75}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl);
—$(CH_2)_oNR^{20}CONR^{33}R^{81}$ (where $R^{20}$: H; or lower alkyl; $R^{33}$: H; lower alkyl; or lower alkenyl; $R^{81}$: H; or lower alkyl; or $R^{33}$ and $R^{81}$ taken together form: —$(CH_2)_{2-6}$—; —$(CH_2)_2O(CH_2)_2$—; —$(CH_2)_2S(CH_2)_2$—; or —$(CH_2)_2 NR^{57}(CH_2)_2$— (where $R^{57}$: H; or lower alkyl);
—$(CH_2)_oN(R^{20})COR^{64}$ (where $R^{20}$: H; or lower alkyl; $R^{64}$: lower alkyl; or lower alkenyl);
—$(CH_2)_oCOOR^{57}$ (where $R^{57}$: lower alkyl; or lower alkenyl);
—$(CH_2)_oCONR^{58}R^{59}$ (where $R^{58}$: lower alkyl, or lower alkenyl; and $R^{59}$: H; or lower alkyl; or $R^{58}$ and $R^{59}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl);
—$(CH_2)_oPO(OR^{60})_2$ (where $R^{60}$: lower alkyl; or lower alkenyl);
—$(CH_2)_oSO_2R^{62}$ (where $R^{62}$: lower alkyl; or lower alkenyl); or
—$(CH_2)_qC_6H_4R^8$ (where $R^8$: H; F; Cl; $CF_3$; lower alkyl; lower alkenyl; or lower alkoxy)

$R^{28}$ is lower alkyl; lower alkenyl;
—$(CH_2)_oOR^{55}$ (where $R^{55}$: lower alkyl; or lower alkenyl);
—$(CH_2)_oSR^{56}$ (where $R^{56}$: lower alkyl; or lower alkenyl);
—$(CH_2)_oNR^{33}R^{34}$ (where $R^{33}$: lower alkyl; or lower alkenyl; $R^{34}$: H; or lower alkyl; or $R^{33}$ and $R^{34}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl);
—$(CH_2)_oOCONR^{33}R^{75}$ (where $R^{33}$: H; lower alkyl; or lower alkenyl; $R^{75}$: lower alkyl; or $R^{33}$ and $R^{75}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl);
—$(CH_2)_oNR^{20}CONR^{33}R^{81}$ (where $R^{20}$: H; or lower alkyl; $R^{33}$: H; lower alkyl; or lower alkenyl; $R^{81}$: H; or lower alkyl; or $R^{33}$ and $R^{81}$ taken together form: —$(CH_2)_{2-6}$—;
—$(CH_2)_2O(CH_2)_2$—; —$(CH_2)_2S(CH_2)_2$—; or —$(CH_2)_2 NR^{57}(CH_2)_2$— (where $R^{57}$: H; or lower alkyl);
—$(CH_2)_oN(R^{20})COR^{64}$ (where $R^{20}$: H; or lower alkyl; $R^{64}$: lower alkyl; or lower alkenyl);
—$(CH_2)_oCOOR^{57}$ (where $R^{57}$: lower alkyl; or lower alkenyl);
—$(CH_2)_oCONR^{58}R^{59}$ (where $R^{58}$: lower alkyl, or lower alkenyl; and $R^{59}$: H; or lower alkyl; or $R^{58}$ and $R^{59}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl);
—$(CH_2)_oPO(OR^{60})_2$ (where $R^{60}$: lower alkyl; or lower alkenyl);
—$(CH_2)_oSO_2R^{62}$ (where $R^{62}$: lower alkyl; or lower alkenyl); or
—$(CH_2)_qC_6H_4R^8$ (where $R^8$: H; F; Cl; $CF_3$; lower alkyl; lower alkenyl; or lower alkoxy)

$R^{29}$ is lower alkyl; lower alkenyl;
—$(CH_2)_oOR^{55}$ (where $R^{55}$: lower alkyl; or lower alkenyl);
—$(CH_2)_oSR^{56}$ (where $R^{56}$: lower alkyl; or lower alkenyl);
—$(CH_2)_oNR^{33}R^{34}$ (where $R^{33}$: lower alkyl; or lower alkenyl; $R^{34}$: H; or lower alkyl; or $R^{33}$ and $R^{34}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl);
—$(CH_2)_oOCONR^{33}R^{75}$ (where $R^{33}$: H; lower alkyl; or lower alkenyl; $R^{75}$: lower alkyl; or $R^{33}$ and $R^{75}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl);
—$(CH_2)_oNR^{20}CONR^{33}R^{81}$ (where $R^{20}$: H; or lower alkyl; $R^{33}$: H; lower alkyl; or lower alkenyl; $R^{81}$: H; or lower alkyl; or $R^{33}$ and $R^{81}$ taken together form:

—(CH$_2$)$_{2-6}$—; —(CH$_2$)$_2$O(CH$_2$)$_2$—; —(CH$_2$)$_2$S (CH$_2$)$_2$—; or —(CH$_2$)$_2$NR$^{57}$(CH$_2$)$_2$— (where R$^{57}$: H; or lower alkyl);

—(CH$_2$)$_o$N(R$^{20}$)COR$^{64}$ (where R$^{20}$: H; or lower alkyl; R$^{64}$: lower alkyl; or lower alkenyl); particularly favored are NR$^{20}$CO-lower-alkyl (where R$^{20}$: H; or lower alkyl);

—(CH$_2$)$_o$COOR$^{57}$ (where R$^{57}$: lower alkyl; or lower alkenyl);

—(CH$_2$)$_o$CONR$^{58}$R$^{59}$ (where R$^{58}$: lower alkyl, or lower alkenyl; and R$^{59}$: H; or lower alkyl; or R$^{58}$ and R$^{59}$ taken together form: —(CH$_2$)$_{2-6}$—; —(CH$_2$)$_2$O (CH$_2$)$_2$—; —(CH$_2$)$_2$S(CH$_2$)$_2$—; or —(CH$_2$)$_2$NR$^{57}$ (CH$_2$)$_2$— (where R$^{57}$: H; or lower alkyl);

—(CH$_2$)$_o$PO(OR$^{60}$)$_2$ (where R$^{60}$: lower alkyl; or lower alkenyl);

—(CH$_2$)$_o$SO$_2$R$^{62}$ (where R$^{62}$: lower alkyl; or lower alkenyl); or

—(CH$_2$)$_q$C$_6$H$_4$R$^8$ (where R$^8$: H; F; Cl; CF$_3$; lower alkyl; lower alkenyl; or lower alkoxy).

5. Compounds according to claim 1 wherein B is a group of formula —NR$^{20}$CH(R$^{71}$)—, or —NR$^{20}$CH(R$^{72}$)—, or —NR$^{20}$CH(R$^{73}$)—, or —NR$^{20}$CH(R$^{74}$)—, or —NR$^{20}$CH (R$^{84}$)—, or an enantiomer of one of the groups A5 (with R$^2$ being H); A8; A22; A25; A38 (with R$^2$ being H); A42; A47 and A50.

6. Compounds according to claim 5 wherein B—CO is Ala; Arg; Asn; Asp; Cys; Gln; Glu; Gly; His; Ile; Leu; Lys; Met; Phe; Pro; Ser; Thr; Trp; Tyr; Val; Cit; Orn; tBuA; Sar; t-BuG; 4AmPhe; 3AmPhe; 2AmPhe; Phe(mC(NH$_2$)=NH); Phe(pC (NH$_2$)=NH); Phe(mNHC (NH$_2$)=NH); Phe(pNHC (NH$_2$)=NH); Phg; Cha; C$_4$al; C$_5$al; Nle; 2-Nal; 1-Nal; 4Cl-Phe; 3Cl-Phe; 2Cl-Phe; 3,4Cl$_2$Phe; 4F-Phe; 3F-Phe; 2F-Phe; Tic; Thi; Tza; Mso; AcLys; Dpr; A$_2$Bu; Dbu; Abu; Aha; Aib; Y(Bzl); Bip; S(Bzl); T(Bzl); hCha; hCys; hSer, hArg; hPhe; Bpa; Pip; MePhe; MeNle; MeAla; MeIle; MeVal; MeLeu; 4Hyp1; 4Hyp2; 4Mp1; 4Mp2.

7. Compounds according to claim 1 wherein B is a group, having (L)-configuration, of formula

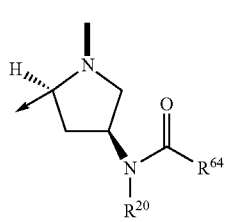

A8″ wherein R$^{20}$ is H or lower alkyl and R$^{64}$ is alkyl; alkenyl; —[(CH$_2$)$_u$—X]$_t$—CH$_3$ (where X is —O—; —NR$^{20}$—, or —S—; u=1-3, and t=1-6), aryl; aryl-lower alkyl; or heteroaryl-lower alkyl; especially those wherein R$^{64}$ is n-hexyl (A8″-21); n-heptyl (A8″-22); 4-(phenyl)benzyl (A8″-23); diphenylmethyl (A8″-24); 3-amino-propyl (A8″-25); 5-amino-pentyl (A8″-26); methyl (A8″-27); ethyl (A8″-28); isopropyl (A8″-29); isobutyl (A8″-30); n-propyl (A8″-31); cyclohexyl (A8″-32); cyclohexyl-methyl (A8″-33); n-butyl (A8″-34); phenyl (A8″-35); benzyl (A8″-36); (3-indolyl)methyl (A8″-37); 2-(3-indolyl) ethyl (A8″-38); (4-phenyl)-phenyl (A8″-39); n-nonyl (A8″-40); CH$_3$—OCH$_2$CH$_2$—OCH$_2$— (A8″-41) and CH$_3$—(OCH$_2$CH$_2$)$_2$—OCH$_2$— (A8″-42).

8. Compounds according to claim 1 wherein Xaa$^{13}$ is $^D$Pro, $^D$Cha, NMe$^D$Ile, $^D$Tyr, $^D$His, $^D$His(Bzl), $^D$4 Pal, NMe$^D$Tyr, NMe$^D$Lys, (ABu)G, $^D$Ile, NMe$^D$Ala, $^D$Lys, or $^D$Dab; Xaa$^{14}$ is $^L$Pro; the aforesaid $^D$Pro moiety and/or the aforesaid $^L$Pro moiety being optionally substituted as shown in formulae A8′ and, respectively, A8″.

9. Compounds according to claim 1 wherein the amino acid residues in Cyclo(-Xaa$^1$-Xaa$^2$-Xaa$^3$-Xaa$^4$-Xaa$^5$-Xaa$^6$-Xaa$^7$-Xaa$^8$-Xaa$^9$-Xaa$^{10}$-Xaa$^{11}$-Xaa$^{12}$-Xaa$^{13}$-Xaa$^{14}$-) are:

Xaa$^1$: Trp;
Xaa$^2$: Arg, Dab or Orn;
Xaa$^3$: Ile;
Xaa$^4$: Arg, Dab or Orn;
Xaa$^5$: Ile;
Xaa$^6$: $^D$Arg, Dab, $^D$Dab, Orn;
Xaa$^7$: Asn, Gln, Thr, Leu or Tyr;
Xaa$^8$: Lys, Gln, Trp or His;
Xaa$^9$: Arg or Dab;
Xaa$^{10}$: Asn, Leu, Cha, Tyr or Trp;
Xaa$^{11}$: Arg or Gln;
Xaa$^{12}$: Arg, Dab, Ala or Gln;
Xaa$^{13}$: DPro;
Xaa$^{14}$: LPro.

10. A compound according to claim 1 wherein the amino acid residues are:
Xaa$^1$: Trp;
Xaa$^2$: Arg;
Xaa$^3$: Ile;
Xaa$^4$: Arg;
Xaa$^5$: Ile;
Xaa$^6$: $^D$Arg;
Xaa$^7$: Asn;
Xaa$^8$: Lys;
Xaa$^9$: Arg;
Xaa$^{10}$: Leu;
Xaa$^{11}$: Arg;
Xaa$^{12}$: Gln;
Xaa$^{13}$: $^D$Pro;
Xaa$^{14}$: $^L$Pro;
or wherein the amino acid residues are:
Xaa$^1$: Trp;
Xaa$^2$: Dab;
Xaa$^3$: Ile;
Xaa$^4$: Arg;
Xaa$^5$: Ile;
Xaa$^6$: $^D$Arg;
Xaa$^7$: Asn;
Xaa$^8$: Gln;
Xaa$^9$: Arg;
Xaa$^{10}$: Leu;
Xaa$^{11}$: Gln;
Xaa$^{12}$: Ala;
Xaa$^{13}$: $^D$Pro;
Xaa$^{14}$: $^L$Pro;
or wherein the amino acid residues are:
Xaa$^1$: Trp;
Xaa$^2$: Arg;
Xaa$^3$: Ile;
Xaa$^4$: Arg;
Xaa$^5$: Ile;
Xaa$^6$: $^D$Arg;
Xaa$^7$: Asn;
Xaa$^8$: Gln;
Xaa$^9$: Arg;
Xaa$^{10}$: Trp;
Xaa$^{11}$: Gln;
Xaa$^{12}$: Ala;

Xaa$^{13}$: $^D$Pro;
Xaa$^{14}$: $^L$Pro;
or wherein the amino acid residues are:
Xaa$^1$: Trp;
Xaa$^2$: Arg;
Xaa$^3$: Ile;
Xaa$^4$: Arg;
Xaa$^5$: Ile;
Xaa$^6$: $^D$Dab;
Xaa$^7$: Asn;
Xaa$^8$: Trp;
Xaa$^9$: Dab;
Xaa$^{10}$: Asn;
Xaa$^{11}$: Arg;
Xaa$^{12}$: Dab;
Xaa$^{13}$: $^D$Pro;
Xaa$^{14}$: LPro.

11. Enantiomers of the compounds as defined in claim 1.

12. Compounds according to claim 1 for use as therapeutically active substances, particularly as substances having selective anti-infective activity, especially as substances having selective antibacterial activity against *Bacillus subtilis* and/or *Shigella boydii*.

13. A pharmaceutical composition containing a compound according to claim 1 and a pharmaceutically inert carrier, particularly in a form suitable for oral, topical, transdermal, injection, buccal, transmucosal, pulmonary or inhalation administration such as tablets, dragees, capsules, solutions, liquids, gels, plaster, creams, ointments, syrup, slurries, suspensions, spray, nebuliser or suppositories.

14. The use of compounds according to claim 1 for the manufacture of a medicament, particularly intended to be used for preventing or treating infections or diseases related to such infections, particularly infections related to respiratory diseases or skin or soft tissue diseases or gastrointestinal diseases or eye diseases or ear diseases or CNS diseases or bone diseases or cardiovascular diseases or gastrourinal diseases, liver diseases, sexually transmitted diseases or diseases such as common cold, influenza, parotitis or gingivostomatitis, or as a disinfectants or preservatives for foodstuffs, cosmetics, medicaments and other nutrient-containing materials.

15. A process for the manufacture of compounds according to claim 1 which process comprises
 (a) coupling an appropriately functionalized solid support with an appropriately N-protected derivative of that amino acid which in the desired end-product corresponds to Xaa$^n$, wherein n is 14, 13, 12, 7, 6 or 5, any functional group which may be present in said N-protected amino acid derivative being likewise appropriately protected;
 (b) removing the N-protecting group from the product thus obtained;
 (c) coupling the product thus obtained with an appropriately N-protected derivative of that amino acid which in the desired end-product corresponds to Xaa$^{n-1}$, any functional group which may be present in said N-protected amino acid derivative being likewise appropriately protected;
 (d) removing the N-protecting group from the product obtained in step (c);
 (e) effecting steps substantially corresponding to steps (c) and (d) using appropriately N-protected derivatives of amino acids which in the desired end-product are in positions n−2 to 1, any functional group(s) which may be present in said N-protected amino acid derivatives being likewise appropriately protected;
 (f) if n is not 14, further effecting steps substantially corresponding to steps (c) and (d) using appropriately N-protected derivatives of amino acids which in the desired end-product are in positions 14 to n+1, any functional group(s) which may be present in said N-protected amino acid derivatives being likewise appropriately protected;
 (g) forming an interstrand linkage between side-chains of appropriate amino acid residues at P2 and P11; or alternatively, forming the aforesaid linkage subsequent to step (j), as described herein below;
 (h) detaching the product thus obtained from the solid support;
 (i) cyclizing the product cleaved from the solid support;
 (j) removing any protecting groups present on functional groups of any members of the chain of amino acid residues and, if desired, any protecting group(s) which may in addition be present in the molecule; and
 (k) if desired, converting the product thus obtained into a pharmaceutically acceptable salt or converting a pharmaceutically acceptable, or unacceptable, salt thus obtained into the corresponding free compound or into a different, pharmaceutically acceptable, salt.

16. A modification of the processes according to claim 15 for the manufacture of compounds in which enantiomers of all chiral starting materials are used.

* * * * *

SEQUENCE LISTING

<160> NUMBER OF SEQ ID NOS: 18

<210> SEQ ID NO 1
<211> LENGTH: 14
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (6)..(6)
<223> OTHER INFORMATION: Xaa is D-Arginine
<220> FEATURE:
<221> NAME/KEY: misc_feature
<222> LOCATION: (9)..(9)
<223> OTHER INFORMATION: Xaa is Dab (2,4 Diaminobutyric acid)
<220> FEATURE:
<221> NAME/KEY: misc_feature
<222> LOCATION: (13)..(13)
<223> OTHER INFORMATION: Xaa is D-Proline

<400> SEQUENCE: 1

Trp Arg Ile Arg Ile Xaa Asn Lys Xaa Leu Arg Arg Xaa Pro
1               5                   10

<210> SEQ ID NO 2
<211> LENGTH: 14
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (6)..(6)
<223> OTHER INFORMATION: Xaa is D-Arginine
<220> FEATURE:
<221> NAME/KEY: misc_feature
<222> LOCATION: (13)..(13)
<223> OTHER INFORMATION: Xaa is D-Proline

<400> SEQUENCE: 2

Trp Arg Ile Arg Ile Xaa Asn Lys Arg Leu Arg Gln Xaa Pro
1               5                   10

<210> SEQ ID NO 3
<211> LENGTH: 14
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (6)..(6)
<223> OTHER INFORMATION: Xaa is D-Arginine
<220> FEATURE:
<221> NAME/KEY: misc_feature
<222> LOCATION: (13)..(13)
<223> OTHER INFORMATION: Xaa is D-Proline

<400> SEQUENCE: 3

Trp Arg Ile Arg Ile Xaa Asn Lys Arg Asn Arg Ala Xaa Pro
1               5                   10

<210> SEQ ID NO 4
<211> LENGTH: 14
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (6)..(6)
<223> OTHER INFORMATION: Xaa is D-Arginine
<220> FEATURE:
<221> NAME/KEY: misc_feature
<222> LOCATION: (10)..(10)
<223> OTHER INFORMATION: Xaa is Cha (L-Cyclohexylalanine)
<220> FEATURE:
<221> NAME/KEY: misc_feature
<222> LOCATION: (13)..(13)
<223> OTHER INFORMATION: Xaa is D-Proline

<400> SEQUENCE: 4

Trp Arg Ile Arg Ile Xaa Asn Gln Arg Xaa Gln Ala Xaa Pro
1               5                   10

<210> SEQ ID NO 5
<211> LENGTH: 14
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (2)..(2)
<223> OTHER INFORMATION: Xaa is Dab (L- 2,4 Diaminobutyric acid)
<220> FEATURE:
<221> NAME/KEY: misc_feature
<222> LOCATION: (6)..(6)
<223> OTHER INFORMATION: Xaa is D-Arginine
<220> FEATURE:
<221> NAME/KEY: misc_feature
<222> LOCATION: (13)..(13)
<223> OTHER INFORMATION: Xaa is D-Proline

<400> SEQUENCE: 5

Trp Xaa Ile Arg Ile Xaa Asn Gln Arg Leu Gln Ala Xaa Pro
1               5                   10

<210> SEQ ID NO 6
<211> LENGTH: 14
<212> TYPE: PRT
<213> ORGANISM: Artificial Sequence
<220> FEATURE:
<223> OTHER INFORMATION: Synthetic peptide

```
<220> FEATURE:
<221> NAME/KEY: misc_feature
<222> LOCATION: (2)..(2)
<223> OTHER INFORMATION: Xaa is Orn (L-Ornithine)
<220> FEATURE:
<221> NAME/KEY: misc_feature
<222> LOCATION: (6)..(6)
<223> OTHER INFORMATION: Xaa is D-Arginine
<220> FEATURE:
<221> NAME/KEY: misc_feature
<222> LOCATION: (13)..(13)
<223> OTHER INFORMATION: Xaa is D-Proline

<400> SEQUENCE: 6

Trp Xaa Ile Arg Ile Xaa Asn Gln Arg Leu Gln Ala Xaa Pro
1               5                   10

<210> SEQ ID NO 7
<211> LENGTH: 14
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (4)..(4)
<223> OTHER INFORMATION: Xaa is Dab (L-2,4 Diaminobutyric acid)
<220> FEATURE:
<221> NAME/KEY: misc_feature
<222> LOCATION: (6)..(6)
<223> OTHER INFORMATION: Xaa is D-Arginine
<220> FEATURE:
<221> NAME/KEY: misc_feature
<222> LOCATION: (13)..(13)
<223> OTHER INFORMATION: Xaa is D-Proline

<400> SEQUENCE: 7

Trp Arg Ile Xaa Ile Xaa Asn Gln Arg Leu Gln Ala Xaa Pro
1               5                   10

<210> SEQ ID NO 8
<211> LENGTH: 14
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (4)..(4)
<223> OTHER INFORMATION: Xaa is Orn (L-Ornithine)
<220> FEATURE:
<221> NAME/KEY: misc_feature
<222> LOCATION: (6)..(6)
<223> OTHER INFORMATION: Xaa is D-Arginine
<220> FEATURE:
<221> NAME/KEY: misc_feature
<222> LOCATION: (13)..(13)
<223> OTHER INFORMATION: Xaa is D-Proline

<400> SEQUENCE: 8

Trp Arg Ile Xaa Ile Xaa Asn Gln Arg Leu Gln Ala Xaa Pro
1               5                   10

<210> SEQ ID NO 9
<211> LENGTH: 14
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (6)..(6)
<223> OTHER INFORMATION: Xaa is Orn (L-Ornithine)
```

```
<220> FEATURE:
<221> NAME/KEY: misc_feature
<222> LOCATION: (13)..(13)
<223> OTHER INFORMATION: Xaa is D-Proline

<400> SEQUENCE: 9

Trp Arg Ile Arg Ile Xaa Asn Gln Arg Leu Gln Ala Xaa Pro
1               5                   10

<210> SEQ ID NO 10
<211> LENGTH: 14
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (6)..(6)
<223> OTHER INFORMATION: Xaa is Dab (L- 2,4 Diaminobutyric acid)
<220> FEATURE:
<221> NAME/KEY: misc_feature
<222> LOCATION: (13)..(13)
<223> OTHER INFORMATION: Xaa is D-Proline

<400> SEQUENCE: 10

Trp Arg Ile Arg Ile Xaa Asn Gln Arg Leu Gln Ala Xaa Pro
1               5                   10

<210> SEQ ID NO 11
<211> LENGTH: 14
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (6)..(6)
<223> OTHER INFORMATION: Xaa is D-Arginine
<220> FEATURE:
<221> NAME/KEY: misc_feature
<222> LOCATION: (13)..(13)
<223> OTHER INFORMATION: Xaa is D-Proline

<400> SEQUENCE: 11

Trp Arg Ile Arg Ile Xaa Gln Gln Arg Leu Gln Ala Xaa Pro
1               5                   10

<210> SEQ ID NO 12
<211> LENGTH: 14
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (6)..(6)
<223> OTHER INFORMATION: Xaa is D-Arginine
<220> FEATURE:
<221> NAME/KEY: misc_feature
<222> LOCATION: (13)..(13)
<223> OTHER INFORMATION: Xaa is D-Proline

<400> SEQUENCE: 12

Trp Arg Ile Arg Ile Xaa Thr Gln Arg Leu Gln Ala Xaa Pro
1               5                   10

<210> SEQ ID NO 13
<211> LENGTH: 14
<212> TYPE: PRT
<213> ORGANISM: Artificial Sequence
<220> FEATURE:
```

```
<223> OTHER INFORMATION: Synthetic peptide
<220> FEATURE:
<221> NAME/KEY: misc_feature
<222> LOCATION: (6)..(6)
<223> OTHER INFORMATION: Xaa is D-Arginine
<220> FEATURE:
<221> NAME/KEY: misc_feature
<222> LOCATION: (13)..(13)
<223> OTHER INFORMATION: Xaa is D-Proline

<400> SEQUENCE: 13

Trp Arg Ile Arg Ile Xaa Leu Gln Arg Leu Gln Ala Xaa Pro
1               5                   10

<210> SEQ ID NO 14
<211> LENGTH: 14
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (6)..(6)
<223> OTHER INFORMATION: Xaa is D-Arginine
<220> FEATURE:
<221> NAME/KEY: misc_feature
<222> LOCATION: (13)..(13)
<223> OTHER INFORMATION: Xaa is D-Proline

<400> SEQUENCE: 14

Trp Arg Ile Arg Ile Xaa Tyr Gln Arg Leu Gln Ala Xaa Pro
1               5                   10

<210> SEQ ID NO 15
<211> LENGTH: 14
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (6)..(6)
<223> OTHER INFORMATION: Xaa is D-Arginine
<220> FEATURE:
<221> NAME/KEY: misc_feature
<222> LOCATION: (13)..(13)
<223> OTHER INFORMATION: Xaa is D-Proline

<400> SEQUENCE: 15

Trp Arg Ile Arg Ile Xaa Asn Gln Arg Tyr Gln Ala Xaa Pro
1               5                   10

<210> SEQ ID NO 16
<211> LENGTH: 14
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (6)..(6)
<223> OTHER INFORMATION: Xaa is D-Arginine
<220> FEATURE:
<221> NAME/KEY: misc_feature
<222> LOCATION: (13)..(13)
<223> OTHER INFORMATION: Xaa is D-Proline

<400> SEQUENCE: 16

Trp Arg Ile Arg Ile Xaa Asn Gln Arg Trp Gln Ala Xaa Pro
1               5                   10
```

```
<210> SEQ ID NO 17
<211> LENGTH: 14
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (6)..(6)
<223> OTHER INFORMATION: Xaa is dDab (D-2,4 Diaminobutyric acid)
<220> FEATURE:
<221> NAME/KEY: misc_feature
<222> LOCATION: (9)..(9)
<223> OTHER INFORMATION: Xaa is Dab (L-2,4 Diaminobutyric acid)
<220> FEATURE:
<221> NAME/KEY: misc_feature
<222> LOCATION: (12)..(12)
<223> OTHER INFORMATION: Xaa is Dab (L-2,4 Diaminobutyric acid)
<220> FEATURE:
<221> NAME/KEY: misc_feature
<222> LOCATION: (13)..(13)
<223> OTHER INFORMATION: Xaa is D-Proline

<400> SEQUENCE: 17

Trp Arg Ile Arg Ile Xaa Asn Trp Xaa Asn Arg Xaa Xaa Pro
1               5                   10

<210> SEQ ID NO 18
<211> LENGTH: 14
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (6)..(6)
<223> OTHER INFORMATION: Xaa is D-Arginine
<220> FEATURE:
<221> NAME/KEY: misc_feature
<222> LOCATION: (13)..(13)
<223> OTHER INFORMATION: Xaa is D-Proline

<400> SEQUENCE: 18

Trp Arg Ile Arg Ile Xaa Asn His Arg Asn Arg Arg Xaa Pro
1               5                   10
```